(12) United States Patent
Capobianco et al.

(10) Patent No.: US 12,077,508 B2
(45) Date of Patent: *Sep. 3, 2024

(54) INHIBITORS OF THE NOTCH TRANSCRIPTIONAL ACTIVATION COMPLEX KINASE ("NACK") AND METHODS FOR USE OF THE SAME

(71) Applicant: UNIVERSITY OF MIAMI, Miami, FL (US)

(72) Inventors: Anthony J. Capobianco, Miami Beach, FL (US); Stephan C. Schürer, Coral Gables, FL (US); Xiaoxia Zhu, Palmetto Bay, FL (US); Tanya T. Kelley, Miami, FL (US)

(73) Assignee: University of Miami, Miami, FL (US)

( * ) Notice: Subject to any disclaimer, the term of this patent is extended or adjusted under 35 U.S.C. 154(b) by 60 days.

This patent is subject to a terminal disclaimer.

(21) Appl. No.: 17/929,957

(22) Filed: Sep. 6, 2022

(65) Prior Publication Data
US 2023/0113546 A1    Apr. 13, 2023

Related U.S. Application Data

(63) Continuation of application No. 16/967,652, filed as application No. PCT/US2019/016868 on Feb. 6, 2019, now Pat. No. 11,649,214.

(60) Provisional application No. 62/626,870, filed on Feb. 6, 2018.

(51) Int. Cl.
C07D 231/54    (2006.01)

(52) U.S. Cl.
CPC .......... *C07D 231/54* (2013.01); *C12Y 207/00* (2013.01); *C12Y 306/01003* (2013.01)

(58) Field of Classification Search
CPC .................................................. C07D 231/54
USPC ........................................................ 514/406
See application file for complete search history.

(56) References Cited

U.S. PATENT DOCUMENTS 11,649,214 B2    5/2023    Capobianco et al.

FOREIGN PATENT DOCUMENTS

| WO | WO-2013/088256 A1 | 6/2013 |
| WO | WO-2016/077841 A1 | 5/2016 |
| WO | WO-2016/154255 A1 | 9/2016 |

OTHER PUBLICATIONS

Aster et al., Oncogenic forms of NOTCH1 lacking either the primary binding site for RBP-Jkappa or nuclear localization sequences retain the ability to associate with RBP-Jkappa and activate transcription, J. Biol. Chem., 272(17):11336-11343 (1997).
Astudillo et at, The small molecule IMR-1 inhibits the notch transcriptional activation complex to suppress tumorigenesis, Cancer Research, 76(12):3593-3603 (2016).
Berezovska et al., Aspartate mutations in presenilin and gamma-secretase inhibitors both impair notch1 proteolysis and nuclear translocation with relative preservation of notch1 signaling, J. Neurochem., 75(2):583-593 (2000).
Fischer et al., Anti-DLL4 inhibits growth and reduces tumor-initiating cell frequency in colorectal tumors with oncogenic KRAS mutations, Cancer Res, 71(5):1520-1525 (2011).
International Application No. PCT/US2019/016868, International Search Report and Written Opinion, mailed Jun. 14, 2019.
International Preliminary Report on Patentability for corresponding International Application No. PCT/US2019/016868, dated Aug. 11, 2020.
Jeffries et at, Characterization of a high-molecular-weight Notch complex in the nucleus of Notch(ic)-transformed RKE cells and in a human T-cell leukemia cell line, Mol. Cell Biol., 22(11):3927-3941 (2002).
Kloe et al., Small molecules that inhibit Notch signaling, Methods Mol. Biol., 1187:311-322 (2014).
Kovall et al., Crystal structure of the nuclear effector of Notch signaling, CSL, bound to DNA, EMBO J., 23(17):3441-3451 (2004).
Kovall, More complicated than it looks: assembly of Notch pathway transcription complexes, Oncogene, 27(38):5099-5109 (2008).
McGuffin et al., IntFOLD: an integrated server for modelling protein structures and functions from amino acid sequences, Nucleic Acids Res, 43(WI):W169-W173 (2015).
Moellering et al., Direct inhibition of the NOTCH transcription factor complex, Nature, 462:182-188 (2009).
Nam et al., Structural basis for cooperativity in recruitment of MAML coactivators to Notch transcription complexes, Cell, 124(5):973-983 (2006).
PubChem-CID-50848794, Create Date: (Feb. 22, 2011), 2 page.

(Continued)

*Primary Examiner* — Taofiq A Solola
(74) *Attorney, Agent, or Firm* — Mintz, Levin, Cohn, Ferris, Glovsky and Popeo, P.C.

(57) ABSTRACT

Disclosed herein are Notch transcriptional activation complex kinase ("MACK") inhibitors, and methods for their use in treating or preventing diseases, such as cancer. The inhibitors described herein include compounds of Formula (Ia) and pharmaceutically acceptable salts thereof: wherein the substituents are as described.

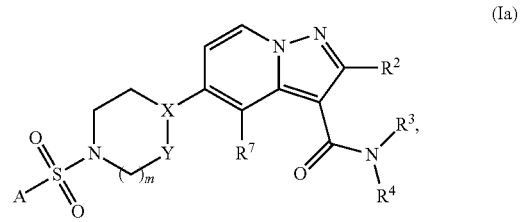

(Ia)

19 Claims, 26 Drawing Sheets

Specification includes a Sequence Listing.

(56) References Cited

OTHER PUBLICATIONS

PubChem-CID-50848832, Create Date: (Feb. 22, 2011), 2 page.
PubChem-CID-83829010, Create Date: (Oct. 20, 2014), 2 page.
Ranganathan et al., Notch signalling in solid tumours: a little bit of everything but not all the time, Nat. Rev. Cancer 11(5):338-351 (2011).
Sharma et al., A monoclonal antibody against human Notch1 ligand-binding domain depletes subpopulation of putative breast cancer stem-like cells, Mol. Cancer Ther 11(1):77-86 (2012).
Shih et al., Notch signaling, gamma-secretase inhibitors, and cancer therapy, Cancer Res., 67(5):1879-1882 (2007).
Supplementary European Application No. 19750817.9, European Search Report and Opinion, mailed Feb. 1, 2022.
Takebe et al., Targeting notch signaling pathway in cancer: clinical development advances and challenges, Pharmacol_ Ther., 141(2):140-149 (2014).
Tamura et al., Physical interaction between a novel domain of the receptor Notch and the transcription factor RBP-J kappa/Su(H), Curr_ Biol., 5(12):1416-1423 (1995).
Taylor, Protein kinases: a diverse family of related proteins, Bioessays, 7(1):24-29 (1987).
Tiyanont et al., Insights into Notch3 activation and inhibition mediated by antibodies directed against its negative regulatory region, J. Mol. Biol., 425(17):3192-3204 (2013).
Wang et al., Notch signaling drives stemness and tumorigenicity of esophageal adenocarcinoma, Cancer Research, 74(21):6364-6374(2014)_.
Weaver et al., NACK is an integral component of the Notch transcriptional activation complex and is critical for development and tumorigenesis, Cancer Research, 74(17):4741-4751 (2014).
Williams et al., Structural basis for the potent and selective binding of LDN-212854 to the BMP receptor kinase ALK2, Bone_, 109:251-258 (2018).

FIG. 2A

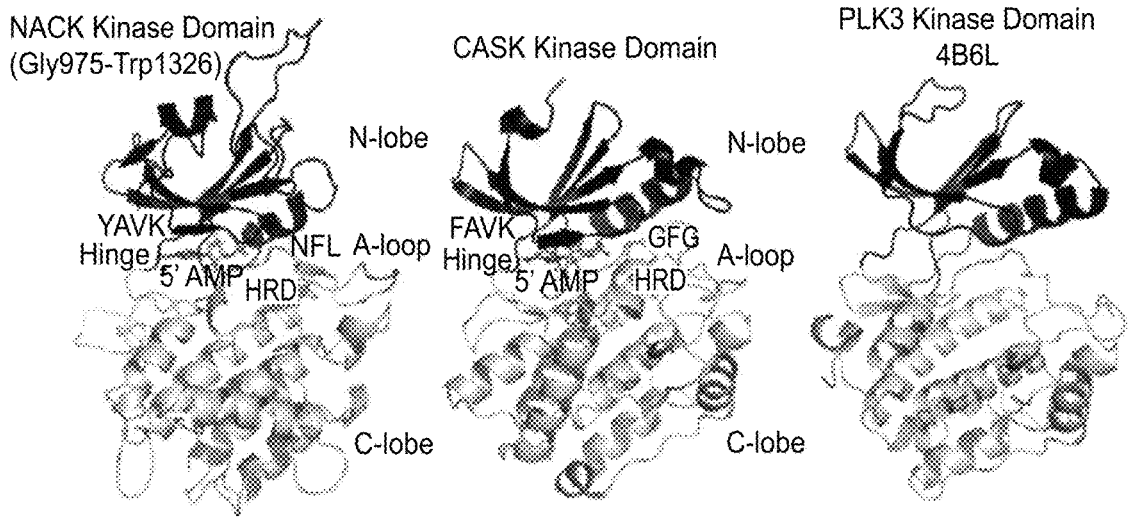

FIG. 2B

Comparisons of key motifs among NACK, CASK and PLK3

| Motifs Overlap | NACK (Human) | CASK (PDB: 3C0I) | PLK3 (PDB: 4B6L) |
|---|---|---|---|
| HRD motif (Catalytic residues) | HRD | HRD | HRD |
| | His1141 | His139 | His183 |
| | Arg1142 | Arg140 | Arg184 |
| | Asp1143 (H acceptor) | Asp141 | Asp185 |
| VAIK motif (Position α- and β-phosphate of ATP for phosphoryl transfer) | YAVK | FAVK | VAIK |
| | Tyr1019 | Phe38 | Val88 |
| | Ala1020 | Ala39 | Ala89 |
| | Val1021 | Val40 | Ile90 |
| | Lys1022 (ATP binding) | Lys41 | Lys91 |
| DFG motif (Metal binding) | NFL | GFG | DFG |
| | Asn1212 | Gly162 | Asp203 |
| | Phe1213 | Phe163 | Phe204 |
| | Leu1214 | Gly164 | Gly205 |

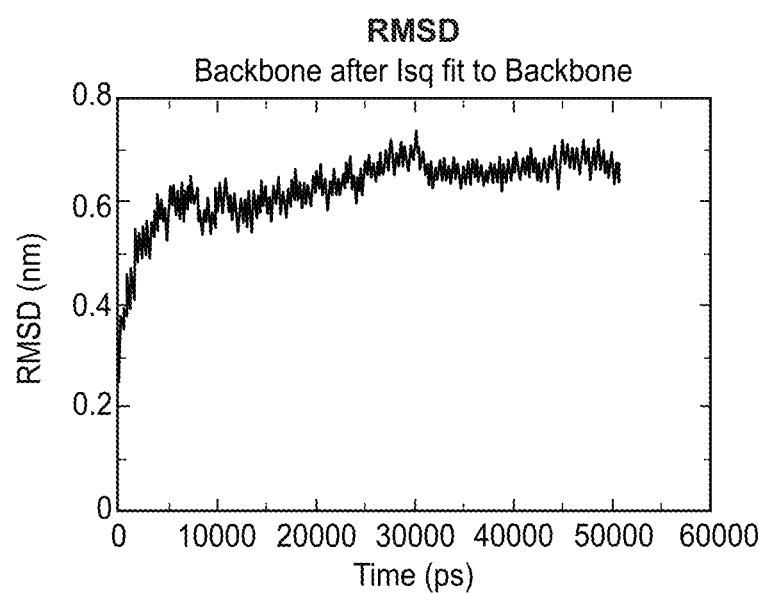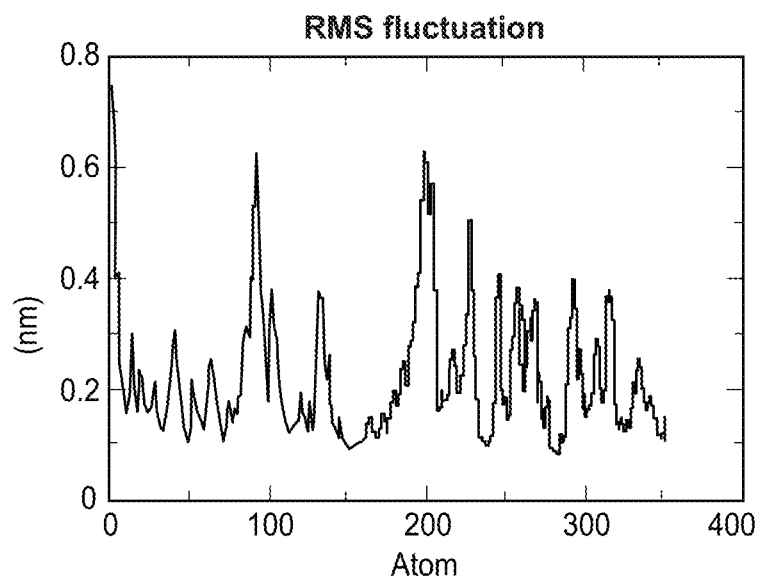

FIG. 3E
| NACK Residues | ATP Molecule | Interactions |
|---|---|---|
| Lys 1022 | Phosphate group | Salt bridge |
| Asn 1212 | Beta phosphate | H bond |
| His 1095 (backbone H) | Alpha phosphate O | H bond |
| Cys 999 | Gamma phosphate O | H bond |
| Asp 1048 (backbone O) | Adenine ring | H bond |
| Tyr 1006 | Gamma phosphate O | H bond |
FIG. 4A
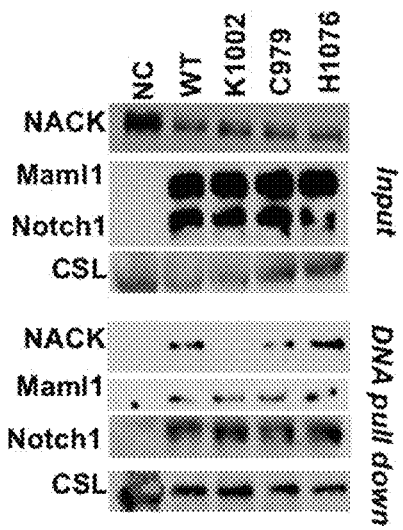
FIG. 4B
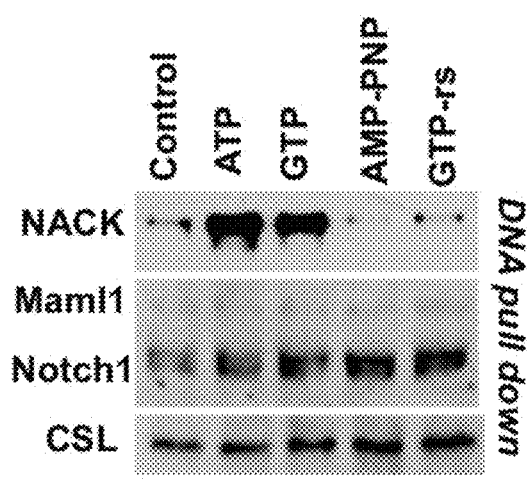
FIG. 4C
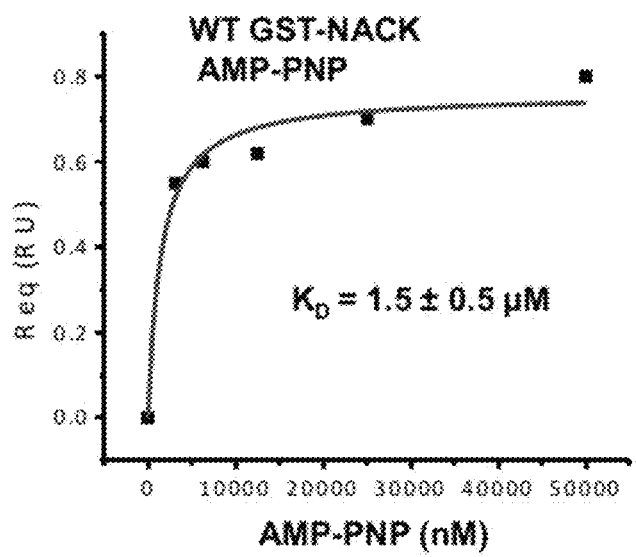

Inhibition via shRNA

FIG. 10A
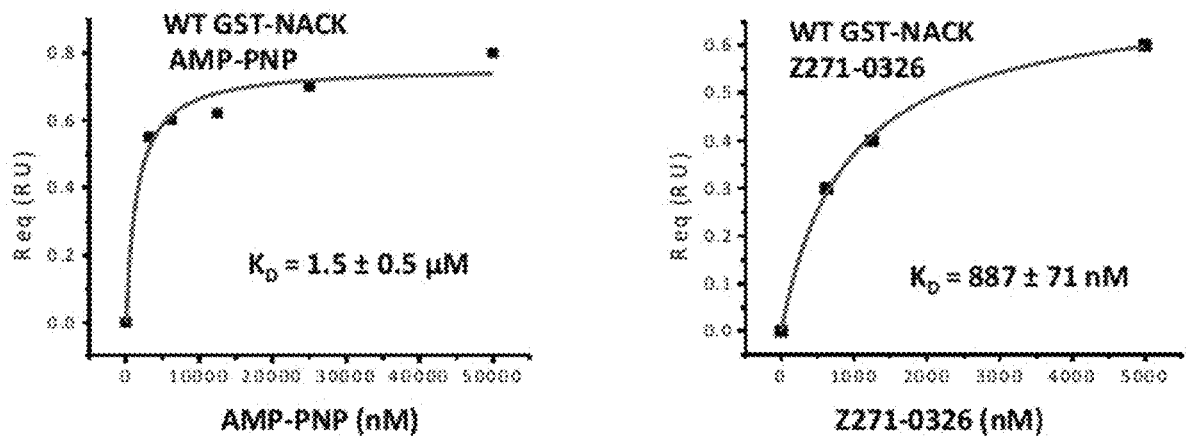
FIG. 10B
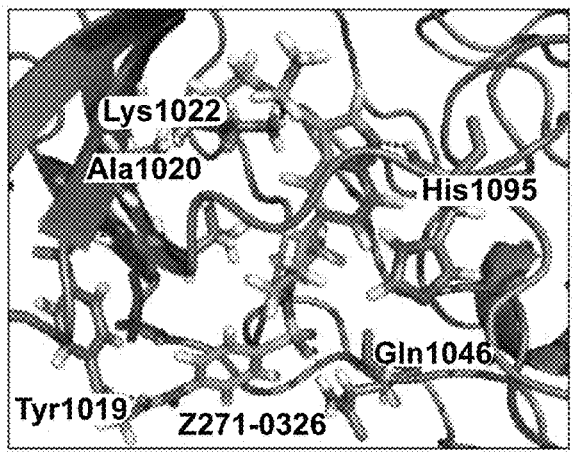
FIG. 10C
Important NACK residues responsible for Z271-0326 binding
| Residue | | Interaction |
|---|---|---|
| Lys 1022 | Side chain -$NH_3^+$ | H bond |
| His 1095 | Backbone -NH- | H bond |
| Gln 1046 | Side chain -$NH_2$ | H bond |
| Tyr 1019 | Side chain -OH | H bond |
| Ala 1020 | Side chain -$CH_3$ | Hydrophobic |

FIG. 11E
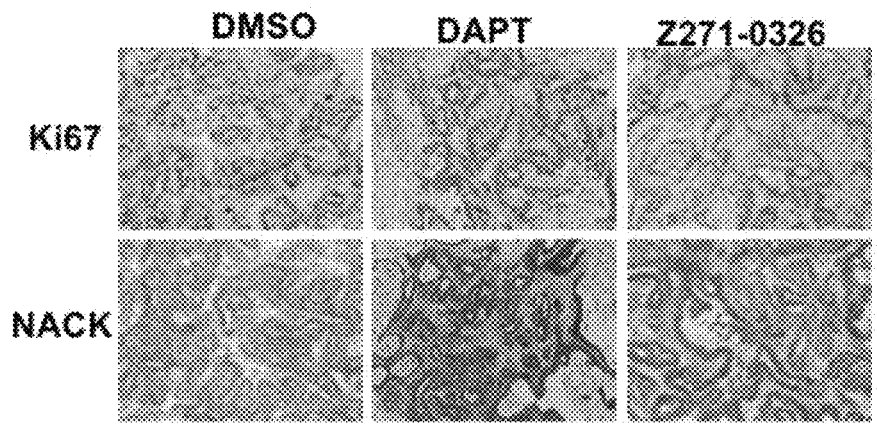
FIG. 12A
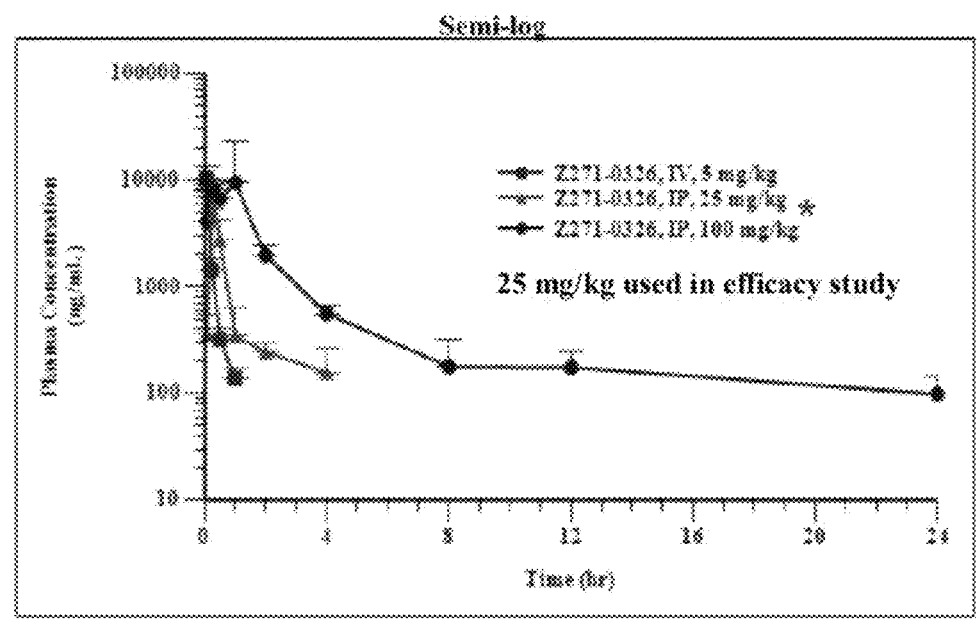
FIG. 12B
Pharmacokinetic parameters of Z271-0326 in plasma following a single intravenous (5 mg/kg) and intraperitoneal (25 and 100 mg/kg) administration to male C57 BL/6 mice
| Route | Dose (mg/kg) | $T_{max}$ (hr) | $C/C_{max}$ (ng/mL) | $AUC_{last}$ (hr*ng/mL) | $AUC_{inf}$ (hr*ng/mL) | $T_{1/2}$ (hr) | CL (mL/min/kg) | Vss (L/kg) |
|---|---|---|---|---|---|---|---|---|
| IV | 5 | - | 25078.74 | 2729.79 | 2769.49 | 0.23 | 30.09 | 0.21 |
| IP | 25 | 0.25 | 5344.40 | 2989.93 | 3592.33 | - | - | - |
| IP | 100 | 1.00 | 9481.07 | 19196.18 | 21767.19 | - | - | - |

SEQUENCE LISTING

```
Sequence total quantity: 3
SEQ ID NO: 1              moltype = AA  length = 1406
FEATURE                   Location/Qualifiers
source                    1..1406
                          mol_type = protein
                          organism = Homo sapiens
SEQUENCE: 1
MHQTLCLNPE SLKMSACSDF VEHIWKPGSC KNCFCLRSDH QLVAGPPQPR AGSLPPPPRL   60
PPRPENCRLE DEGVNSSPYS KPTIAVKPTM MSSEASDVWT EANLSAEVSQ VIWRRAPGKL  120
PLPKQEDAPV VYLGSFRGVQ KPAGPSTSPD GNSRCPPAYT MVGLHNLEPR GERNIAFHPV  180
SFPEEKAVHK EKPSFPYQDR PSTQESFRQK LAAFAGTTSG CHQGPGPLRE SLPSEDDSDQ  240
RCSPSGDSEG GEYCSILDCC PGSPVAKAAS QTAGSRGRHG GRDCSPTCWE QGKCSGPAEQ  300
EKRGPSFPKE CCSQGPTAHP SCLGPKKLSL TSEAAISSDG LSCGSGSGSG SGASSPFVPH  360
LESDYCSLMK EPAPEKQQDP GCPGVTPSRC LGLTGEPQPP AHPREATQPE PIYAESTKRK  420
KAAPVPSKSQ AKIEHAAAAQ GQGQVCTGNA WAQKAASGWG RDSPDPTPQV SATITVMAAH  480
PEEDHRTIYL SSPDSAVGVQ WPRGPVSQNS EVGEEETSAG QGLSSRESHA HSASESKPKE  540
RPAIPPKLSK SSPVGSPVSP SAGGPPVSPL ADLSDGSSGG SSIGPQPPSQ GPADPAPSCR  600
TNGVAISDPS RCPQPAASSA SEQRRPRFQA GTWSRQCRIE EEEEVEQELL SHSWGRETKN  660
GPTDHSNSTT WHRLHPTDGS SGQNSKVGTG MSKSASFAFE FPKDRSGIET FSPPPPPPKS  720
RHLLKMNKSS SDLEKVSQGS AESLSPSFRG VHVSFTTGST DSLASDSRTC SDGGPSSELA  780
HSPTNSGKKL FAPVPFPSGS TEDVSPSGPQ QPPPLPQKKI VSRAASSPDG FFWTQGSPKP  840
GTASPKLNLS HSETNVHDES HFSYSLSPGN RHHPVFSSSD PLEKAFKGSG HWLPAAGLAG  900
NRGGCGSPGL QCKGAPSASS SQLSVSSQAS TGSTQLQLHG LLSNISSKEG TYAKLGGLYT  960
QSLARLVAKC EDLFMGGQKK ELHFNENNWS LFKLTCNKPC CDSGDAIYYC ATCSEDPGST 1020
YAVKICKAPE PKTVSYCSPS VPVHFNIQQD CGHFVASVPS SMLSSPDAPK DPVPALPTHP 1080
PAQEQDCVVV ITREVPHQTA SDFVRDSAAS HQAEPEAYER RVCFLLLQLC NGLEHLKEHG 1140
IIHRDLCLEN LLLVHCTLQA GPGPAPAPAP APAPAAAAPP CSSAAPPAGG TLSPAAGPAS 1200
PEGPREKQLP RLIISNFLKA KQKPGGTPNL QQKKSQARLA PEIVSASQYR KFDEFQTGIL 1260
IYELLHQPNP FEVRAQLRER DYRQEDLPPL PALSLYSPGL QQLAHLLLEA DPIKRIRIGE 1320
AKRVLQCLLW GPRRELVQQP GTSEEALCGT LHNWIDMKRA LMMMKFAEKA VDRRRGVELE 1380
DWLCCQYLAS AEPGALLQSL KLLQLL                                     1406

SEQ ID NO: 2              moltype = DNA  length = 19
FEATURE                   Location/Qualifiers
misc_feature              1..19
                          note = Synthetic Primer
source                    1..19
                          mol_type = other DNA
                          organism = synthetic construct
SEQUENCE: 2
cgtgtctcct cctcccatt                                               19

SEQ ID NO: 3              moltype = AA  length = 18
FEATURE                   Location/Qualifiers
REGION                    1..18
                          note = Synthetic Primer
source                    1..18
                          mol_type = protein
                          organism = synthetic construct
SEQUENCE: 3
GGGGGATTCC GCTGTTAT                                                18
```

INHIBITORS OF THE NOTCH TRANSCRIPTIONAL ACTIVATION COMPLEX KINASE ("NACK") AND METHODS FOR USE OF THE SAME

CROSS-REFERENCE TO RELATED APPLICATIONS

This application is a continuation of U.S. patent application Ser. No. 16/967,652, filed Aug. 5, 2020, which is a U.S. National Stage of International Application No. PCT/US2019/016868, filed Feb. 6, 2019, which claims priority to U.S. Provisional Patent Application. No. 62/626,870, filed Feb. 6, 2018, the disclosures of which are hereby incorporated by reference in their entirety.

STATEMENT OF GOVERNMENT SUPPORT

This invention was made with government support under grant number 1R01CA169805-01, awarded by the National Cancer Institute National Institutes of Health. The Government has certain rights in the invention. The invention also was made with support under grant number 7BC01, awarded by the Bankhead-Coley Cancer Research Program.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 51617B Seqlisting. XML; Size: 5,680 bytes; Created: Aug. 31, 2022.

BACKGROUND

Field of the Invention

The present disclosure relates to inhibitors of the Notch activation complex kinase ("NACK"), and methods of using the inhibitors to treat and prevent diseases, such as cancer.

Description of Related Technology

The Notch pathway, a highly conserved cell signaling system present in most multicellular organisms, is widely used in development to govern cell fate specification, and to balance proliferative capacity and differentiation state. Notch drives a context-dependent cellular response by initiating and maintaining a transcriptional cascade. See Tamura et al. Curr Biol 5, 1416-23 (1995); Aster et al. J Biol Chem 272, 11336-43 (1997). Notch mediates this transcriptional response by directing the formation of a core Notch transcriptional activation complex ("NTC"), which is composed of the DNA binding protein CSL, the intracellular domain of Notch ("NICD") and the co-activator protein Mastermind ("MAML1"). Jeffries et al., Mol Cell Biol 22, 3927-41 (2002); Nam et al., Cell 124, 973-83 (2006); Kovall et al., EMBO J 23, 3441-51 (2004). Notch signaling activation is initiated by the binding of Notch ligands (Jagged and Delta-like) to the transmembrane Notch receptor through cell-to-cell contact. This event triggers the cleavage of the Notch receptor proteins to go through sequential cleavages, which result in the release of the active NICD from the plasma membrane and the translocation of NICD to the nucleus. See Ranganathan et al., Nat Rev Cancer 11, 338-351 (2011); Kovall, Oncogene 27, 5099-5109 (2008).

In the adult, the Notch pathway is restricted to small populations of progenitor and stem cells of regenerating tissues, such as the colon and brain. However, in many human cancers, the Notch pathway becomes reactivated. The deregulation of the Notch pathway underlies many aspects of cancer physiology, depending on cell type and context. Aberrant Notch activity has been demonstrated to play a role in the initiation and maintenance of the neoplastic phenotype, as well as playing a central role in cancer stem cells, which may underlie a role in metastasis and resistance to therapy. See Ranganathan et al., Nat Rev Cancer 11, 338-351 (2011).

Current compounds that regulate the Notch pathway include small molecule inhibitors that target the presenilin-dependent γ-secretase, an enzyme complex that is responsible for ligand-induced cleavage and activation of Notch, and monoclonal antibodies that target and disrupt Notch-DSL. See Takebe et al., Pharmacol Ther 141, 140-9 (2014); Shih et al., Cancer Res 67, 1879-82 (2007); Tiyanont et al., J Mol Biol 425, 3192-204 (2013); Sharma et al., Mol Cancer Ther 11, 77-86 (2012); Fischer et al, Cancer Res 71, 1520-5 (2011); Berezovska et al., J Neurochem 75, 583-93 (2000); De Kloe et al., Methods Mol Biol 1187, 311-22 (2014). Both of these approaches act at the top of the Notch signaling cascade to block ligand-dependent production of NICD. Moreover, γ-secretase is known to have many substrates in addition to the Notch pathway, which could contribute to off target effects. See Shih et al., Cancer Res 67, 1879-82 (2007).

Therefore, there is a need for inhibitors that directly target the Notch transcription complex (see Astudillo et al., Cancer Research 76, 3593-3603 (2016); Moellering et al., Nature 462, 182-8 (2009)), either by blocking the assembly of Notch transcriptional activation complex, or by inhibiting the activation of the Notch mediated transcription.

SUMMARY OF THE DISCLOSURE

In one aspect, the disclosure provides compounds of Formula (Ia), or pharmaceutically acceptable salts thereof:

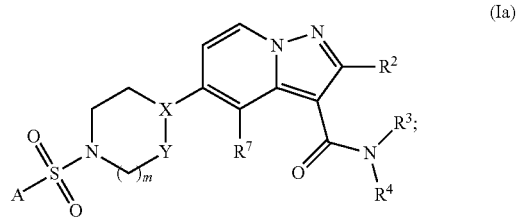

wherein A is $C_{1-4}$alkyl or

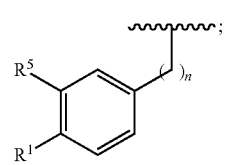

X is CH or N; Y is $CH_2$ or N, and when X is N, then Y is $CH_2$; m is 0 or 1, and when m is 1 then Y is $CH_2$; n is 0 or 1; $R^1$ is H, $C_{1-6}$ alkyl, $C_{0-6}$ alkyleneC(=O)$R^6$, halo, cyano, aryloxy, amino, $C_{0-3}$ alkylene-amido, carbamyl, S-thiocarbamyl, or ureido; $R^2$ is H, halo, $C_{1-6}$alkyl, $C_{3-8}$ cycloalkyl, or heteroaryl; each $R^3$ and $R^4$ independently is H, $C_{1-6}$ alkyl, or $C_{1-3}$aralkyl, or $R^3$ and $R^4$ and the nitrogen to which they are attached join together to form a 3-6 membered ring optionally comprising 1 to 3 additional heteroatoms selected from N, O, and S; $R^5$ is H, or $R^1$ and $R^5$ together with the atoms to which they are attached form a 5- or 6-membered heterocyclic ring comprising 1 to 3 ring heteroatoms selected from N, O, and S; $R^6$ is OH, $C_{1-6}$alkyl, or $OC_{1-6}$alkyl; and $R^7$ is H, halo or amino; with the proviso that the compound is not

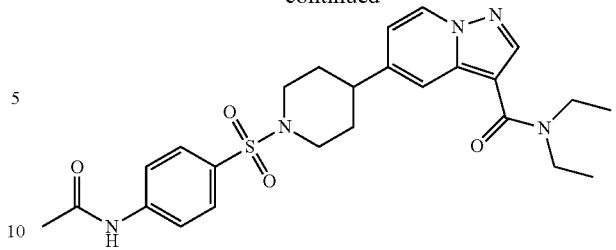

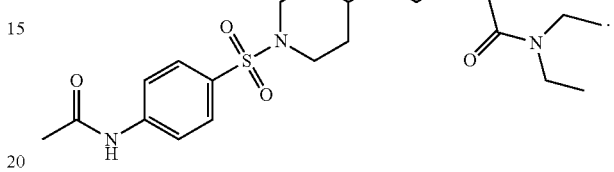

In some embodiments, A is methyl, ethyl, propyl, isopropyl, n-butyl, s-butyl, isobutyl, or t-butyl. In various embodiments, A is methyl. In some cases, A is

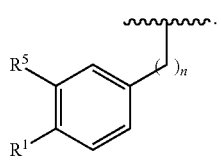

In various cases, n is 0. In some embodiments, n is 1. In various embodiments, $R^1$ and $R^5$ together with the atoms to which they are attached form a 5- or 6-membered heterocyclic ring comprising 1 to 3 ring heteroatoms selected from N, O, and S. In some cases, A is selected from the group consisting of

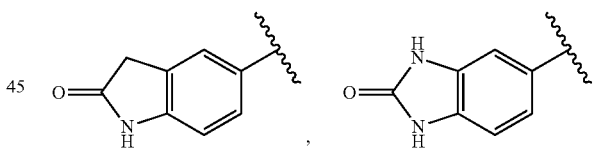

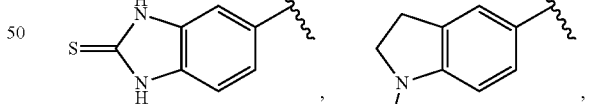

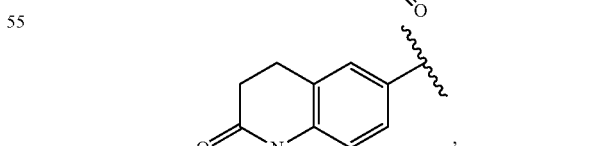

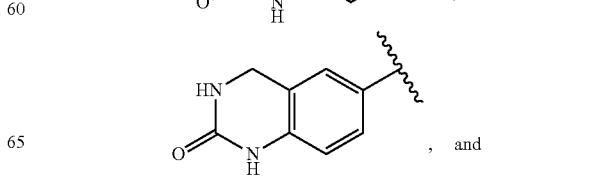

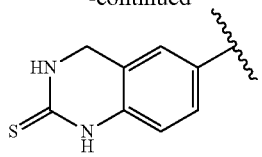

In various cases, $R^5$ is H. In some embodiments, $R^1$ is H. In various embodiments, $R^1$ is $C_{1-6}$alkyl. In some cases, $R^1$ is methyl, ethyl, fluoromethyl, or trifluoromethyl. In various cases, $R^1$ is $C_{0-6}$ alkyleneC(=O)$R^6$. In some embodiments, $R^1$ is

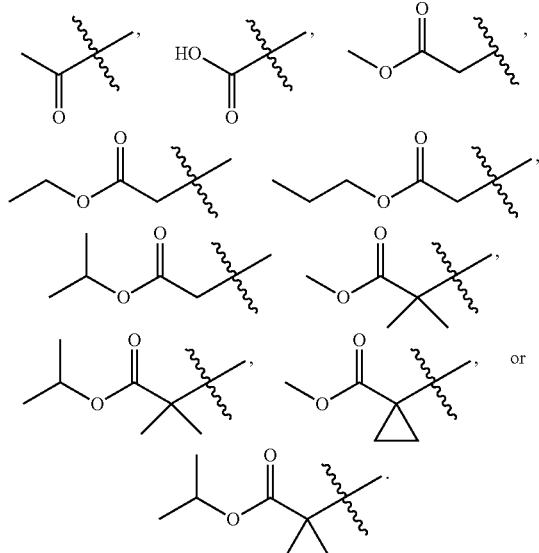

In various embodiments, $R^1$ is halo. In some cases, $R^1$ is F. In various cases, $R^1$ is cyano or aryloxy. In some embodiments, $R^1$ is CN or —OPh. In various embodiments, $R^1$ is amino. In some cases, $R^1$ is —NH$_2$, —N(CH$_3$)$_2$ or —NH$_2$Ph. In various cases, $R^1$ is $C_{0-3}$ alkylene-amido, carbamyl, S-thiocarbamyl, or ureido. In some embodiments, $R^1$ is selected from the group consisting of

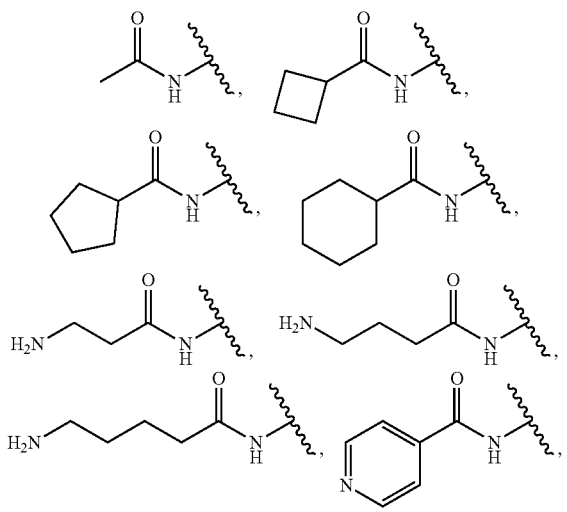

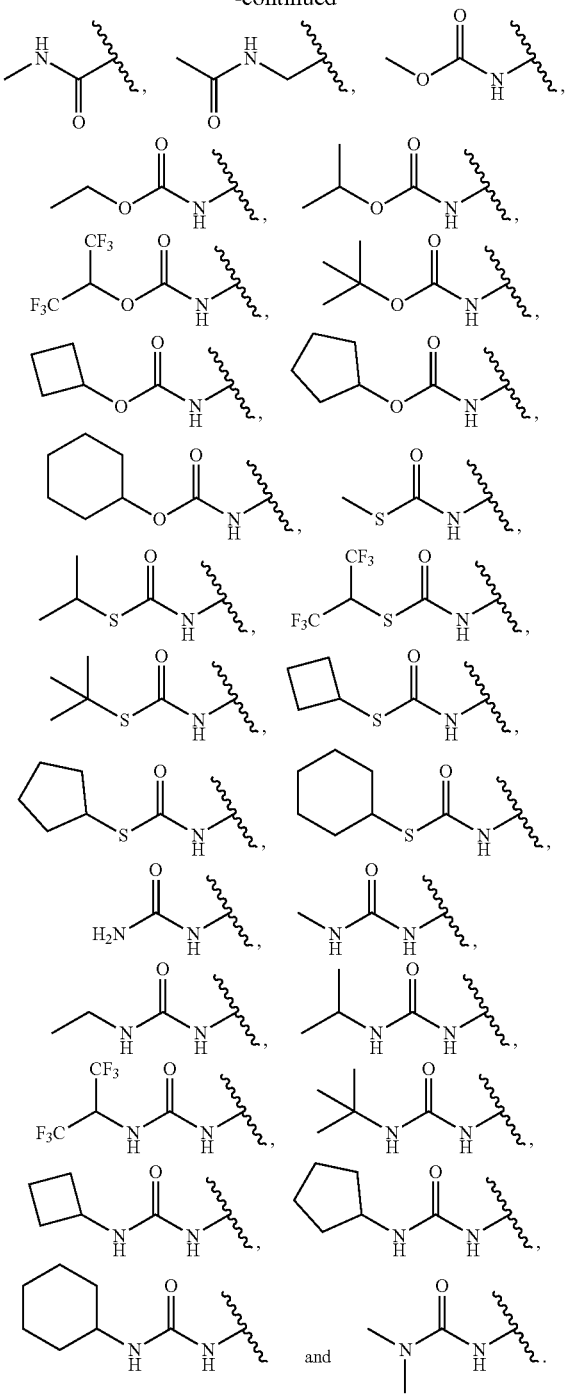

In various embodiments, A is selected from the group consisting of CH$_3$,

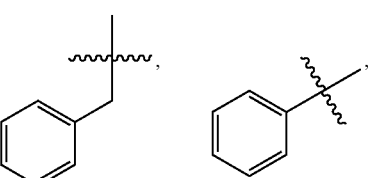

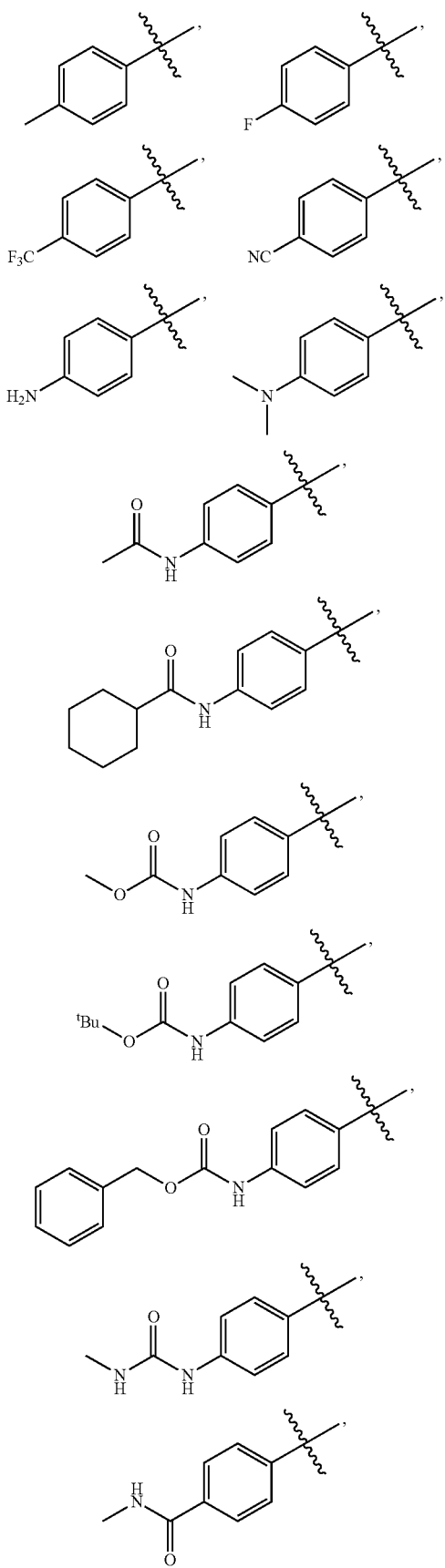
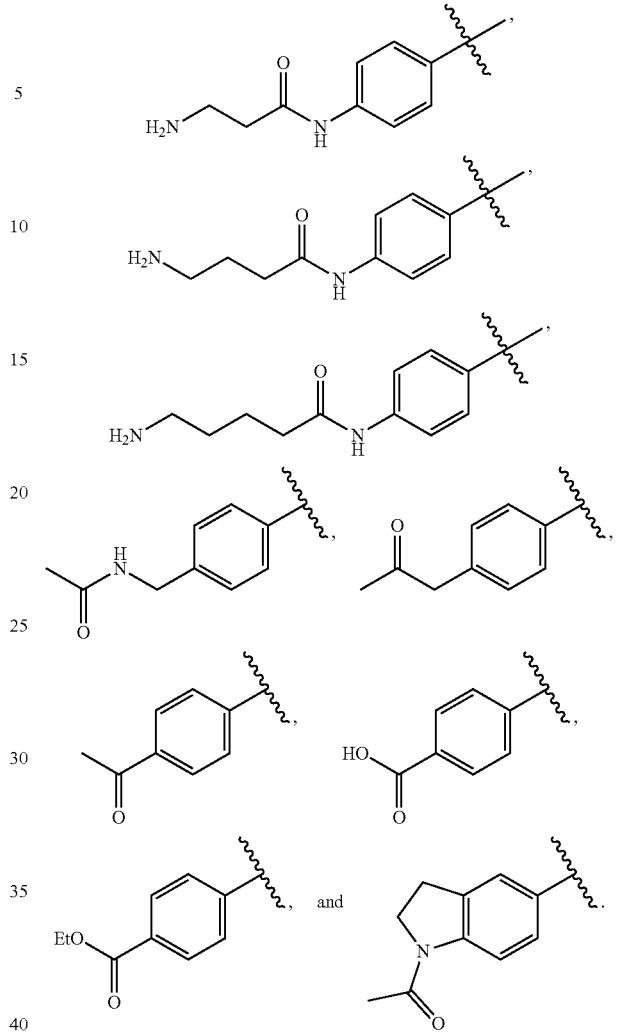

In some cases, X is CH. In various cases, X is N. In some embodiments, Y is $CH_2$. In various embodiments, Y is N. In some cases, m is 0. In various cases, m is 1.

In some embodiments, $R^2$ is H. In various embodiments, $R^2$ is Br or Cl. In some cases, $R^2$ is $CH_3$, $CF_3$, $CH_2OH$, or $CH_2OCH_3$. In various cases, $R^2$ is cyclopropyl, cyclobutyl, cyclopentyl, or cyclohexyl. In some embodiments, $R^2$ is 3-furanyl. In various embodiments, $R^2$ is selected from the group consisting of H, $CH_3$, $CF_3$, and cyclopropyl.

In some cases, each of $R^3$ and $R^4$ independently is H, $C_{1-6}$ alkyl, or $C_{1-3}$ aralkyl. In various cases, each of $R^3$ and $R^4$ independently is H, $CH_3$, $CH_2CH_3$, $^tBu$, or $CH_2Ph$. In some embodiments,

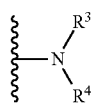

is selected from the group consisting of

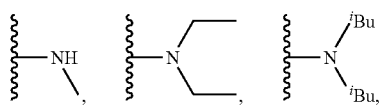

and

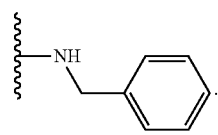 [SMILES: *NCc1ccccc1]

In various embodiments, R³ and R⁴ and the nitrogen to which they are attached join together to form a 5-6 membered ring. In some cases,

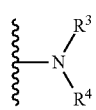

is selected from the group consisting of

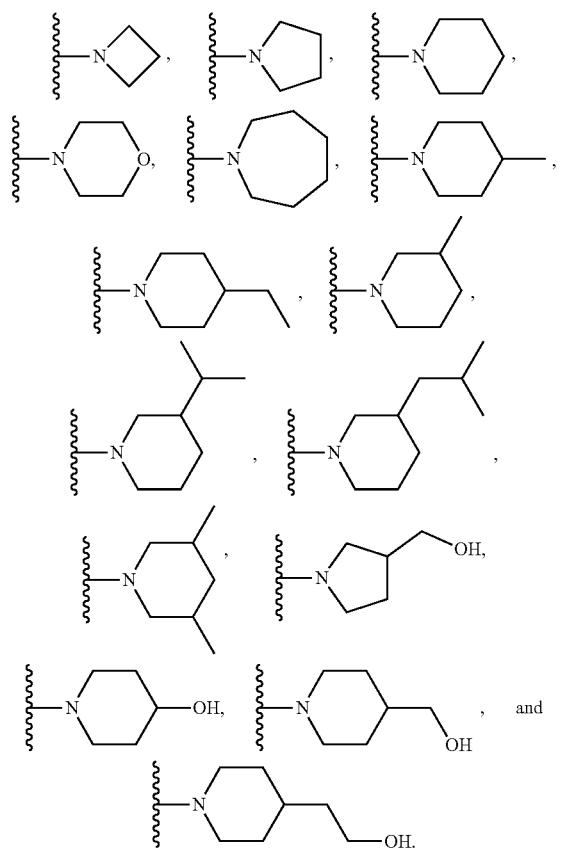

In various cases,

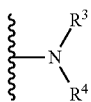

is selected from the group consisting of

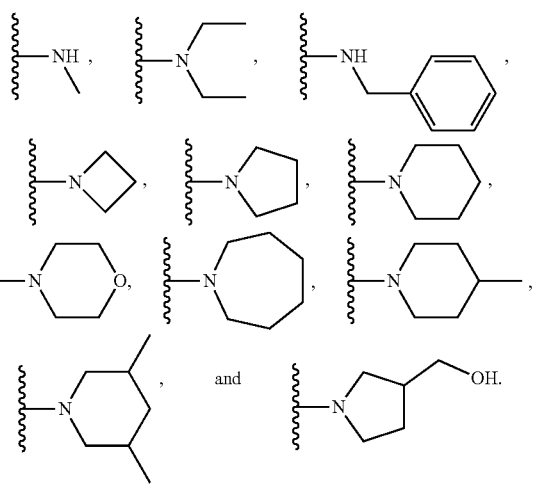

In some embodiments, $R^7$ is H. In various embodiments, $R^7$ is $NH_2$, Br, Cl, or F.

In some cases, provided herein is a compound listed in Table A, Table B, Table C, or a pharmaceutically acceptable salt of any of the foregoing.

In another aspect, the disclosure provides a pharmaceutical composition comprising a compound disclosed herein and a pharmaceutically acceptable carrier.

In yet another aspect, the disclosure provides a method of inhibiting the Notch activation complex kinase ("NACK") in a cell, comprising contacting the cell with a compound disclosed herein, or a pharmaceutically acceptable salt thereof, in an amount effective to inhibit NACK. In some embodiments, the compound or salt inhibits NACK recruitment to the Notch transcriptional complex ("NTC"). In various embodiments, the contacting comprises administering to a patient in need thereof. In various cases, the patient suffers from a disease associated with deregulation of the Notch transcriptional activation complex. In some embodiments, the disease is Tetralogy of Fallot ("TOF") or Alagille syndrome. In some cases, the disease is cancer. In some cases, the cancer is selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, cerebral autosomal-dominant ateriopathy with sub-cortical infarcts and leukoencephalophathy ("CADASIL"), chronic lymphocytic leukemia ("CLL"), hepatocellular carcinoma ("HCC"), myelomonocytic leukemia ("CMML"), pancreatic ductal adenocarcinoma ("PDAC"), head and neck squamous cell carcinoma ("HNSCC"), renal cell adenocarcinoma, and fibrosarcoma. In some cases, the disease is multiple sclerosis ("MS").

In yet another aspect, the disclosure provides a method of inhibiting kinase activity, ATPase activity, or both in a cell, comprising contacting the cell with a compound described herein, or a pharmaceutically acceptable salt thereof), in an amount effective to inhibit kinase and/or ATPase activity in the cell.

Further aspects and advantages will be apparent to those of ordinary skill in the art from a review of the following detailed description, taken in conjunction with the drawings. While the compounds and methods disclosed herein are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

FIG. 1A shows the mRNA of clinical samples derived from surgically resected primary EAC (tumor tissue compared to its corresponding normal tissue), and demonstrates that mRNA levels of NACK and Notch1 are elevated in most of the tumor tissues compared to their corresponding normal tissues. FIG. 1B shows that a high level of NACK and activated Notch1 expression are both observed in chemo-naïve esophageal adenocarcinoma samples from endoscopic ultrasound ("EUS") biopsies. FIG. 1C shows the expression of NACK in EAC cell lines (OE33, OE19, Flo-1 and JH-1) by qPCR. FIG. 1D shows that NACK knockdown was verified by Q-PCR. FIG. 1E shows that NACK knockdown was verified by Western blot. FIG. 1F shows that knockdown of NACK in EAC cells (OE33, OE19 and Flo-1) led to dramatic inhibition of the clonogenic potential of these cells.

FIGS. 2A-2E show the homology modeling and the MD simulation of the kinase domain of NACK. FIG. 2A is a representation of the three-dimensional model for NACK kinase domain sequence using the IntFOLD method, compared with CASK kinase domain (PDB code: 3C0I) and PLK3 (PDB: 4B6L). The image was shown using PyMol. FIG. 2B shows comparisons between the key motifs of NACK, CASK and PLK3. FIG. 2C depicts a plot showing the RMSD levels off to ~0.1 nm, indicating that the structure is very stable. FIG. 2D is an RMSF showing the dynamic regions of NACK (Cys1049-Asp1084 and Cys1154-Leu1205). FIG. 2E depicts the most representative structure of NACK.

FIGS. 3A-3E show a MD simulation of NACK coupled with ATP reveals the catalytic domain of NACK. FIG. 3A is a RMSD plot demonstrating that during the simulation the structure is very stable. FIG. 3B shows that for the last 50 ns run, the radius of gyration of NACK maintains a relatively steady value of Rg. FIG. 3C is a plot showing that around 5 hydrogen bonds were formed between NACK and ATP during 50 to 100 ns simulation. FIG. 3D depicts the most representative structure of NACK and ATP during the last 50 ns simulation. FIG. 3E depicts the important NACK residues for ATP binding.

FIGS. 4A-4E demonstrate that NACK binds to the Notch transcription complex in an ATP-dependent manner. FIG. 4A shows NACK (K1002 or C979) mutations in mouse NACK blocks NACK recruitment to the Notch complex. FIG. 4B show that ATP and GTP hydrolysis is required for NACK recruitment. FIG. 4C shows the binding between NACK and ATP analog AMP-PNP using surface plasmon resonance (SPR). FIG. 4D shows that equal amounts of ADP and Pi were detected by ADP-Glo in vitro kinase assay and colorimetric phosphate assay after incubating NACK with ATP. FIG. 4E shows that NACK "kinase-dead" mutant K1002A failed to hydrolyze ATP to ADP in the ADP-Glo assay.

FIG. 5A shows that knockdown of NACK affects the viability of OE33 cell line, but not HC11. FIG. 5B shows that the compounds described herein selectively inhibit the viability of Notch/NACK dependent cell line.

FIG. 6A shows that the NACK inhibitors described herein can selectively inhibit NACK recruitment to the Notch transcription complex. FIG. 6B shows that the NACK inhibitors described herein cause down regulation of Notch transcription activity. FIG. 6C shows the $EC_{50}$ of Z271-0326 and Z271-0191 estimated by colony formation titration assay.

FIG. 7A shows that the NACK inhibitors described herein can attenuate the secondary sphere formation in OE33 cell line. FIG. 7B shows that treatment of OE33 spheres with Z271-0326 affects Notch target genes transcription. FIG. 7C shows that a NACK inhibitor can attenuate the secondary sphere formation in HC11/N1ICD. FIG. 7D shows that treatment of HC11/N1ICD spheres with Z271-0326 causes a decrease in HES1 gene expression as well as several other stem-cell marker genes. The figures show that HC11 cells are insensitive to inhibition of Notch/NACK. HC11 cells cannot form spheres themselves, but are transformed by Notch efficiently to form spheres and are tumorigenic in mice. The Notch-transformed HC11 cells are sensitive to NACK inhibition.

FIG. 8A shows Q-PCR and western blot results of NACK knock down in OE33 stable cell lines harboring doxycycline (DOX) inducible small hairpin RNA (shRNA) constructs. FIG. 8B depicts ChIP experiments to measure Notch1, NACK and activated Pol II occupancies on the HES1 promoter following NACK depletion in clone 1A3. FIG. 8C depicts ChIP experiments to measure Notch1, NACK and activated Pol II occupancies on the HES1 promoter after drug treatment in OE33 cell line.

FIG. 9A shows that Z271-0326 induces cell apoptosis in OE33 cell line. FIG. 9B shows that the senescence β-galactosidase staining was measured after treatment of the OE33 cells with either the drugs or DMSO (vehicle) for 3 weeks.

FIGS. 10A-10D show surface plasmon resonance (SPR) analysis of Z271-0326 binding to NACK. FIG. 10A depicts surface plasmon resonance (SPR) analysis of Z271-0326 and AMP-PNP binding to GST tagged NACK protein (GST as control). FIG. 10B shows interactions between Z271-0326 and NACK. FIG. 10C shows the important residues responsible of Z271-0326 binding. FIG. 10D shows that NACK (Y999F or Q1024E) mutations in mouse NACK failed to abolish NACK binding to the Notch complex in the condition of adding Z271-0326.

FIGS. 11A-11E demonstrate that Z271-0326 inhibits tumor growth of EAC47 PDX. FIG. 11A shows the tumor growth of EAC47 PDX after treatment with either vehicle (DMSO), DAPT or Z271-0326 for 20 days. FIG. 11B shows the tumor weights collected at end point. FIG. 11C shows the tumors collected at the end point. FIG. 11D shows the body weights of EAC47 PDX during treatment. FIG. 11E shows representative images of EAC47 PDX treated by DMSO, DAPT and Z271-0326 with Ki67 staining.

FIG. 12A and FIG. 12B show the pharmacokinetic profile of Z271-0326 in a mouse.

DETAILED DESCRIPTION

Figure 1A:
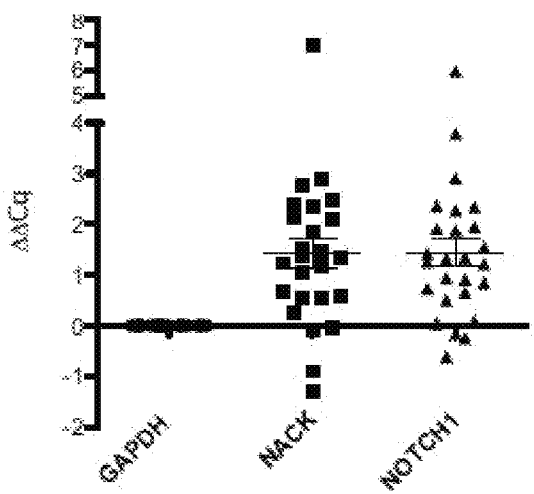
FIGS. 1A-1F demonstrate that NACK is a novel therapeutic target in the Notch pathway.

Provided herein are compounds that inhibit the Notch activation complex kinase ("NACK"), and methods of using the compounds to treat and prevent diseases associated with the Notch transcriptional activation complex ("NTC"), such as cancer. "Notch activation complex kinase" or "NACK" generally refers to a Notch-associated protein that functions as a co-activator of Notch transcriptional activity. NACK proteins can include a protein having a SEQ ID NO: 1; PEAK1 Related Kinase Activating Pseudokinase; Sugen Kinase 223; Pragmin, RND2 Effector Protein; SGK223; Tyrosine-Protein Kinase SgK223; Homolog Of Rat Pragma Of Rnd2; EC 2.7.10.2; PRAGMIN; and PEAK2.

The compounds and methods provided herein can complement existing strategies by providing rescue to resistance of the mAb or GSI therapies, resulting in therapeutic depth in the attack on an activated Notch pathway. By exploiting multiple targets within a particular cancer pathway, superior outcomes in individuals afflicted with the cancer can occur.

NACK acts as a Notch transcriptional co-activator, and an essential regulator of Notch-mediated tumorigenesis and development. See Weaver et al., Cancer Research 74, 4741-4751 (2014). NACK functions in an ATP dependent manner to bind to the Notch transcription complex and to activate Notch-mediated transcription. Because of NACK's prominent role in the Notch pathway, it can act as a suitable drug target.

Without being bound by any particular theory, the compounds described herein can interrupt recruitment of NACK to the Notch transcription complex, which inhibits Notch-mediated transcriptional cascade, and suppresses tumor growth in patients. In some cases, the compounds disclosed herein are specific inhibitors for Notch dependent cells, and therefore, do not inhibit or kill cells that are not dependent on Notch.

The Notch signaling pathway is a particularly attractive target for inhibitor development. Prior to ligand activation and cleavage, the Notch intracellular domain ("NICD") is bound to the cell membrane, and therefore, accessible to potential inhibitors. Further, the NTC is constantly being recycled, thus requiring constant reformation on chromatin for maintenance of the Notch transcriptional cascade driving the neoplastic phenotype. Therefore, ample opportunity exists for a small molecule to target the exposed interaction surfaces on the NTC components and prevent complex formation.

In various cases, the compounds of the disclosure can inhibit recruitment of NACK to the NTC by about 50%, 55%, 60%, 65%, 70%, 75%, 80%, 85%, 90%, 95%, 97%, or 99% or more of the positive control. In some embodiments, the compounds of the disclosure can inhibit recruitment by about 75%, 80%, 85%, 90%, 95%, 97%, or 99% or more of the positive control. For example, the compounds disclosed herein can inhibit recruitment by about 85%, 86%, 87%, 88%, 89%, 90%, 91%, 92%, 93%, 94%, 95%, 96%, 97%, 98%, or 99% or more of the positive control. Furthermore, the compounds disclosed herein can inhibit NACK with an $IC_{50}$ of about 5 μM or less, or about 4 μM or less, or about 3 μM or less, or about 2 μM or less, or about 1 μM or less, or about 0.6 μM or less, or about 0.5 μM or less, or about 0.4 μM or less, or about 0.3 μM or less, or about 0.2 μM or less, or about 0.1 μM or less, or about 0.05 μM or less. In some embodiments, the compounds of the disclosure can inhibit NACK with an $IC_{50}$ of about 1 μM or less, or about 0.6 μM or less, or about 0.5 μM or less, or about 0.4 μM or less, or about 0.3 μM or less, or about 0.2 μM or less, or about 0.1 μM or less, or about 0.05 μM or less. In some cases, the compounds of the disclosure can inhibit NACK with an $IC_{50}$ of about 0.5 μM or less, or about 0.4 μM or less, or about 0.3 μM or less, or about 0.2 μM or less, or about 0.1 μM or less, or about 0.05 μM or less. For example, the compounds of the disclosure can inhibit NACK with an $IC_{50}$ of about 0.2 μM or less, or about 0.19 μM or less, or about 0.18 μM or less, or about 0.17 μM or less, or about 0.16 μM or less, or about 0.15 μM or less, or about 0.14 μM or less, or about 0.13 μM or less, or about 0.12 μM or less, or about 0.11 μM or less, or about 0.10 μM or less, or about 0.09 μM or less, or about 0.08 μM or less, or about 0.07 μM or less, or about 0.06 μM or less, or about 0.05 μM or less. The compounds described herein can inhibit NACK by disrupting recruitment of NACK to the NTC.

The compounds of the disclosure have several advantageous properties and effects. The compounds can, for example: (1) selectively disrupt the recruitment of NACK to the NTC with $IC_{50}$s in the low micromolar range; (2) cause down regulation of Notch transcription activity; (3) block Notch transcription complex binding to the Hes1 promoter; (4) induce cell apoptosis and senescence; and/or (5) inhibit tumor growth.

Definitions

As used herein, "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), isobutyl (2,2-dimethylethyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkylene" refers to an alkyl group having a substituent. For example, the term "alkylenearyl" refers to an alkyl group substituted with an aryl group. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups. Unless otherwise indicated, the alkylene group itself can be unsubstituted or substituted.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated, share a carbon atom with another cycloalkyl or heterocycloalkyl group, or fused to another cycloalkyl group, a heterocycloalkyl group, an aryl group and/or a heteroaryl group. Cycloalkyl groups can be saturated or partially unsaturated ring systems optionally substituted with, for example, one to three groups, independently selected alkyl, alkylene-OH, $C(O)NH_2$, $NH_2$, oxo (=O), aryl, haloalkyl, halo, and OH.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group. Unless otherwise indicated, an aryl group can be fused to a cycloalkyl or heterocycloalkyl group.

As used herein, the term "aryloxy" refers to —O-aryl.

As used herein, the term "aralkyl" refers to an alkyl group that is substituted with an aryl moiety. The term $C_n$ indicates n carbon atoms of the alkyl group of the aralkyl.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thiophenyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "halo" refers to a fluoro, chloro, bromo, or iodo group. The term "haloalkyl" refers to an alkyl group that is substituted with at least one halogen.

As used herein, the term "alkoxyl" refers to —OR, wherein 'R' is a radical.

As used herein, the term "amino" refers to a —$NH_2$ or —NH— group, wherein each hydrogen in each Formula can be replaced with an alkyl, cycloalkyl, aryl, heteroaryl, or heterocycloalkyl group.

As used herein, the term "amido" refers to an amino group that is substituted with a carbonyl moiety (e.g., —NRC(=O)— or —C(=O)NR—), wherein R is a substituent on the nitrogen (e.g., alkyl or H).

As used herein, the term "carbamyl" refers to the following functional group —NR(C=O)O— or —OC(=O)NR—, wherein R is a substituent on the nitrogen (e.g., alkyl or H).

As used herein, the term "S-thiocarbamyl" refers to the following functional group —SC(=O)NR— or —NRC(=O)S—, wherein R is a substituent on the nitrogen atom (e.g., H or alkyl).

As used herein, the term "ureido" refers to the following functional group —NR(C=O)NR—, wherein each R is a substituent on the nitrogen (e.g., alkyl or H).

A used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "therapeutically effective amount" means an amount of a compound or combination of therapeutically active compounds (e.g., an inhibitor described herein, or a combination of inhibitors) that ameliorates, attenuates or eliminates one or more symptoms of a particular disease or condition (e.g., cancer), or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients are mammals (e.g., humans). The term patient includes males and females.

As used herein, the term "pharmaceutically acceptable" means that the referenced substance, such as a compound of the present invention, or a formulation containing the compound, or a particular excipient, are safe and suitable for administration to a subject or patient. The term "pharmaceutically acceptable carrier" refers to a medium that does not interfere with the effectiveness of the biological activity of the active ingredient(s) and is not toxic to the host to which it is administered.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

As used herein, the term "Notch transcriptional activation complex" ("NTC") refers to a complex of three proteins, the DNA binding protein CSL, the intracellular domain of Notch ("NICD") and the co-activator protein Mastermind ("MAML1"), which functions to activate transcription of target genes.

As used herein, the phrase "deregulation of the Notch transcriptional activation complex" or "deregulation of the NTC" refers to an abnormality in the regulatory ability of the NTC, resulting in reactivation of gene transcription.

Notch Transcriptional Activation Complex Kinase ("NACK") Inhibitors

Disclosed herein are compounds that can inhibit Notch activation complex kinase ("NACK").

In some embodiments, the disclosure provides a compound of Formula (Ia), or a pharmaceutically acceptable salt thereof:

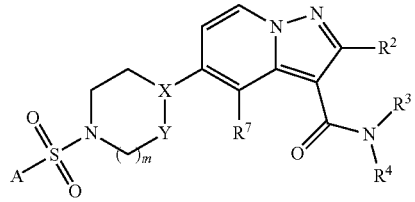

(Ia)

wherein:

A is $C_{1-4}$alkyl or

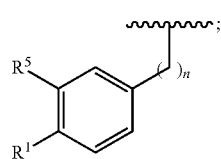

X is CH or N;

Y is $CH_2$ or N, and when X is N, then Y is $CH_2$;

m is 0 or 1, and when m is 1 then Y is $CH_2$;

n is 0 or 1;

$R^1$ is H, $C_{1-6}$alkyl, $C_{0-6}$alkyleneC(=O)$R^6$, halo, cyano, aryloxy, amino, $C_{0-3}$alkylene-amido, carbamyl, S-thiocarbamyl, or ureido;

$R^2$ is H, halo, $C_{1-6}$alkyl, $C_{3-8}$cycloalkyl, or heteroaryl;

each $R^3$ and $R^4$ independently is H, $C_{1-6}$ alkyl, or $C_{1-3}$ aralkyl, or $R^3$ and $R^4$ and the nitrogen to which they are attached join together to form a 3-6 membered ring optionally comprising 1 to 3 additional heteroatoms selected from N, O, and S;

$R^5$ is H, or $R^1$ and $R^5$ together with the atoms to which they are attached form a 5- or 6-membered heterocyclic ring comprising 1 to 3 ring heteroatoms selected from N, O, and S;

$R^6$ is OH, $C_{1-6}$alkyl, or O$C_{1-6}$alkyl;

$R^7$ is H, halo or amino;

with the proviso that the compound is not

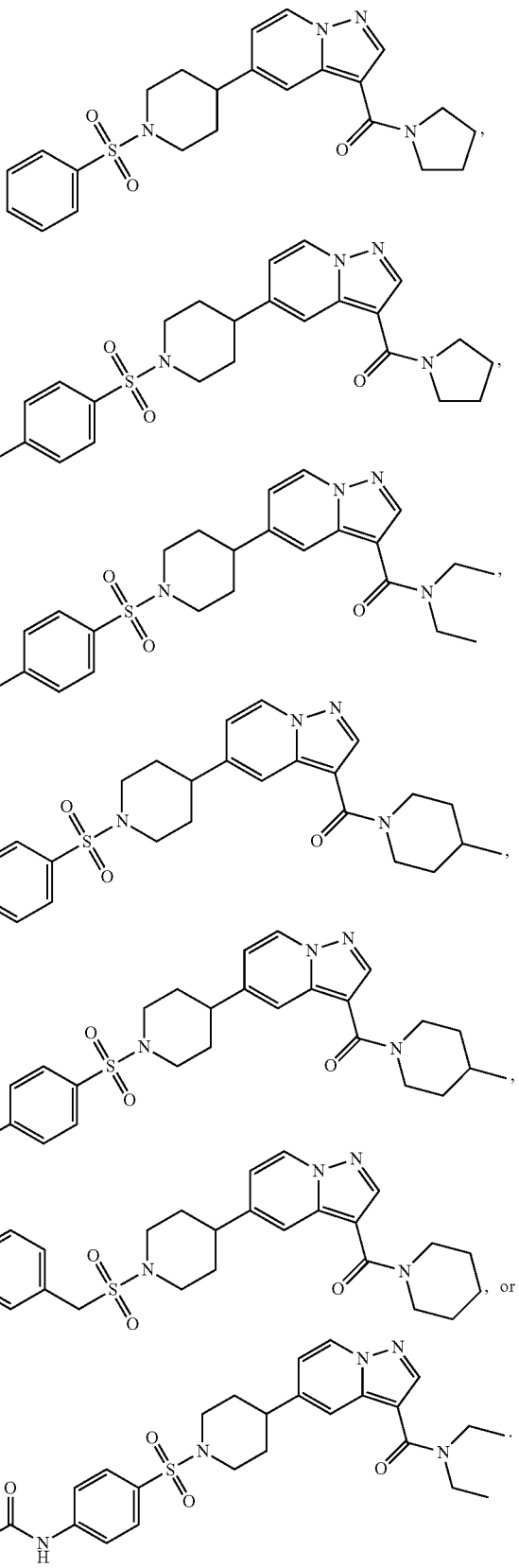

In some embodiments, the disclosure provides a compound of Formula (I), or a pharmaceutically acceptable salt thereof:

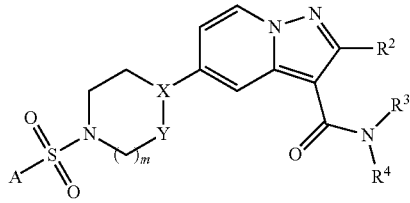

wherein A is $C_{1-4}$alkyl or

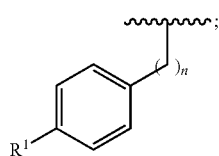

X is CH or N; Y is $CH_2$ or N, and when X is N, then Y is $CH_2$; m is 0 or 1, and when m is 1 then Y is $CH_2$; n is 0 or 1; $R^1$ is H, $C_{1-6}$alkyl, halo, cyano, aryloxy, amino, amido, carbamyl, or ureido; $R^2$ is H, halo, $C_{1-6}$ alkyl, $C_{3-8}$ cycloalkyl, or heteroaryl; and each $R^3$ and $R^4$ independently is H, $C_{1-6}$ alkyl, or $C_{1-3}$aralkyl, or $R^3$ and $R^4$ and the nitrogen to which they are attached join together to form a 5-6 membered ring; with the proviso that the compound is not

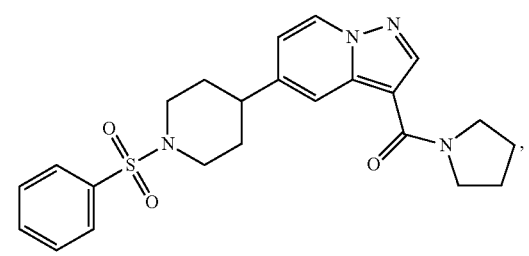

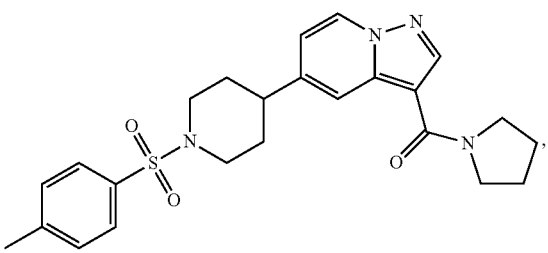

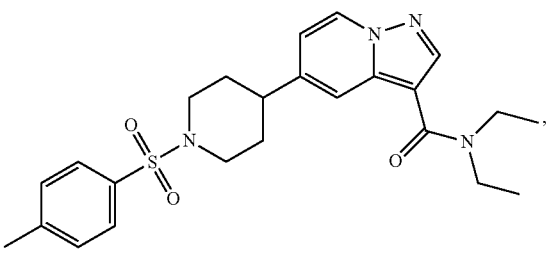

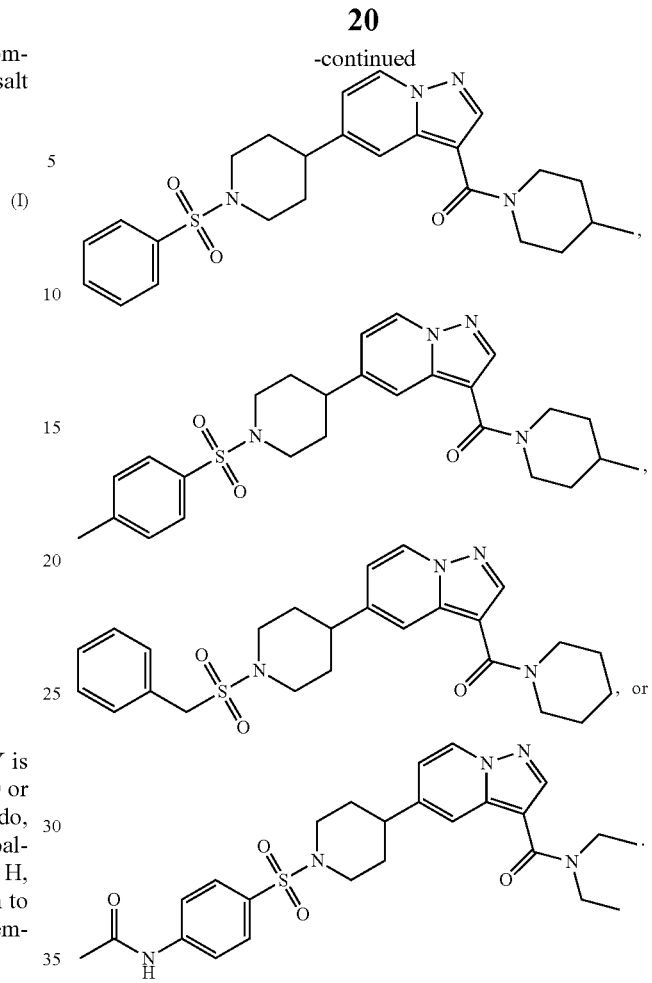

In some embodiments, A is $C_{1-4}$alkyl. Suitable A groups can include, for example, methyl, ethyl, propyl, isopropyl, n-butyl, s-butyl, isobutyl, or t-butyl. In some cases, A is methyl. In some embodiments, A is not $C_{1-4}$alkyl.

In some embodiments, A is

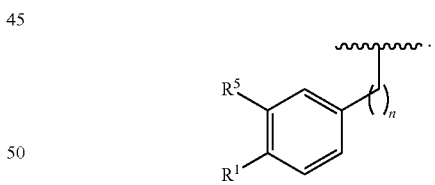

In some embodiments, n is 0. In various cases, n is 1. In some embodiments, $R^1$ and $R^5$ together with the atoms to which they are attached form a 5- or 6-membered heterocyclic ring comprising 1 to 3 ring heteroatoms selected from N, O, and S. In some cases, A is selected from the group consisting of

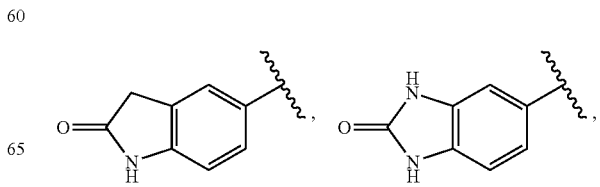

-continued

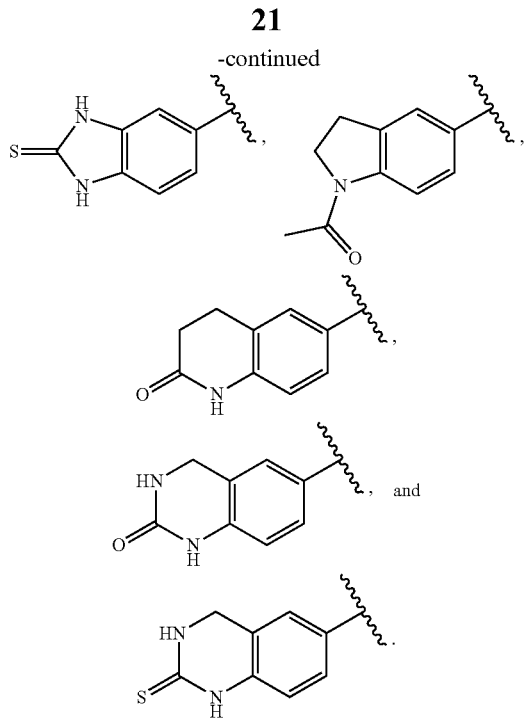

In some cases, A is

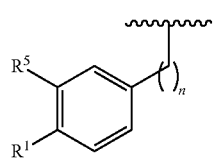

and $R^5$ is H. In some cases, $R^1$ is H. In some embodiments, $R^1$ is $C_{1-6}$ alkyl. Suitable $R^1$ groups can include methyl, ethyl, propyl, isopropyl, n-butyl, s-butyl, isobutyl, t-butyl, pentyl, or hexyl. In some cases, $R^1$ is unsubstituted. For example, $R^1$ can be methyl or ethyl. In some cases, $R^1$ is substituted. For example, $R^1$ can be fluoromethyl or trifluoromethyl. In some embodiments, $R^1$ is $C_{0-6}$alkyleneC(=O)$R^6$. In some cases, $R^1$ is $C_{1-3}$ alkyleneC(=O)$R^6$. In various embodiments, the alkylene group is unsubstituted. In some cases, the alkylene group is substituted with one or more alkyl groups (e.g., one or more methyl groups, such as

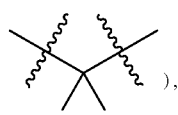), or a spiro group (e.g.,

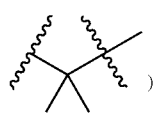 [SMILES: *C(*)(C)C])

In some embodiments, $R^6$ is OH or $OC_{1-6}$alkyl (e.g., OMe, OEt, OPr, OiPr, 2-ethyl). In various embodiments, $R^6$ is $C_{1-6}$alkyl (e.g., methyl, ethyl, or propyl). Suitable $R^1$ groups can include

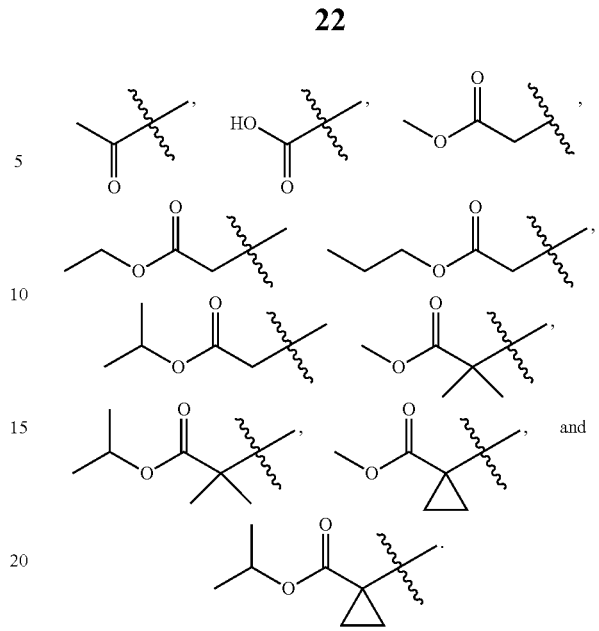

In some cases, $R^1$ is halo (e.g., F). In some embodiments, $R^1$ is cyano. In various embodiments, $R^1$ is aryloxy. For example, $R^1$ can be —CN or —OPh. In some cases, $R^1$ is amino (e.g., $NH_2$). In some embodiments, the amino is mono-substituted with a $C_{1-3}$alkyl group (e.g., methyl, ethyl, propyl). In various cases, the amino is di-substituted with the same or different $C_{1-3}$alkyl groups. For example, $R^1$ can be —$NH_2$, —$N(CH_3)_2$ or —$NH_2Ph$. In various cases, $R^1$ is $C_{0-3}$alkylene-amido. In some cases, $R^1$ is $C_0$alkylene-amido. In various cases, $R^1$ is $C_1$alkylene-amido. In some embodiments, the $C_{0-3}$alkylene-amido group terminates in a $C_{1-6}$alkyl group, a $C_{3-8}$cycloalkyl group, an amino group, or a heteroaryl group. Suitable $C_{0-3}$alkylene-amido groups can include

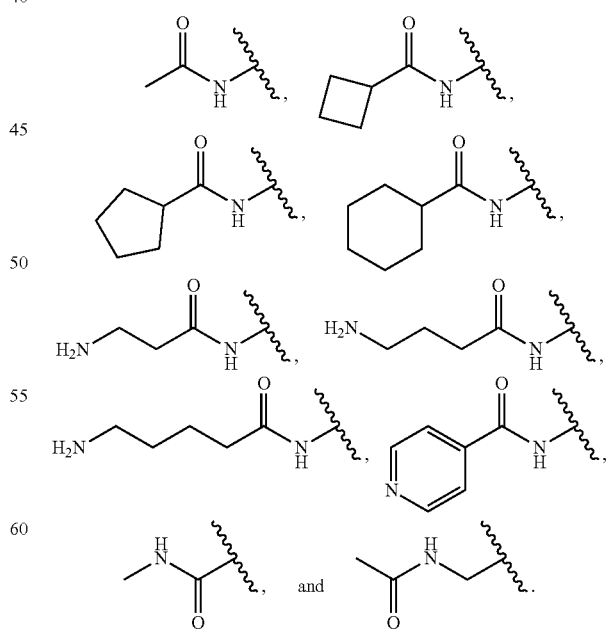

In some embodiments, $R^1$ is a carbamyl group. In some cases, the carbamyl group terminates in a $C_{1-6}$alkyl group or a $C_{3-8}$cycloalkyl group. In some embodiments, the alkyl group is substituted (e.g., with fluorine). Suitable carbamyl groups can include, for example,

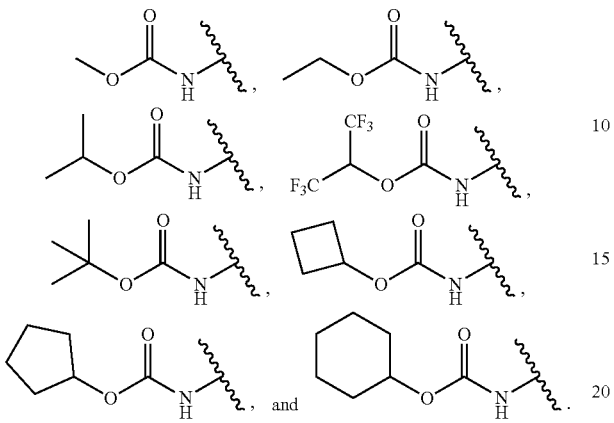

In some embodiments, $R^1$ is a S-thiocarbamyl group. In various embodiments, the S-thiocarbamyl group can terminate in a $C_{1-6}$alkyl group or a $C_{3-8}$cycloalkyl group. In some embodiments, the alkyl group is substituted (e.g., with fluorine). Suitable S-thiocarbamyl groups can include, for example,

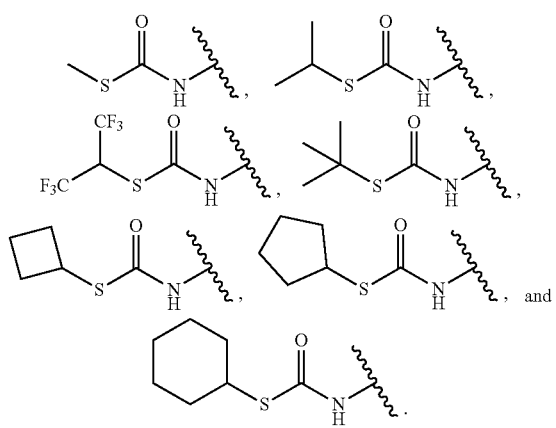

In some cases, $R^1$ is ureido group. In various cases, the ureido group can terminate in a $C_{1-6}$alkyl group or a $C_{3-8}$cycloalkyl group. In some embodiments, the alkyl group is substituted (e.g., with fluorine). Suitable ureido groups can include, for example,

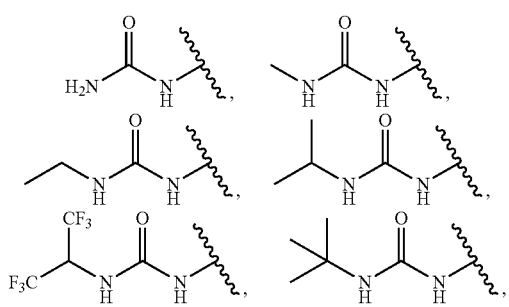

-continued

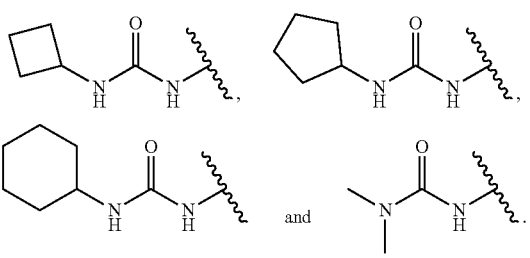

In various cases, $R^1$ is amido, carbamyl, or ureido.

In some cases, A is selected from the group consisting of $CH_3$,

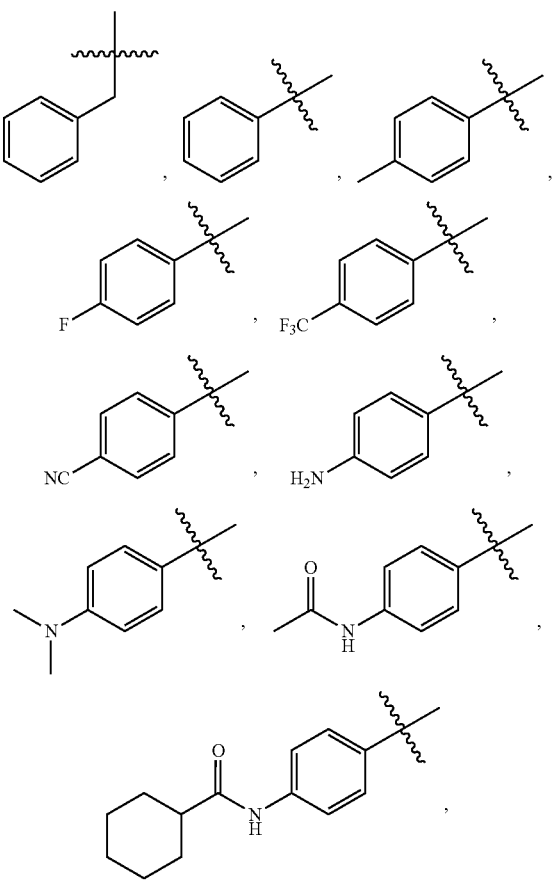

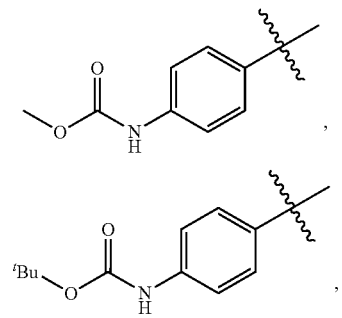

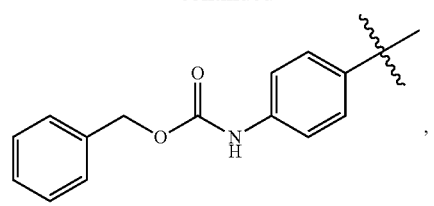

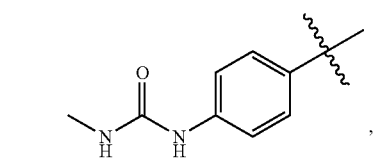

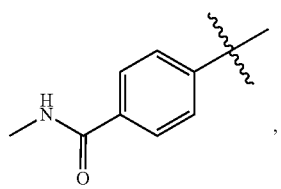

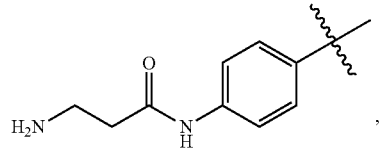

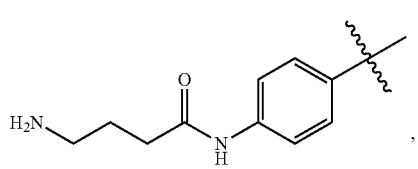

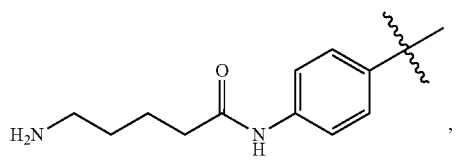

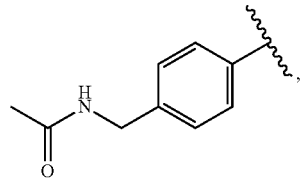

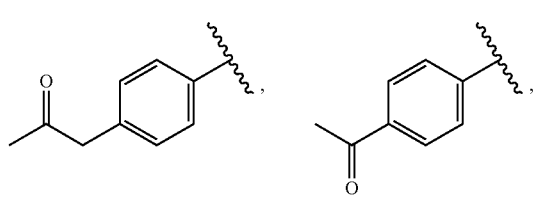

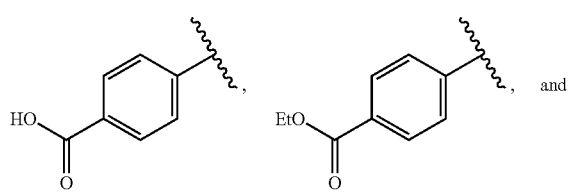

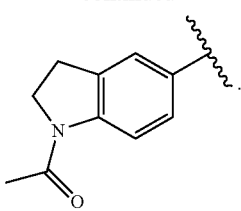

In various cases, A is selected from the group consisting of CH₃,

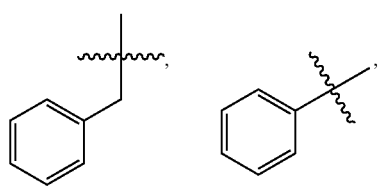

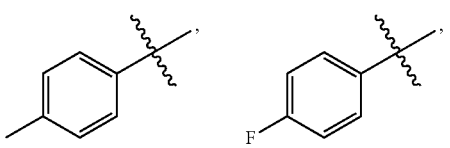

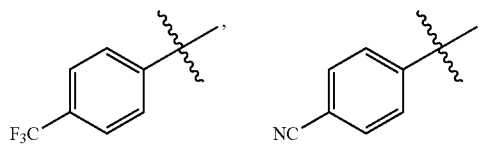

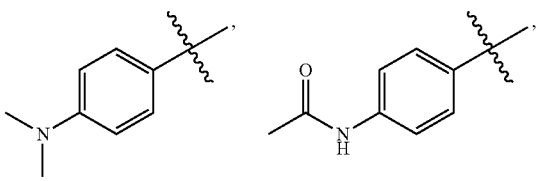

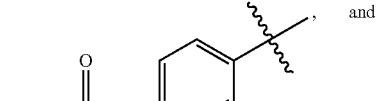

and

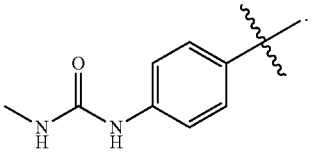

In some embodiments, X is CH. In various embodiments, X is N. In some cases, Y is CH₂. In various cases, Y is N. In some cases, m is 0. In various cases, m is 1. In some embodiments, X is CH, Y is CH₂, and m is 1. In various embodiments, X is CH, Y is CH₂, and m is 0. In some cases, X is N, Y is CH₂, and m is 1. In various cases, X is CH, Y is N, and m is 0. In some embodiments, the compound of Formula (Ia) has a structure of Formula (Ia'):

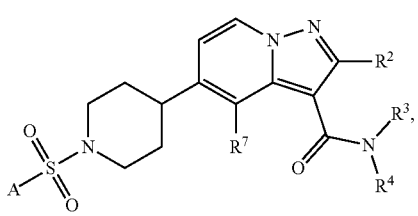

(Ia')

wherein the substituents are as previously defined.

In some embodiments, $R^2$ is H. In various embodiments, $R^2$ is halo. For example, $R^2$ can be Br or Cl. In some cases, $R^2$ is $C_{1-6}$ alkyl. Suitable $R^2$ groups can include methyl, ethyl, propyl, isopropyl, n-butyl, s-butyl, isobutyl, t-butyl, pentyl, or hexyl. In some cases, $R^2$ is unsubstituted. For example, $R^2$ can be methyl or ethyl. In some cases, $R^2$ is substituted. In various cases, $R^2$ can be substituted with a fluoro, hydroxyl, or alkoxyl group. For example, $R^2$ can be $CH_3$, $CF_3$, $CH_2OH$, or $CH_2OCH_3$. In some embodiments, $R^2$ is $C_{3-8}$cycloalkyl. In some cases, $R^2$ is cyclopropyl, cyclobutyl, cyclopentyl, or cyclohexyl. In various cases, $R^2$ is heteroaryl. In various embodiments, $R^2$ is selected from the group consisting of H, $CH_3$, $CF_3$, and cyclopropyl.

In some embodiments, $R^7$ is H. In various embodiments, $R^7$ is halo or amino. In some embodiments, $R^7$ is F, Cl, or Br. In some embodiments, $R^7$ is —$NH_2$. In some embodiments, each of $R^2$ and $R^7$ is H. In some cases, the compound of Formula (Ia) has a structure of Formula (Ia"):

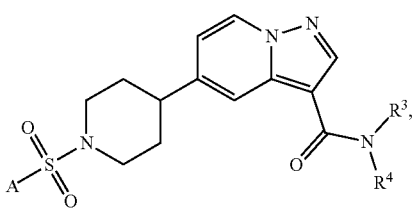

(Ia")

wherein the substituents are as previously defined.

In some embodiments, each of $R^3$ and $R^4$ independently is H, $C_{1-6}$ alkyl, or $C_{1-3}$aralkyl. Suitable alkyl groups include, for example, methyl, ethyl, propyl, isopropyl, n-butyl, s-butyl, isobutyl, t-butyl, pentyl, and hexyl. In some cases, each $R^3$ and $R^4$ independently is H, $CH_3$, $CH_2CH_3$, $^iBu$, or $CH_2Ph$. In various cases,

is selected from the group consisting of

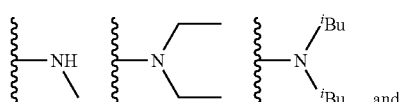

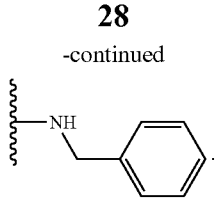

In some embodiments, $R^3$ and $R^4$ and the nitrogen to which they are attached join together to form a 3-6-membered ring. In some embodiments, $R^3$ and $R^4$ and the nitrogen to which they are attached join together to form a 4-membered ring. In some embodiments, $R^3$ and $R^4$ and the nitrogen to which they are attached join together to form a 5-6 membered ring. In various embodiments, the 5-6 membered ring is a pyrrolidine or piperidine ring. In some embodiments, the 3-6 membered ring comprises 1 to 3 additional heteroatoms selected from N, O, and S. In some cases,

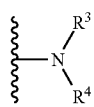

is selected from the group consisting of

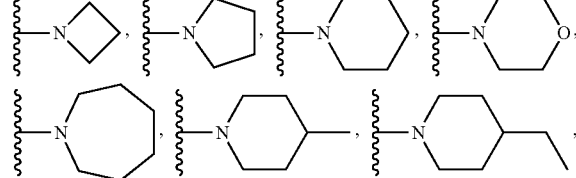

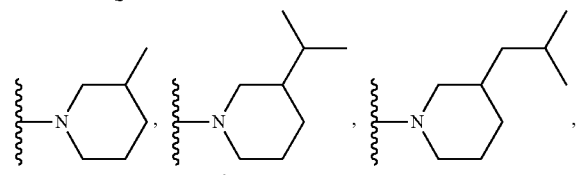

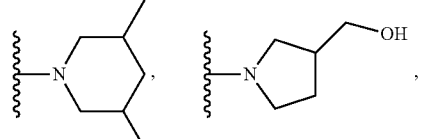

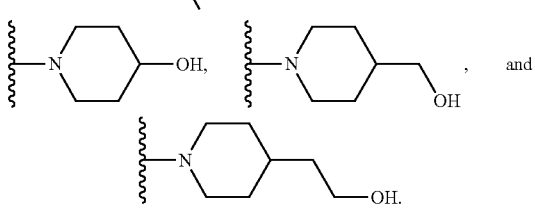

In various cases,

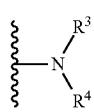

is selected from the group consisting of
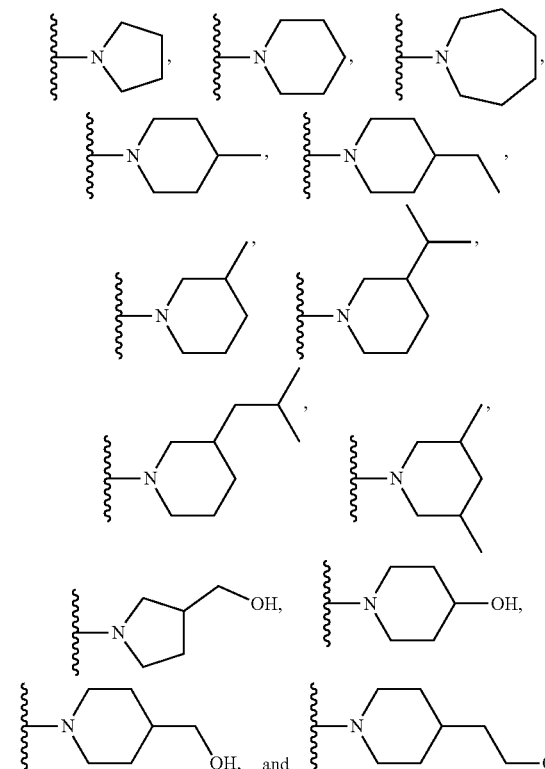
For example,
can be selected from the group consisting of
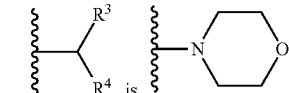
In some cases,
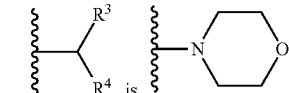R³/R⁴ is azetidinyl.
In some cases, R³/R⁴ is morpholinyl.
Contemplated compounds of the disclosure include the compounds listed in Table A and pharmaceutically acceptable salts thereof:
TABLE A
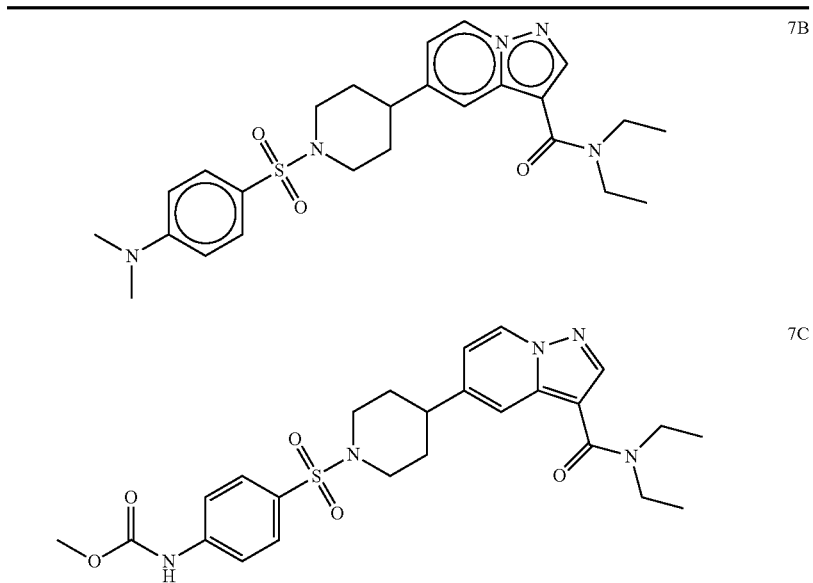

TABLE A-continued
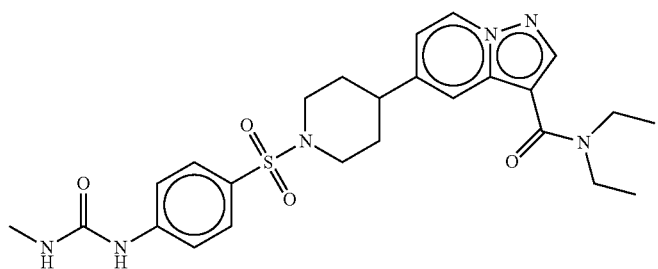
7D
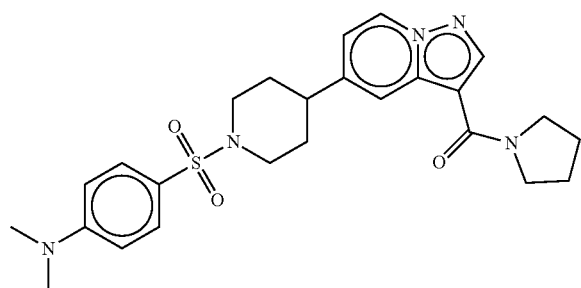
7F
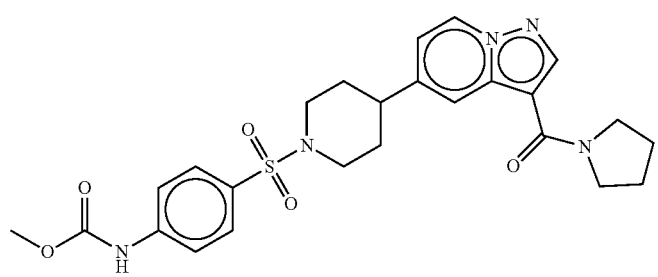
7G
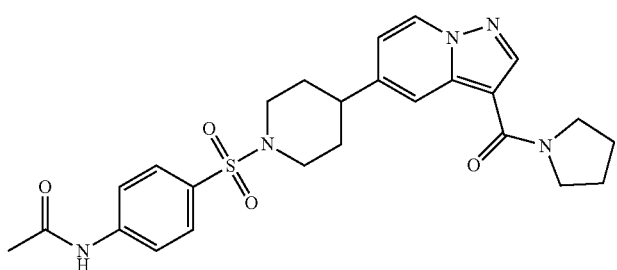 [SMILES: CC(=O)Nc1ccc(S(=O)(=O)N2CCC(c3ccn4ncc(C(=O)N5CCCC5)c4c3)CC2)cc1]
7H
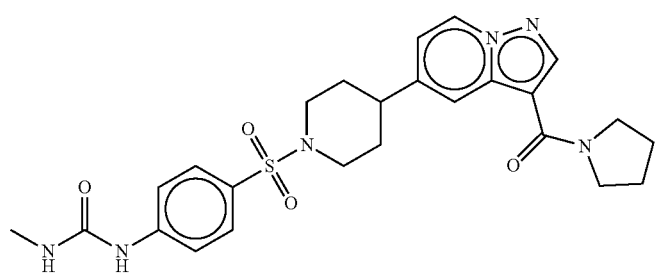
7I TABLE A-continued
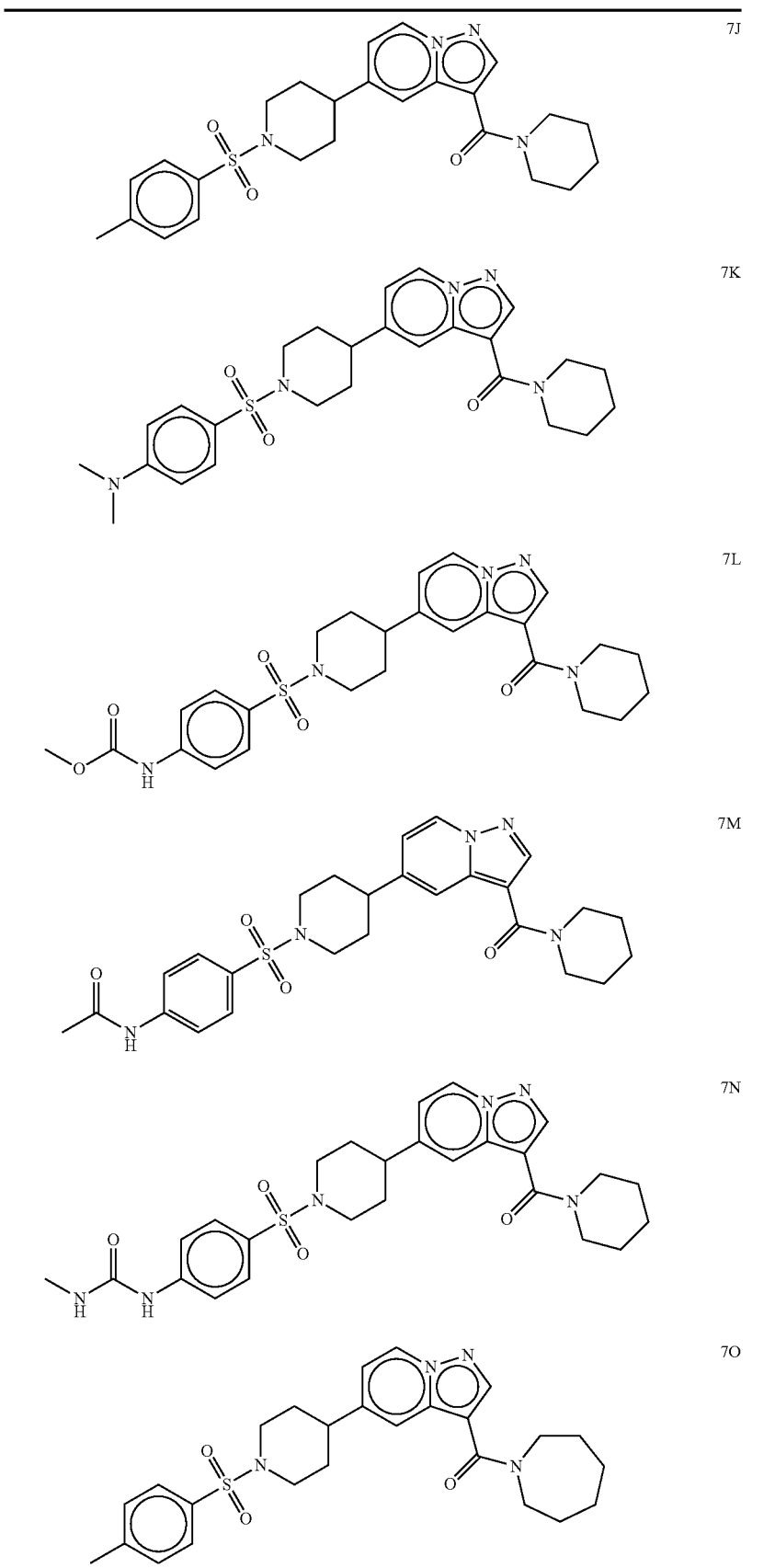

TABLE A-continued
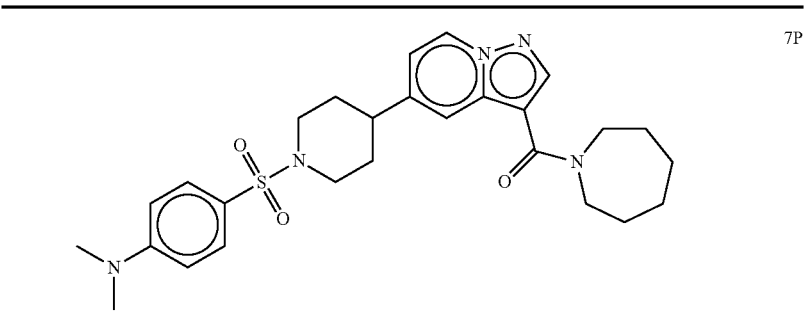
7P
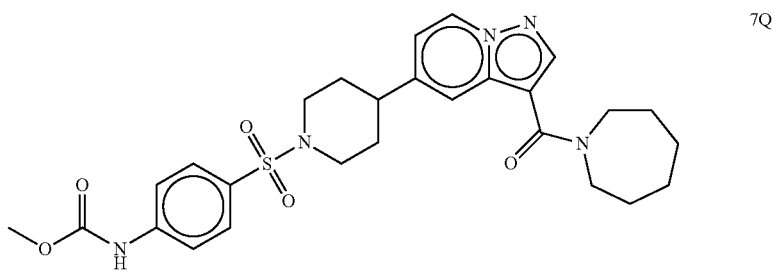
7Q
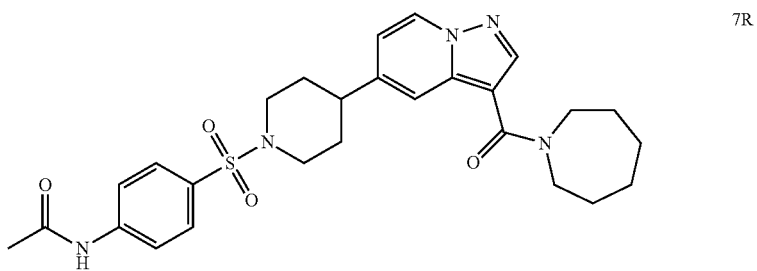
7R
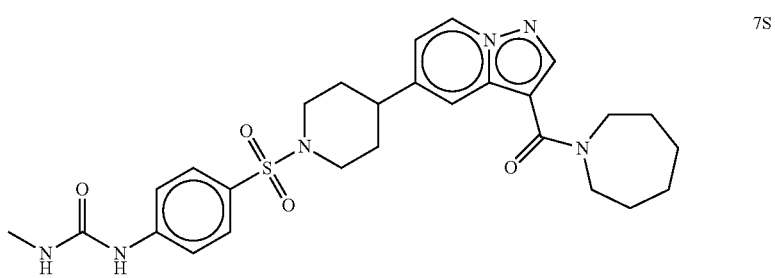
7S
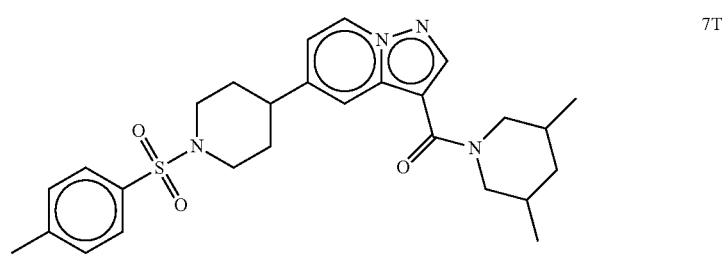
7T TABLE A-continued
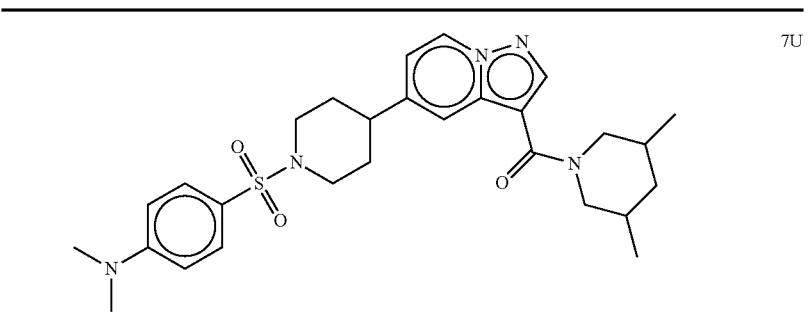
7U
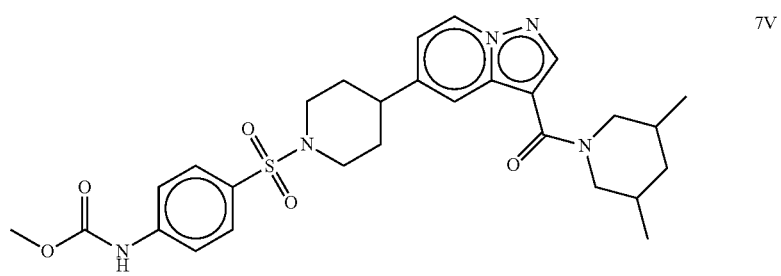
7V
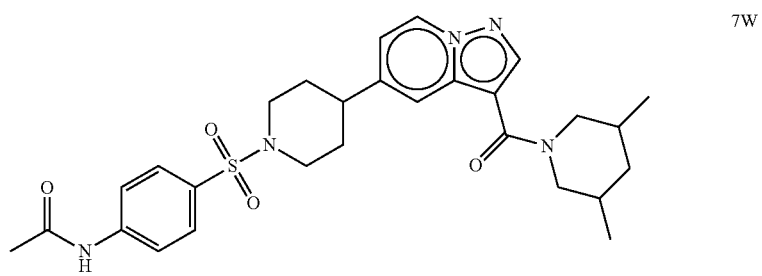
7W
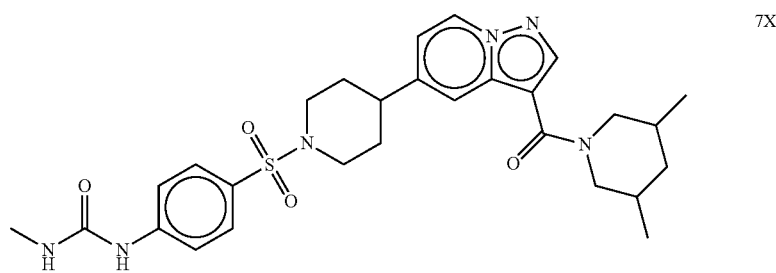
7X
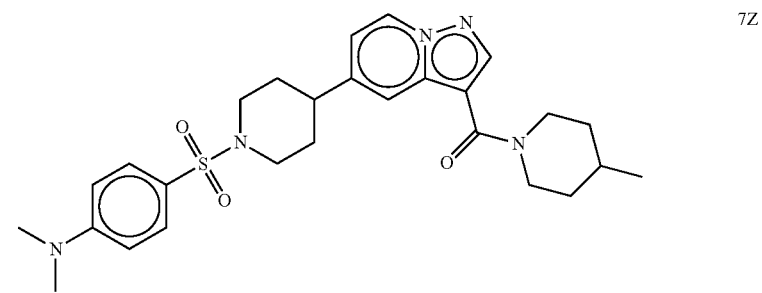
7Z TABLE A-continued
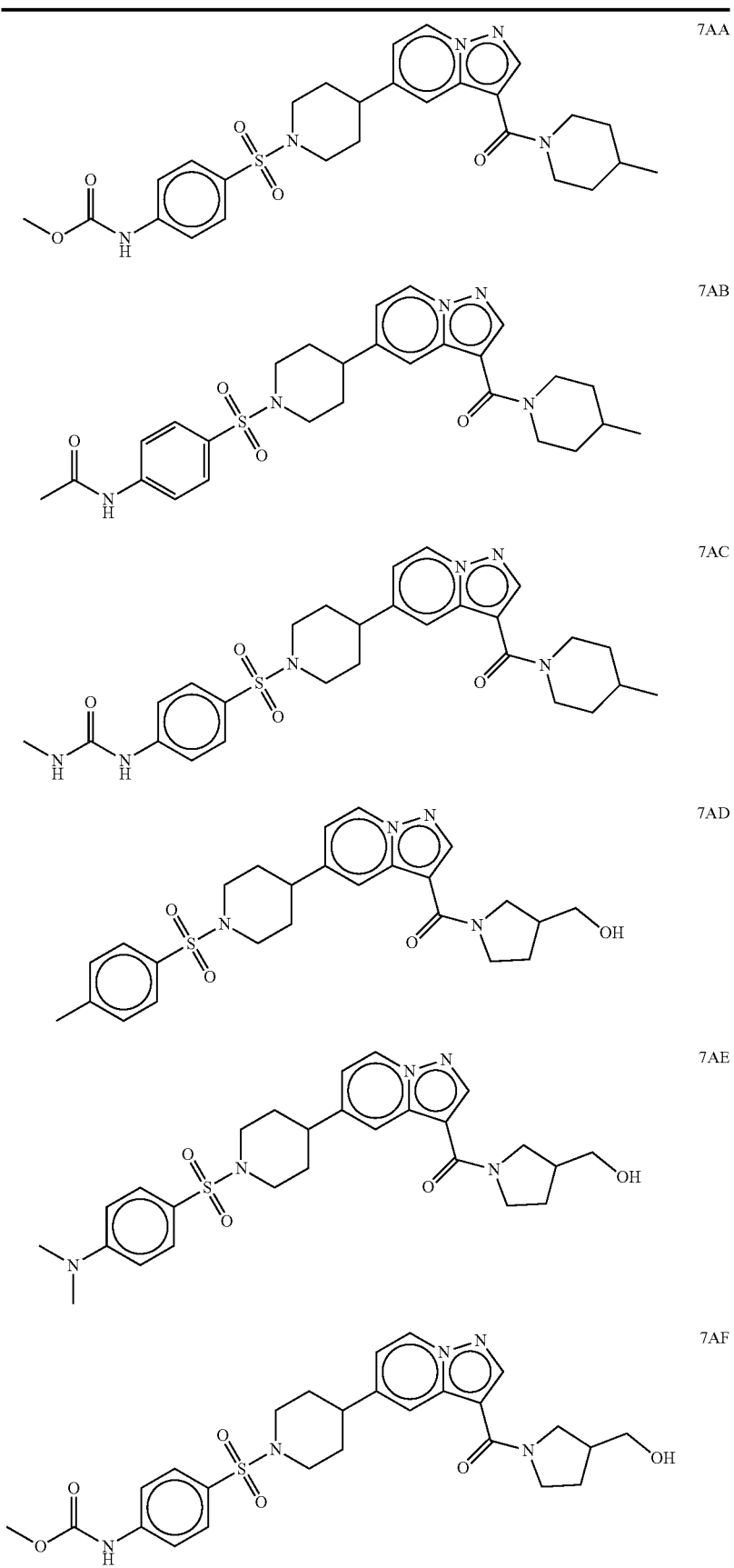
7AA
7AB
7AC
7AD
7AE
7AF TABLE A-continued
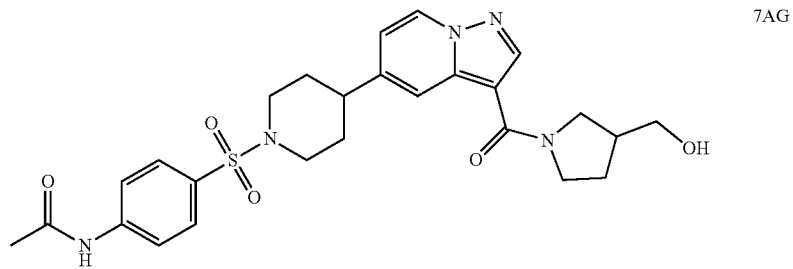
7AG
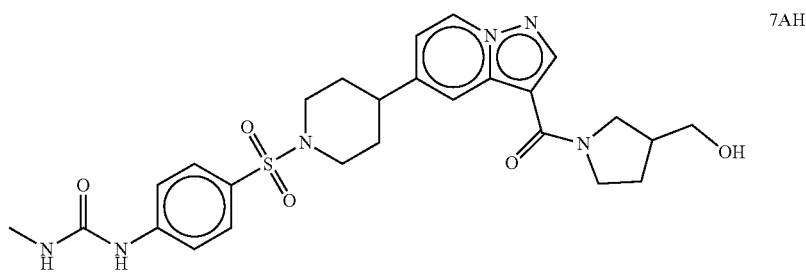
7AH
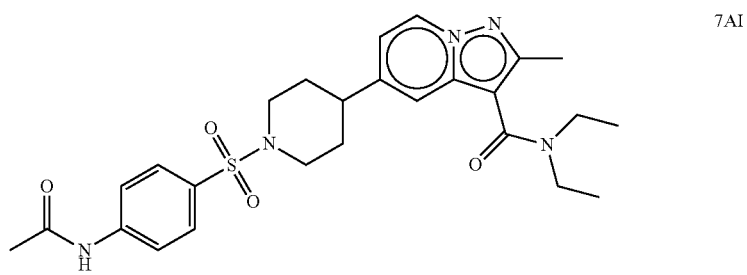
7AI
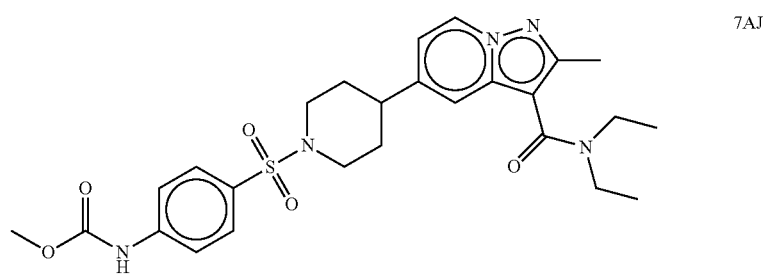
7AJ
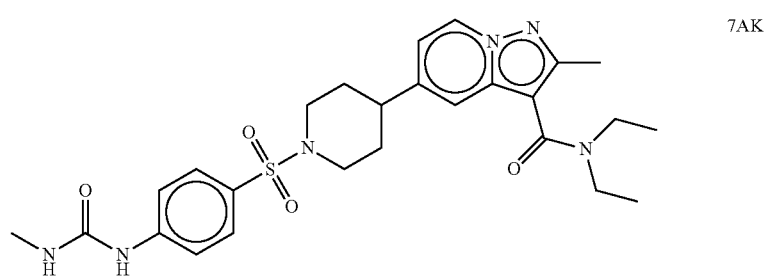
7AK TABLE A-continued
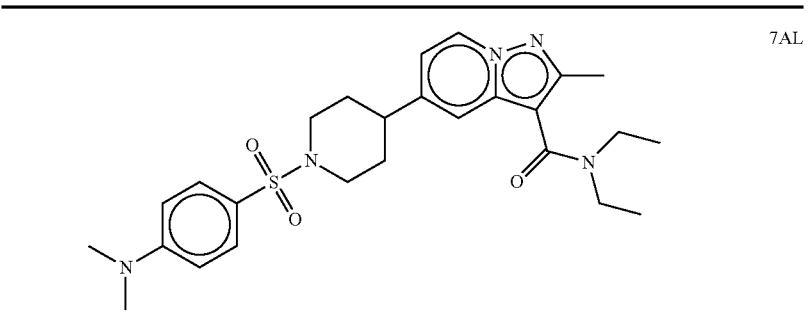
7AL
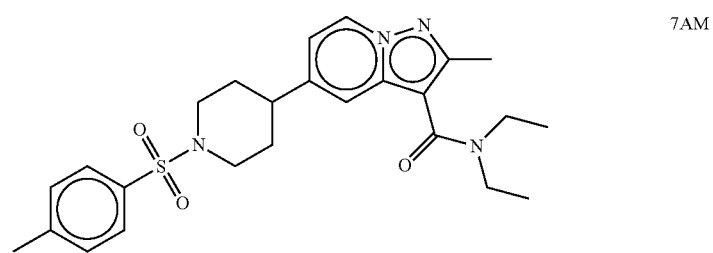
7AM
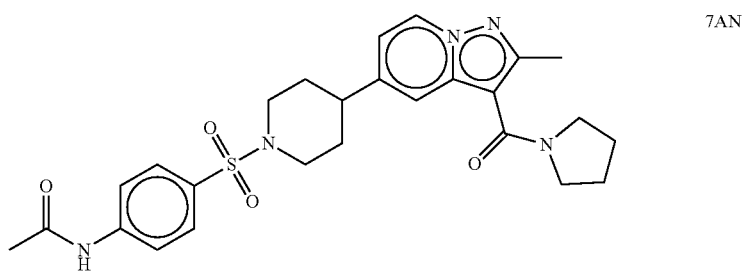
7AN
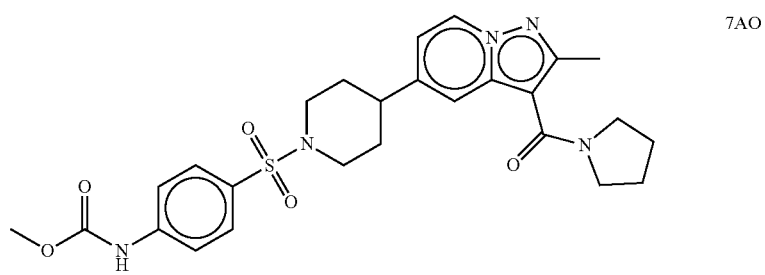
7AO
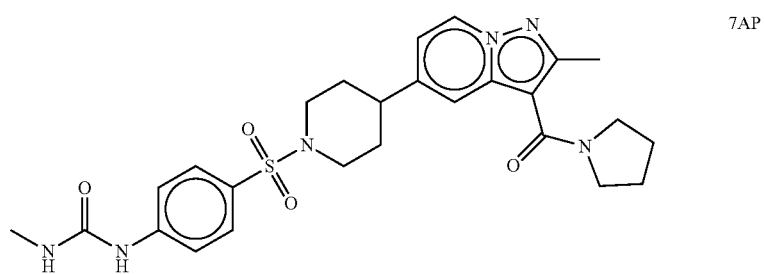
7AP TABLE A-continued
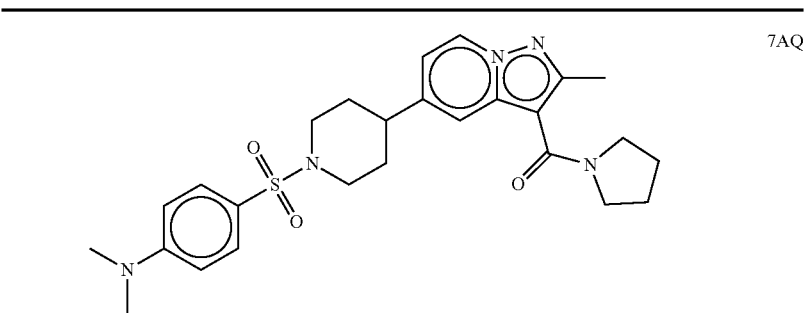
7AQ
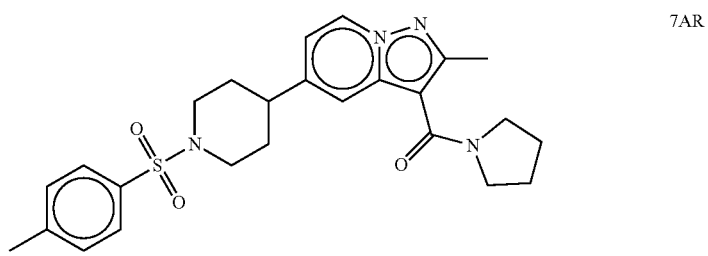
7AR
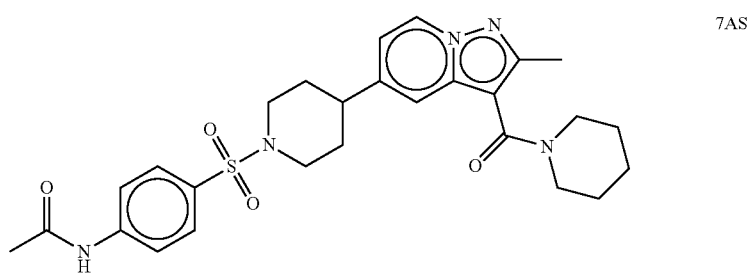
7AS
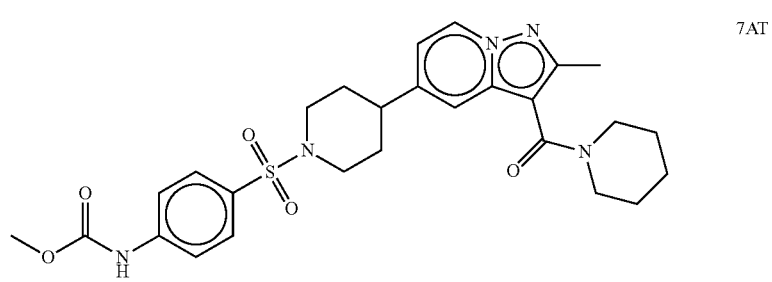
7AT
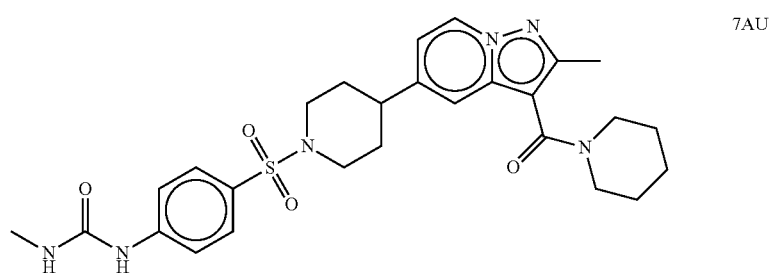
7AU TABLE A-continued
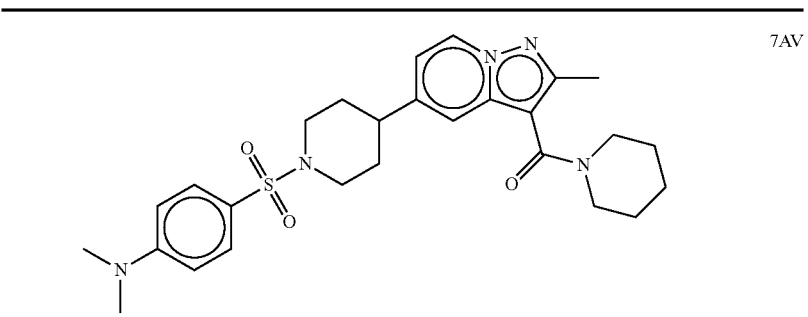
7AV
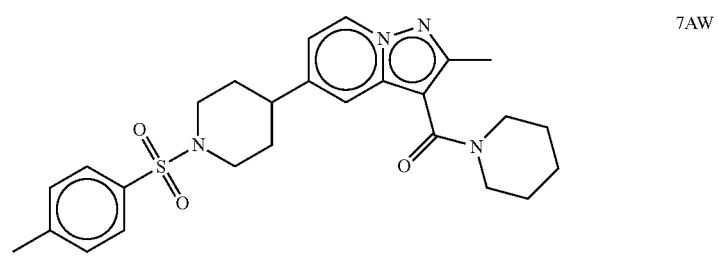
7AW
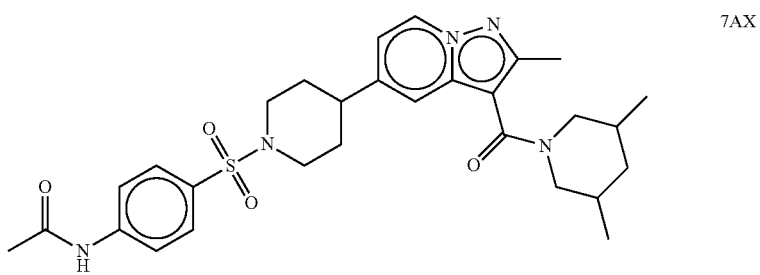
7AX
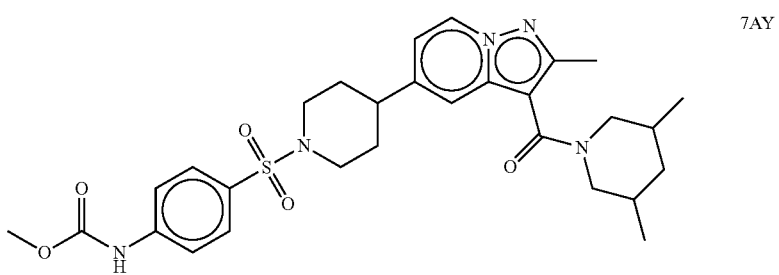
7AY
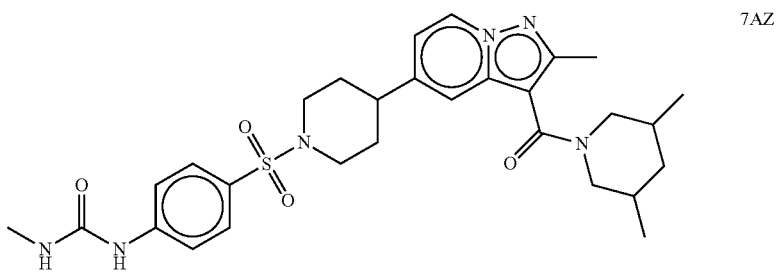
7AZ TABLE A-continued
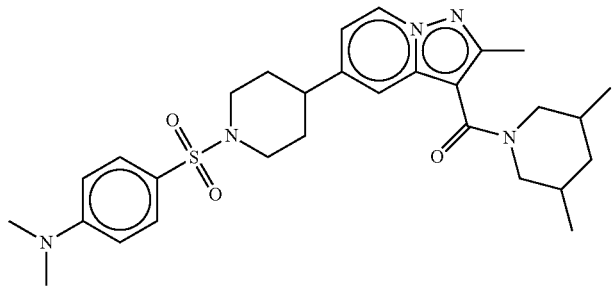
7BA
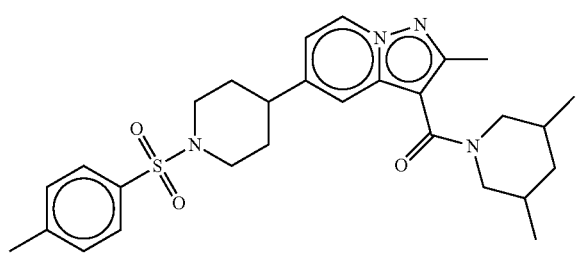
7BB
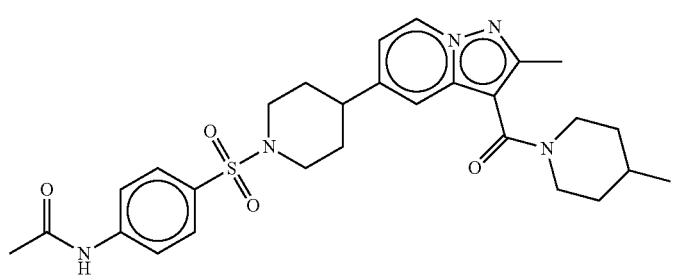
7BC
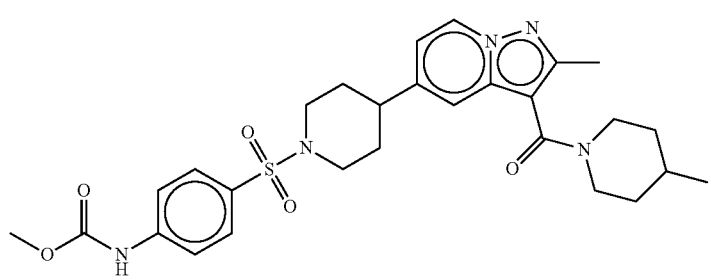
7BD
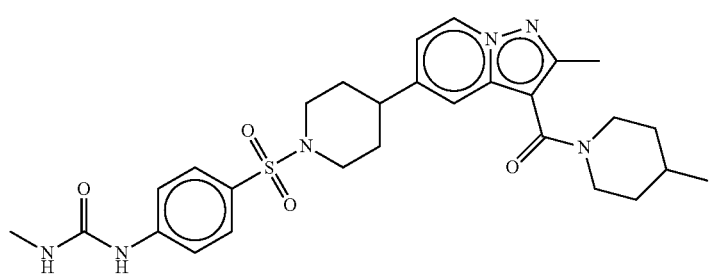
7BE TABLE A-continued
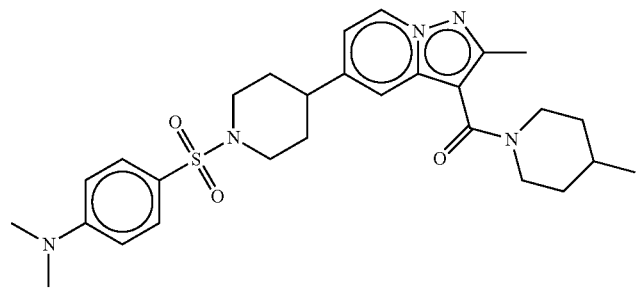
7BF
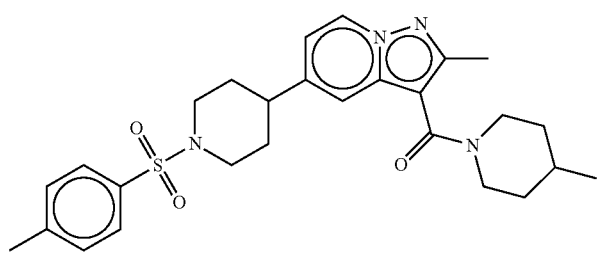
7BG
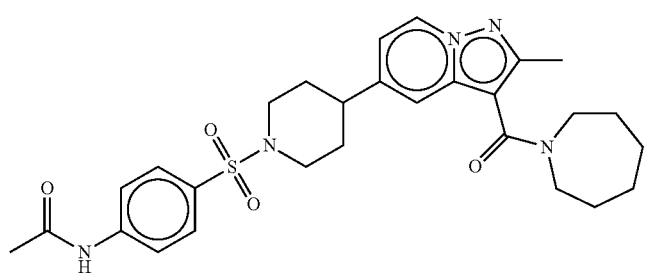
7BH
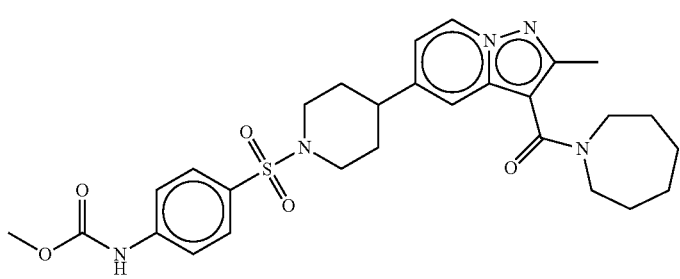
7BI
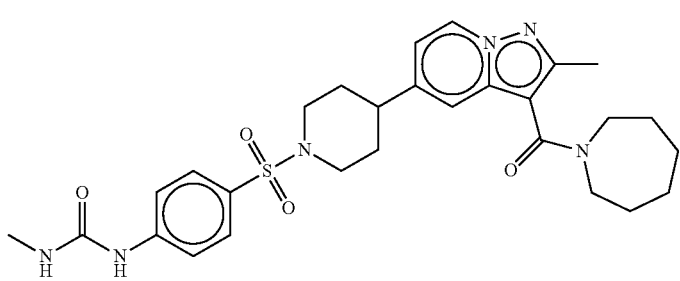
7BJ TABLE A-continued
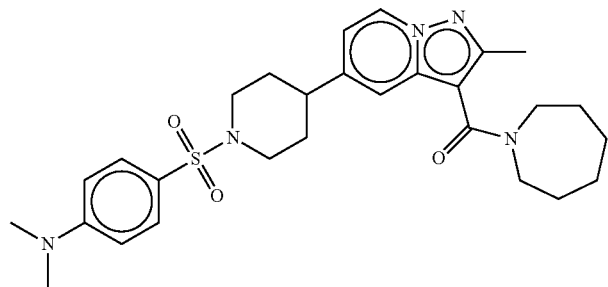
7BK
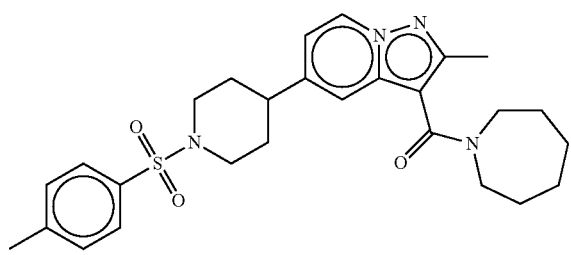
7BL
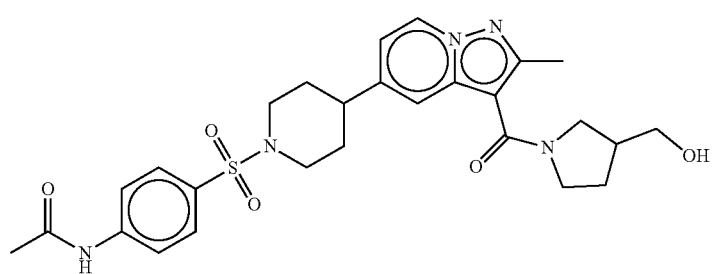
7BM
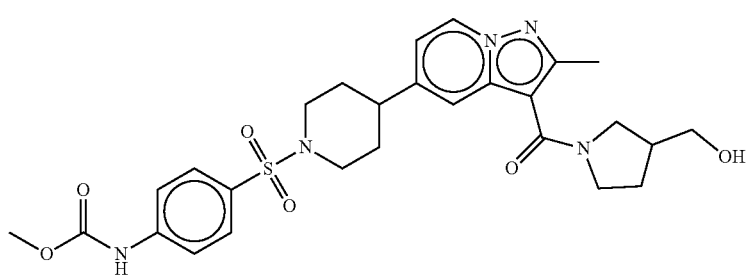
7BN
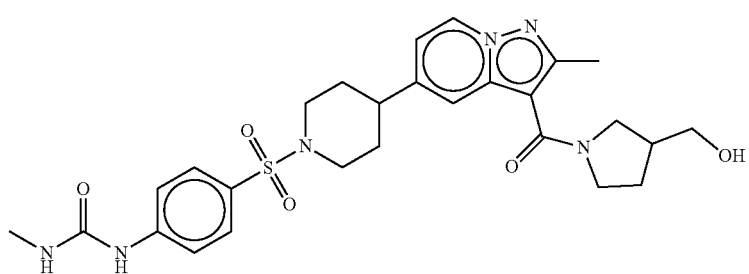
7BO TABLE A-continued
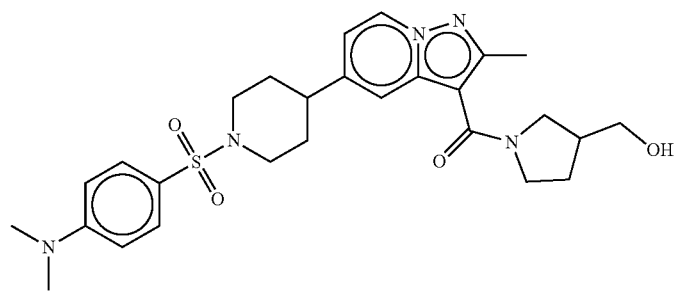
7BP
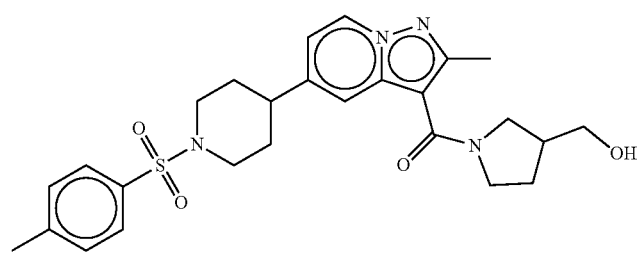
7BQ
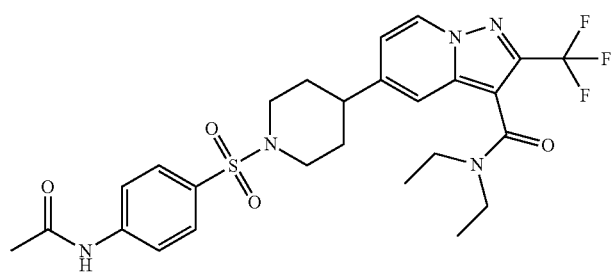 [SMILES: CCN(CC)C(=O)c1c(C(F)(F)F)nn2ccc(C3CCN(S(=O)(=O)c4ccc(NC(C)=O)cc4)CC3)cc12]
7BR
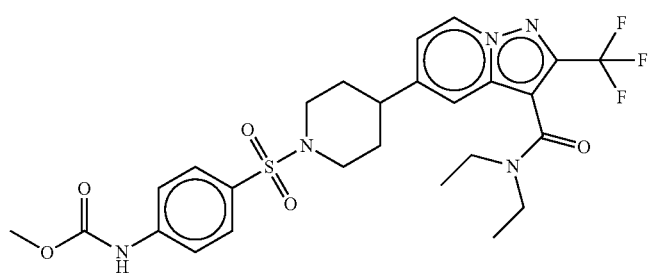
7BS
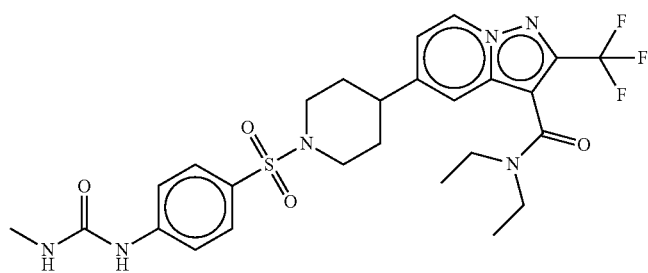
7BT TABLE A-continued
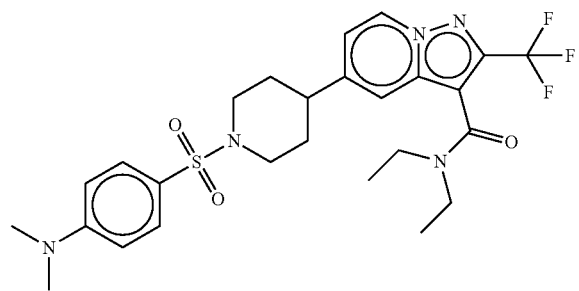
7BU
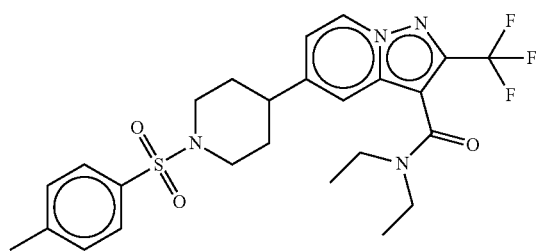
7BV
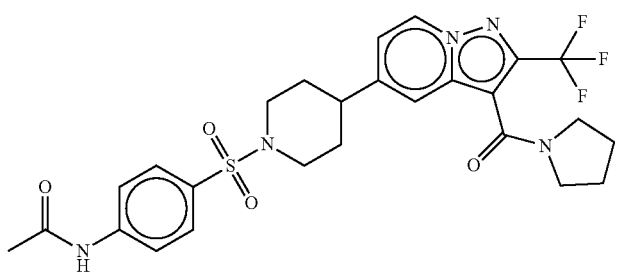
7BW
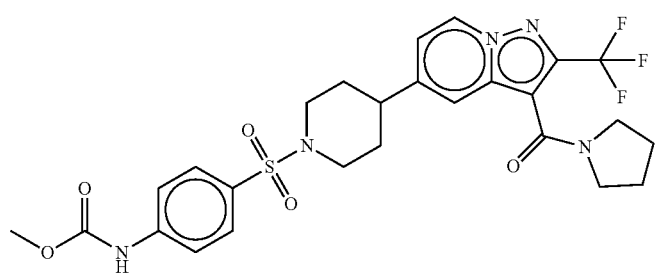
7BX
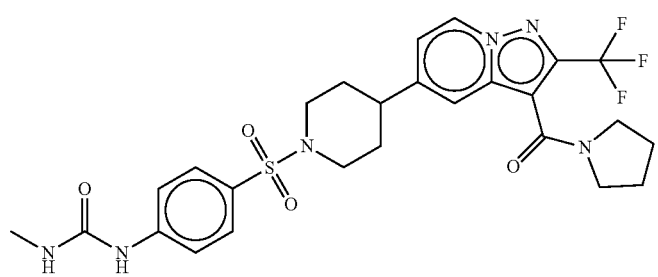
7BY TABLE A-continued
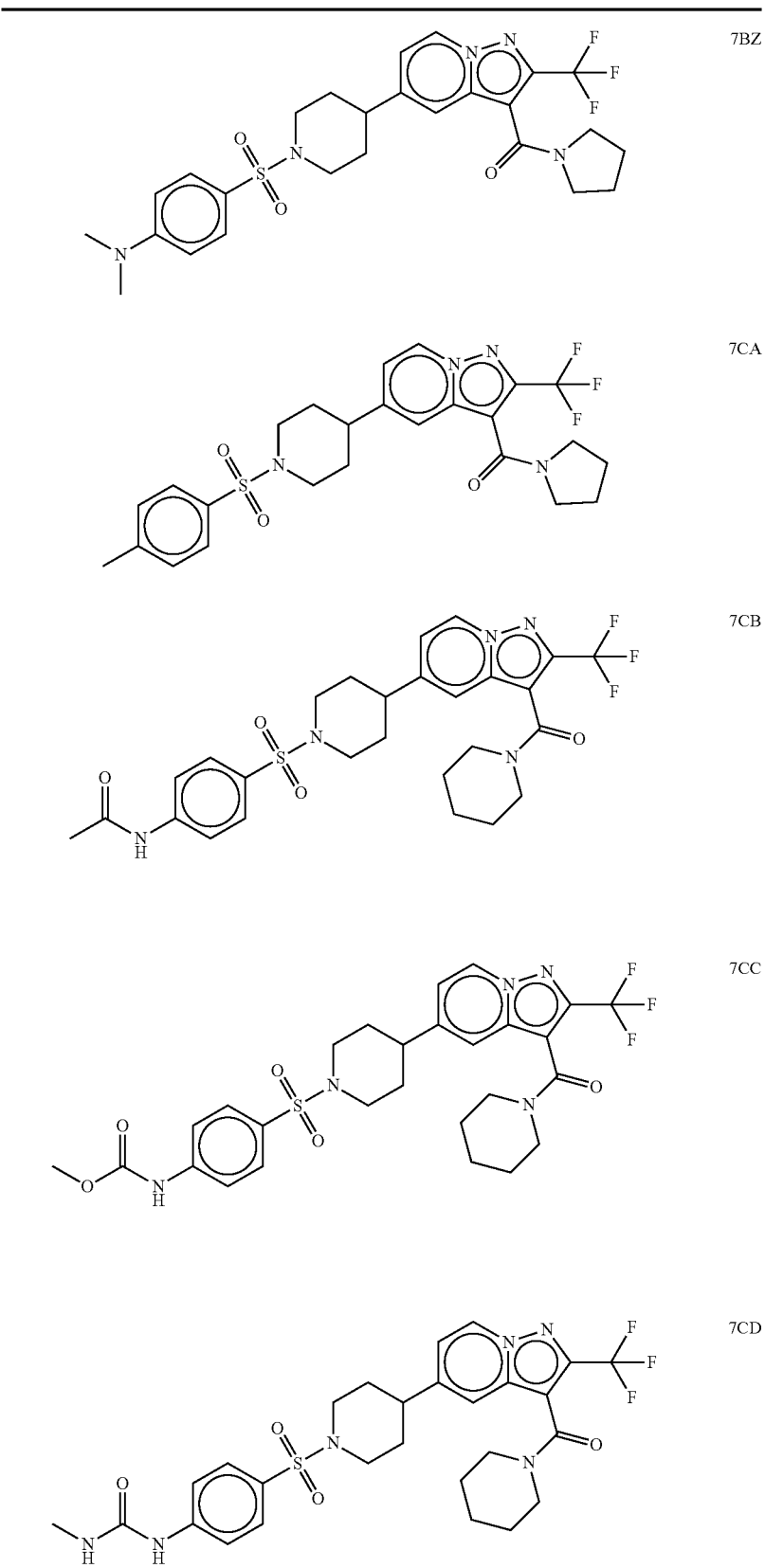

TABLE A-continued
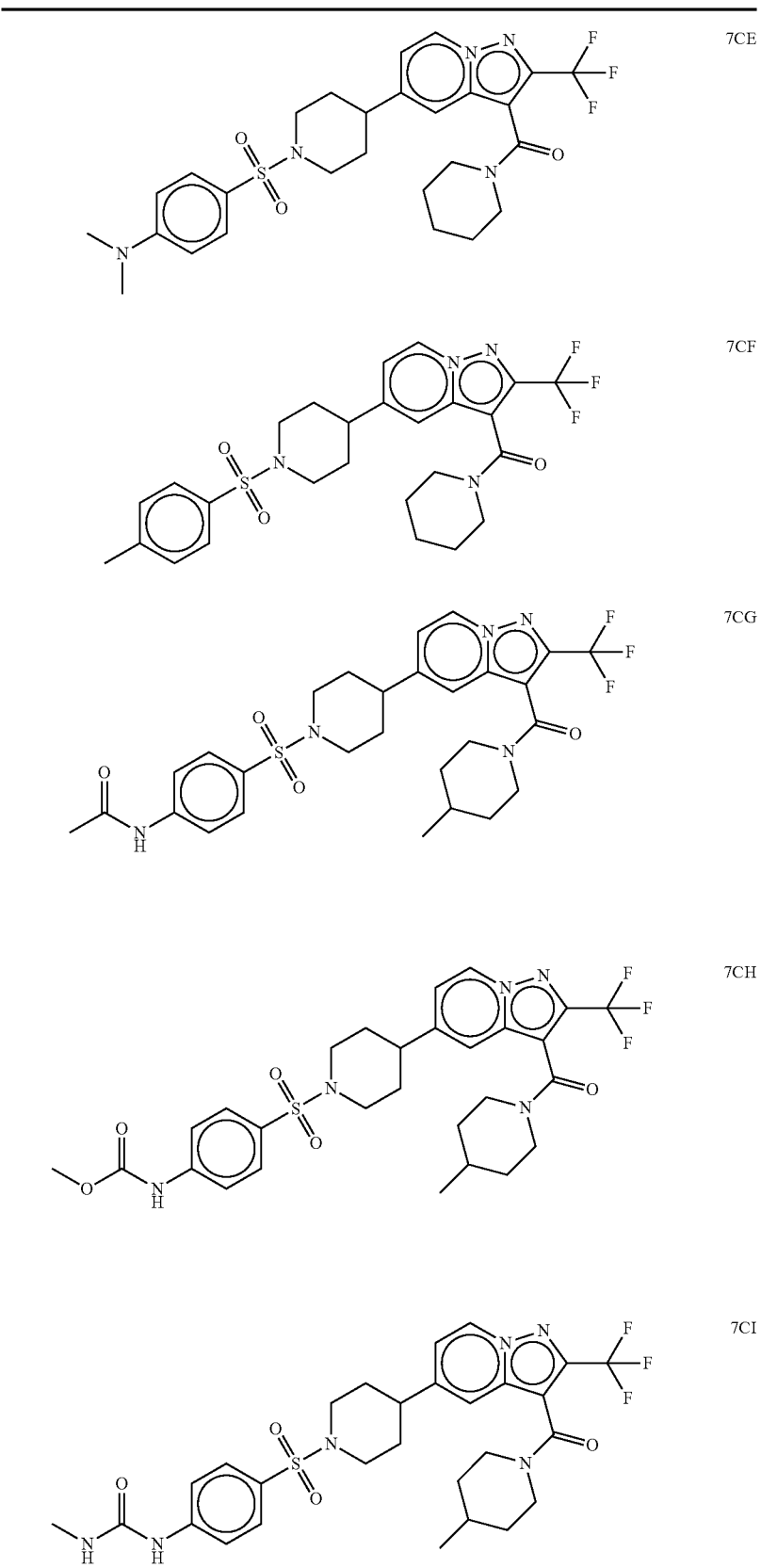
7CE
7CF
7CG
7CH
7CI

TABLE A-continued
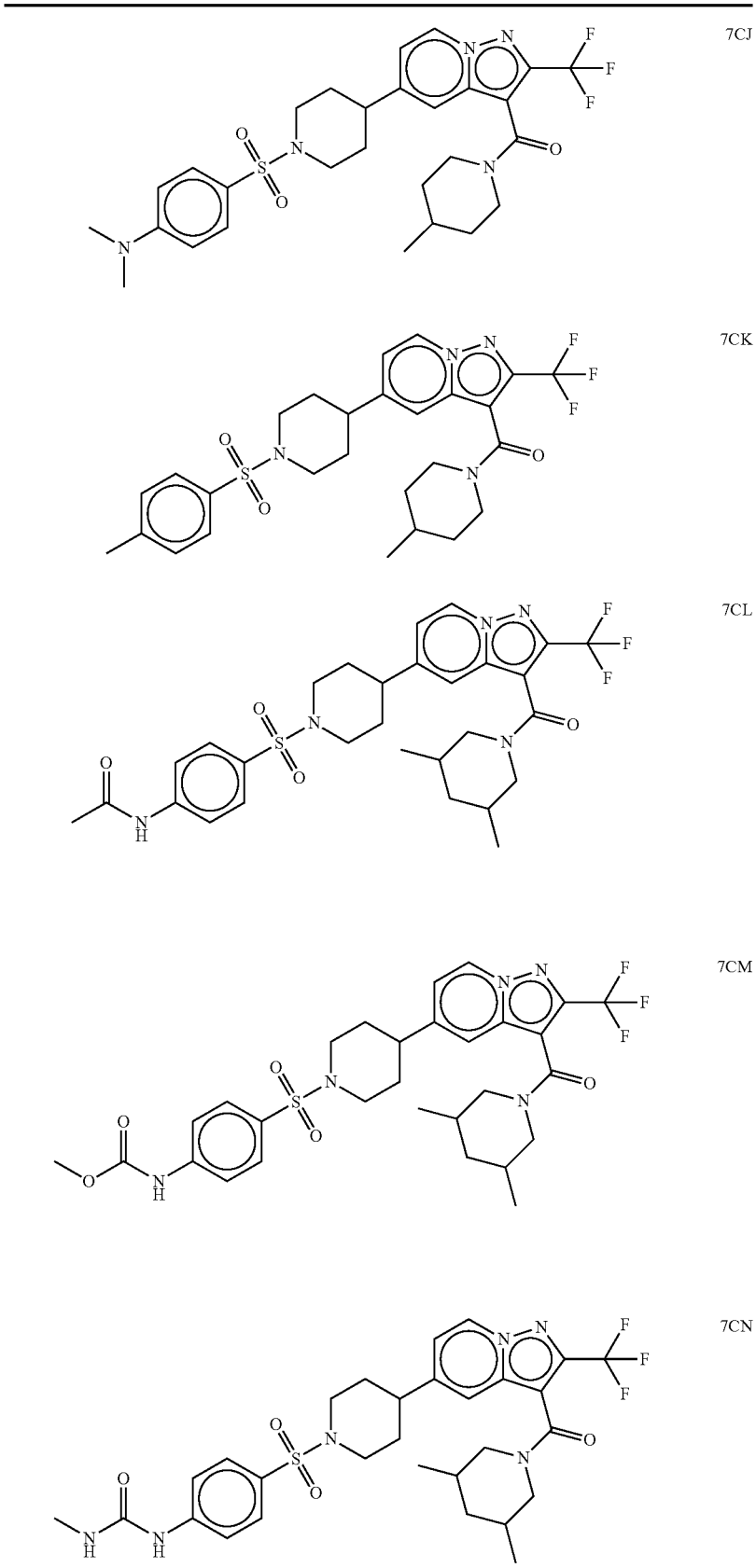
7CJ
7CK
7CL
7CM
7CN

TABLE A-continued
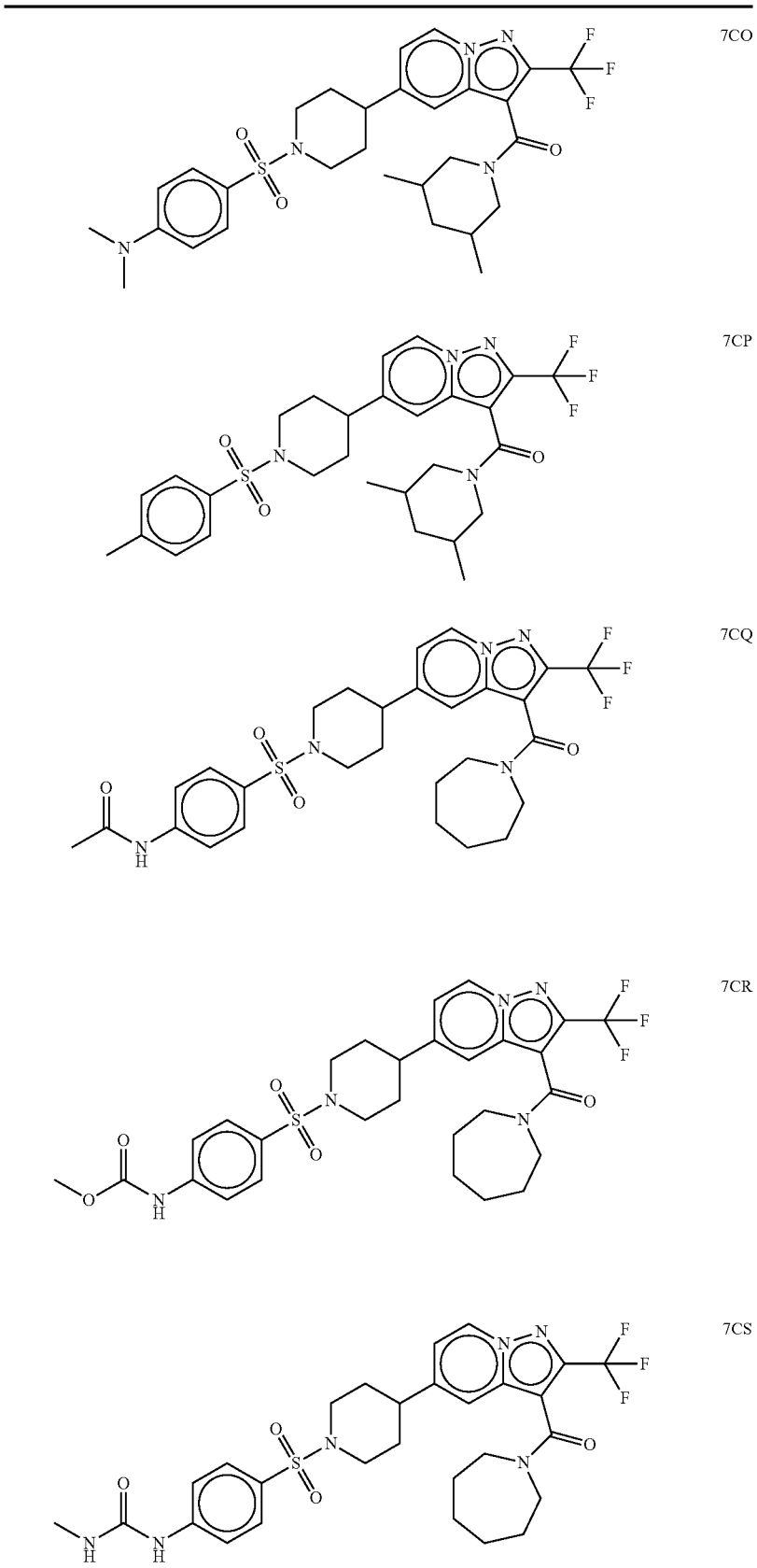
7CO
7CP
7CQ
7CR
7CS

TABLE A-continued
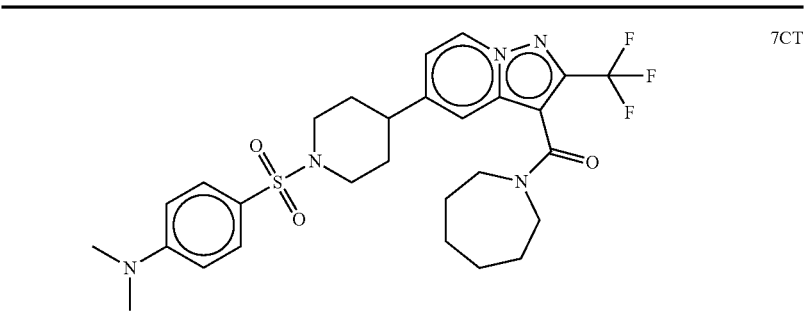
7CT
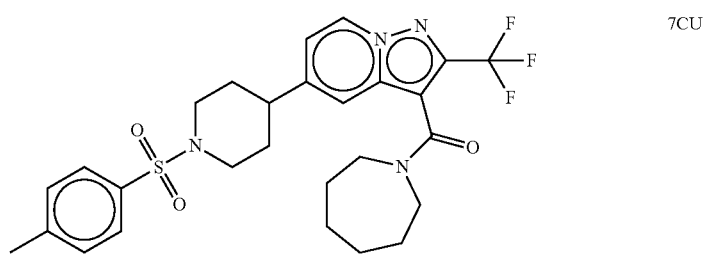
7CU
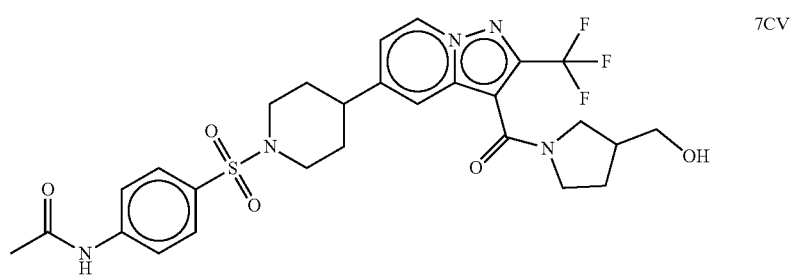
7CV
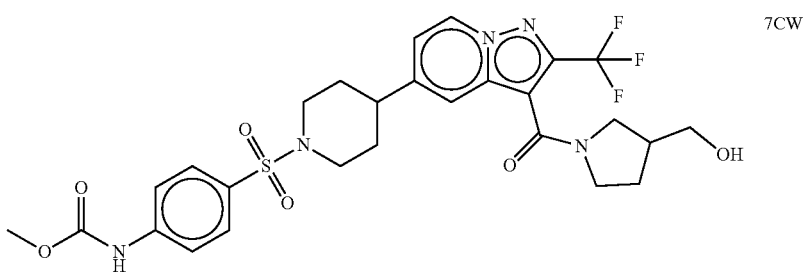
7CW
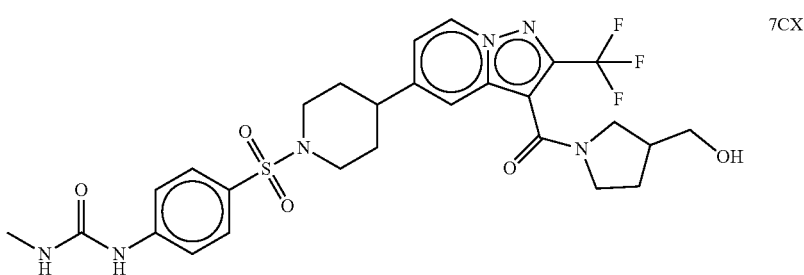
7CX TABLE A-continued
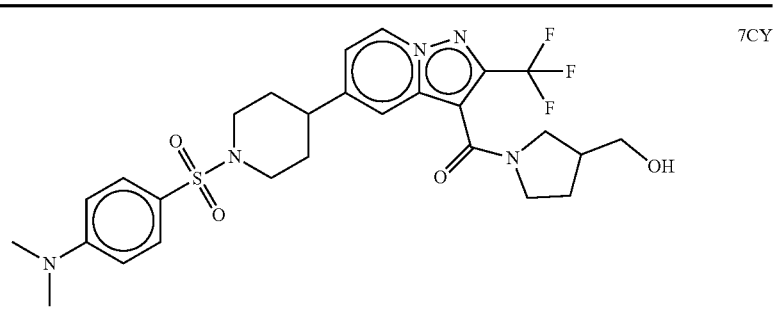 7CY
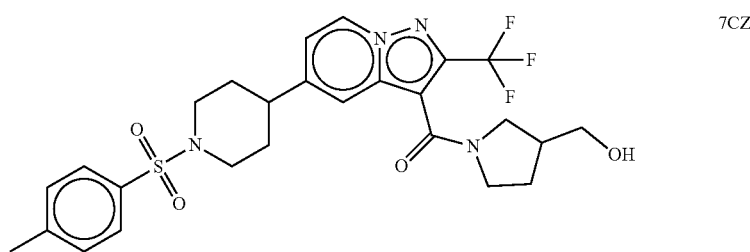 7CZ
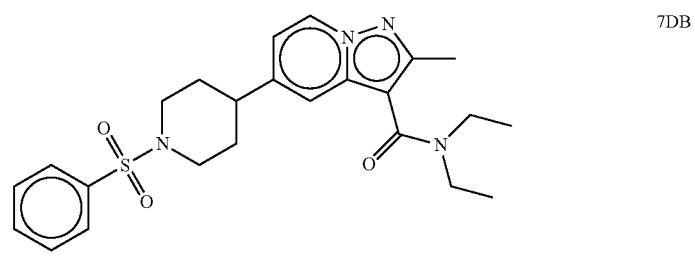 7DB
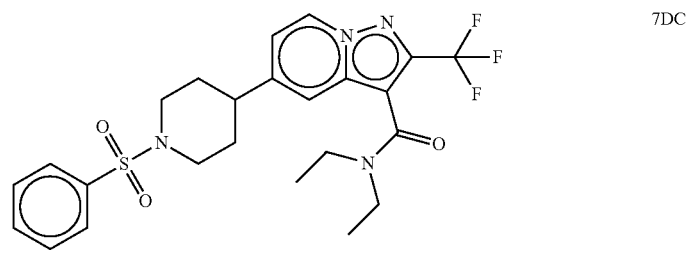 7DC
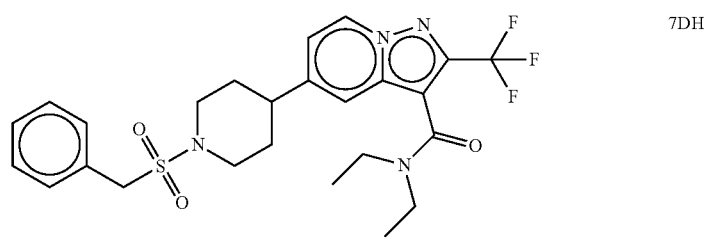 7DH
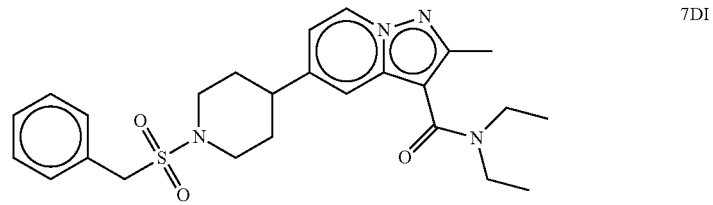 7DI TABLE A-continued
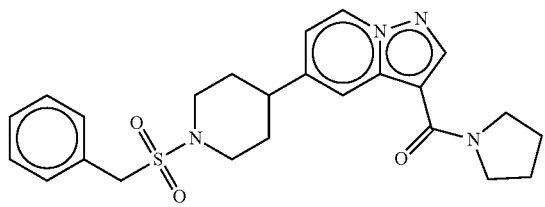 7DK
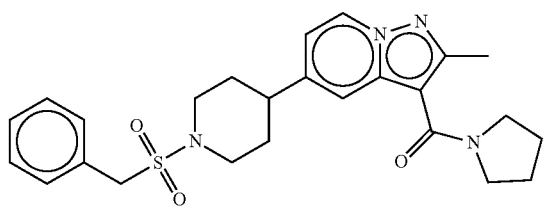 7DL
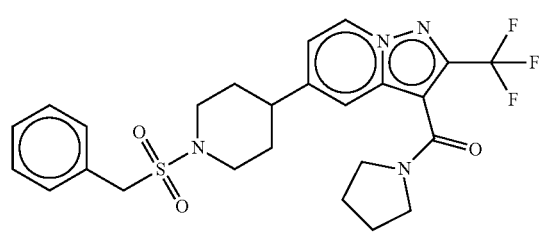 7DM
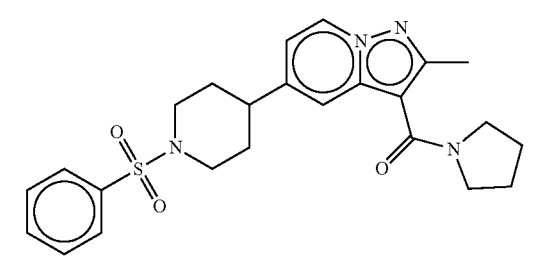 7DQ
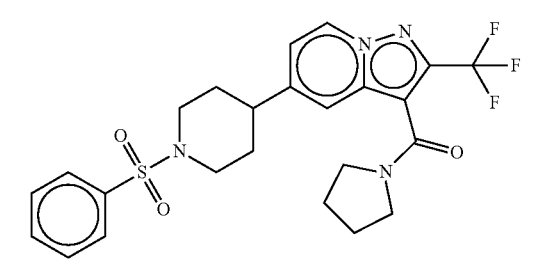 7DR
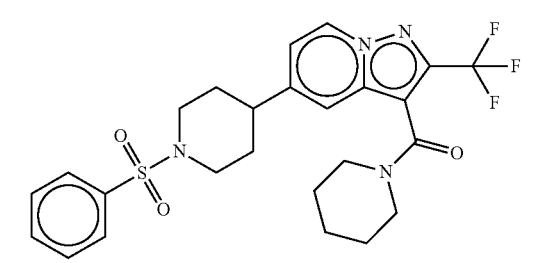 7DS TABLE A-continued

| Structure | ID |
|---|---|
| (structure) | 7DT |
| (structure) | 7DU |
| (structure) | 7DY |
| (structure) | 7DZ |
| (structure) | 7EB |
| (structure) | 7EC |
| (structure) | 7ED |

TABLE A-continued
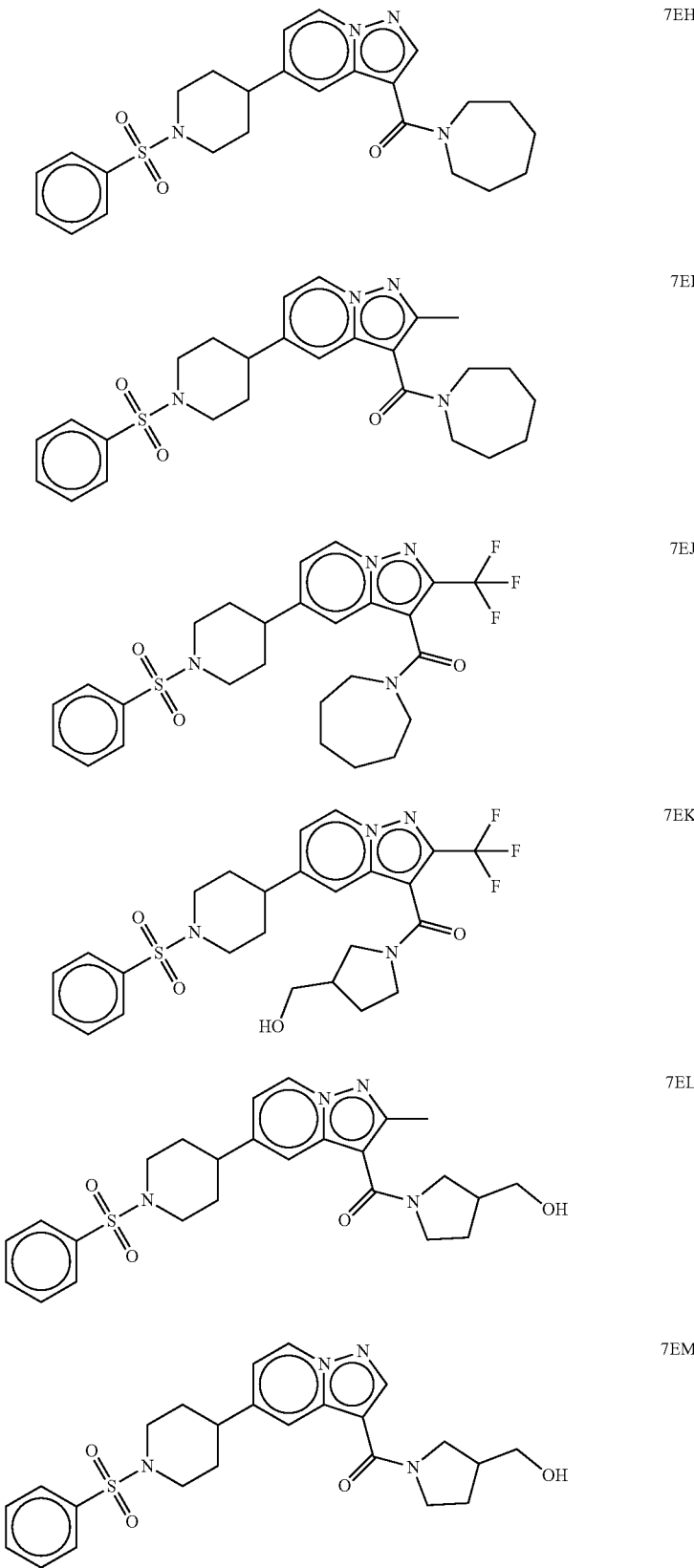
7EH
7EI
7EJ
7EK
7EL
7EM

TABLE A-continued
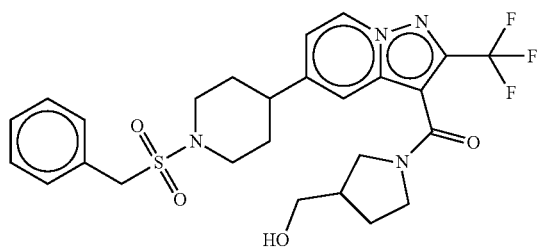 7EQ
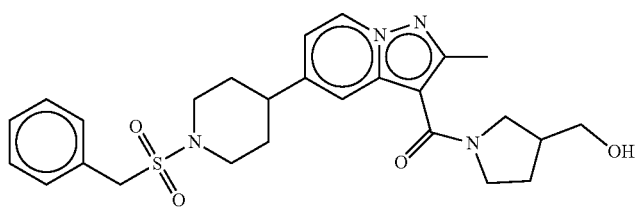 7ER
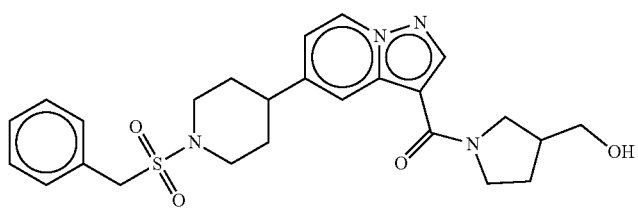 7ES
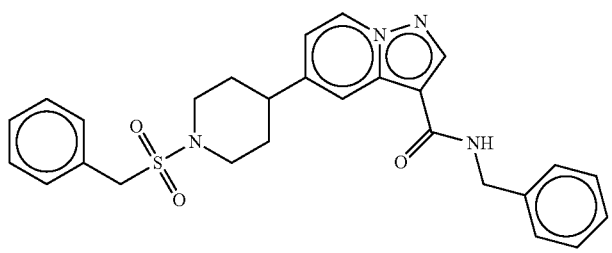 7ET
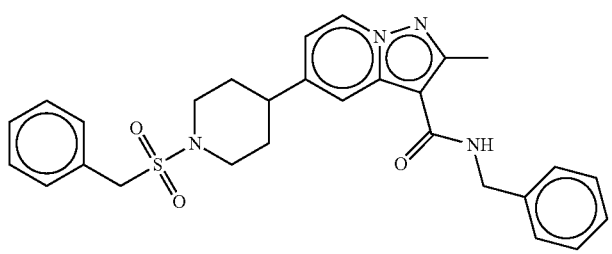 7EU
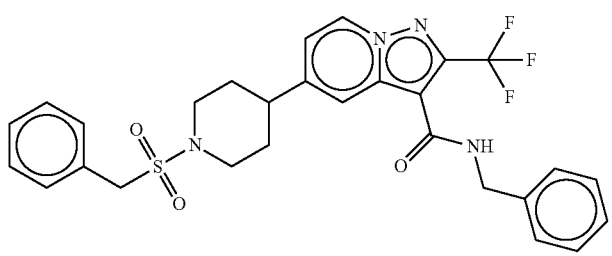 7EV TABLE A-continued
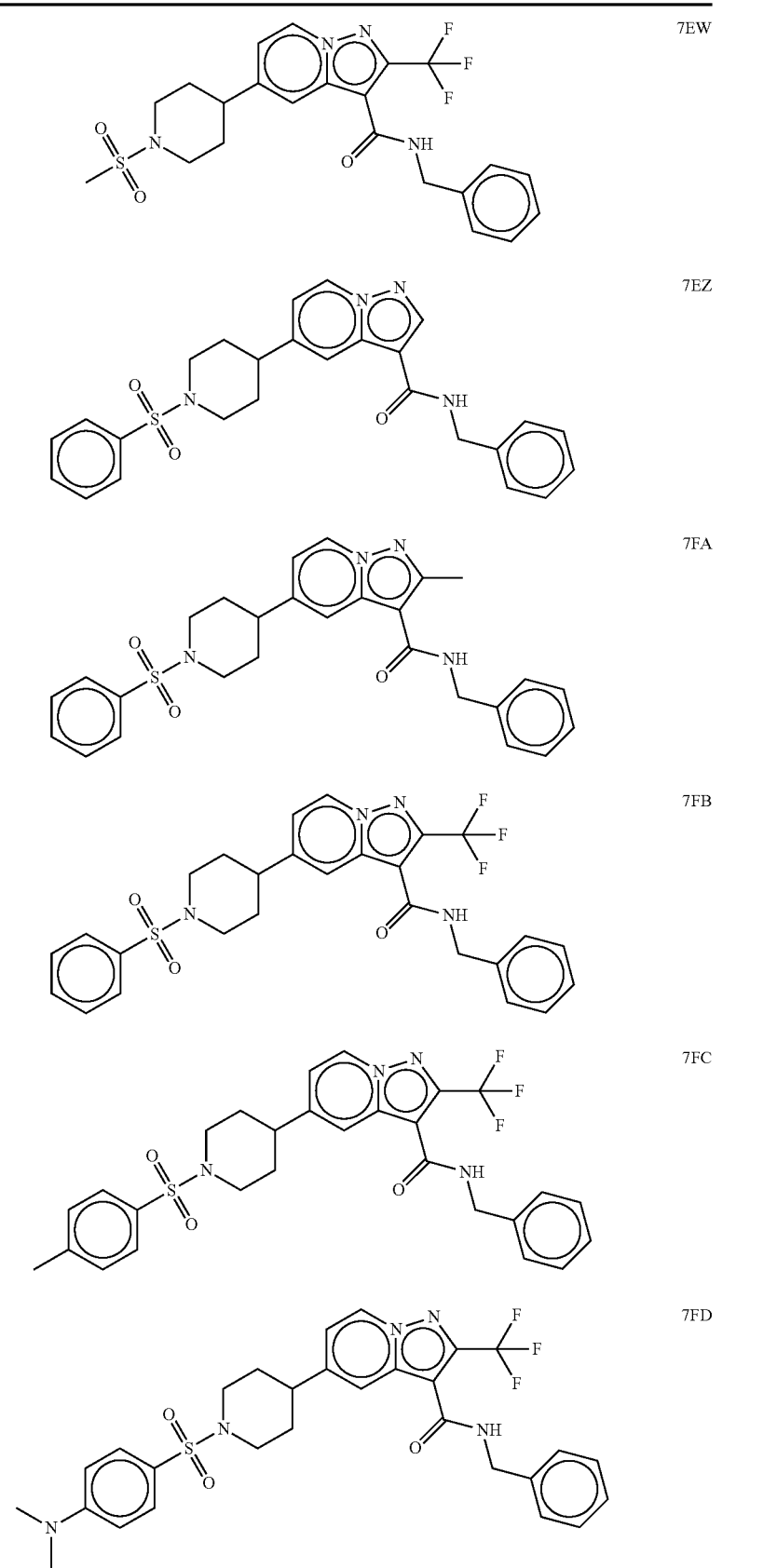

TABLE A-continued
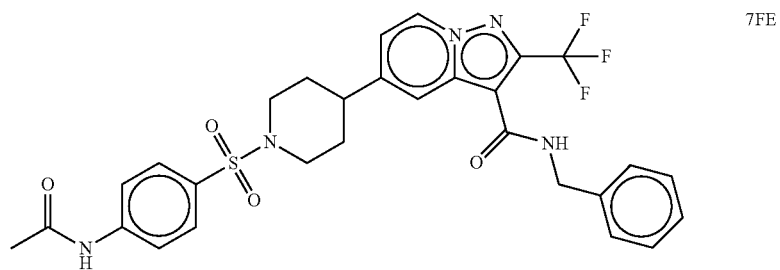 7FE
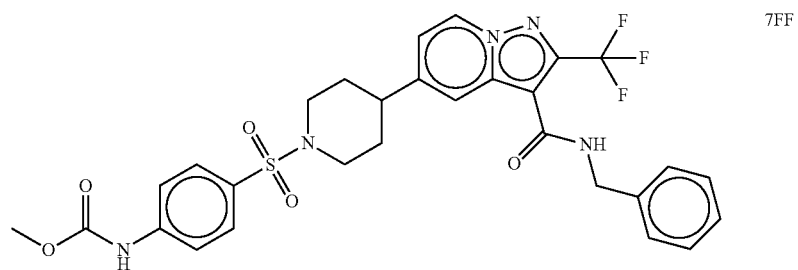 7FF
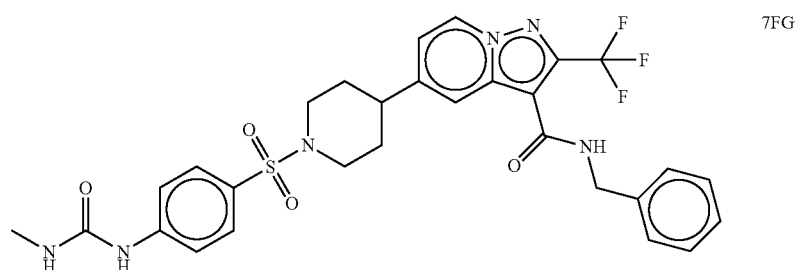 7FG
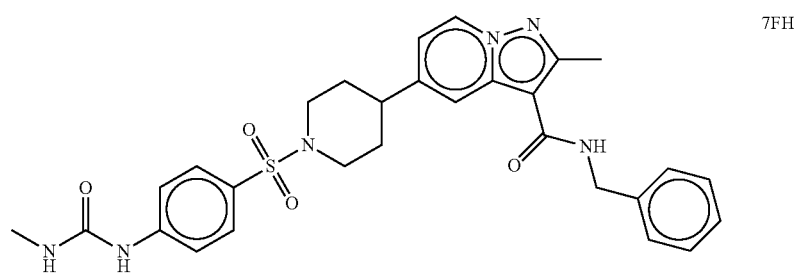 7FH
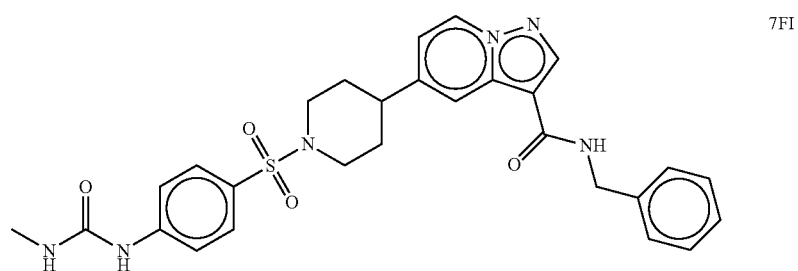 7FI
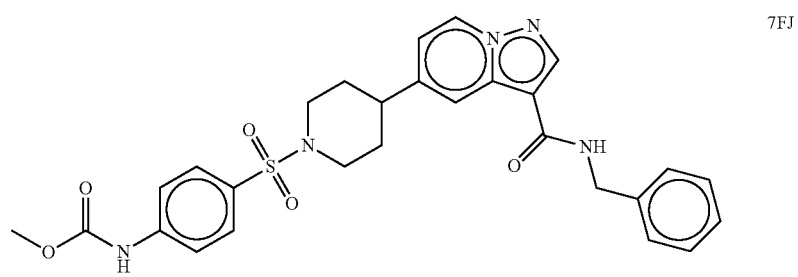 7FJ TABLE A-continued
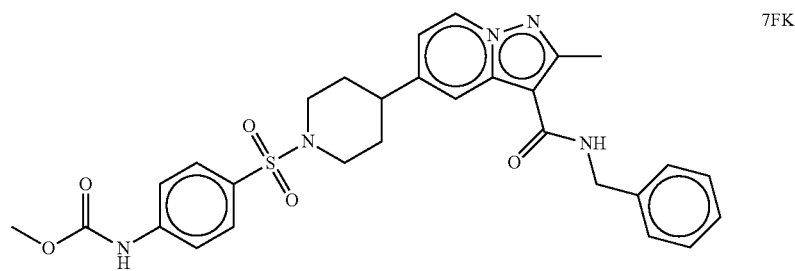
7FK
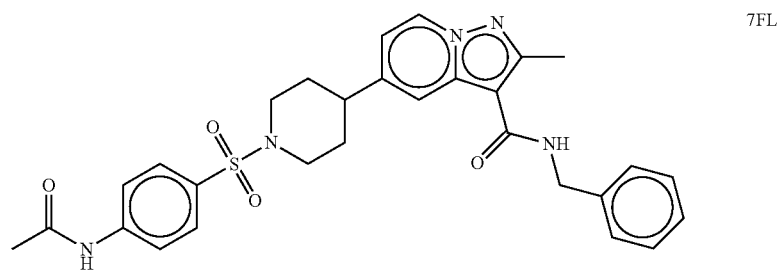
7FL
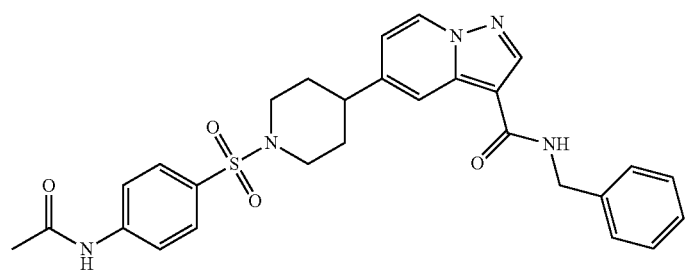 [SMILES: CC(=O)Nc1ccc(S(=O)(=O)N2CCC(c3ccn4ncc(C(=O)NCc5ccccc5)c4c3)CC2)cc1]
7FM
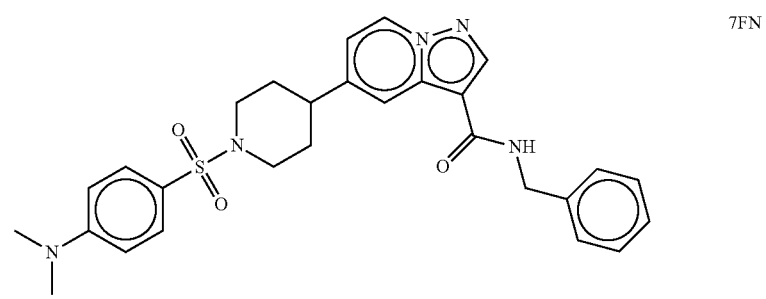
7FN
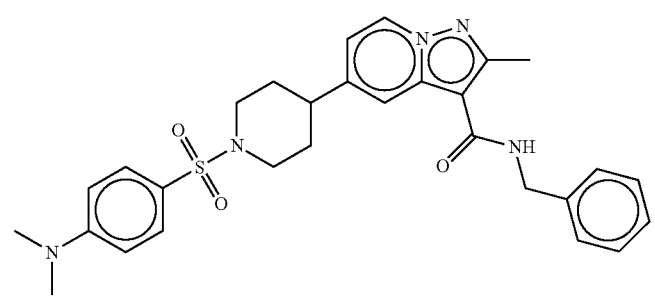
7FO TABLE A-continued
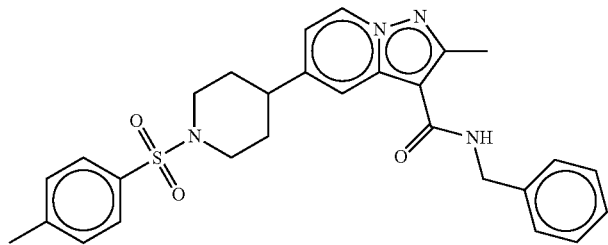
7FP
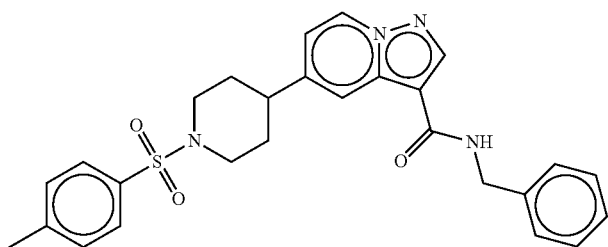
7FQ
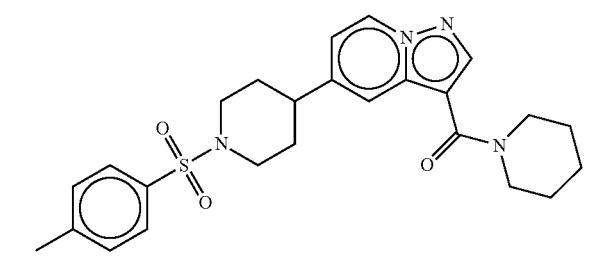
7FR
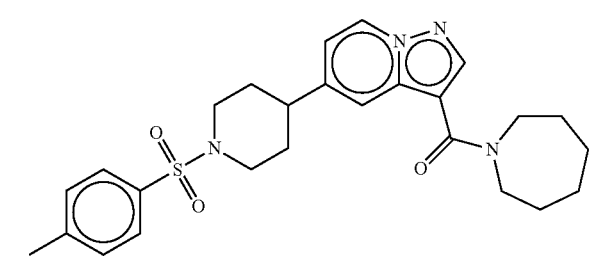
7FS
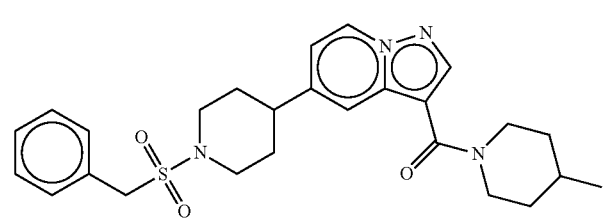
7FT
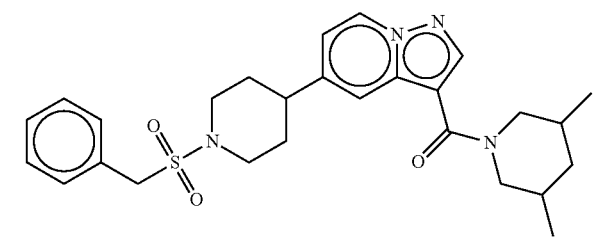
7FU TABLE A-continued
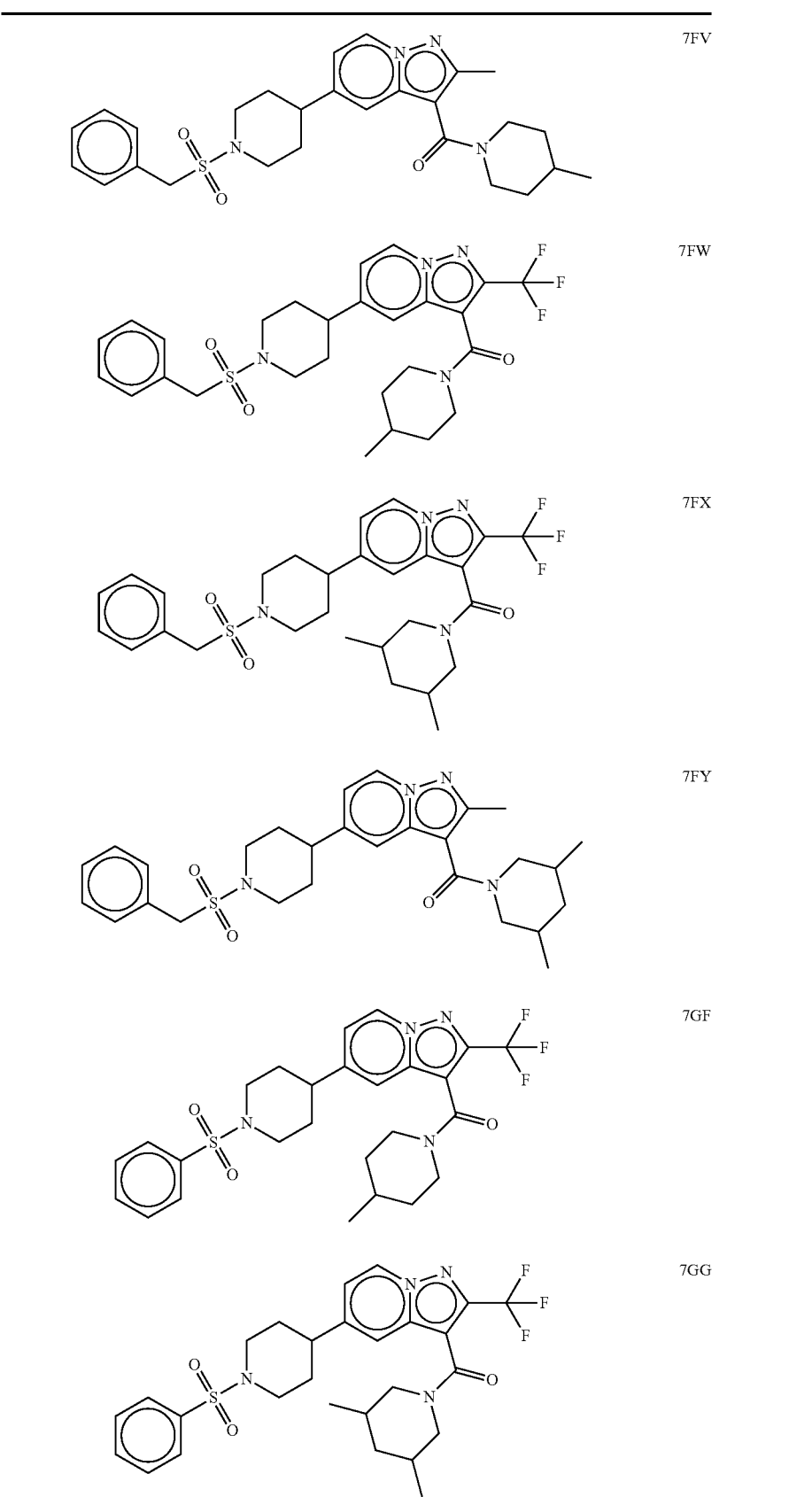

TABLE A-continued
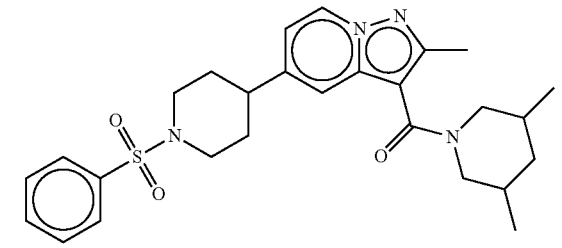
7GH
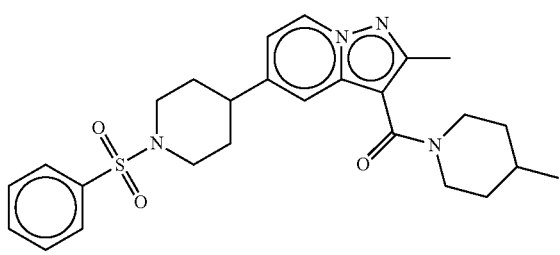
7GI
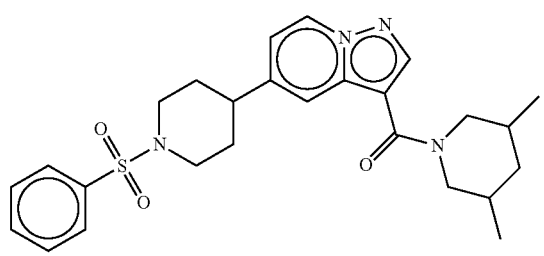
7GJ
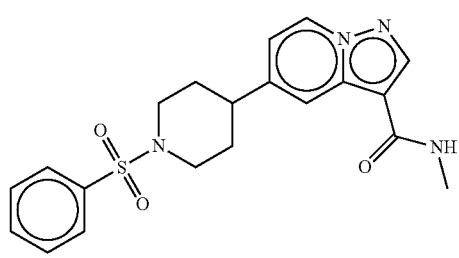
7GL
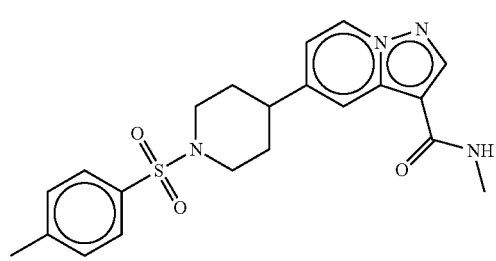
7GM
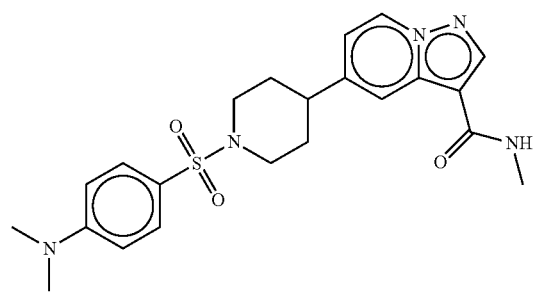
7GN TABLE A-continued
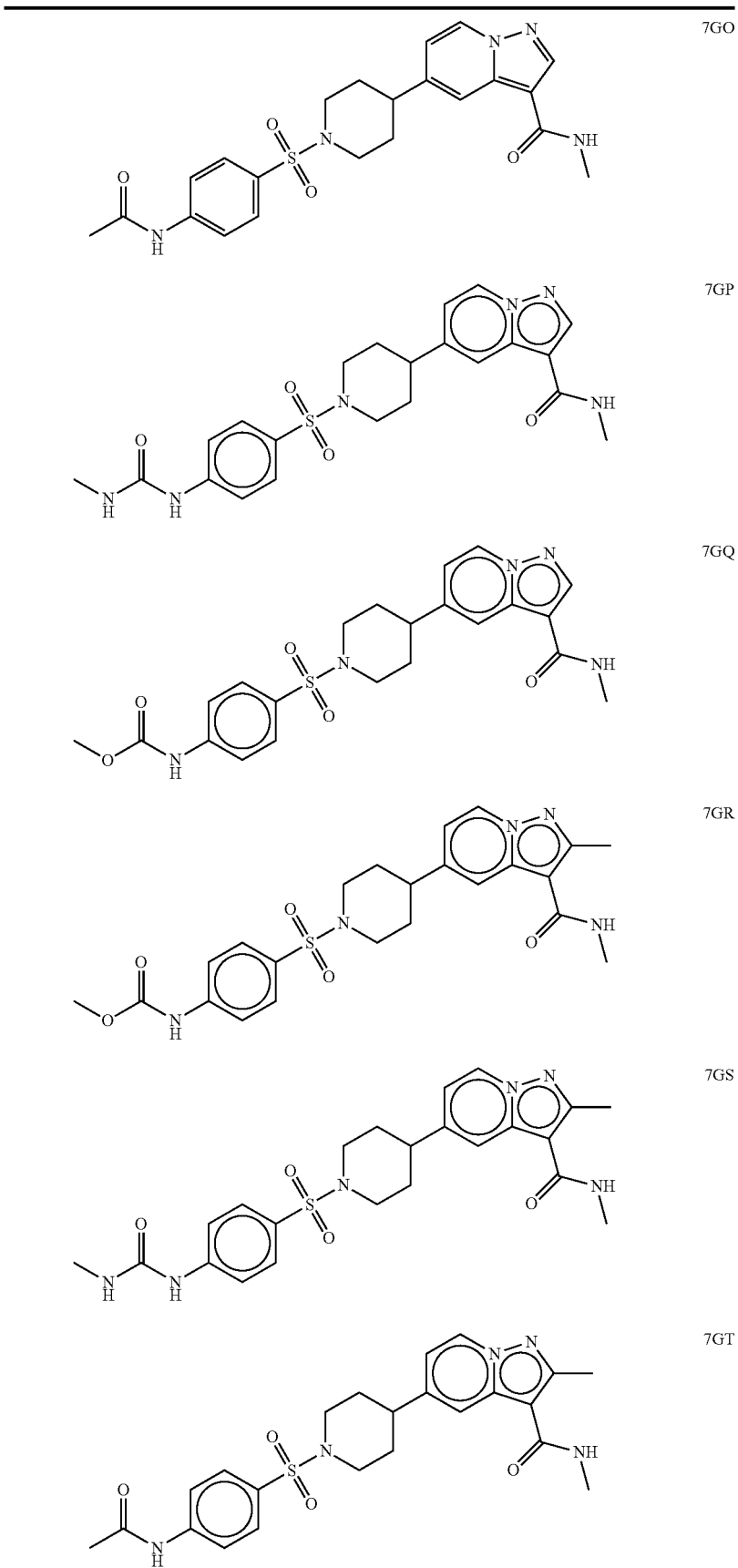
7GO
7GP
7GQ
7GR
7GS
7GT TABLE A-continued
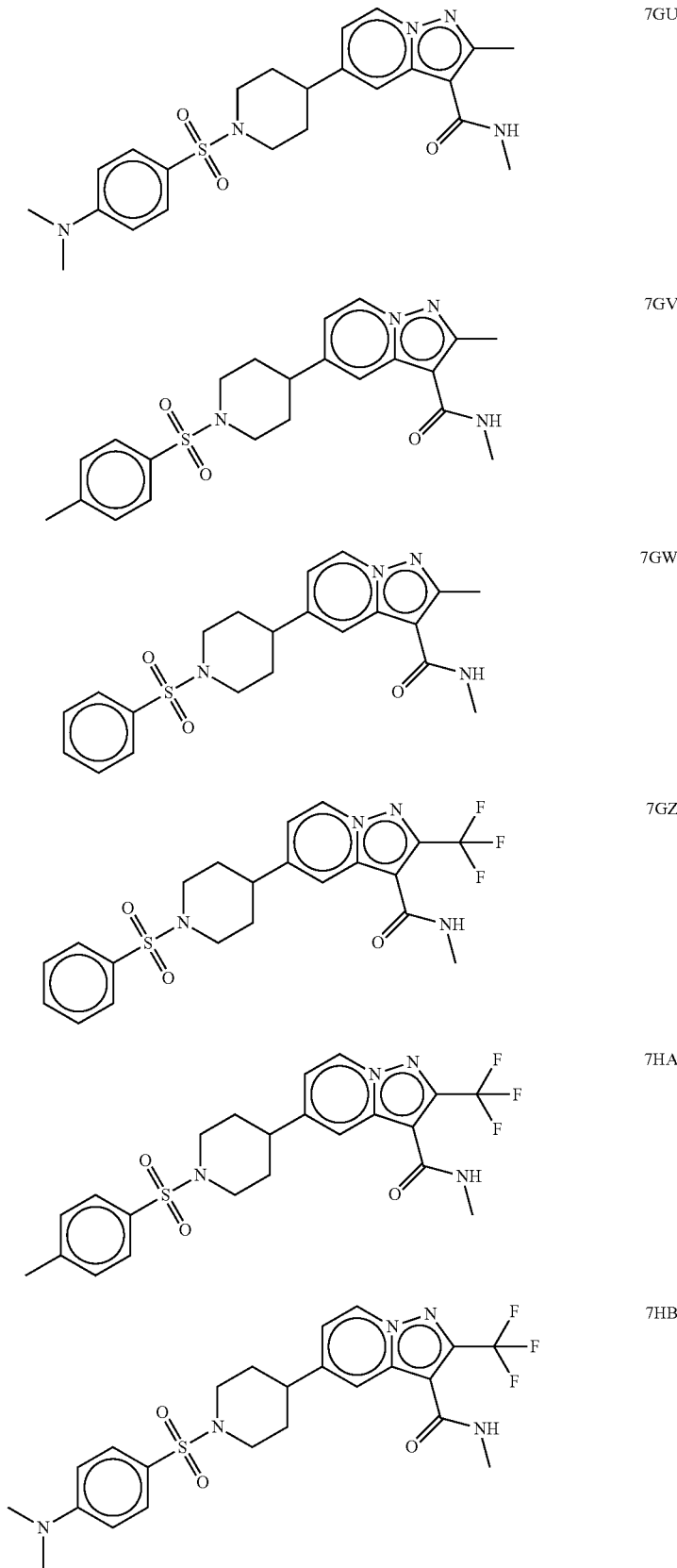
7GU
7GV
7GW
7GZ
7HA
7HB TABLE A-continued
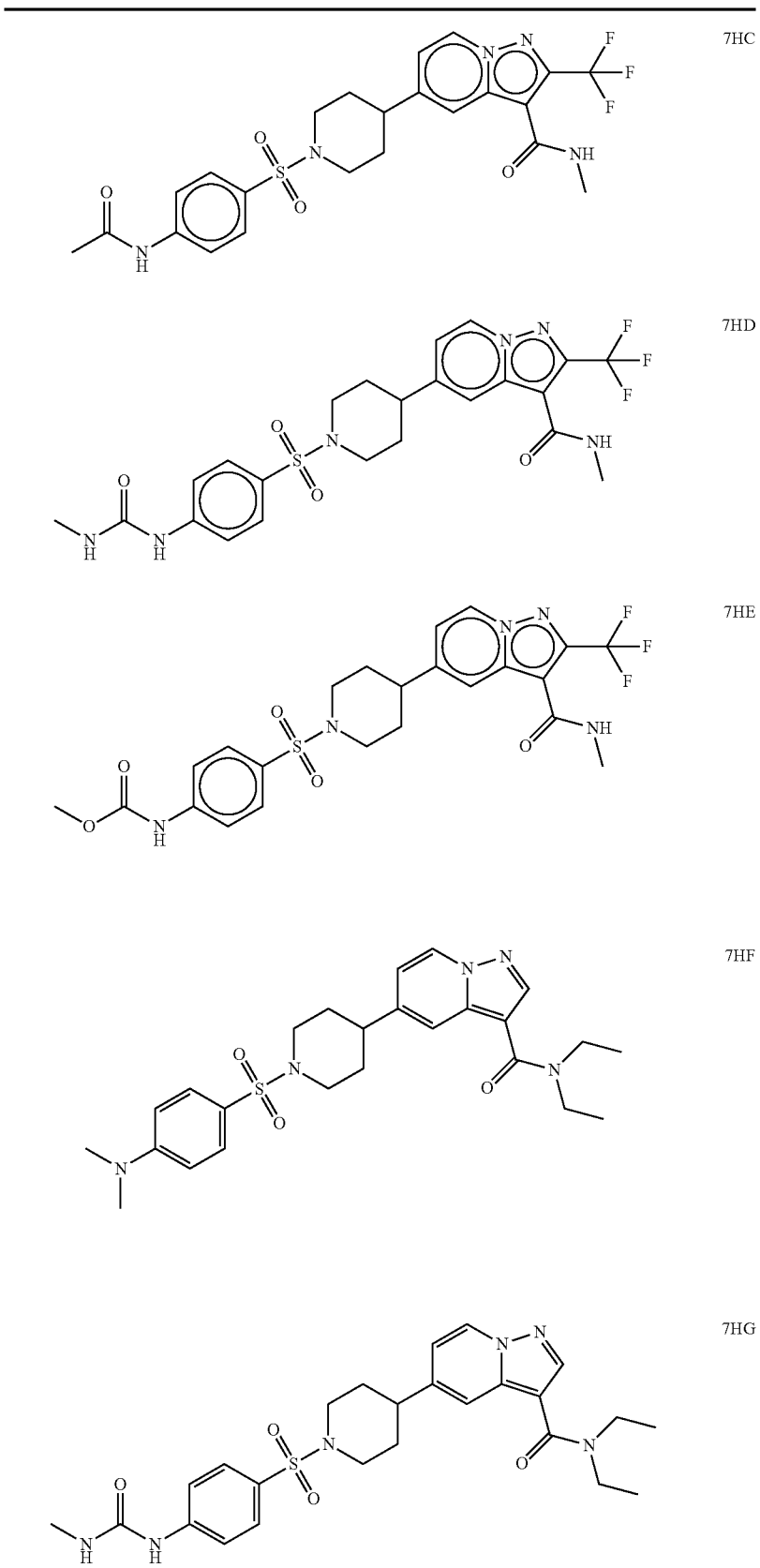

TABLE A-continued
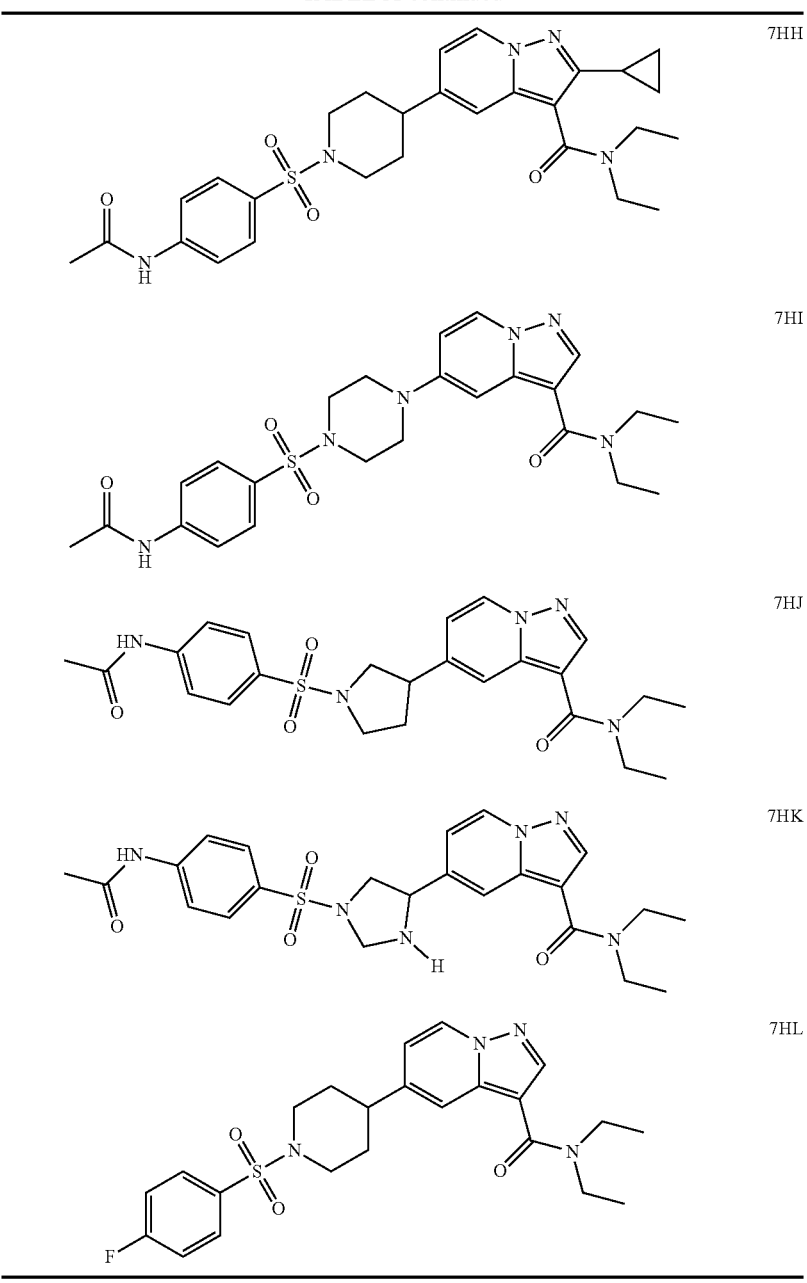
Additional contemplated compounds of the disclosure include the compounds listed in Table B and pharmaceutically acceptable salts thereof:
TABLE B
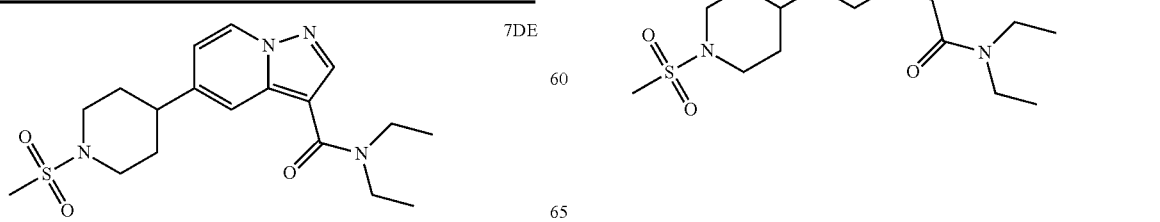

TABLE B-continued
| | |
|---|---|
| 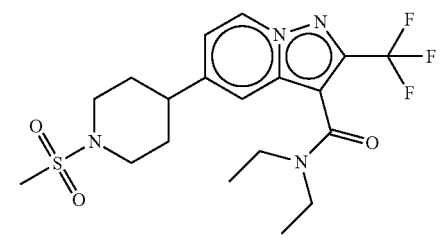 7DG | 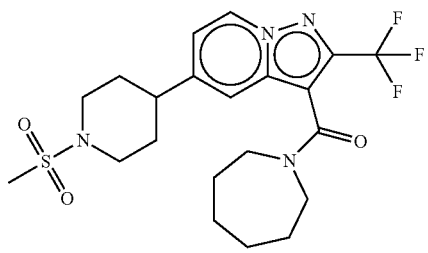 7EE |
| 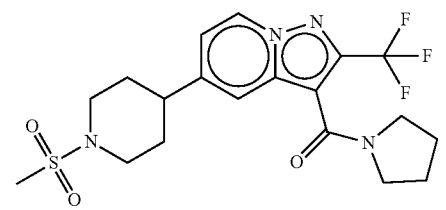 7DN | 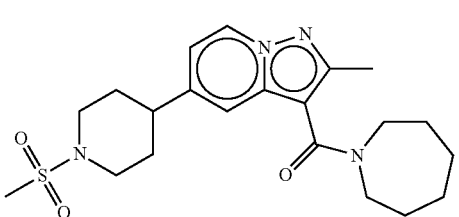 7EF |
| 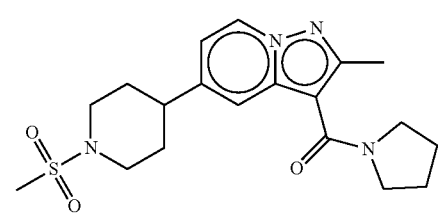 7DO | 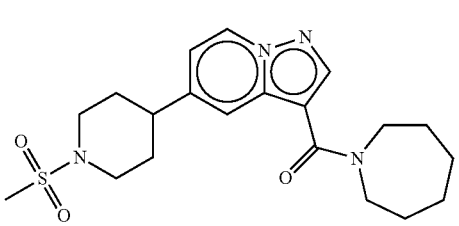 7EG |
| 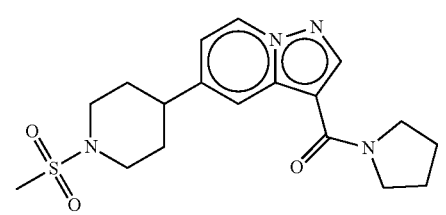 7DP | 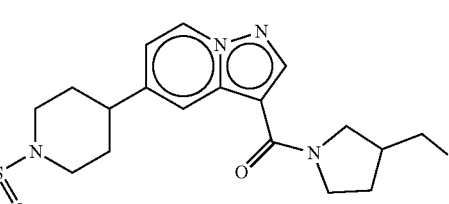 7EN |
| 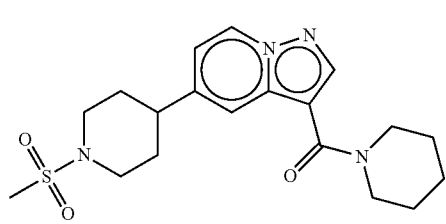 7DV | 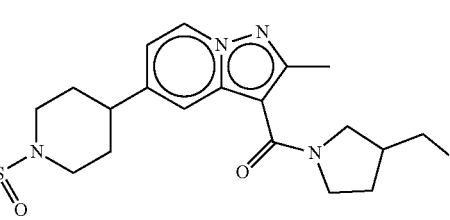 7EO |
| 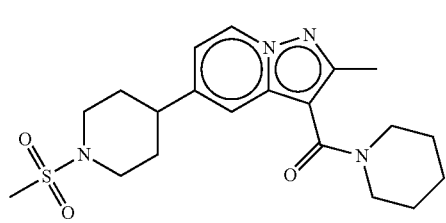 7DW | 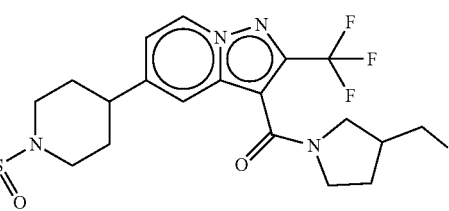 7EP |
| 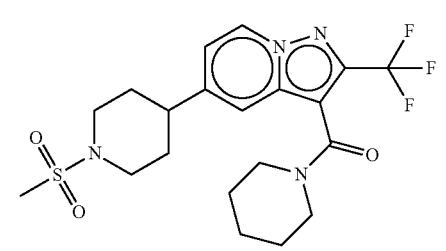 7DX | 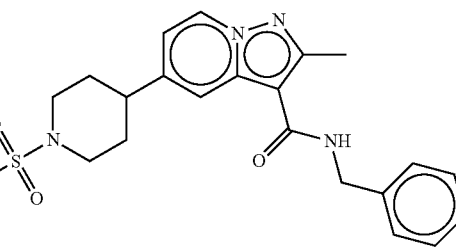 7EX |

TABLE B-continued
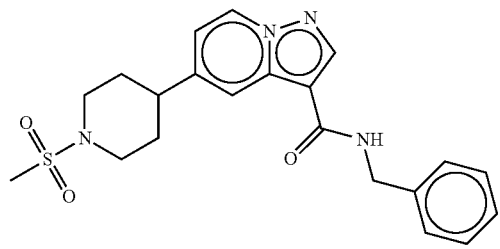
7EY
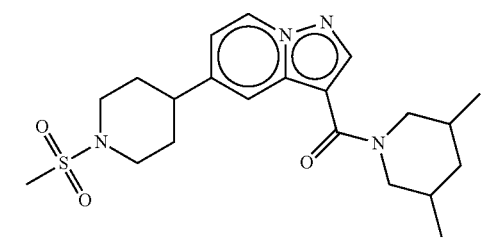
7FZ
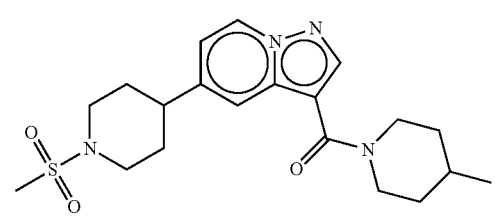
7GA
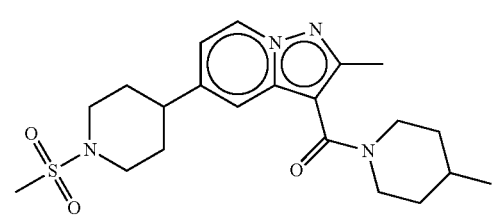
7GB
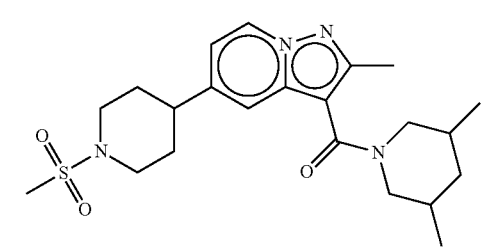
7GC
TABLE B-continued
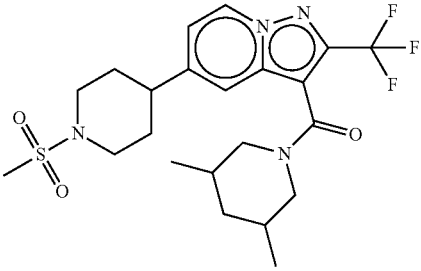
7GD
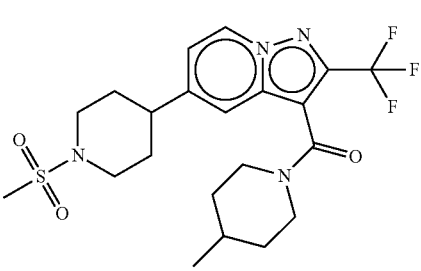
7GE
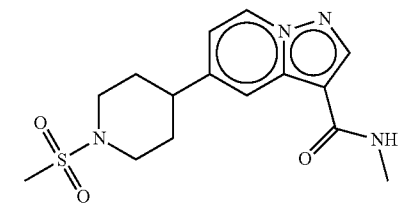
7GK
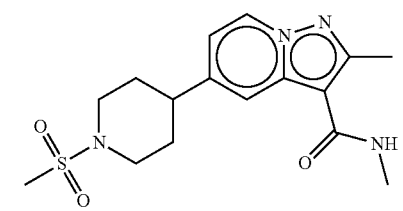
7GX
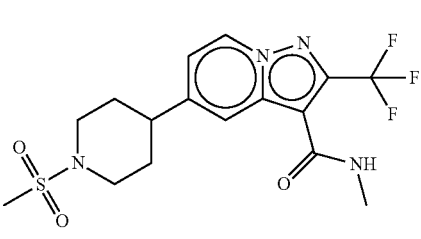
7GY
Additional contemplated compounds of the disclosure include the compounds listed in Table C and pharmaceutically acceptable salts thereof:

TABLE C
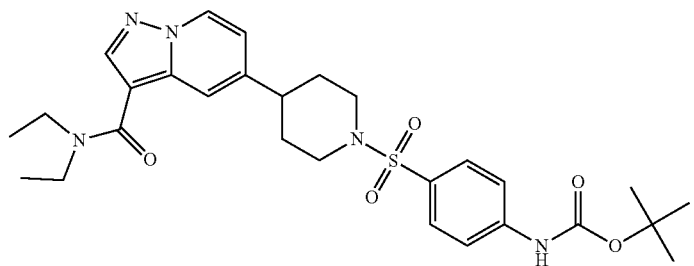 [SMILES: CCN(CC)C(=O)c1cnn2ccc(C3CCN(S(=O)(=O)c4ccc(NC(=O)OC(C)(C)C)cc4)CC3)cc12]
7HM
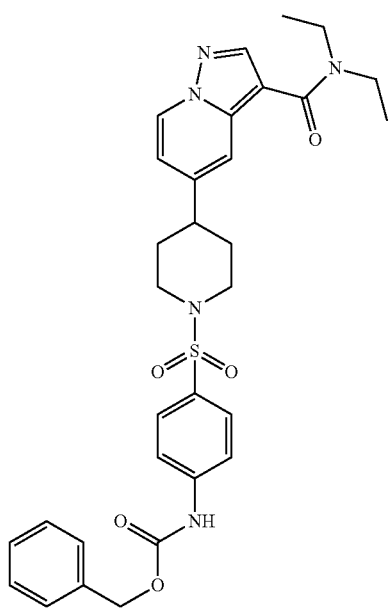 [SMILES: CCN(CC)C(=O)c1cnn2ccc(C3CCN(S(=O)(=O)c4ccc(NC(=O)OCc5ccccc5)cc4)CC3)cc12]
7HN
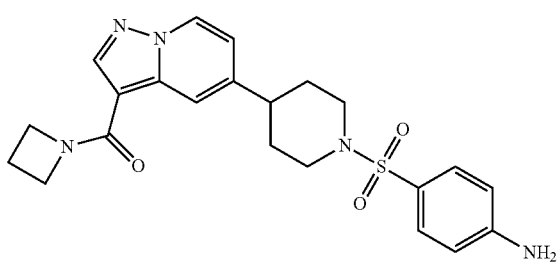 [SMILES: Nc1ccc(S(=O)(=O)N2CCC(c3ccn4ncc(C(=O)N5CCC5)c4c3)CC2)cc1]
7HO
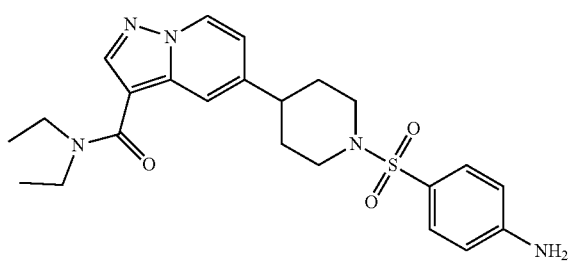 [SMILES: CCN(CC)C(=O)c1cnn2ccc(C3CCN(S(=O)(=O)c4ccc(N)cc4)CC3)cc12]
7HP

TABLE C-continued
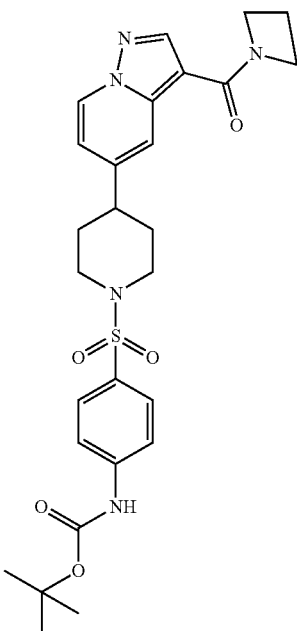 [SMILES: CC(C)(C)OC(=O)Nc1ccc(S(=O)(=O)N2CCC(c3ccn4ncc(C(=O)N5CCC5)c4c3)CC2)cc1]
7HQ
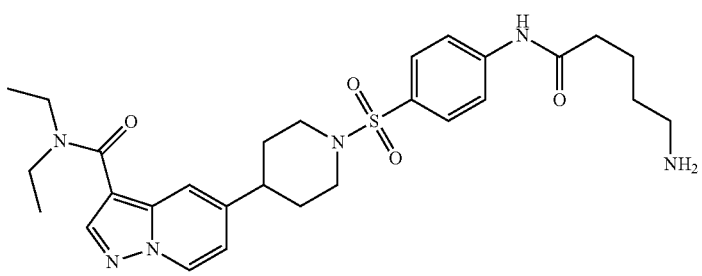 [SMILES: CCN(CC)C(=O)c1cnn2ccc(C3CCN(S(=O)(=O)c4ccc(NC(=O)CCCCN)cc4)CC3)cc12]
7HR
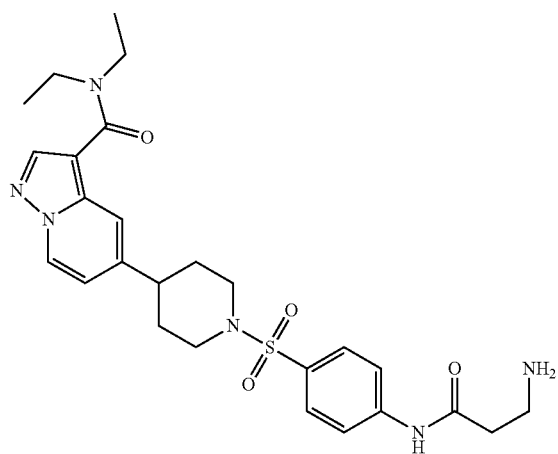 [SMILES: CCN(CC)C(=O)c1cnn2ccc(C3CCN(S(=O)(=O)c4ccc(NC(=O)CCN)cc4)CC3)cc12]
7HS
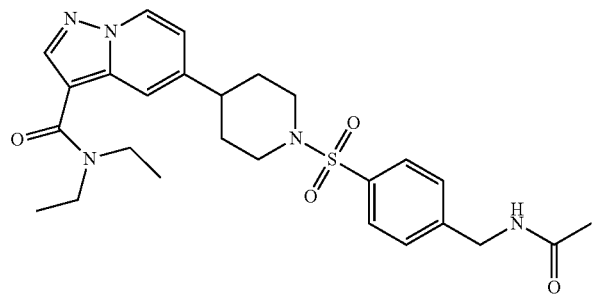 [SMILES: CCN(CC)C(=O)c1cnn2ccc(C3CCN(S(=O)(=O)c4ccc(CNC(C)=O)cc4)CC3)cc12]
7HT TABLE C-continued
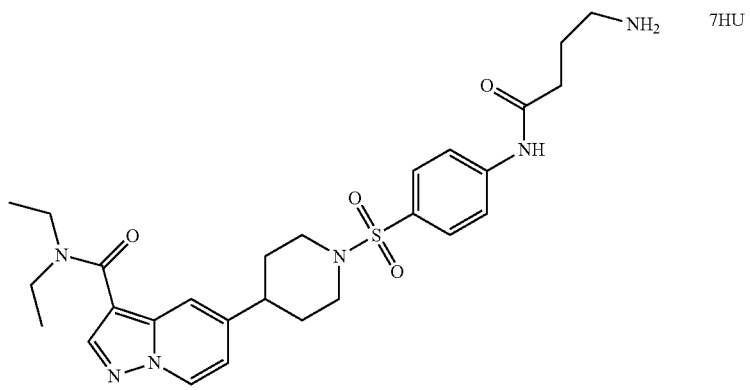
7HU
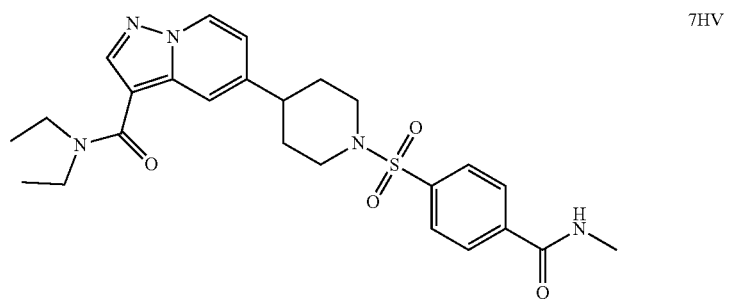
7HV
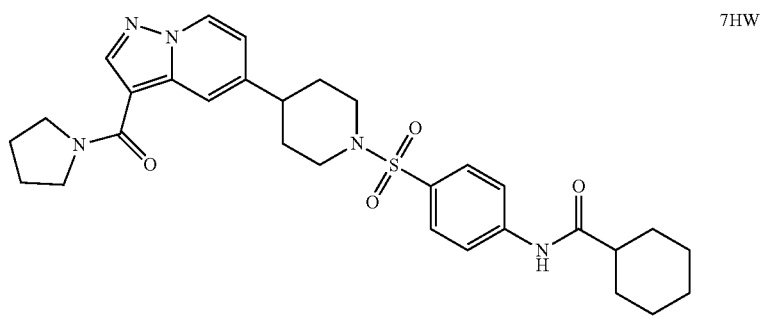
7HW
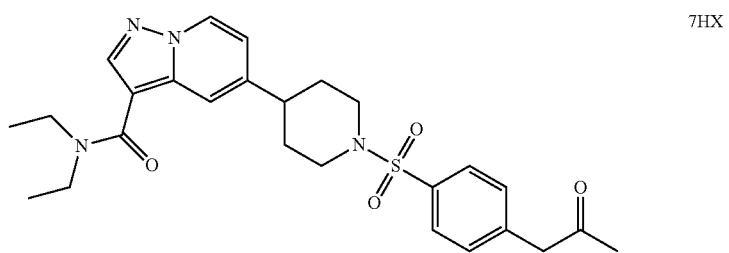
7HX TABLE C-continued
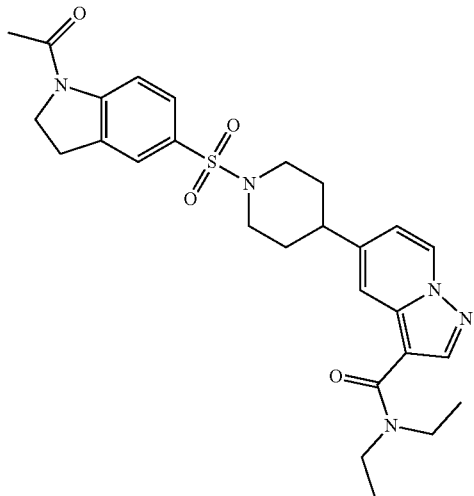 [SMILES: CCN(CC)C(=O)c1cnn2ccc(C3CCN(S(=O)(=O)c4ccc5c(c4)CCN5C(C)=O)CC3)cc12]
7HY
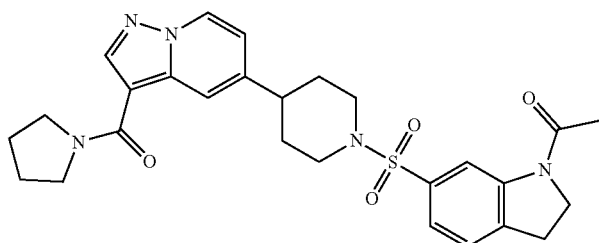
7HZ
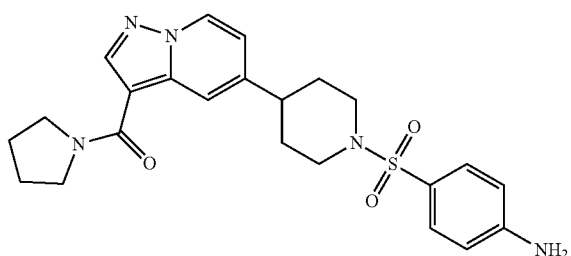
7IA
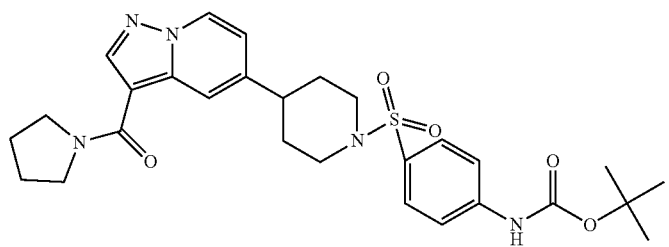 [SMILES: CC(C)(C)OC(=O)Nc1ccc(S(=O)(=O)N2CCC(c3ccn4ncc(C(=O)N5CCCC5)c4c3)CC2)cc1]
7IB
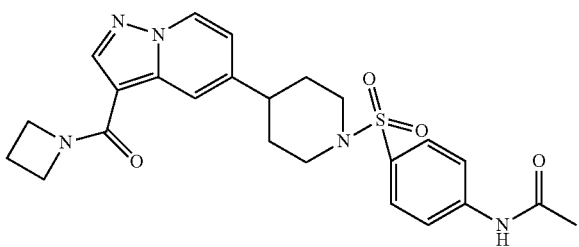 [SMILES: CC(=O)Nc1ccc(S(=O)(=O)N2CCC(c3ccn4ncc(C(=O)N5CCC5)c4c3)CC2)cc1]
7IC TABLE C-continued
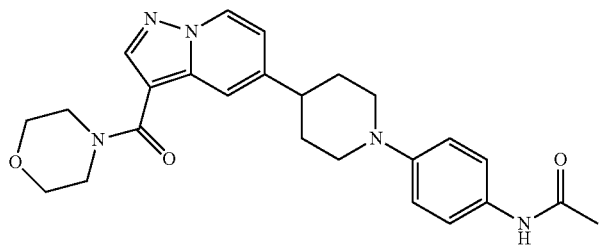 [SMILES: CC(=O)Nc1ccc(N2CCC(c3ccn4ncc(C(=O)N5CCOCC5)c4c3)CC2)cc1]
7ID
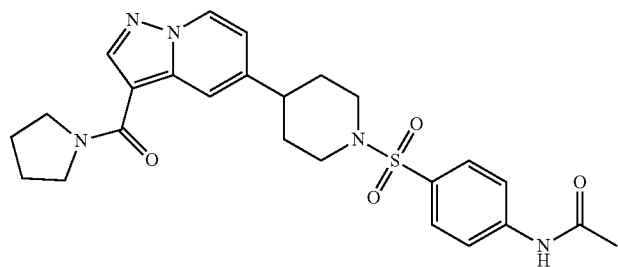 [SMILES: CC(=O)Nc1ccc(S(=O)(=O)N2CCC(c3ccn4ncc(C(=O)N5CCCC5)c4c3)CC2)cc1]
7IE
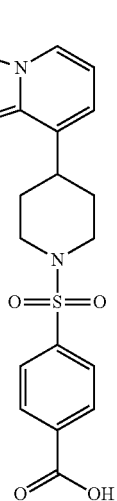
7IF
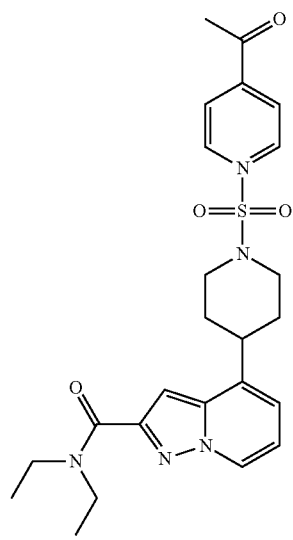
7IG TABLE C-continued

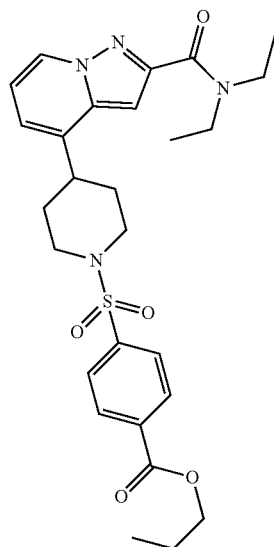 [SMILES: CCCOC(=O)c1ccc(S(=O)(=O)N2CCC(c3cccn4nc(C(=O)N(CC)CC)cc34)CC2)cc1]

7IH

In some embodiments, the compounds disclosed herein include an aryl sulfonyl group, which participates in hydrogen bonding interactions with Tyr1019 on NACK, as well as additional hydrogen bond donor and acceptor atoms that participate in favorable water interactions. The compounds disclosed herein also include an alkyl amide, the nitrogen of which forms a hydrogen bond with Lys1022, and the alkyl groups of which participate in hydrophobic interactions deep within the binding pocket of NACK. It was found that an increase in carbon atoms on the alkyl chains of the alkyl amide improve interaction of the compound with the binding pocket, and particularly so for cyclic moieties (e.g., when $R^3$ and $R^4$ together with the nitrogen to which they are attached form a ring). Without being bound to any particular theory, straight chain alkyl moieties can increase steric hindrance and entropy. The compounds disclosed herein also include an azaindole moiety, which participates in hinge interactions with His1095.

Synthesis of the NACK Inhibitors

The compounds of the disclosure can be synthesized by any method known to one skilled in the art. Scheme 1, below, depicts one method for synthesizing the compounds of the disclosure. For example, 4-(piperidine-4-yl)pyridine (1) can be protected (e.g., with BOC) to result in 2, which can reacted with, for example, mesitylenesulfonylhydroxylamine ("MSH") to form an aminopyridinium salt. The aminopyridinium salt can undergo a 3+2 cycloaddition with a desired propiolate to form a desired methyl-pyrazolo[1,5-a]pyridine-carboxylate (3). The methyl carboxylate 3 can undergo hydrolysis (e.g., with LiOH) to result in carboxylic acid (4), which can be reacted with a desired amine using standard coupling chemistry to form a desired amide (5). The amide can then be deprotected (6) and reacted with a desired sulfonyl chloride to result in an inhibitor of the disclosure (7).

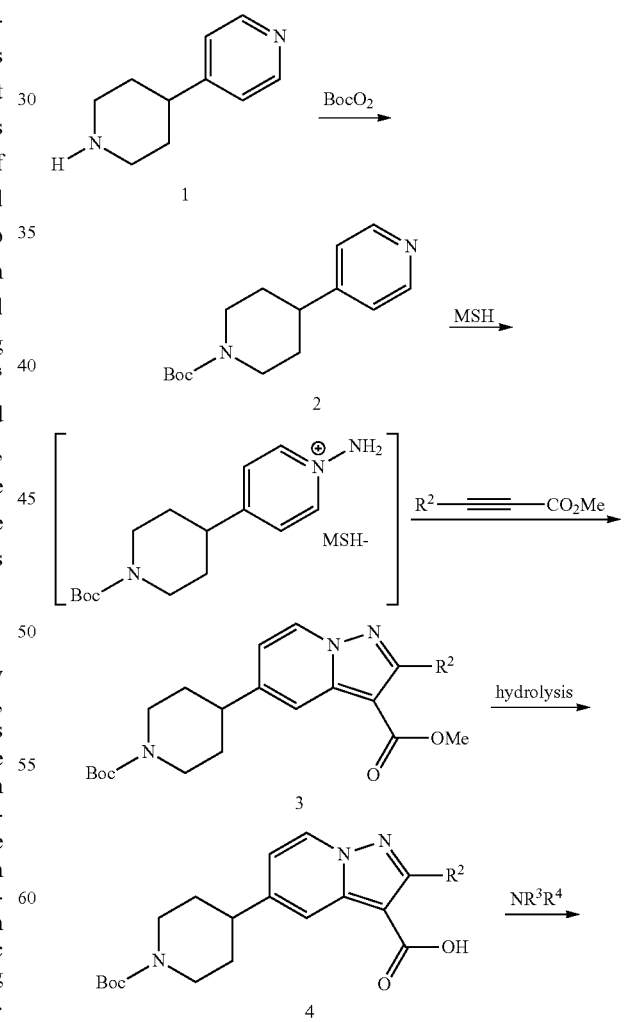

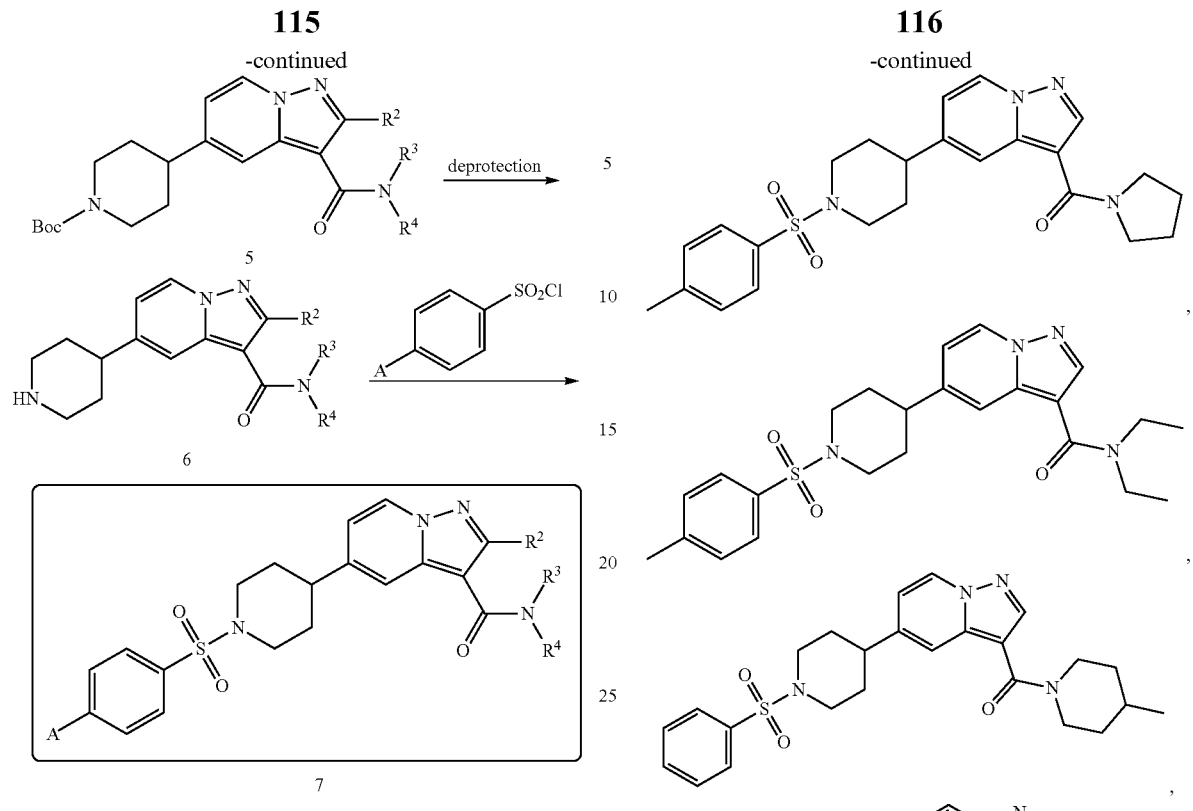

Additional synthetic procedures for preparing the compounds disclosed herein can be found in the Examples section.

Methods of Using the NACK Inhibitors

The compounds of the disclosure can inhibit Notch activation complex kinase ("NACK") by disrupting recruitment of NACK to the Notch transcription complex ("NTC") in a cell, which is useful in preventing or treating diseases associated with deregulation of the Notch transcriptional activation complex.

The Notch pathway is restricted to small populations of progenitor and stem cells of regenerating tissues, such as the colon and brain. However, in many human cancers, the Notch pathway becomes reactivated, and this deregulation of the Notch pathway underlies many aspects of cancer physiology, depending on cell type and context.

Therefore, one aspect of the disclosure relates to a method of inhibiting the Notch activation kinase complex ("NACK") in a cell, comprising contacting the cell with one or more compounds as disclosed herein (e.g., a compound of Formula (I), a compound of Formula (Ia), a compound listed in Table A, Table B, Table C,

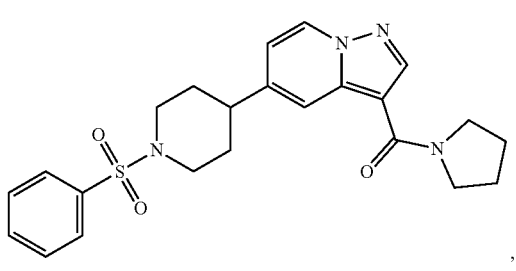

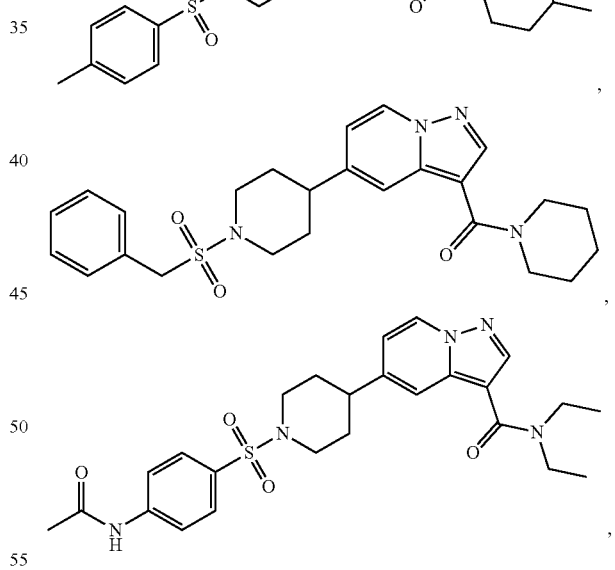

and pharmaceutically acceptable salts of any of the foregoing) in an amount effective to inhibit NACK.

In particular, provided herein is a method of inhibiting NACK recruitment to the Notch transcriptional complex ("NTC") in a cell by contacting the cell with one or more compounds disclosed herein in an amount effective to inhibit NACK recruitment to the NTC.

The compounds disclosed herein can inhibit NACK in a cell by contacting the cell in vitro or in vivo. In some embodiments, the contacting occurs in vitro. In other embodiments, the contacting occurs in vivo. The compounds can contact NACK in vivo by administering the compound to a subject or patient in need of regulation of NACK. Put another way, in various embodiments, the invention includes administering one or more compounds of the disclosure to a subject or patient, such as a human, in need thereof. In some of these embodiments, the patient suffers from a disease associated with deregulation of the Notch transcriptional activation complex (e.g., Tetralogy of Fallot ("TOF"), Alagille syndrome, multiple sclerosis, or cancer).

Another aspect of the disclosure relates to a method of treating a disease associated with deregulation of the Notch transcriptional activation complex in a patient, comprising administering to the patient a therapeutically effective amount of one or more compounds disclosed herein.

In some embodiments, the disease associated with deregulation of the Notch transcriptional activation complex is Tetralogy of Fallot ("TOF"), or Alagille syndrome. In some cases, the disease associated with deregulation of the Notch transcriptional activation complex is cancer. In various embodiments, the cancer is selected from the group consisting of T-cell acute lymphoblastic leukemia ("T-ALL"), B-cell acute lymphoblastic leukemia ("B-ALL"), breast cancer, medulloblastoma, colorectal cancer, non-small cell lung carcinoma ("NSCLC"), melanoma, cerebral autosomal-dominant ateriopathy with sub-cortical infarcts and leukoencephalophathy ("CADASIL"), chronic lymphocytic leukemia ("CLL"), hepatocellular carcinoma ("HCC"), myelomonocytic leukemia ("CMML"), pancreatic ductal adenocarcinoma ("PDAC"), head and neck squamous cell carcinoma ("HNSCC"), renal cell adenocarcinoma, fibrosarcoma, and combinations thereof. In some embodiments, the disease associated with deregulation of the Notch transcriptional activation complex is multiple sclerosis ("MS").

Use of a compound, or pharmaceutically acceptable salt thereof, as disclosed herein (e.g., a compound of Formula (I), a compound of Formula (Ia), a compound listed in Table A, Table B, Table C,

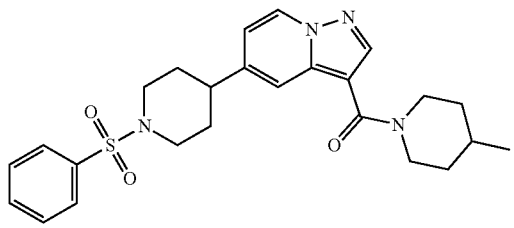

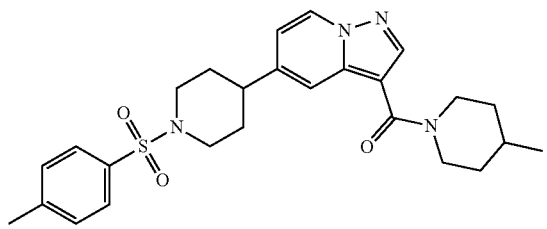

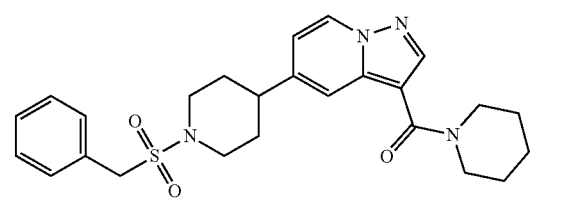

, and

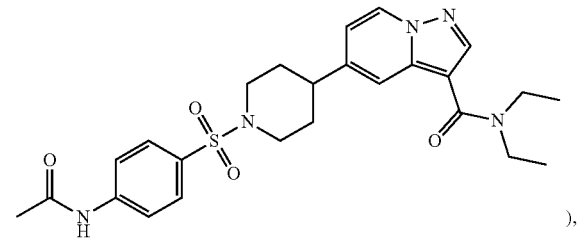

),

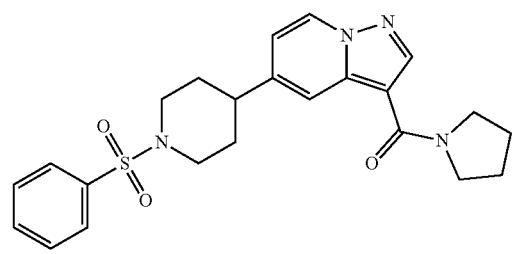

,

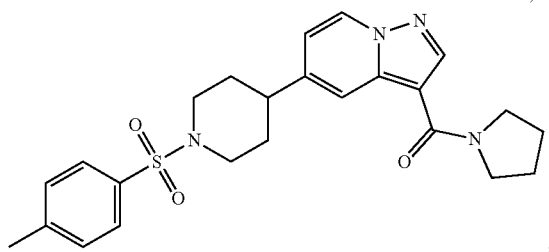

,

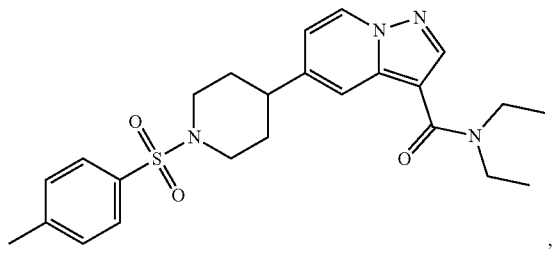

to treat a condition resulting from deregulation of the Notch transcriptional activation complex in a patient, as well as use of the compound in the preparation of a medicament for treating the condition, also are contemplated.

Another aspect of the disclosure provides a method of inhibiting kinase activity, ATPase activity, or both in a cell, comprising contacting the cell with one or more compounds as disclosed herein (e.g., a compound of Formula (I), a compound of Formula (Ia), a compound listed in Table A, Table B, Table C,

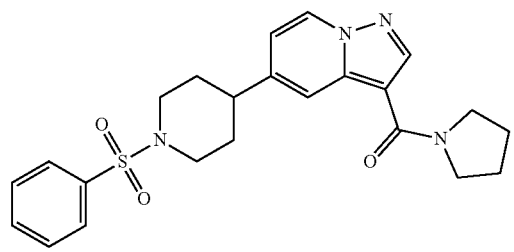

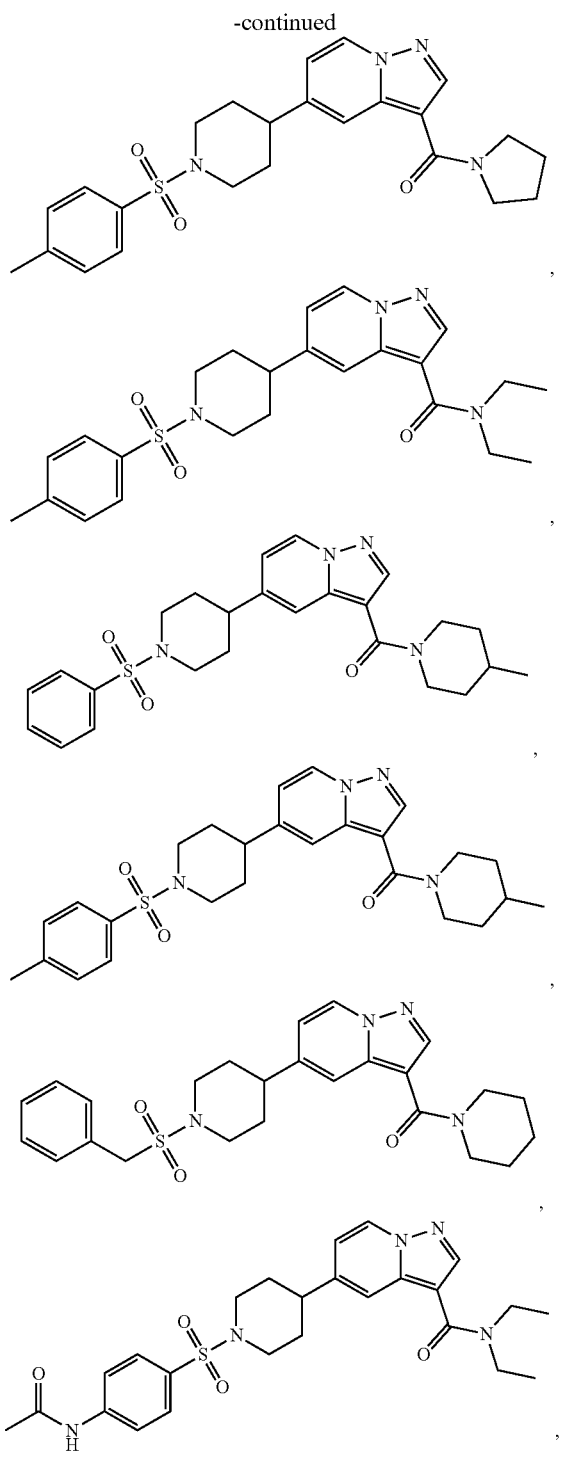

and pharmaceutically acceptable salts of any of the foregoing), in an amount effective to inhibit kinase and/or ATPase activity.

Elevated NACK Expression in Esophageal Adenocarcinoma ("EAC")

NACK plays an important role in activating Notch transcription and regulating the Notch-mediated tumorigenesis and development. See Weaver et al., Cancer Research 74, 4741-4751 (2014). Further, Notch drives stemness and tumorgenicity of esophageal adenocarcinoma ("EAC"). See Wang et al., Cancer Research 74, 6364-6374 (2014).

Figure 1B:
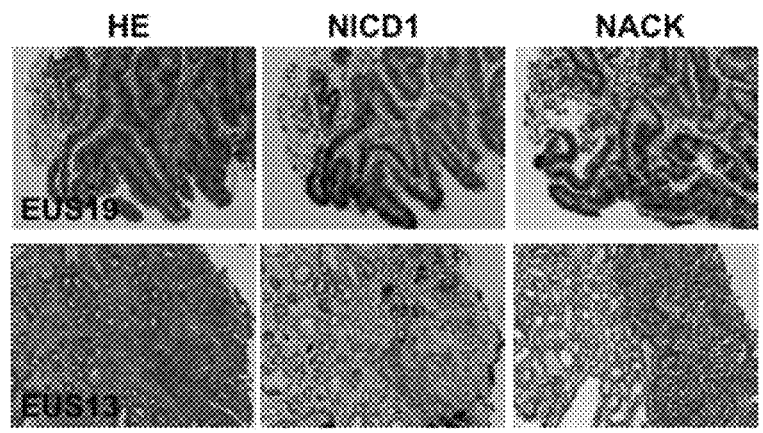

To evaluate the expression level of NACK in EAC, clinical samples derived from surgically resected primary esophageal adenocarcinoma were analyzed. As illustrated in FIG. 1A, the mRNA levels of NACK and Notch1 are elevated in tumor samples compared to their corresponding normal tissues. Consistently, high levels of NACK were observed in chemo-naïve esophageal adenocarcinoma samples from endoscopic ultrasound ("EUS") biopsies, which also have elevated levels of activated Notch1 (FIG. 1B).

Figure 1C:
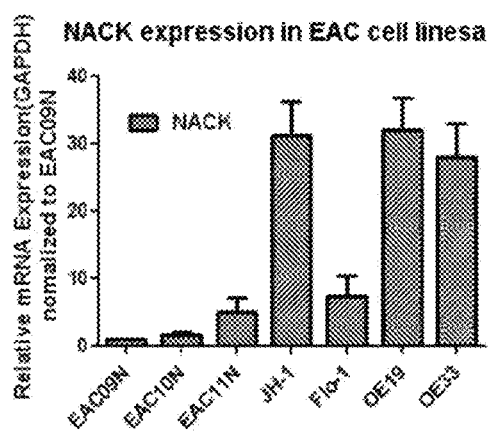

The expression of NACK in esophageal adenocarcinoma cell lines (OE33, OE19, Flo-1 and JH-1) by qPCR was also analyzed (FIG. 1C). Increased NACK expression was also observed in these esophageal adenocarcinoma cells compared to immortalized cells derived from normal tissue. These results demonstrate that the expression level of NACK is elevated and linked with the expression of activated Notch1 in esophageal adenocarcinoma tumor and cells.

Figure 1D:
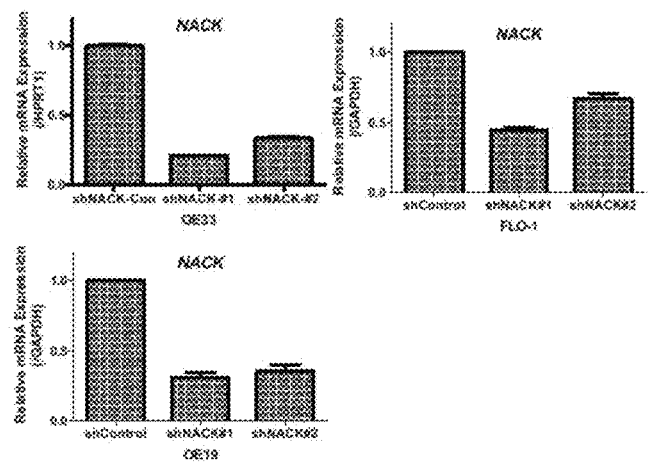
Figure 1E:
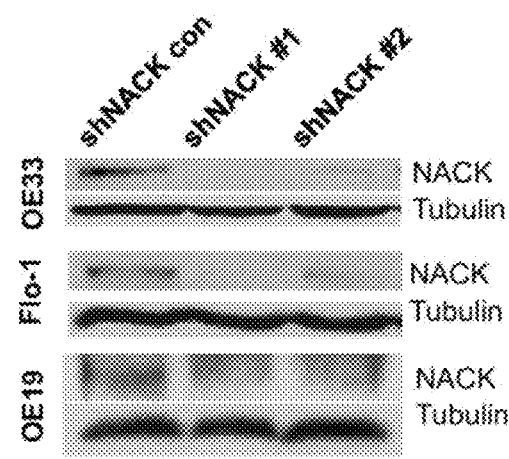
Figure 1F:
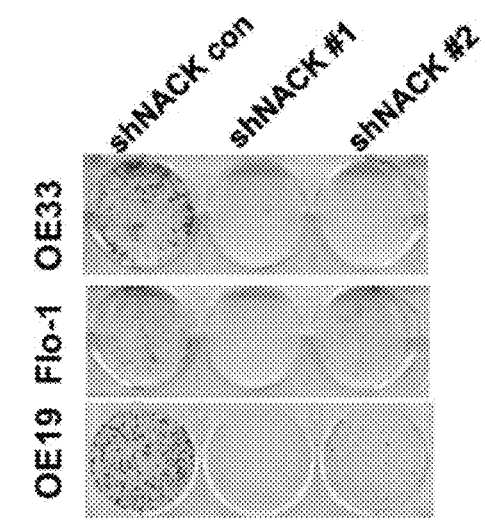

To assess the importance of NACK in EAC, the viability of EAC cells was assessed by knocking down endogenous expression of NACK. Cell lines were infected with lentivirus expressing control shRNA or shRNA against NACK. Knockdown of NACK in esophageal adenocarcinoma cells (OE33, OE19 and Flo-1), as verified by qPCR and Western blot (FIGS. 1D and 1E), led to dramatic inhibition of the clonogenic potential of these cells (FIG. 1F). These data indicated that NACK is essential for the survival of EAC cells, which provide the rationale for targeting NACK as a therapeutic target.

Homology Modeling and Molecular Dynamic ("MD") Simulation of the Kinase Domain of NACK The NACK structure was constructed using homology modeling. The three-dimensional model of NACK was produced using the IntFOLD server, which adopted the multiple-template modeling method based on global and local sequence quality estimates and additional sequence-structure alignment methods. See McGuffin et al., Nucleic Acids Res 43, W169-73 (2015).

A good quality model was obtained based on the structure templates of protein kinases PKR (2A1A), STK16 (2BUJ), NEK1 (4APC) and CaMKII (2BDW). The three-dimensional model for NACK (full length) shows a largely disordered N-terminal domain (Met1-Gly974), an ordered kinase catalytic domain (Gly975-Trp1326), followed by a disordered C-terminal domain (Gly1327-Leu1402). The catalytic core of the protein kinase domain is composed of a β-sheet characterized N-lobe and an α-helix dominated C-lobe. In this regard, only the kinase domain model of NACK was employed for further molecular dynamic (MD) simulation.

To investigate the structural features of the NACK kinase domain, the NACK kinase domain model was compared to the crystallographic structure of PLK3 (PDB: 4B6L), which is a typical kinase. PLK3 is structurally similar to NACK, with an RMSD of 1.748 Å over 182 aligned residues, and 27.47% sequence identity calculated by YASARA (shown using PyMOL, FIGS. 2A and 2B). This model kinase domain structure of NACK is also similar to that of the atypical kinase CASK. The 3D structural superimposition using YASARA between the kinase domain of NACK and CASK (PDB: 3C0I) has an RMSD of 1.69 Å over 176 aligned residues, with 21.59% sequence identity (shown using PyMOL, FIG. 2A). Superimposition of CASK with the NACK structure suggests that the adenine ring of 5'AMP can interact with the "hinge" residues of the NACK kinase domain. The hinge region contains several conserved residues that are essential for ATP binding and catalytic activity.

There are several key motifs in typical kinase domain structures that are needed for ATP binding, hydrolysis, and transfer. The HRD motif, containing a catalytic residue, functions to cleave the gamma-phosphate group and transfer it to the substrate. The VAIK motif is used to position the alpha and beta phosphate of ATP. The DFG motif contains the $Mg^{2+}$ binding site, which is required for ATP hydrolysis. NACK has several major protein kinase features such as the HRD motif, which includes a conserved aspartate (ASP1143) that is directly involved in catalytic activity (FIG. 2A). Moreover, the VAIK motif, with the alteration of the YAVK motif in NACK adopts a β-sheet secondary structure (FIG. 2A) is very similar to the corresponding regions of PLK3 and CASK (FAVK motif). In the loop between the N- and C-lobes, Arg1091 and Val1093 form a hinge that is structurally similar to that formed between Glu92 and Met94 in CASK. However, NACK lacks the conserved DFG motif that is involved in metal binding (FIG. 2A). As for CASK, it may still function as active kinase without metal binding site.

Figure 2E:
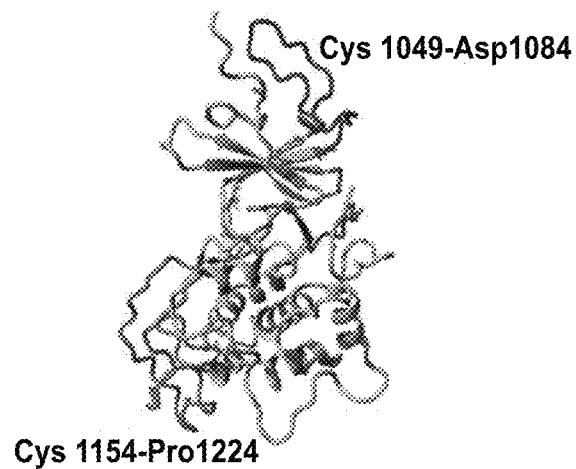

Following the homology modeling of NACK structure, a 50 ns all-atom MD simulation was performed in explicit water solvent to evaluate the stability of the NACK kinase domain model. Throughout the simulation, the Root Mean Square Deviation (RMSD) values increased up to 0.6 nm at 5 ns and remained around 0.7 nm as the time evolved (FIG. 2C). Moreover, the Root Mean Square Fluctuation (RMSF) was calculated to evaluate the flexibility of NACK kinase domain structure (FIG. 2D). Two regions appear to be the most flexible, which were Cys1049-Asp1084 and Cys1154-Leu1205 (shown in FIG. 2E respectively). The Cys1049-Aps1084 region forms a flexible loop between strands of the beta sheet in the N-lobe of NACK kinase domain, and Cys1154-Leu1205 constitutes the kinase insert domain.

MD Simulation Between NACK and ATP Reveals a Putative ATP Binding Pocket

Figure 3A:
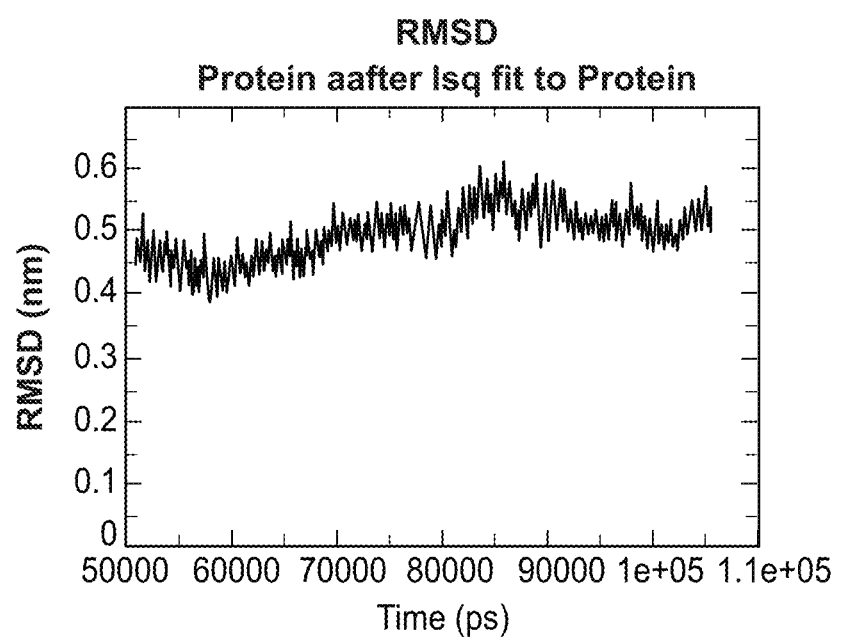
Figure 3B:
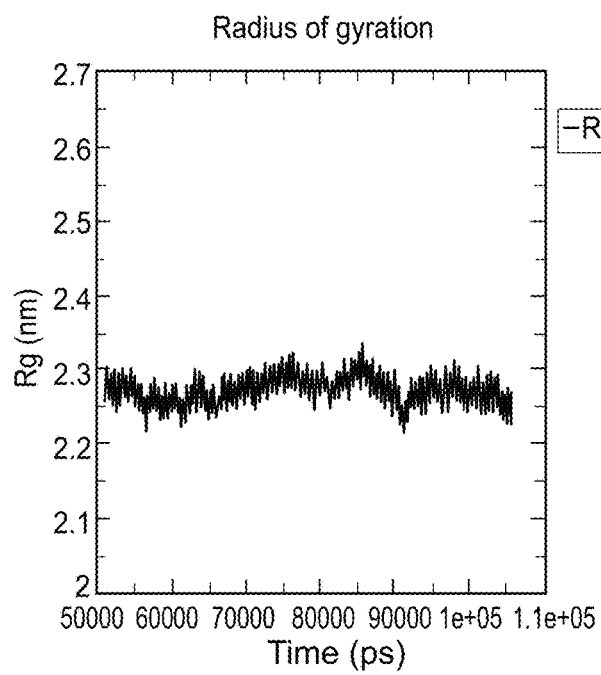

In order to identify the catalytic pocket of NACK, a MD simulation between NACK and the ATP ligand was conducted. The most representative structure of NACK derived from the initial MD study served as the starting conformation for the NACK-ATP interaction simulation. The ATP molecule was pre-positioned in the kinase domain of NACK according to the proposed interactions (see Taylor, S. S. Bioessays 7, 24-9 (1987), with phosphate groups making interaction with Lys1022 and adenine head making contact with His1095 at hinge region of the kinase domain. A 100 ns MD simulation was conducted. During the second 50 ns the binding model stabilized with RMSD between 4 and 5.5 Å (FIG. 3A). The stability of the MD simulation was further validated by the Radius of Gyration (Rg). Rg is the distance of the atoms of the structure from its center of gravity during the simulation time. Rg reached plateau averaging around 2.3 nm, which further demonstrated that the simulation reached equilibrium (FIG. 3B).

Figure 3C:
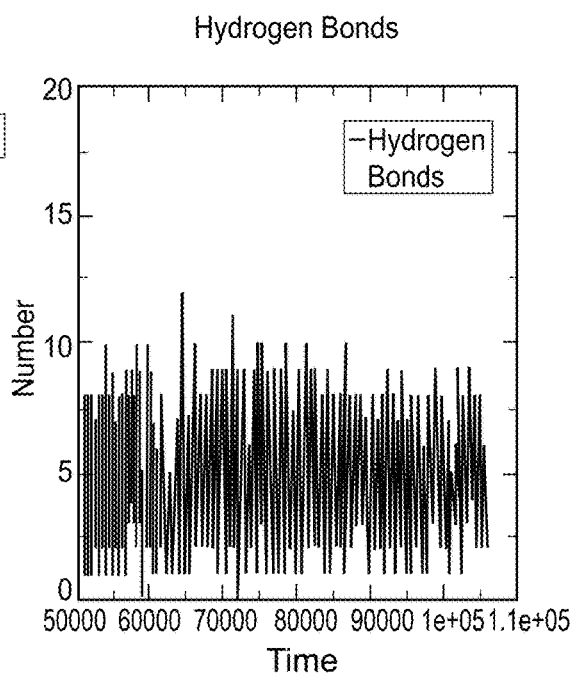
Figure 3D:
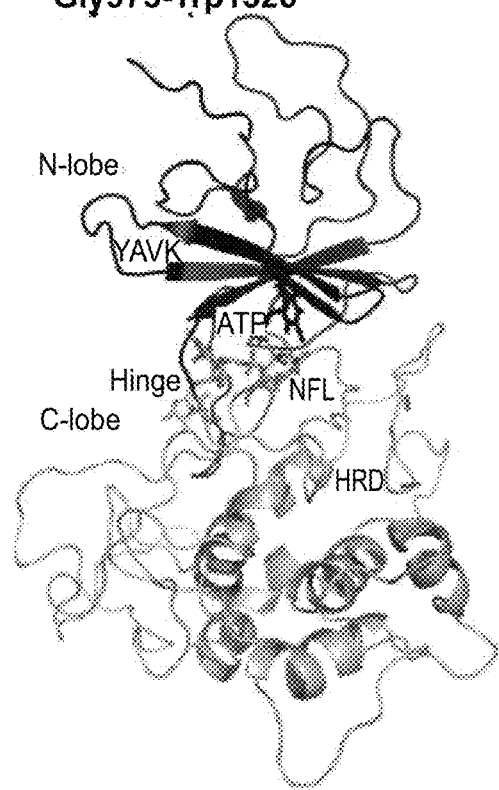
Figure 3D:
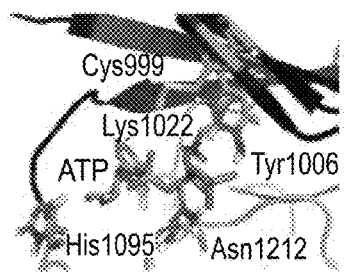

The molecular interactions between NACK and ATP were evaluated by calculating the number of hydrogen bonds. Five hydrogen bonds were consistently present between ATP and NACK in the last 50 ns of simulation (FIG. 3C). As for typical kinases, ATP was found to make seven to eight hydrogen bonds with residues at the active site. See Kuriyan, J., Konforti, B. & Wemmer, D. The molecules of life: Physical and chemical principles (Garland Science, 2012). The most representative structure of NACK with ATP molecule is shown in FIG. 3D. Several residues in the kinase domain of NACK were found to make important contacts with ATP (FIG. 3E). Notably, the salt bridge between Lys1022 and the beta phosphate group of ATP remained intact during the simulation. A hydrogen bond was found between the backbone hydrogen of His1095 and alpha phosphate oxygen ATP, whereas His1095 was in the position to make contact with adenine ring of ATP at the starting point of simulation. Residues Asn1212, Cys999 and Tyr1006 also formed hydrogen bonds with the phosphate groups of ATP. Asp1048 was found to make contact with adenine ring of ATP through a hydrogen bond (FIG. 3E). These results suggested that ATP could make stable contacts at the active site of NACK.

NACK Binds to the Notch Transcription Complex in an ATP-Dependent Manner

Previously, it had been demonstrated that NACK can be coprecipitated concomitantly with N1ICD and Maml1 in a CSL-dependent manner from 293T cells transfected with N1ICD, Maml1 and NACK in the CSL DNA affinity precipitation (CSL-DAP) assay. See Weaver, K. L. et al. Cancer Research 74, 4741-4751 (2014). To validate the model, residues Lys1002, Cys979, Tyr986 and His1076 were mutated in mouse NACK, which were found to make important interactions between NACK and ATP in the MD simulation (FIGS. 3D and 3E). The binding between ATP and mutated NACK was evaluated by the CSL-DAP experiment. NACK mutants (NACK-Lys1002, NACK-Cys979) showed decreased NACK binding to N1ICD and Maml1 in a CSL-dependent manner, suggesting their importance for ATP binding (FIG. 4A). While the NACK-His1076 mutant does not alter the NACK recruitment as His residue interacted with ATP through backbone.

Figure 4D:
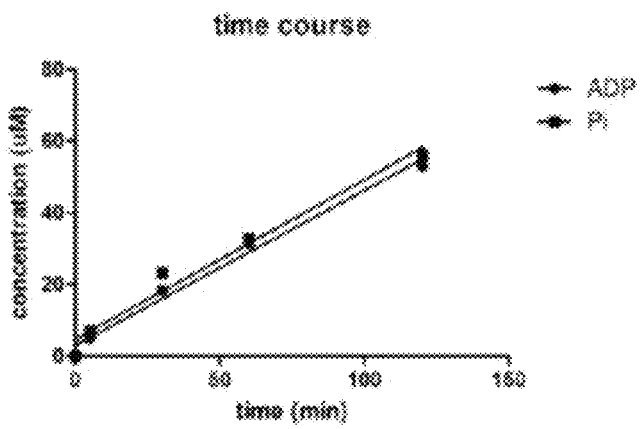
Figure 4E:
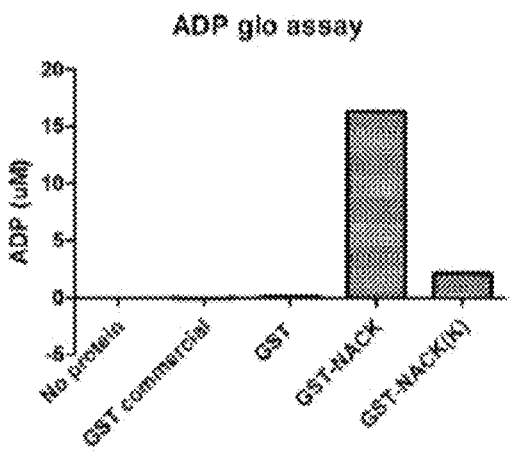

To further explore the effect of ATP on NACK binding to the Notch transcription complex, a CSL-DAP assay was conducted by adding ATP or GTP to the cell lysate. Compared to the control, NACK recruitment was dramatically increased (FIG. 4B). In contrast, NACK was not observed in the condition of non-hydrolysable ATP or GTP (AMPPNP or GTP-gS) (FIG. 4B), suggesting that ATP or GTP hydrolysis is required for the recruitment of NACK to the Notch transcription complex. Moreover, the binding between NACK and ATP was confirmed by measuring the binding between NACK and ATP analog AMP-PNP using surface plasmon resonance (SPR). The binding constant was determined to be approximately 1.5 uM (FIG. 4C). Therefore, it has been demonstrated that NACK can hydrolyze ATP to ADP and Pi (FIG. 4D). In contrast, NACK "kinase-dead" mutant K1002A failed to hydrolyze ATP to ADP in the ADP-Glo assay (FIG. 4E). Taken together, these results suggested that NACK functions in an ATP dependent manner to bind to the Notch transcription complex and to activate Notch-mediated transcription.

NACK Inhibitors Selectively Inhibit the Viability of Notch/NACK Dependent Cell Line To establish a criterion for Notch/NACK-dependence, cell lines were classified into two groups based on their sensitivity to DAPT (a GSI) and NACK knockdown. In this scenario, it was reasoned that inhibition of cell growth and Notch target genes by either DAPT or NACK knockdown indicates specific inhibition of Notch/NACK activity. Therefore, cell lines in which cell growth and Notch target gene transcription were affected by either DAPT treatment or NACK knockdown were classified as Notch/NACK dependent cell lines. On the other hand, those in which cell growth and transcription did not significantly change upon DAPT treatment or NACK knockdown were defined as Notch/NACK independent cell lines.

Figure 5A:
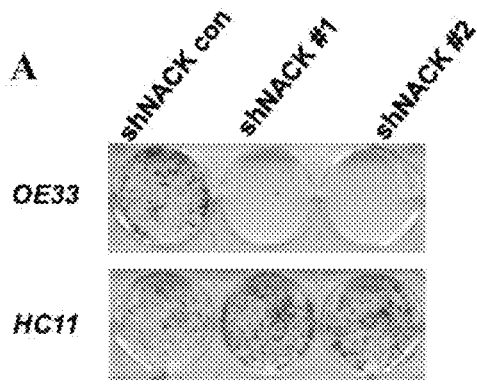
FIGS. 5A and 5B show a cell-based assay to screen for inhibitors that selectively inhibit the viability of Notch/NACK dependent cell lines.
Figure 5B:
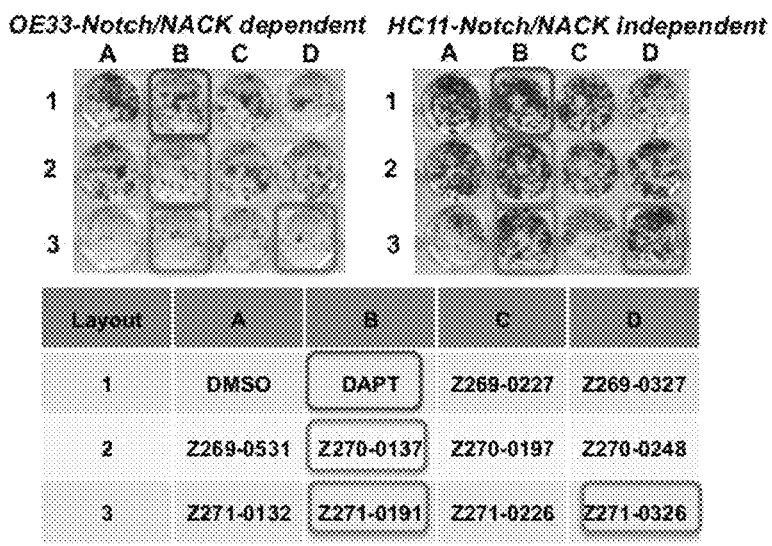
Figure 5C:
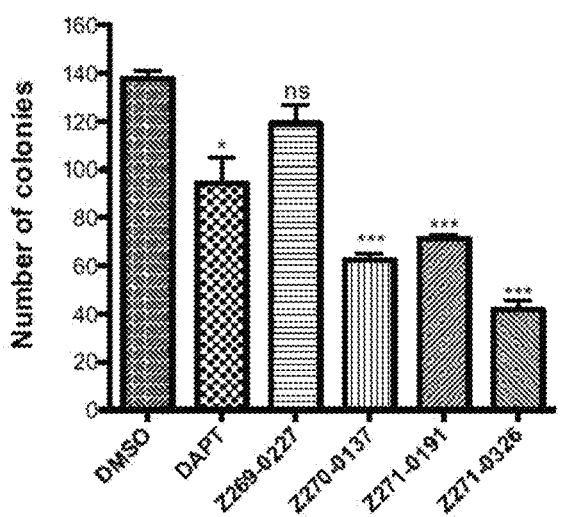
FIG. 5C show a summary of the colony formation assay.

A cell based colony formation assay was used in these experiments. Normal mouse mammary epithelia HC11 cells have little or no endogenous NACK expression, and NACK knockdown had no effect on the growth of HC11 cells (FIG. 5A, lower panel). On the other hand, knockdown of NACK in esophageal adenocarcinoma cell line OE33 showed significant inhibition of colony formation. Knockdown of NACK was confirmed by western blot and qPCR (FIGS. 1D and 1E). Furthermore, OE33 cell lines were responsive to gamma secretase inhibitor (GSI) DAPT treatment with a reduction in the colony formation compared to the mock treated cells, whereas DAPT treatment did not alter the viability of HC11 cells (FIG. 5B). Therefore, compounds that affect OE33 colony formation but not HC11 were desired. In order to screen the compounds, cells were treated with test compounds every other day. As shown in FIGS. 5B and 5C, compounds Z270-0137, Z271-0191, and Z271-0326 (depicted below) displayed remarkable potency and selectivity, which can effectively inhibit OE33 colony formation but not HC11 cell. These results suggested that a competitive inhibitor of NACK would affect the viability of Notch/NACK dependent cell lines, while have little or no impact on Notch/NACK-independent cells.

Figure 6A:
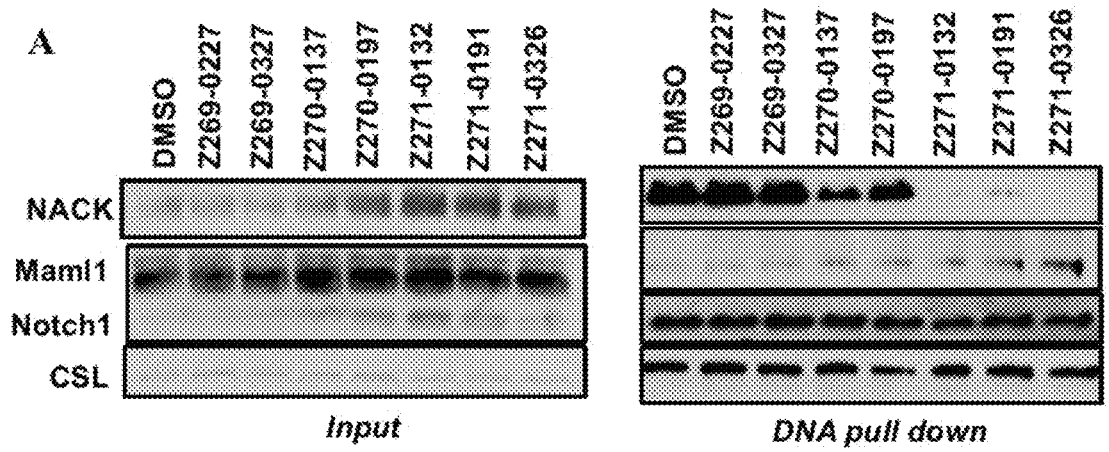
FIGS. 6A-6C show in vitro biochemical assays to screen for the NACK inhibitors (iNACK) described herein.

To determine whether the inhibitors that were selective in the colony assay could inhibit NACK recruitment to the Notch transcription complex, compounds were tested by the CSL-DAP assay. Inhibitors that can block ATP from binding to NACK were sought, resulting in attenuation of NACK binding to N1ICD, Maml1 and CSL. Z271-0326, Z271-0191 and Z271-0132 (depicted below) were found to dramatically inhibit NACK binding to the NOTCH transcription complex compared to the control group (FIG. 6A).

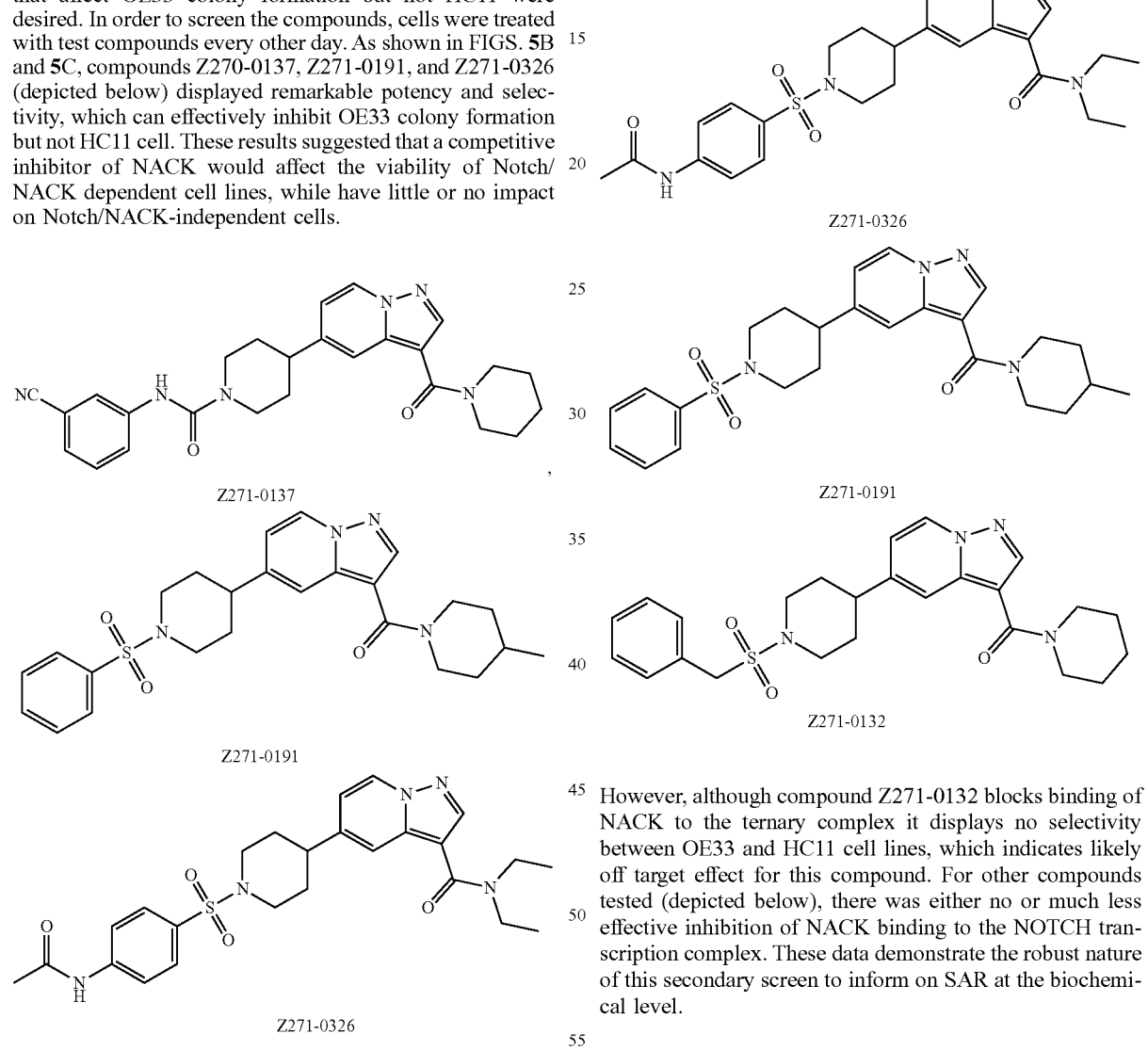

NACK Inhibitors can Selectively Inhibit NACK Recruitment to the Notch Transcription Complex Previously, NACK and Notch were observed at the Hes1 promoter by ChIP assay, demonstrating that Notch and NACK can be co-localized at CSL sites on chromatin and supporting the model that NACK is a component of the Notch transcriptional regulatory complex. See Weaver, K. L. et al. Cancer Research 74, 4741-4751 (2014). Moreover, it was demonstrated that ATP binding and hydrolysis is required to drive NACK binding to Notch, CSL and Maml (FIG. 4B).

However, although compound Z271-0132 blocks binding of NACK to the ternary complex it displays no selectivity between OE33 and HC11 cell lines, which indicates likely off target effect for this compound. For other compounds tested (depicted below), there was either no or much less effective inhibition of NACK binding to the NOTCH transcription complex. These data demonstrate the robust nature of this secondary screen to inform on SAR at the biochemical level.

-continued

Z270-0137
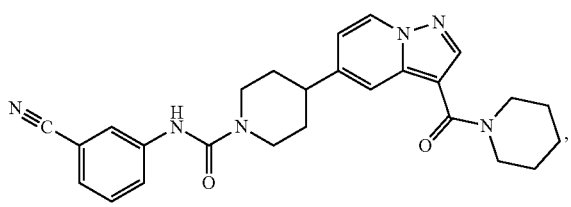

Z069-0327
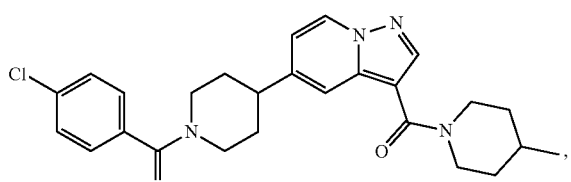

Z270-0197
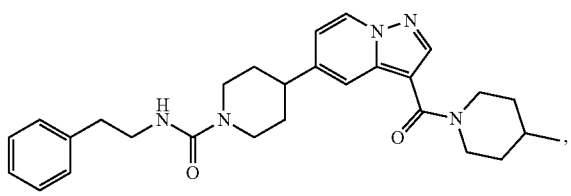

Z269-0386
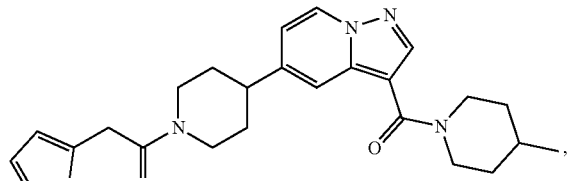

Z270-0248
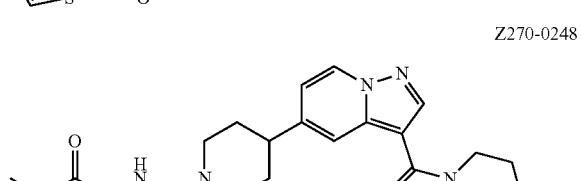

Z269-0437
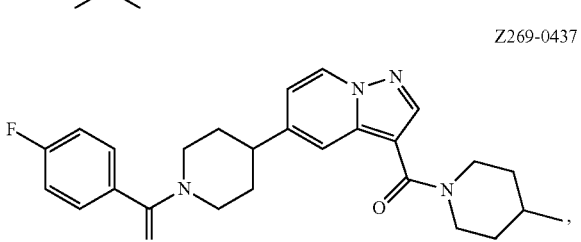

Z269-0441
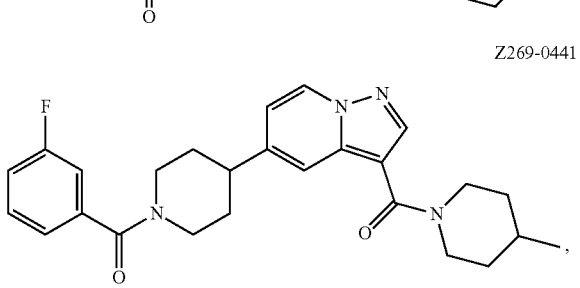

-continued

Z269-0516
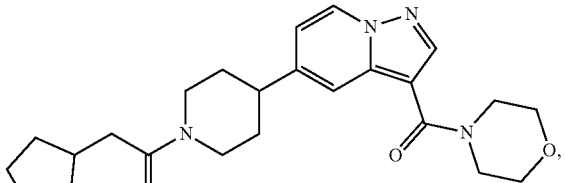

Z271-0226
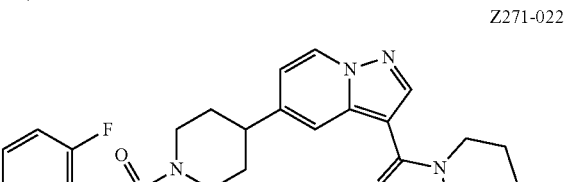

Z269-0531
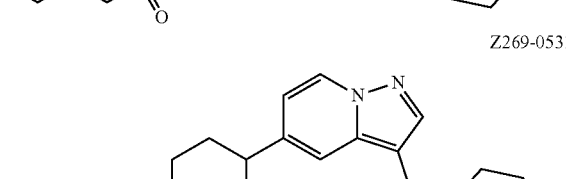

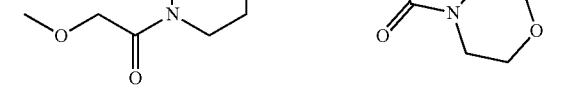

Compounds Inhibit Notch-Directed Transcriptional Activation

Figure 6B:
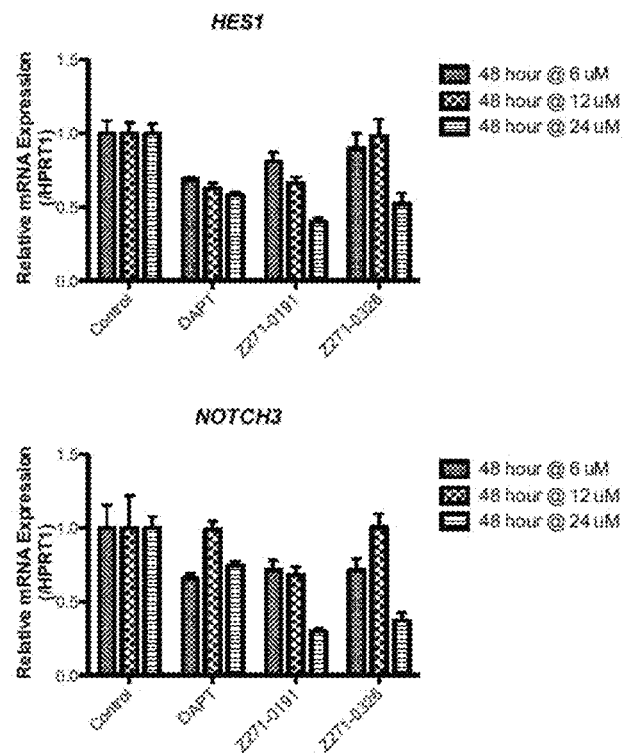
Figure 6C:
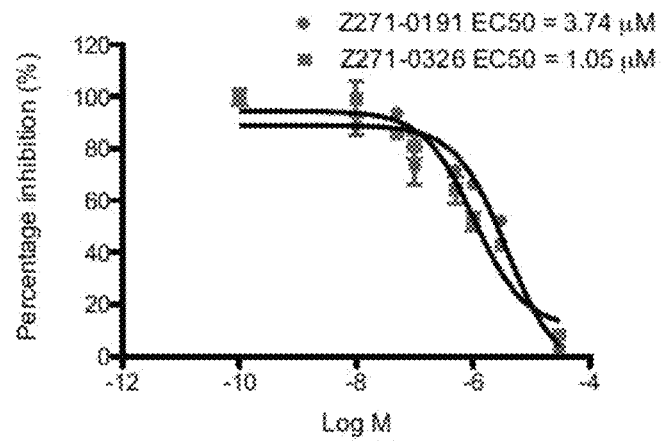

To further explore the effects of NACK inhibitors on transcription of Notch target genes, it was demonstrated that treatment of OE33 with Z271-0191 and Z271-0326 decrease the mRNA levels of Notch target genes Hes1 and Notch3 (FIG. 6B). This result demonstrates that the inhibitors effectively attenuate the activity of NACK, which further down-regulated Notch mediated transcriptional activity. Based on colony formation titration assay, $EC_{50}$ of Z271-0326 and Z271-0191 were estimated to be 1.05 and 3.74 µM, respectively (FIG. 6C).

Secondary Sphere Formation is Effectively Attenuated by Inhibitors

Figure 7A:
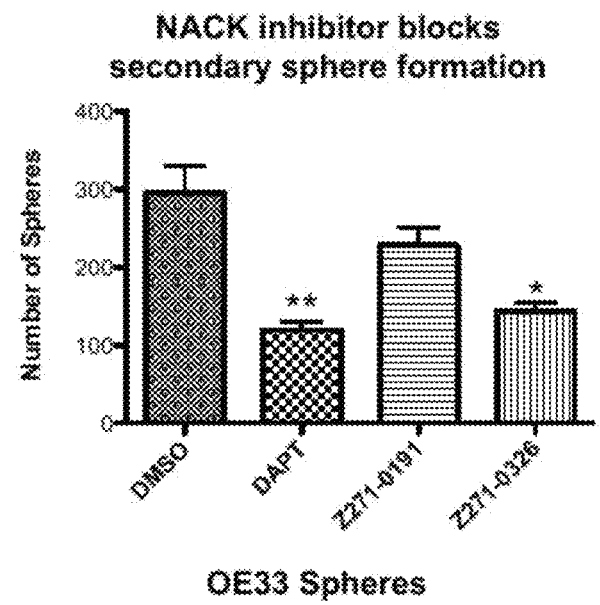
FIGS. 7A-7D show that the NACK inhibitors described herein block secondary sphere formation.
Figure 7B:
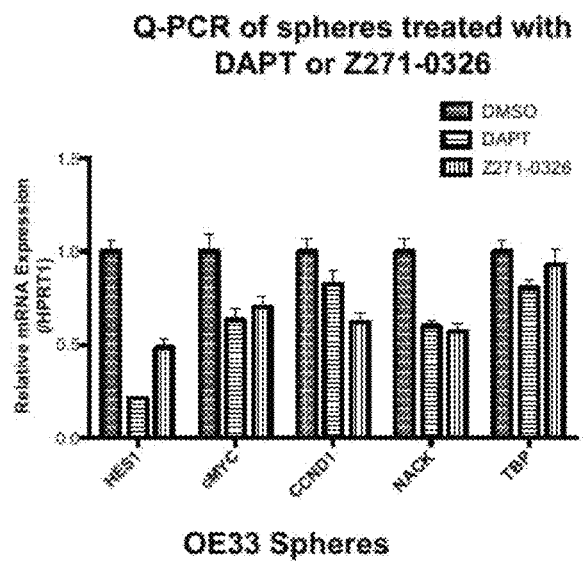

Two compounds were tested by conducting tumor sphere assays. Compared to the vehicle group, the treatment of OE33 with Z271-0326 showed decrease in the ability of cell spheres to form secondary spheres, which works comparable with the DAPT group. While compound Z271-0191, it is less effective compared to Z271-0326 (FIG. 7A). Treatment of OE33 spheres with Z271-0326 also affected Notch target genes HES1, MYC, CCND1 and NACK transcription (FIG. 7B).

Figure 7C:
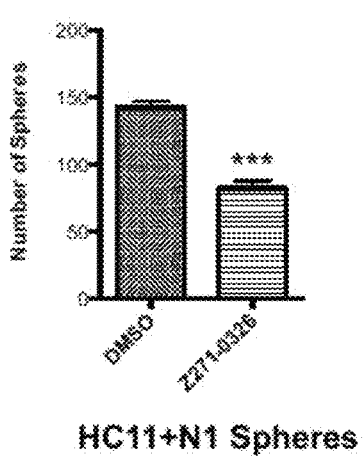
Figure 7D:
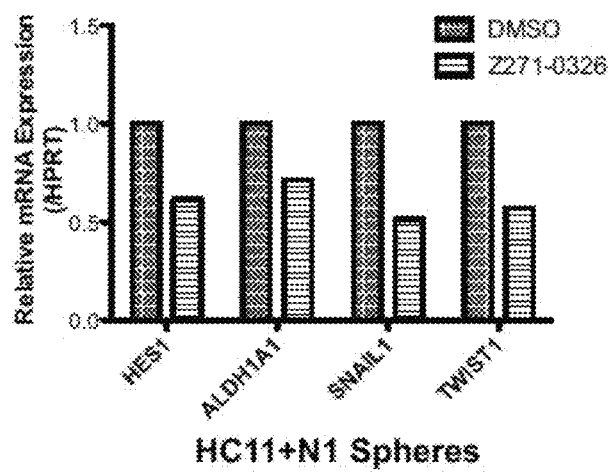

To further explore the effect of NACK inhibitors targeting Notch pathway, ectopic expression of Notch in HC11 mammary epithelial cells was constructed, as HC11 cells have little to no endogenous Notch activity. Moreover, HC11 cells are insensitive to either DAPT or Z271-0326 treatment as shown in previous colony formation assay (FIG. 5B). See Weaver et al., Cancer Research 74, 4741-4751 (2014). Compared to the control, HC11/N1ICD cells showed elevated Notch target gene transcription. Z271-0326 treatment inhibits the ability of HC11/N1ICD spheres to form secondary spheres (FIG. 7C). Furthermore, treatment of HC11/N1ICD spheres with Z271-0326 also causes a decrease in HES1 gene expression as well as several other stem-cell marker genes (ALDH1A1, SNAIL1 and TWIST1) (FIG. 7D). Therefore, transformation of HC11 cells by Notch now renders these cells dependent on Notch activity and sensitive to inhibition of NACK by Z271-0326.

NACK Inhibitors Block the NOTCH-NACK Complex Binding at the HES1 Promoter

Figure 8A:
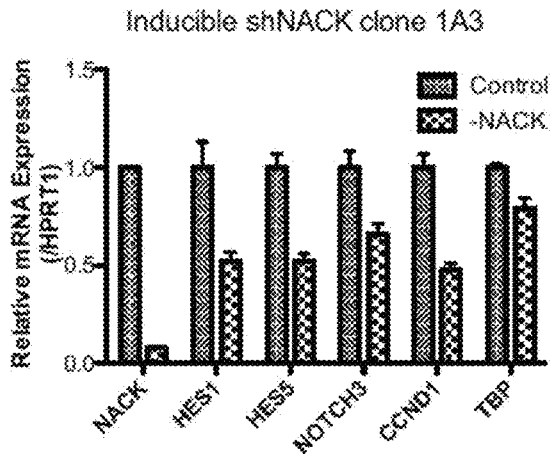
FIGS. 8A-8C show that the NACK inhibitor Z271-0326 blocks Notch transcription complex binding to the Hes1 promoter.
Figure 8A:
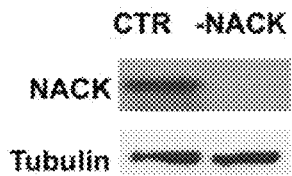
Figure 8B:
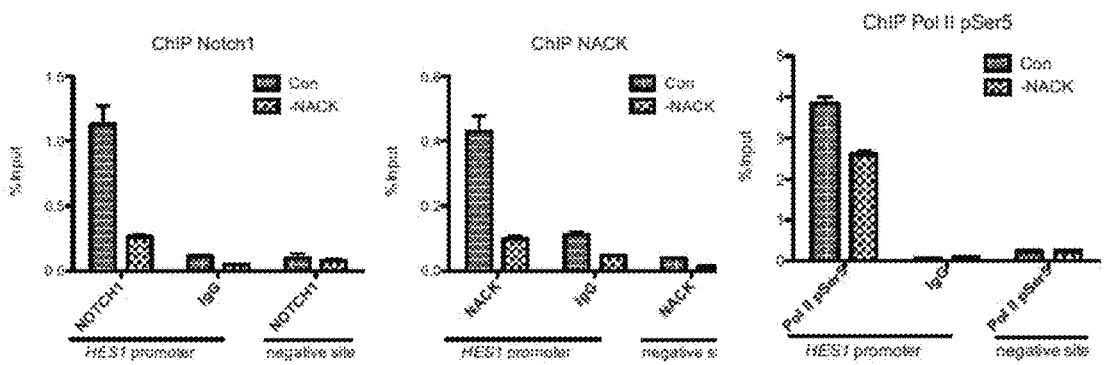

To study the molecular mechanism by which NACK coactivates Notch transcriptional activation of Notch target genes, OE33 stable cell lines were generated harboring doxycycline (DOX) inducible small hairpin RNA (shRNA) constructs. RT-qPCR analysis was performed in a cell clone 1A3 expressing tet-inducible shRNA against NACK, and DOX was added to the culture medium for 72 hrs to deplete the NACK mRNA and protein levels (FIG. 8A). RT-qPCR experiments were performed to determine the effects of NACK depletion on Notch target gene expression. TBP (TATA-binding protein), which is not a Notch target gene, was used as a negative control. Expression was normalized to HPRT1. NACK depletion reduces the expression of Notch target genes HES1, HESS, NOTCH3 and CCND1 (FIG. 8A). These results indicate that NACK inhibition blocks Notch transactivation of target genes. To further determine the mechanism of action of NACK on Notch target genes, ChIP experiments were performed to measure Notch1, NACK and activated Pol II occupancy on the HES1 promoter following NACK depletion in clone 1A3. To measure activated Pol II, antibody against Pol II pSer5 was used as a marker for active Pol II in transcription initiation. NACK depletion resulted in a profound decrease in Notch1, NACK and Pol II pSer5 ChIP signals (FIG. 8B). These results indicate that NACK inhibition by shRNA decreases Notch binding to the HES1 promoter and blocks transcription initiation.

Figure 8C:
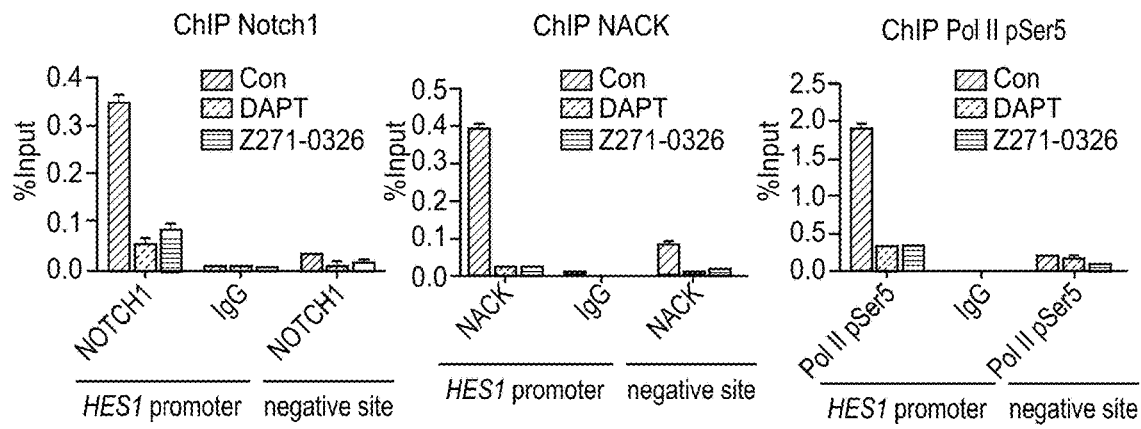

NACK inhibition by shRNA was found to attenuate Notch activity. Experiments were performed to determine whether NACK inhibitors can inhibit Notch transcription activity of the HES1 promoter, as HES1 expression is regulated by N1ICD, MAML1 and CSL transcription complex. See Nam, Y. et al., Cell 124, 973-83 (2006). To explore this, chromatin immunoprecipitation (ChIP) experiments were performed by assaying the protein level of N1ICD and NACK at the HES1 promoter. Treatment of OE33 cells with GSI DAPT or Z271-0326 both abrogated the binding of N1ICD and NACK to the HES1 promoter (FIG. 8C), which supports that NACK inhibitor can attenuate Notch activity at the HES1 promoter. Furthermore, NACK inhibitor Z271-0326 not only blocks Notch components binding to the HES1 promoter, but also decreases the RNA polymerase initiation complex (Pol II pSer5) formation at the HES1 promoter (FIG. 8C). Without being bound by any theory, these data indicate that Z271-0326 blocks NACK binding to NOTCH target HES1 promoter, possibly causing decreased resident time of the Notch activation complex at Notch target promoters.

Figure 9A:
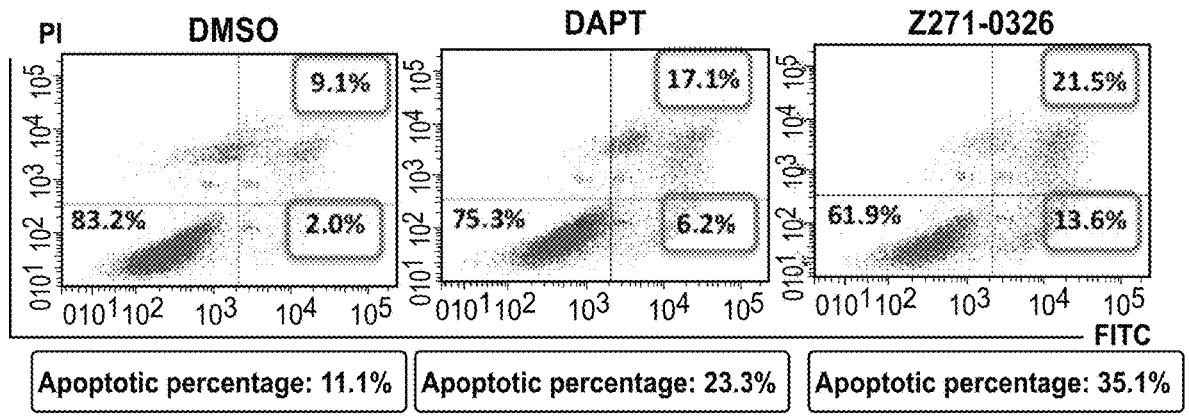
FIGS. 9A and 9B demonstrate that the NACK inhibitor Z271-0326 induces cell apoptosis and senescence.
Figure 9B:
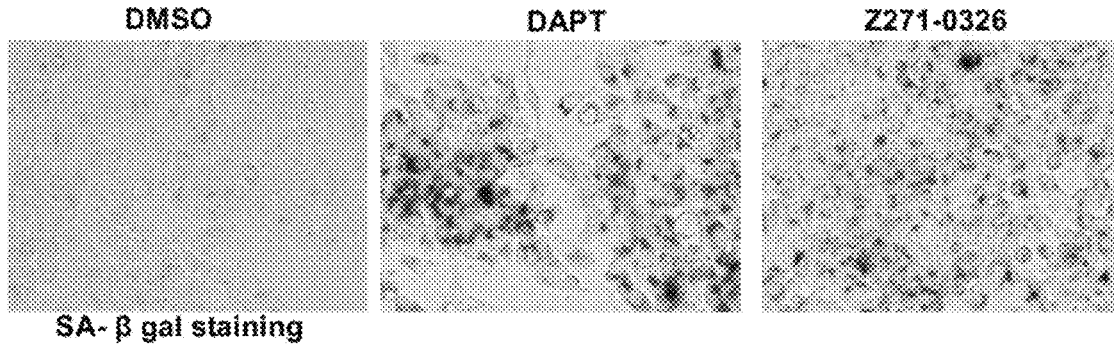

Notch Pathway Inhibition is Associated with Induction of Apoptosis and Senescence in EAC Cell Lines To investigate how Z271-0326 inhibits cell growth in EAC cell lines, the effect of Z271-0326 treatment was evaluated on apoptosis. OE33 cells were treated either with the GSI DAPT or Z271-0326, and their effects on apoptosis were analyzed at various time points after treatment. On day 7 of treatment, DAPT and Z271-0326 treatments result in a twofold and threefold increase in the percent of cells undergoing apoptosis, respectively, compared to the control. This result indicated that Notch pathway inhibition leads to apoptotic cell death, in OE33 cells (FIG. 9A). Similar to DAPT treatment, prolonged Z271-0326 treatment for 3 weeks of live cells of OE33 resulted in the induction of cellular senescence, as measured by senescence-associated β-galactosidase activity (FIG. 9B). These data indicate that inhibition of NACK activity induces apoptosis and cellular senescence to a similar extent as the GSI DAPT.

Characterization of the Interaction Between NACK and the Inhibitors Through SPR

The interaction between inhibitor Z271-0326 and target NACK was characterized using surface plasmon resonance (SPR). For this purpose, GST tagged NACK was captured by a GST antibody that was previously immobilized onto the surface of the chip through standard amide coupling. The dissociation constants associated with binding of the compounds to NACK was determined using the equilibrium approach, which consists of plotting the equilibrium response (Req) as a function of concentration of the compound and fitting the data to a 1:1 binding model. The dissociation constant associated with Z271-0326 binding to NACK ($K_D$=0.89±0.07 µM) is comparable to the affinity observed for AMP-PNP, a non-hydrolysable ATP analog ($K_D$=1.5±0.5 µM), (FIG. 10A).

Figure 10D:
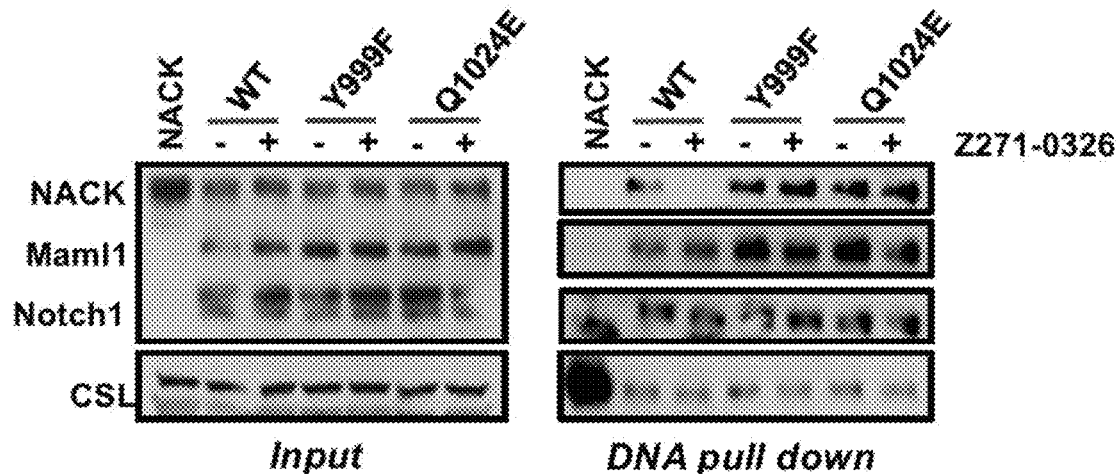

The initial docking results revealed several interactions between NACK and Z271-0326 (FIGS. 10B and 10C). At the active site of NACK, residues Lys1022, His1095, Gln1046 and Tyr1019 were found to form important hydrogen bonds with Z271-0326. In order to validate the importance of these residues, residues Q1024 and Y999 were mutated in mouse NACK. The binding between ATP and mutated NACK was evaluated by the CSL-DAP assay with or without Z271-0326. Z271-0326 was found to block recruitment of NACK to the Notch ternary complex when WT NACK is used (FIG. 10D). However, Y999F NACK and Q1024E NACK were insensitive to inhibition by Z271-026 as indicated by NACK binding to the Notch complex in the presence or absence of Z271-0326.

Figure 11A:
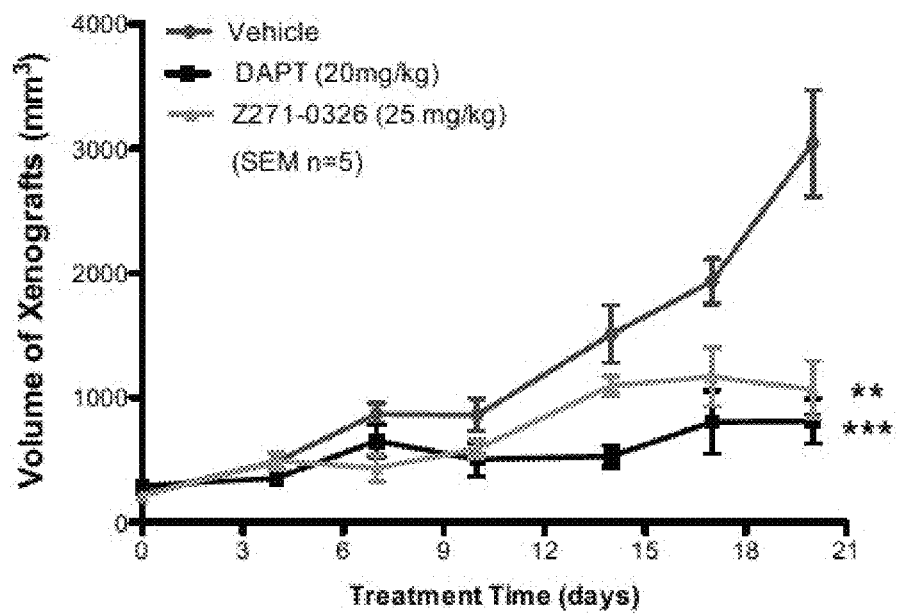
Figure 11B:
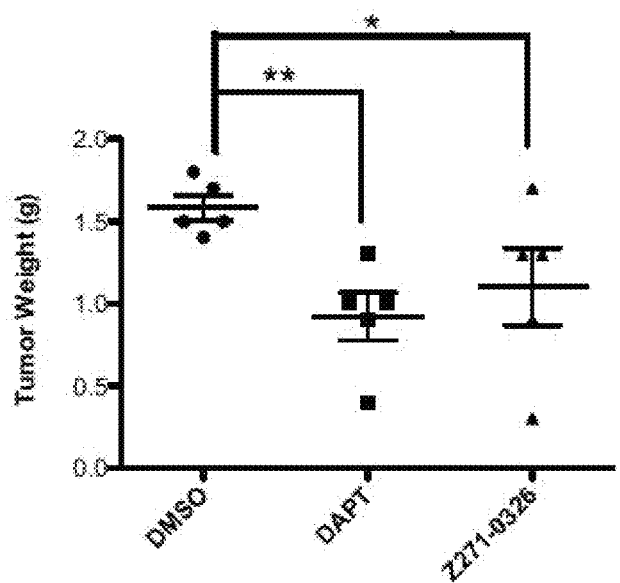
Figure 11C:
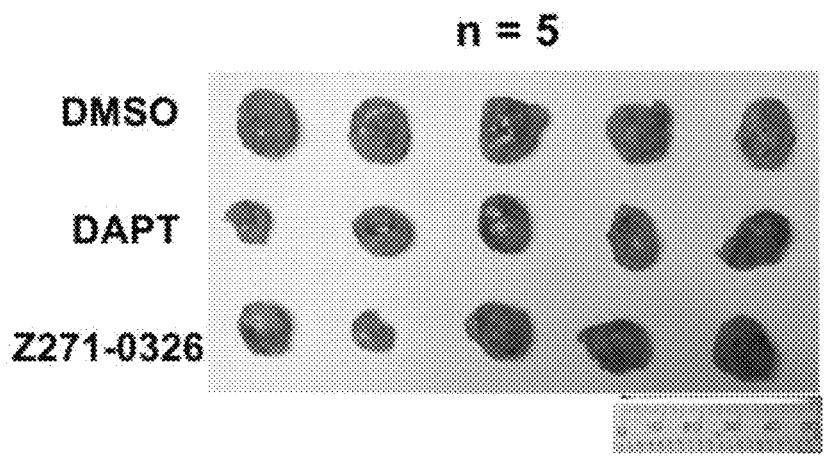
Figure 11D:
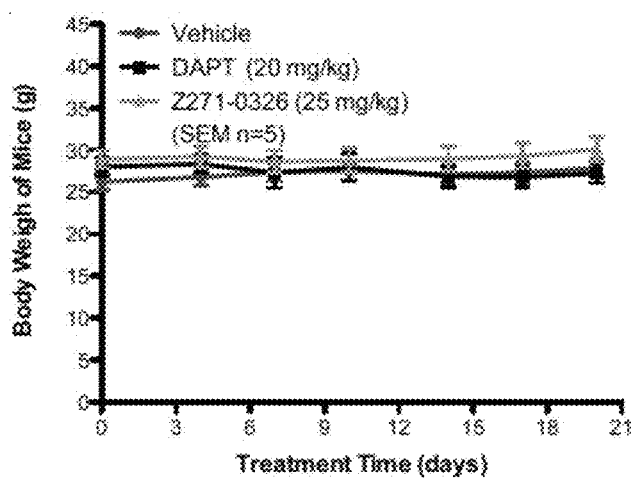
Figure 13A:
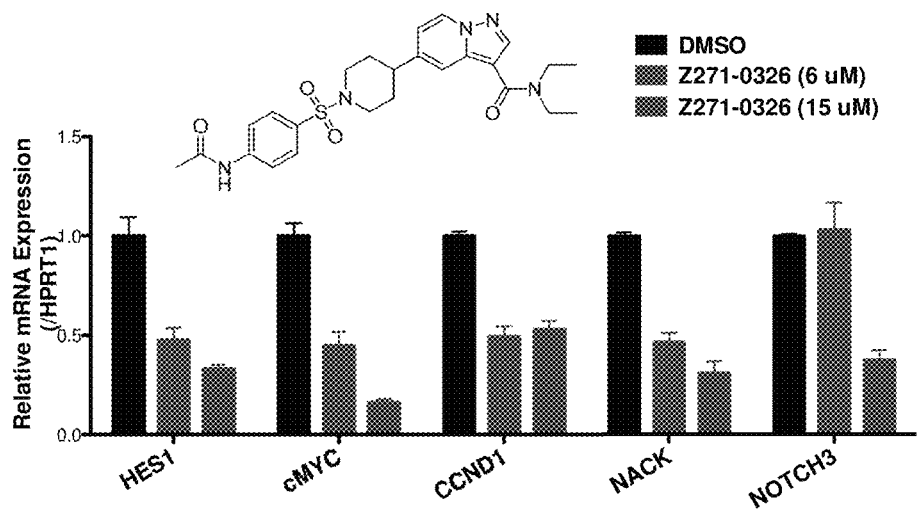
FIGS. 13A-13D show the q-PCR profile of the NACK inhibitor analogs (7W, 7H, 7M). As compared to NACK inhibitor Z271-0326 (FIG. 13A), compound 7W does not show any effect in down regulating Notch target genes (FIG. 13B). Compound 7H performed the best in down regulating Notch target genes, even better than Z271-0326 as seen in qPCR results (FIG. 13C). Compound 7M can also down regulate Notch target genes, but not as good as compound 7H (FIG. 13D).
Figure 13B:
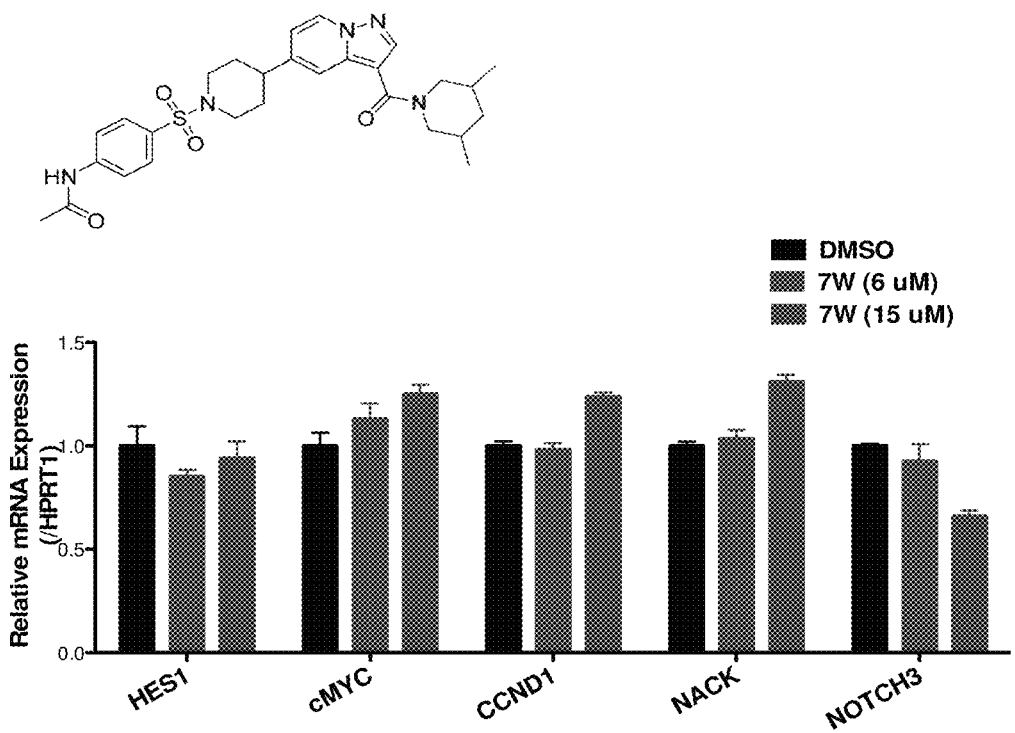
Figure 13C:
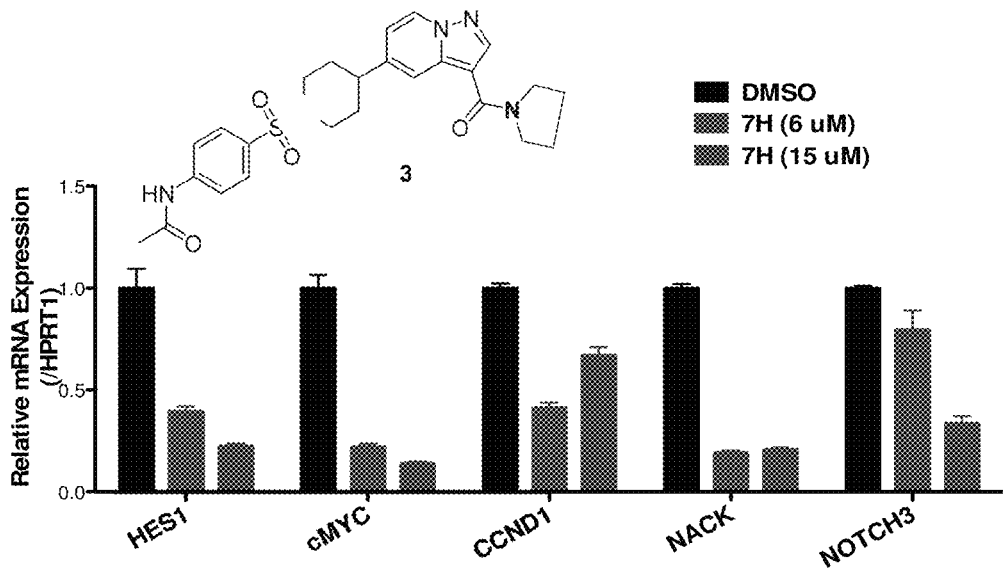
Figure 13D:
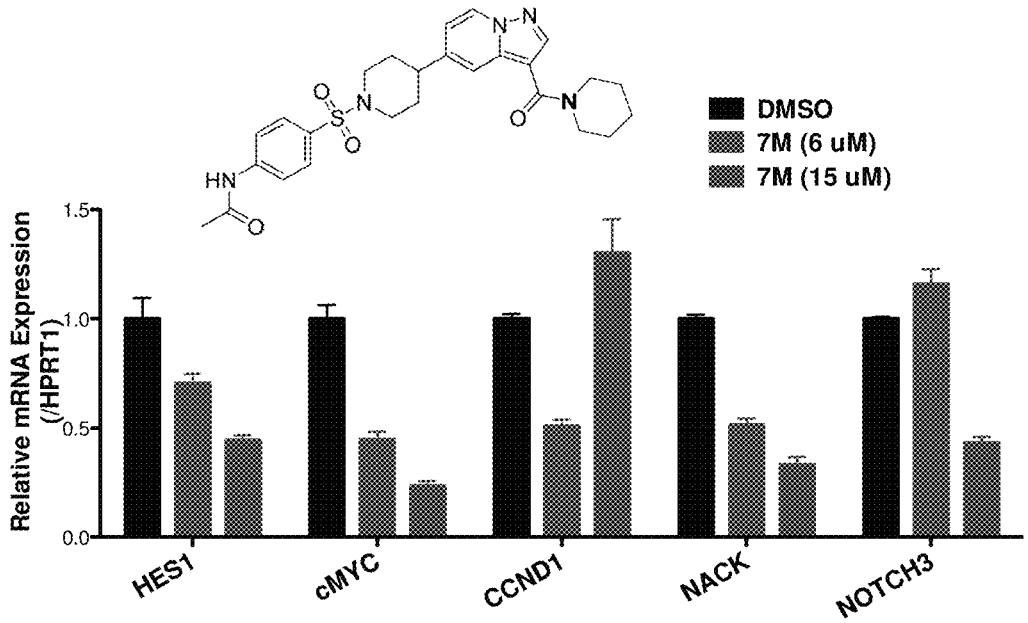

NACK Inhibitors can Suppress Tumor Growth in Esophageal Adenocarcinoma (EAC) PDX Models A well-established xenograft model was employed to assess the effect of Z271-0326 on tumor formation in animal model using PDX. Compared to cell line-based xenografts, PDX models better represent the diversity of human cancer and are more representative of the original tumor. See Wang, Z. et al. Cancer Research 74, 6364-6374 (2014). Two EAC PDX models were constructed (EAC47 and EAC36) from patient tumor samples. Mice harboring established tumors (approx. 200 mm$^3$) were treated with either DAPT (20 mg/kg) or Z271-0326 (25 mg/kg) daily via intraperitoneal injections. Growth of these tumors was significantly attenuated by Z271-0326 treated mice to a comparable level as DAPT compared to the vehicle treated group (FIGS. 11A, 11B and 11C). Moreover, body weights of the treated groups were not statistically different from the vehicle treated group (FIG. 11D). A decrease in proliferation index was also observed in Z271-0326 treated group as compared to the control group, measured via Ki67 staining (FIG. 11E). These results indicate that Z271-0326 can inhibit growth of Notch dependent esophageal adenocarcinoma tumor.

Plasma Pharmacokinetics of Z271-0326

The plasma pharmacokinetic profile of Z271-0326 was investigated following a single intravenous and intraperitoneal dose administration in male C57 BL/6 mice (FIG. 12). Following a single intravenous administration of Z271-0326 at 5 mg/kg, to male C57BL/6 mice, compound exhibited moderate systemic plasma clearance (30 mL/min/kg, normal liver blood flow in mice is 90 mL/min/kg) with terminal elimination half-life of 0.23 hr. The Vss was similar to the normal volume of total body water (0.7 L/kg). The Vss is a pharmacokinetic parameter, which represents the volume distribution of a drug in the body tissue. After a single intraperitoneal administration of Z271-0326 to male C57 BL/6 mice at 25 mg/kg dose, plasma concentrations were quantifiable up to 4 hr with Tmax of 0.25 hr. This dose was MTD for the 4-week efficacy studies shown in preliminary data. Following a single intraperitoneal administration of Z271-0326 to male C57 BL/6 mice at 100 mg/kg dose, plasma concentrations were quantifiable up to 24 hr with Tmax of 1.00 hr.

Effect of NACK Inhibitor on Cell Viability

Figure 14A:
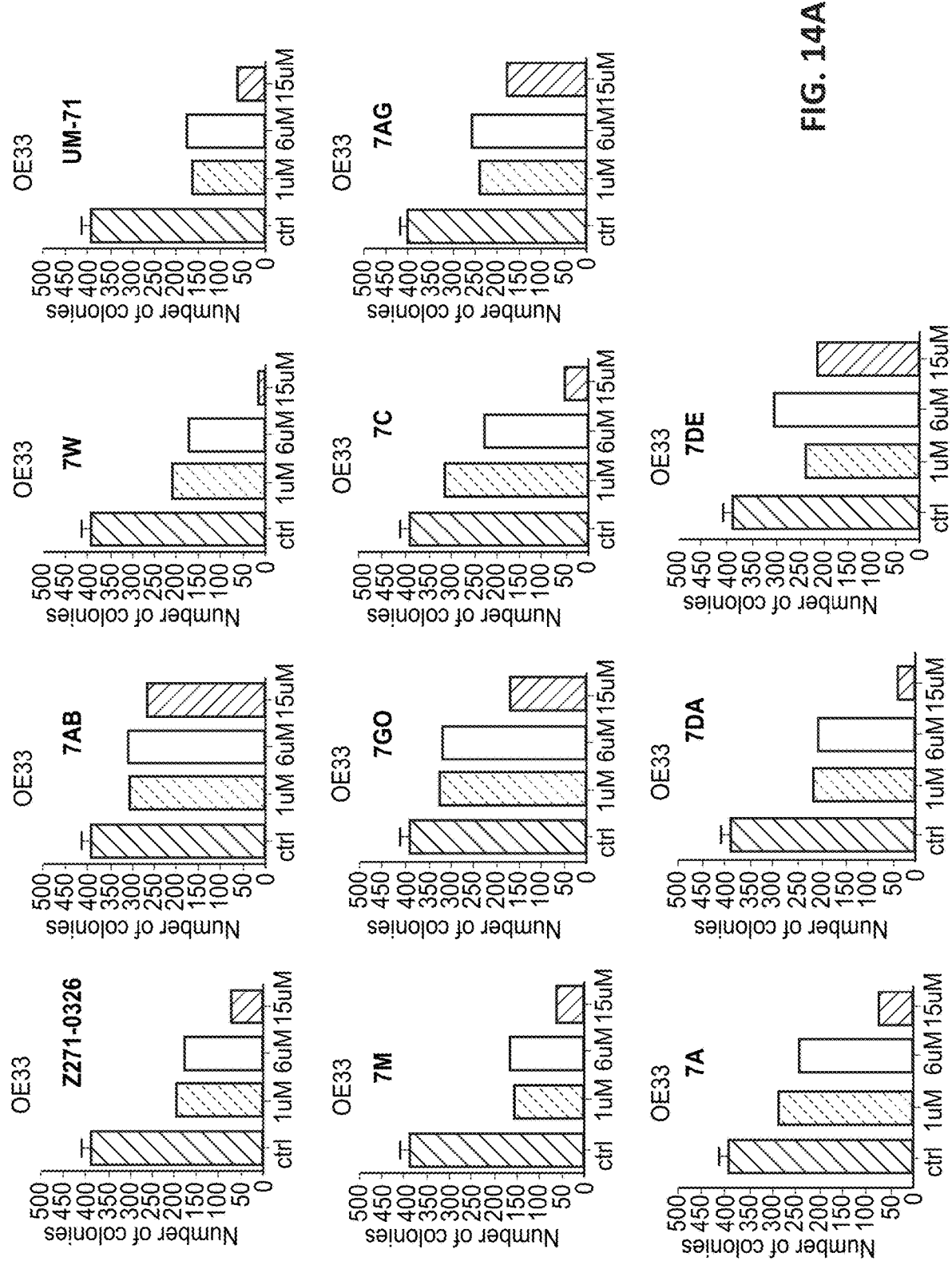
FIG. 14A and FIG. 14B show the inhibition of OE33 cells by compounds disclosed herein as number of colonies (FIG. 14A) or colonies with respect to a control (FIG. 14B).
Figure 14B:
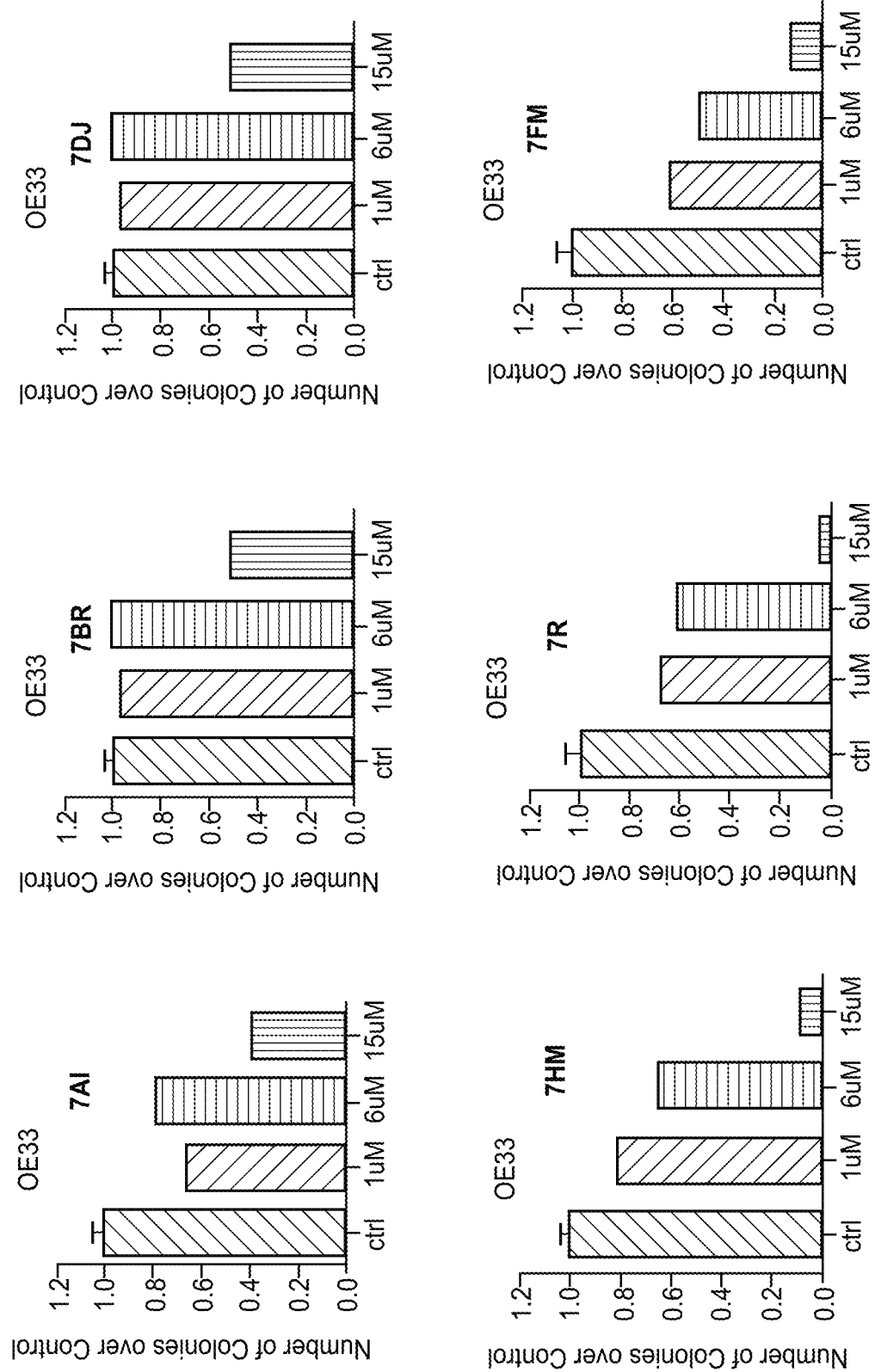
Figure 15:
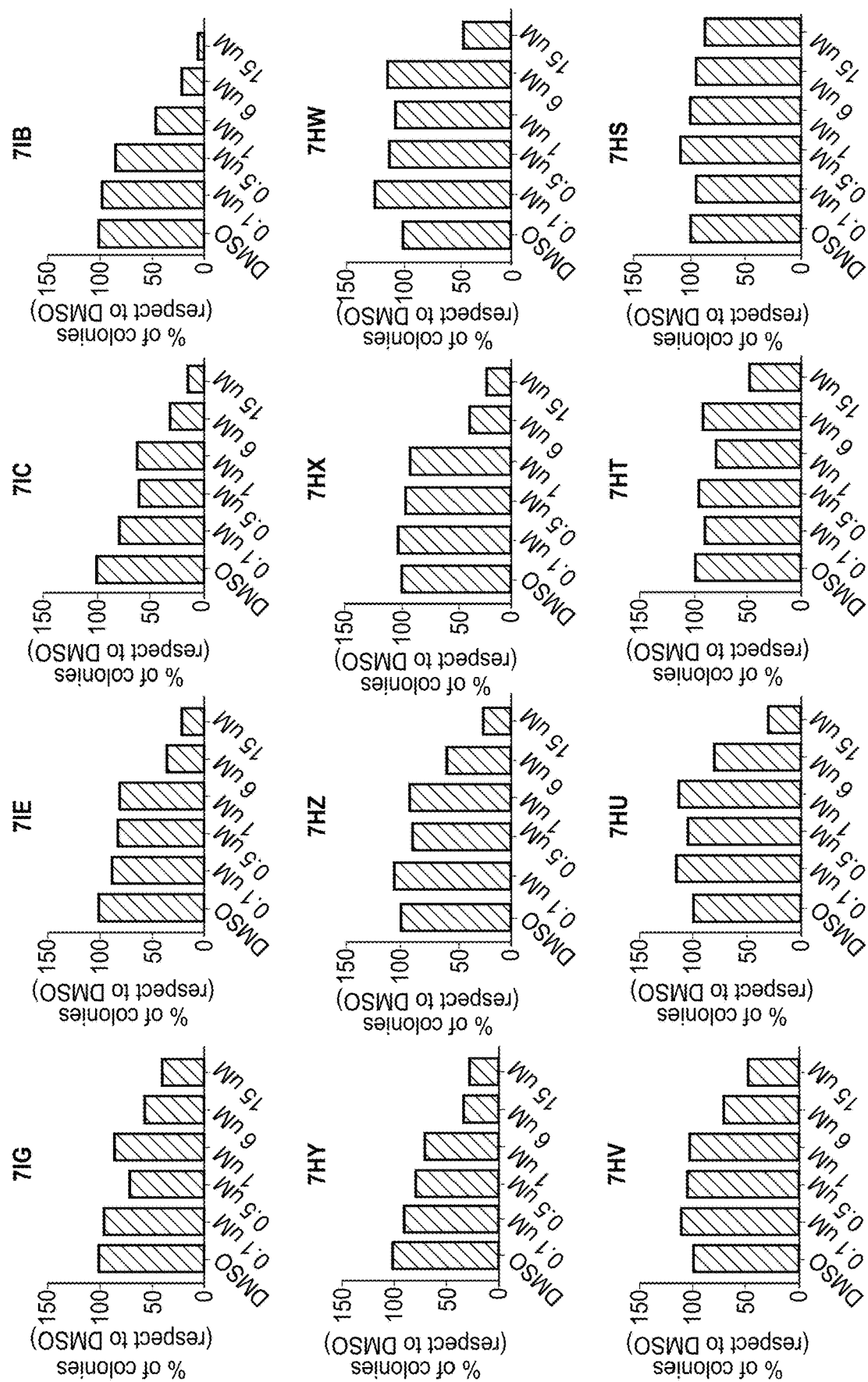
FIG. 15 shows the inhibition of OE33 cells by compounds disclosed herein with respect to number of colonies treated with DMSO.

To assess the effect of NACK inhibitor on Notch target gene transcription, Notch/NACK-dependent cell lines were treated with NACK inhibitors. The cells were also treated with DAPT as a positive control. DMSO treated cells served as a vehicle control for comparison. Gene expression was normalized to HPRT, and TBP served as a negative control to validate normalization. As shown in FIG. 14A, FIG. 14B, and FIG. 15 the compounds disclosed herein can effectively inhibit the number of colonies of OE33 cells.

Effect of NACK Inhibitor on Cell Viability

Figure 16:
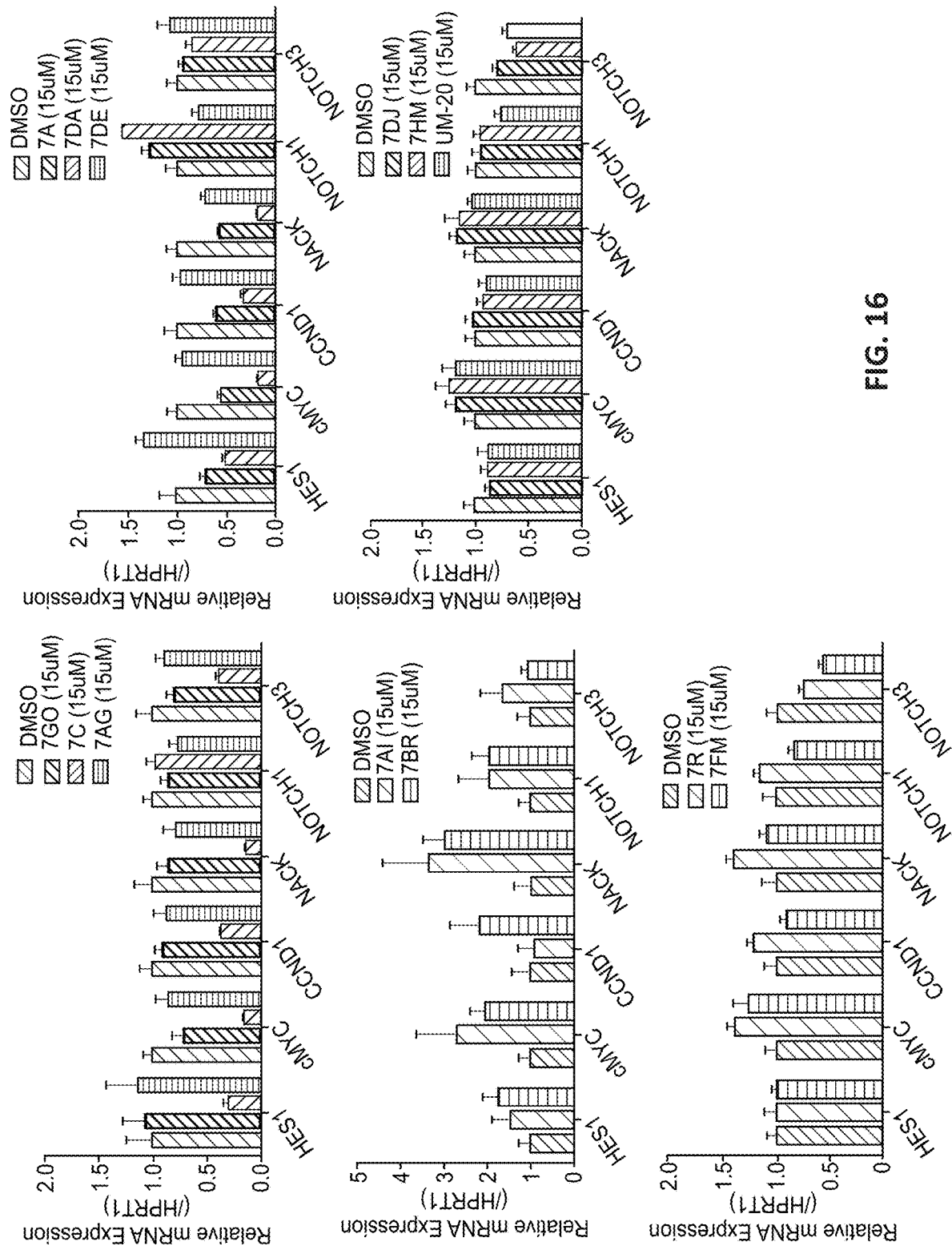
FIG. 16 shows the Q-PCR profile of NACK inhibitor analogs for the expression of several genes.

To assess the effect of NACK inhibitor on Notch target gene transcription, Notch/NACK-dependent cell lines were treated with NACK inhibitors. The cells were also treated with DAPT as a positive control. DMSO treated cells served as a vehicle control for comparison. Gene expression was normalized to HPRT, and TBP served as a negative control to validate normalization. As shown in FIG. 16, the NACK analogues 7C and 7DA downregulate oncogenes cMYC, CCND1, and HES1 with respect to DMSO and Z271-0326 (described previously).

Effect of NACK Inhibitor on Cell Viability

Figure 17A:
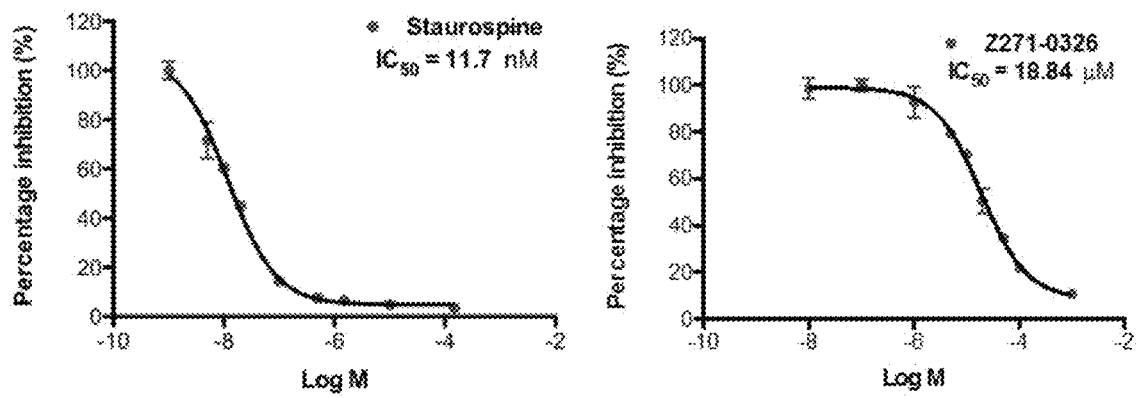
FIGS. 17A-17C show ADP-GLO Kinase assay results using Z271-0326 or inhibitors of the corresponding kinases: MAP4K5 assay (FIG. 17A), LCK kinase assay (FIG. 17B), and TNIK kinase assay (FIG. 17C).
Figure 17B:
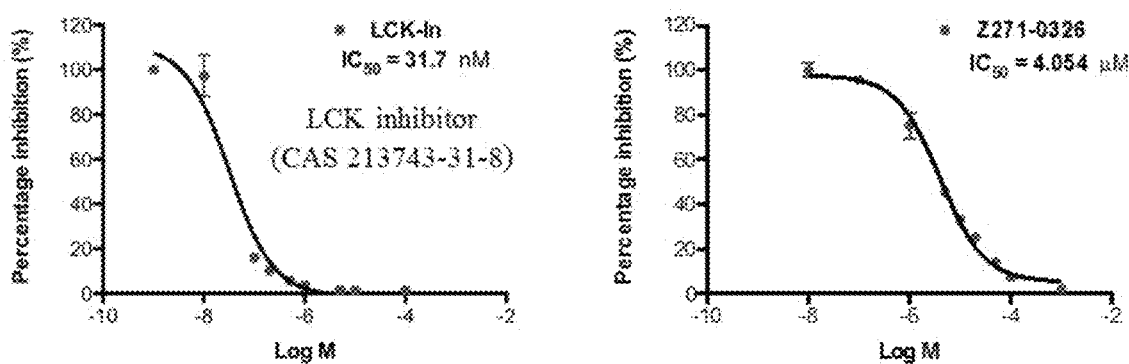
Figure 17C:
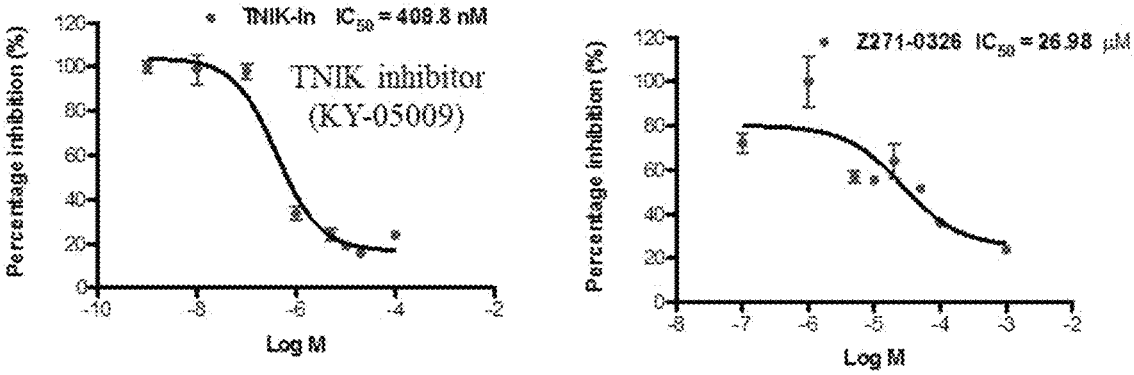
Figure 18:
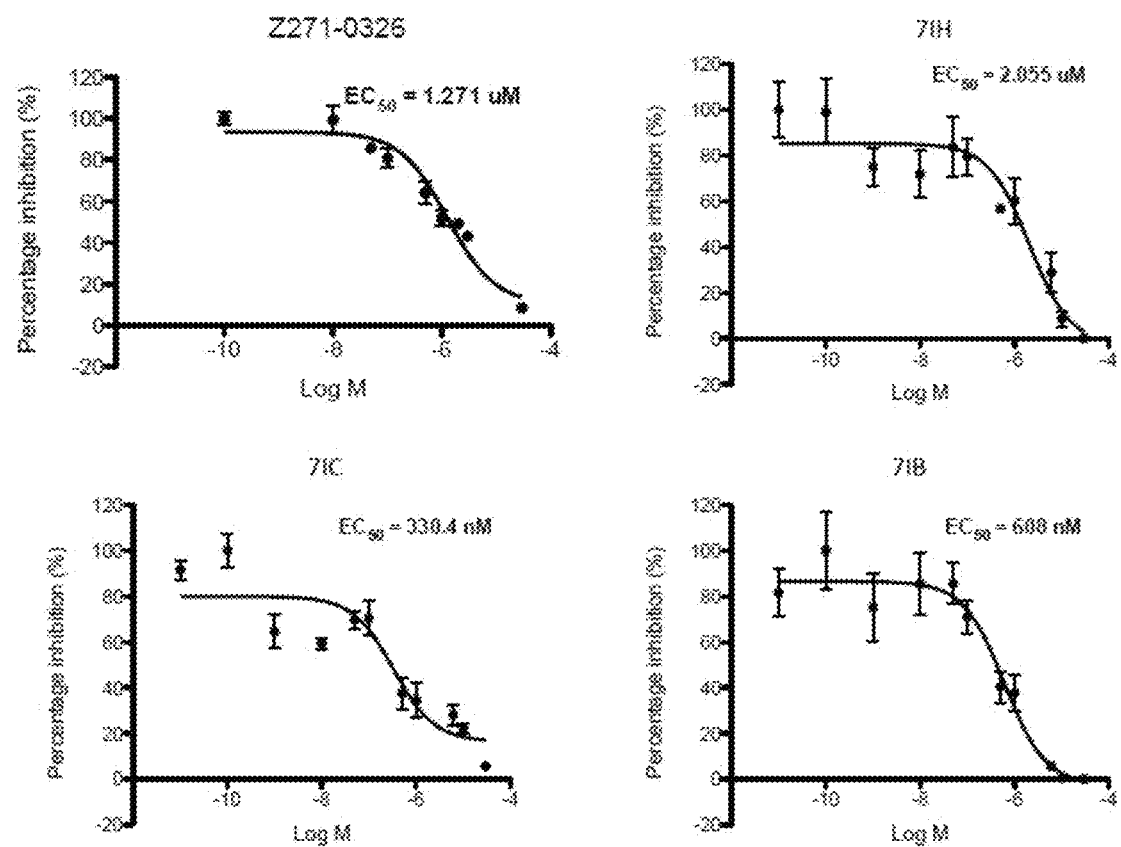
FIG. 18 shows the $EC_{50}$ values of several compounds disclosed herein as estimated by a colony formation titration assay in an OE33 cell line.

To assess the validity of the kinase profile screen results, Z271-0326 was screened in LCK, MAP4K5, and TNIK kinase assay. As shown in FIG. 17, Z271-0326 only meaningfully inhibits LCK out of the three kinases mentioned above Effect of NACK Inhibitor on Cell Viability As shown in FIG. 18, the $EC_{50}$ of Z271-0326 is 1.27 µM, and the analogues 71C and 71B have improved activity with $EC_{50}$s at 330 nM and 608 nM respectively.

LCK Kinase Assay

Figure 19:
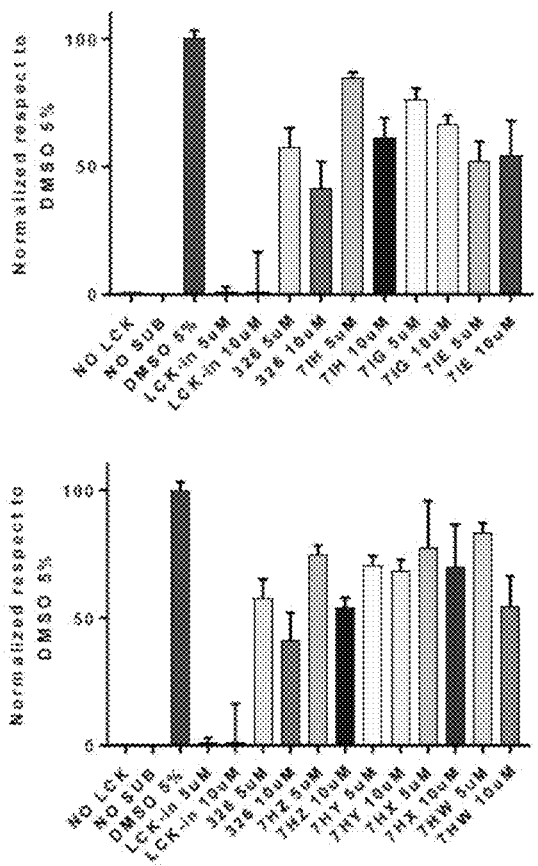
FIG. 19 shows the results of an LCK kinase assay using Z271-0326, a specific kinase inhibitor, and compounds disclosed herein at 10 μM, normalized with respect to DMSO.
Figure 19:
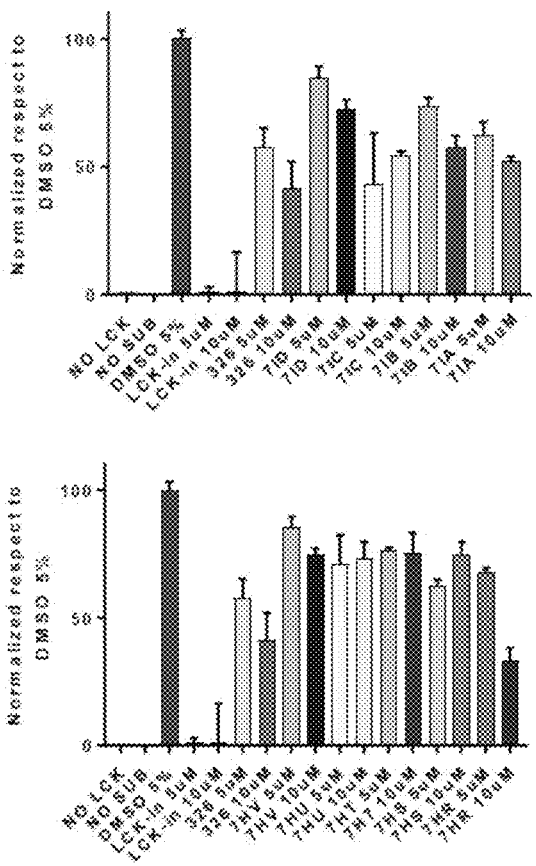
Figure 19:
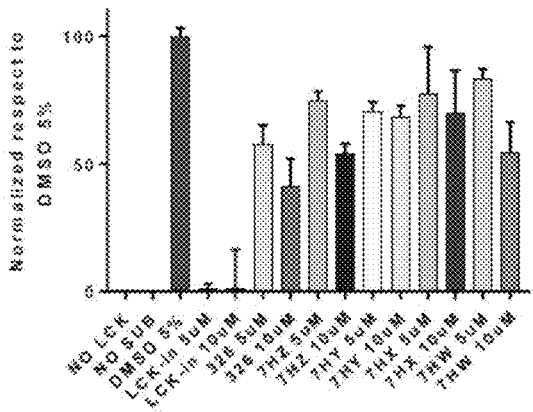
Figure 19:
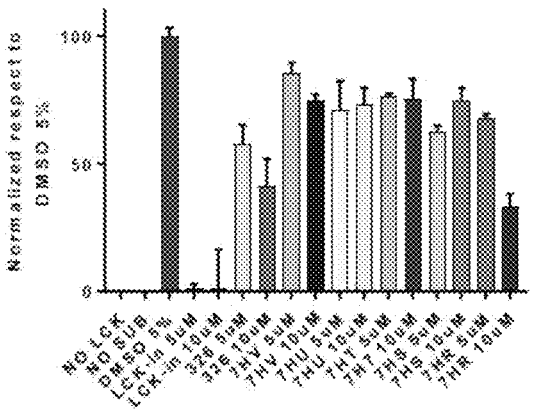

To continue to drive analogue selectivity for NACK, an LCK kinase assay was utilized as a counter screen. As shown in FIG. 19, the compounds described herein show a decreased affinity for LCK over Z271-0326.

Further guidance for using the compounds of the disclosure can be found in the Examples section, below.

Pharmaceutical Formulations

Also provided herein are pharmaceutical formulations that include the compounds of the disclosure, and one or more pharmaceutically acceptable excipients.

The compounds of the disclosure can be administered to a subject or patient in a therapeutically effective amount. The compounds can be administered alone or as part of a pharmaceutically acceptable composition or formulation. In addition, the compounds can be administered all at once, as for example, by a bolus injection, multiple times, e.g. by a series of tablets, or delivered substantially uniformly over a period of time, as for example, using transdermal delivery. It is also noted that the dose of the compound can be varied over time.

The compounds disclosed herein and other pharmaceutically active compounds, if desired, can be administered to a subject or patient by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compounds of the disclosure can be administered to a subject or patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the subject or patient, the severity of the condition or disease being treated, and the pharmacological activity of the compound being administered. The determination of dosage ranges and optimal dosages for a particular subject or patient is within the ordinary skill in the art.

In jurisdictions that forbid the patenting of methods that are practiced on the human body, the meaning of "administering" of a composition to a human subject or patient shall be restricted to prescribing a controlled substance that a human subject or patient will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Examples

The following examples are provided for illustration and are not intended to limit the scope of the invention.

Cell Lines

OE19 and OE33, human esophageal adenocarcinoma cell lines, were obtained from the European Collection of Cell Culture. 293T and HC11 cell lines were obtained from ATCC. All cell lines were propagated in growth media as specified by the provider.

Chromatin Immunoprecipitation ("ChIP") Analysis

Notch/NACK-dependent cells were treated with either DAPT as a positive control, DMSO (vehicle) as a negative control, or compounds for screening for 24 hours. After treatment, cells were cross-linked and sonicated to yield chromatin fragments of approximately 500 bp, as previously described (See Weaver et al., Cancer Research 74, 4741-4751 (2014)). Lysates were immunoprecipitated with either α-Notch1 (Bethyl Laboratories, Montgomery, TX; A301-894A), α-Maml1 (Cell Signaling, 12166s), α-NACK (Bethyl Laboratories, A302-675A), or α-PolII pSer5 (Abcam, ab5131) antibodies. DNA immunoprecipitates were cleaned using the PCR purification Kit (Qiagen). DNA were detected by Syber green qPCR using HES1 specific oligonucleotide primers (forward: 5'CGTGTCTCCTCCTCC-CATT3' (SEQ ID NO: 2); reverse: 5'GGGGGAT-TCCGCTGTTAT3' (SEQ ID NO:3)).

RT-qPCR Analysis.

Reverse transcription and qPCR analysis were performed as described previously (See Weaver et al., Cancer Research 74, 4741-4751 (2014)). Gene expression was normalized to the TATA-binding protein ("TBP") gene. As a control, hypoxanthine phosphoribosyltransferase 1 ("HPRT") gene expression was also monitored.

Colony Assay

Colony formation assay was utilized to determine the effect of small molecule inhibitors on cell proliferation. In general, different cell lines (NACK dependent or independent) will be seeded in 6-well plates at a density of 2000 cells per well and allowed to attach overnight. Inhibitor treatment commenced 24 hours post seeding, and the media containing inhibitor was changed every 48 hours thereafter. After 168 hours, colonies were be stained with Crystal Violet (Millipore) and counted.

CSL-DNA Affinity Precipitation (CSL-DAP) Assay

To determine the specificity of hit-to-lead compounds targeting NACK activity, it was evaluated whether iNACK can block NACK binding to the Notch complex by conducting CSL-DNA affinity precipitation (CSL-DAP) assay. Compounds, which showed selective inhibition on NACK/Notch dependent cells lines, were further assessed in this assay. In the CSL-DAP assay, 293T cells were co-transfected with $N1^{ICD}$, Maml1 and NACK. Transfections were performed using LipoJet transfection reagent (SL100468, SignaGen Laboratories) according to the manufacturer recommended protocol. After two days of transfection, cells were treated with compounds for 2 hours prior collecting the cell lysate. Cell lysates were incubated with DNA streptavidin beads. Proteins that bound to the beads were analyzed by Western blot.

Western Blot

Western blot was performed as described previously (See Weaver et al., Cancer Research 74, 4741-4751 (2014)). Primary antibodies were α-NACK (1:1,000; against aa209-287 of NACK and affinity purified), α-CSL (1:1,000; generated against full-length CSL and affinity purified), α-Maml1 (1:5,000; Cell Signaling Technology), α-cleaved-Notch1 (1:1,000; Cell Signaling Technology).

Tumor Sphere Formation Assay

In order to assess the effect of hit to lead compounds on the proliferation of stem cell like population of Notch/NACK dependent cells, the primary tumor spheres were treated with NACK inhibitor and allow the cells to be propagated as secondary cultures. To obtain tumor spheres, cells were cultured in DMEM/F12 with 2% B-27 serum-free supplement (17604-044; Invitrogen), 20 ng/mL epidermal growth factor (EGF; PHG0311L; Invitrogen), and 20 ng/mL basic fibroblastic growth factor (bFGF; PHG0266; Invitrogen) for 14 days. Resulting tumor spheres were examined and counted under the microscope. Furthermore, the tumor spheres were collected for further RT-qPCR analysis to test the effect of hit to lead compounds on the stem like target genes.

Determination of Affinity of Lead Inhibitors to Target Protein

A GST capture kit (GE Healthcare) were utilized to covalently immobilize an anti-GST antibody, provided in the kit, to the sensor chip surface (CM5 chip, GE Healthcare) by following the manufacturer's instructions. Capture were performed by injecting GST-NACK (1 μg/μL) over the immobilized anti-GST antibody in Hepes buffer (10 mM Hepes, pH 7.5, 150 mM NaCl, 3 mM EDTA, 0.0005% NP-40) for 7 min at 10 μL/min. A reference flow cell was prepared by capturing GST following the procedure described above. The GST capture resulted in a stable baseline. Experiments were performed on a Biacore T200 instrument (GE Healthcare) at 25° C. Small molecule inhibitors binding to NACK were performed in 50 mM Tris buffer, pH 7.5, containing 150 mM NaCl, 10 mM $MgCl_2$ and 5% DMSO (running buffer). The SPR signal arising from the sample was corrected for its respective control containing DMSO. Data visualization and analysis was performed using Biacore T200 software (GE Healthcare) and Origin 8.0 (OriginLab).

Plasma Pharmacokinetics of Z271-0326

The plasma pharmacokinetic profile of Z271-0326 was investigated following a single intravenous and intraperitoneal dose administration in male C57 BL/6 mice.

Efficacy in Mouse Models and Analysis of Biomarkers In Vivo

PDX models were employed to determine the effect of lead candidates on tumor growth. When the tumor size reaches 200 $mm^3$, the corresponding groups were either treated with vehicle (DMSO) or lead compound by IP injection daily.

ADP-Glo Kinase Assay

ADP-Glo kinase assay was performed using ADP-Glo™ Kinase Assay (Promega, V6930) according to the manufacture recommended protocol.

Cell Apoptosis and Cell Senescence Assays

To investigate how Z271-0326 inhibits cell growth in EAC cell lines, the effect of Z271-0326 treatment was evaluated on apoptosis. OE33 was treated either with the GSI DAPT or Z271-0326 every other day, and their effects on apoptosis were analyzed. On day 7 of treatment, cell apoptosis was analyzed using FITC Annexin V/Dead Cell Apoptosis Kit with FIFC annexin V and PI for flow cytometry (Invitrogen, V13242).

After prolonged Z271-0326 or DAPT treatment for 3 weeks of live cells of OE33, cells were measured by senescence-associated β-galaotosidase activity according to the manufacture recommended protocol (Senescence β-Galaotosidase Staining Kit, Cell Signaling, #9860).

SYNTHETIC EXAMPLES

Example 1. Synthesis of 5-(1-((4-acetamidophenyl)sulfonyl)piperidin-4-yl)-N,N-diethylpyrazolo[1,5-a]pyridine-3-carboxamide (Z271-0326

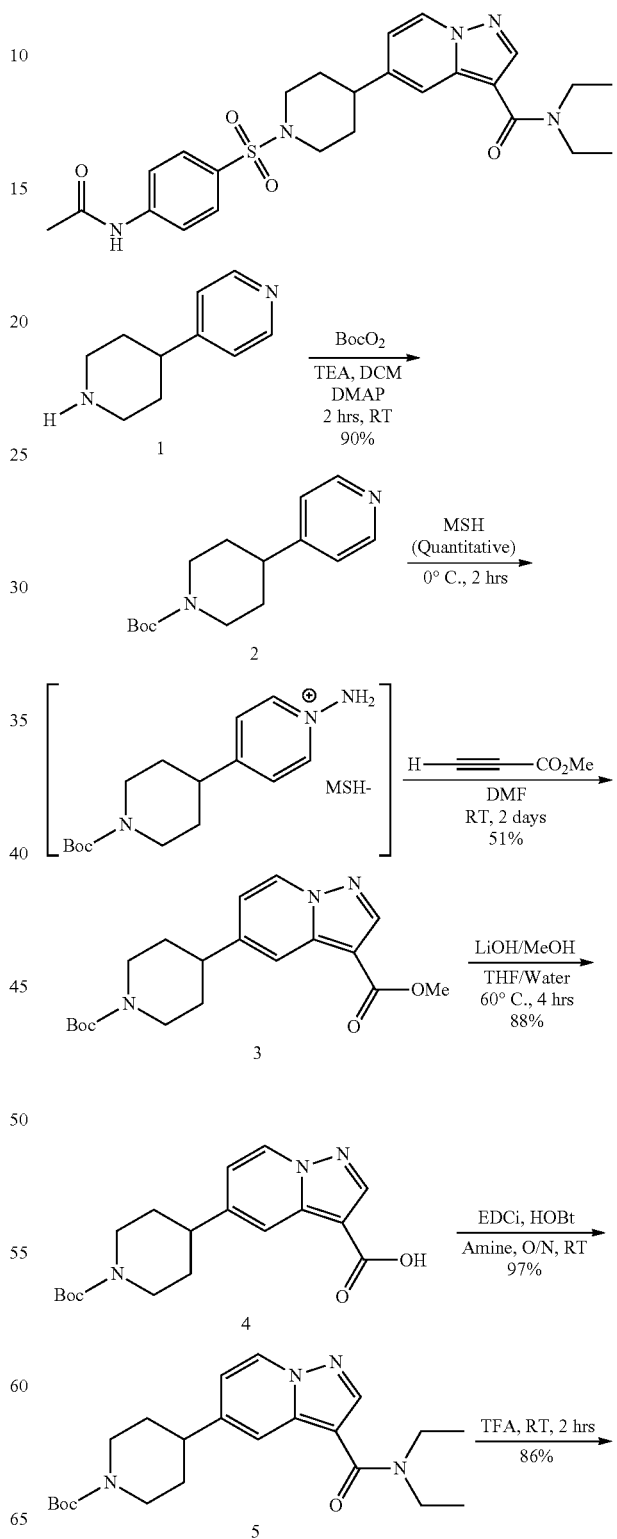

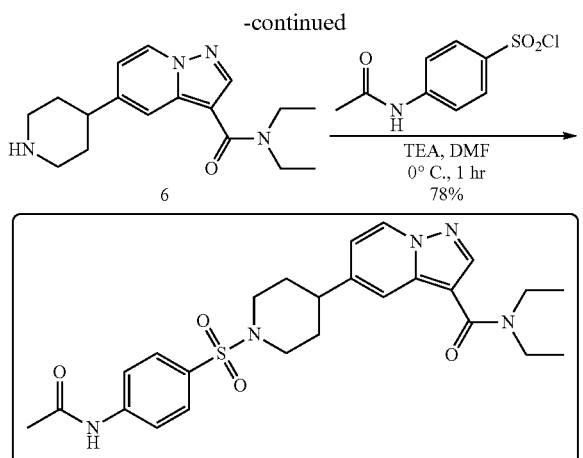

Preparation of Boc-4-pyridin-4-yl-piperidine (2)

Boc anhydride (1.52 g, 6.96 mmol) was added to a flame dried and argon purged round-bottom flask and dissolved in DCM (11 mL). DMAP (7.33 mg, 0.06 mmol), 4-pyridin-4-yl-piperidine (1.00 g, 6.33 mmol), followed by TEA (1.05 mL) was added in that order and the reaction was allowed to stir at room temperature for 2 hours. At this point, all starting material had been converted as seen on TLC. Reaction was washed with water twice, and once again with brine, dried with sodium sulfate and concentrated in vacuo. Product was purified via flash chromatography using a 50/50 EtOAc/Hexane gradient. Yield was 90%, 1.50 g, yellow oil. $^1$H NMR (400 MHz, Chloroform-d) δ 8.52 (dd, J=4.3, 1.9 Hz, 2H), 7.16-7.09 (m, 2H), 4.26 (s, 2H), 2.80 (t, J=12.5 Hz, 2H), 2.69-2.59 (m, 1H), 1.83 (d, J=13.1 Hz, 2H), 1.68-1.53 (m, 2H), 1.48 (s, 9H). m/z: 263.2 [M+H].

Preparation of
N-Boc-O-(mesitylsulfonyl)hydroxylamine
(N-Boc-MSH

2-Mesitylenesufonylchloride (2.00 g, 9.17 mmol) was added to a flame dried and argon purged round-bottom flask and dissolved in ether (18 mL), followed by the addition of N-Boc-hydroxylamine (1.47 g, 11.00 mmol). The flask was cooled to 0° C., and then TEA was added dropwise (1.3 mL). The reaction stirred for 2 hours at 0° C., at which all starting material had been converted as seen by TLC. The TEA-Cl, white solid, was filtered, and washed with ether. The filtrate was concentrated in vacuo, and purified via flash chromatography in 25/75 EtOAc/hexane gradient. Yield was quantitative, 2.16 g, white solid. $^1$H NMR (400 MHz, Chloroform-d) δ 7.77 (1H, s), 6.98 (2H, s), 2.66 (6H, s), 2.31 (3H, s), 1.30 (9H, s). $^{13}$C NMR: (100 MHz, CDCl$_3$) δ 154.5, 144.7, 142.2, 131.9, 128.7, 84.1, 27.9, 23.4, 21.4. m/z: 315.0 [M+H].

Preparation of O-mesitylenesulfonylhydroxylamine
(MSH)

TFA (2.1 mL) was added to a flame dried and argon purged round-bottom flask and cooled to 0° C. N-Boc-O-(mesitylsulfonyl)hydroxylamine (500 mg, 2.1 mmol) was added in 2 portions, and the reaction stirred at 0 C for two hours. After which, all starting material had been converted, as seen by TLC. Ice and cold water was added to the reaction to precipitate MSH. The MSH was filtered, washed with cold water, and dried under high-vacuum overnight to remove excess TFA and water. No further purification was necessary. Compound is a white solid, with a quantitative yield of 422 mg. $^1$H NMR: (400 MHz, Chloroform-d) δ 7.00 (s, 2H), 4.80 (s, 3H), 2.65 (s, 6H), 2.33 (s, 3H). $^{13}$C NMR: (100 MHz, CDCl3): δ 21.1, 22.7, 128.9, 131.7, 141.0, 143.9.

General Procedure for (3)

Boc-4-pyridin-4-yl-piperidine was dissolved in DMF (3.8 mL) and added to a flame dried and argon purged round-bottom flask. MSH was added in two portions (535 mg, 2.5 mmol) and the reaction stirred at RT for two hours. After which, methyl prop-2-ynoate was added (170 µL, 1.9 mmol) followed by K$_2$CO$_3$ (264 mg, 1.91 mmol). The reaction stirred for 2 days at RT, and was then diluted with water and extracted three times with DCM. Compound was purified via flash chromatography and eluted with a 1:1 mixture of EtOAc and hexanes. Fractions were concentrated in-vacuo and dried under high-vac overnight.

Preparation of tert-butyl 4-[3-(methoxycarbonyl)pyrazolo[1,5-a]pyridin-5-yl]piperidine-1-carboxylate (3A): Yield: 53%, light orange solid. $^1$HNMR: (400 MHz, Acetonitrile-d$_3$) δ 8.51 (s, 1H), 8.30 (s, 1H), 7.92 (s, 1H), 6.98 (d, J=7.2 Hz, 1H), 4.21 (d, J=13.3 Hz, 2H), 3.86 (s, 3H), 2.85 (m, J=14.8, 13.1 Hz, 3H), 1.87 (d, J=14.0 Hz, 3H), 1.65-1.53 (m, 3H), 1.48-1.42 (s, 9H). $^{13}$C NMR (101 MHz, Chloroform-d) δ 164.06, 154.88, 146.28, 145.29, 141.21, 129.20, 115.69, 113.92, 103.16, 79.86, 51.35, 42.47, 28.60. m/z: 360.19 [M+H].

Preparation of tert-butyl 4-[3-(ethoxycarbonyl)-2-(trifluoromethyl)pyrazolo[1,5-a]pyridin-5-yl]piperidine-1-carboxylate (3B): 40% yield, light yellow solid. $^1$H NMR (400 MHz, Chloroform-d) δ 8.47 (dd, J=7.5, 3.2 Hz, 1H), 8.10 (s, 1H), 6.97 (d, J=2.1 Hz, OH), 4.49-4.36 (m, 2H), 2.93-2.68 (m, 3H), 1.91 (d, J=13.1 Hz, 2H), 1.69 (t, J=12.6 Hz, 2H), 1.61-1.55 (m, 3H), 1.51 (s, 4H), 1.43 (dq, J=6.7, 3.3 Hz, 2H).

Preparation of tert-butyl4-[3-(methoxycarbonyl)-2-methylpyrazolo[1,5-a]pyridin yl]piperidine-1-carboxylate (3C): 34% yield, light yellow solid, $^1$H NMR (400 MHz, Chloroform-d) δ 8.34 (d, J=7.0 Hz, OH), 7.89 (s, OH), 6.76 (d, J=7.1 Hz, OH), 4.13 (qd, J=7.2, 2.2 Hz, 1H), 3.93 (s, 1H), 1.89 (d, J=13.1 Hz, 1H), 1.72-1.65 (m, 1H), 1.50 (s, 4H). $^{13}$C NMR (101 MHz, Chloroform-d) δ 164.81, 156.10, 154.81, 145.99, 142.47, 128.42, 115.56, 113.24, 100.69, 79.78, 51.06, 42.44, 28.55, 14.51. m/z: 374.21 [M+H].

General Procedure for (4)

tert-butyl 4-[3-(methoxycarbonyl)pyrazolo[1,5-a]pyridin-5-yl]piperidine-1-carboxylate (204 mg, 0.56 mmol) was dissolved in a 2:1:2 solvent mixture of THF:MeOH:Water (2.25 mL, 1.5 mL, 2.25 mL) and added to an argon filled round-bottom flask, equipped with a reflux condenser. LiOH was added (13 mg, 0.56 mmol) and the reaction was heated to 60° C. and stirred at this temperature for 4 hours. After which, all starting material had been converted, as seen by TLC. DCM was added to the reaction, and then washed with 1 M HCl×2, followed by water. Aqueous extracts were combined and extracted once more with DCM. The organic extracts were combined and washed with brine, followed by drying with Na2SO4 and then concentrated in vacuo. Crude product was purified via flash chromatography with a 70:30 solvent mixture of EtOAc/Hexanes.

Preparation of 5-{1-[(tert-butoxy)carbonyl]piperidin-4-yl}pyrazolo[1,5-a]pyridine-3-carboxylic acid (4A): 88% yield, white solid. $^1$H NMR (400 MHz, Chloroform-d) δ 8.39 (dd, J=7.4, 2.8 Hz, 1H), 8.02 (d, J=3.0 Hz, 1H), 7.96 (s, 1H), 6.75 (d, J=7.4 Hz, 1H), 4.27 (s, 2H), 3.66-3.50 (m, 3H), 2.78 (d, J=15.5 Hz, 1H), 2.74-2.68 (m, 0H), 1.87 (d, J=13.1 Hz, 2H), 1.67 (s, 1H), 1.48 (s, 3H). $^{13}$C NMR (101 MHz, Chloroform-d) δ 169.27, 155.20, 146.47, 141.95, 129.71, 116.28, 114.53, 102.99, 80.24, 42.84, 32.82, 28.93. m/z: 344.05 [M+H].

Preparation of 5-{1-[(tert-butoxy)carbonyl]piperidin-4-yl}-2-methylpyrazolo[1,5-a]pyridine-3-carboxylic acid (4B): 78% yield, white solid. $^1$H NMR (400 MHz, Chloroform-d) δ 8.38 (d, J=9.8 Hz, 1H), 7.98 (s, 1H), 6.80 (d, J=7.1 Hz, 1H), 4.30 (s, 1H), 2.92-2.76 (m, 3H), 2.71 (s, 3H), 1.90 (d, J=13.0 Hz, 2H), 1.69 (q, J=12.2, 11.6 Hz, 2H), 1.50 (s, 9H). $^{13}$C NMR (100 MHz, Chloroform-d) δ 169.40, 157.11, 154.85, 146.69, 143.07, 128.60, 115.95, 113.54, 100.05, 79.83, 77.31, 42.54, 28.57. m/z: 360.19 [M+H].

Preparation of 5-{1-[(tert-butoxy)carbonyl]piperidin-4-yl}-2-(trifluoromethyl)pyrazolo[1,5-a]pyridine-3-carboxylic acid (4C): Yield: 75%, white solid. $^1$H NMR (400 MHz, Chloroform-d) δ 8.51 (d, J=8.3 Hz, 1H), 8.15 (s, 1H), 7.01 (d, J=7.2 Hz, 1H), 4.33 (s, 1H), 2.85 (t, J=12.9 Hz, 3H), 1.92 (d, J=13.0 Hz, 2H), 1.70 (q, J=11.3 Hz, 2H), 1.50 (s, 9H). $^{13}$C NMR (101 MHz, CHLOROFORM-D) δ 168.74, 168.70, 154.57, 147.72, 129.03, 122.68 (q, J=3.8) Hz 116.71, 115.56, 79.72, 77.16, 77.16, 76.84, 76.52, 42.34, 32.10, 28.29. m/z: 436.15 [M+Na$^+$]

General Procedure for (5)

5-{1-[(tert-butoxy)carbonyl]piperidin-4-yl}pyrazolo[1,5-a]pyridine-3-carboxylic acid (75 mg, 0.22 mmol) was dissolved in DCM (2.2 mL) and added to an argon filled round-bottom flask. HOBt (60 mg, 0.44 mmol), EDCi (68 mg, 0.44 mmol), and diethylamine (34 µL, 0.33 mmol) were added to the flask in that order. The reaction was stirred at RT overnight after which all starting material had been converted, as seen by TLC. DCM was added to the reaction, and then washed with 1 M NaOH×2, followed by water. Aqueous extracts were combined and extracted once more with DCM. The organic extracts were combined and washed with brine, followed by drying with Na$_2$SO$_4$ and then concentrated in-vacuo. Crude product was purified via flash chromatography with a 60:40 solvent mixture of EtOAc/hexanes.

tert-butyl 4-[3-(diethylcarbamoyl)pyrazolo[1,5-a]pyridin-5-yl]piperidine-1-carboxylate (5A): 75% yield, white solid. $^1$H NMR (400 MHz, Acetonitrile-d$_3$) δ 8.45 (d, J=7.6 Hz, 1H), 8.04 (s, 1H), 7.80 (s, 1H), 6.89 (d, J=7.1 Hz, 1H), 4.26-4.11 (m, 2H), 3.64-3.45 (m, 4H), 2.81 (d, J=15.9 Hz, 3H), 1.56 (dd, J=12.6, 4.4 Hz, 1H), 1.45 (s, 9H), 1.23 (td, J=7.1, 2.7 Hz, 7H); $^{13}$C NMR (100 MHz, Chloroform-d) δ 164.45, 154.81, 144.41, 141.93, 141.13, 128.46, 116.44, 113.59, 106.14, 79.75, 42.38, 32.49, 28.60. m/z: 401.25 [M+H].

tert-butyl 4-[3-(diethylcarbamoyl)-2-(trifluoromethyl)pyrazolo[1,5-a]pyridin-5-yl]piperidine-1-carboxylate (5B): 89% yield, white solid. $^1$H NMR (400 MHz, Chloroform-d) δ 8.41 (d, J=8.5 Hz, 1H), 7.30 (s, 1H), 6.85 (d, J=7.3 Hz, 1H), 2.89-2.76 (m, 2H), 2.71 (t, J=12.4 Hz, 2H), 1.85 (d, J=13.0 Hz, 2H), 1.74-1.53 (m, 4H), 1.48 (s, 9H), 1.33-1.22 (m, 3H). $^{13}$C NMR (100 MHz, Chloroform-d) δ 162.41, 154.51, 144.24, 140.42 (d, J=37.5 Hz), 138.69, 128.47, 122.26, 119.57, 114.84, 113.83, 106.10, 79.62, 77.05, 41.93, 32.05, 28.26, 20.89. m/z: 469.24 [M+H].

tert-butyl 4-[3-(diethylcarbamoyl)-2-methylpyrazolo[1,5-a]pyridin-5-yl]piperidine-1-carboxylate (5C): 74% yield, yellow oil. $^1$H NMR (400 MHz, Chloroform-d) δ 8.28 (d, J=7.6 Hz, 1H), 7.20 (s, 1H), 6.61 (d, J=7.2 Hz, 1H), 4.11 (d, J=7.2 Hz, 2H), 3.49 (d, J=7.4 Hz, 2H), 2.80 (d, J=13.1 Hz, 1H), 2.66 (t, J=12.2 Hz, 1H), 2.46 (s, 3H), 1.84 (d, J=13.0 Hz, 2H), 1.60 (q, J=15.7, 13.9 Hz, 2H), 1.48 (s, 9H), 1.26 (d, J=7.5 Hz, 3H), 1.16 (d, J=7.4 Hz, 6H). $^{13}$C NMR (101 MHz, CHLOROFORM-D) δ 165.95, 154.83, 150.51, 143.38, 139.49, 128.03, 113.20, 112.04, 105.96, 79.75, 77.43, 60.48, 42.21, 32.45, 28.54, 21.14, 14.28, 14.00, 13.02. m/z: 437.25 [M+Na$^+$].

tert-butyl 4-[3-(methylcarbamoyl)pyrazolo[1,5-a]pyridine-5-yl]piperidine-1-carboxylate (5D): Yield: 95%, white solid; $^1$H NMR (400 MHz, Chloroform-d) δ 8.39 (d, J=7.1 Hz, 1H), 8.12 (d, J=9.2 Hz, 2H), 6.77 (d, J=7.2 Hz, 1H), 6.03 (s, 1H), 4.26 (d, J=13.4 Hz, 2H), 3.00 (s, 3H), 2.89-2.67 (m, 3H), 1.86 (d, J=13.1 Hz, 2H), 1.65 (q, J=13.2, 12.6 Hz, 2H), 1.48 (s, 9H). $^{13}$C NMR (101 MHz, CHLOROFORM-D) δ 164.57, 155.15, 145.44, 141.20, 140.98, 128.97, 116.53, 114.08, 106.66, 77.16, 42.69, 32.77, 28.90, 26.56. m/z: 359.10 [M+H].

tert-butyl 4-[3-(pyrrolidine-1-carbonyl)pyrazolo[1,5-a]pyridin-5-yl]piperidine carboxylate (5G): 75% yield. $^1$H NMR (400 MHz, Chloroform-d) δ 8.41 (s, 1H), 8.15 (s, 2H), 6.78 (d, J=7.1 Hz, 1H), 4.26 (d, J=13.5 Hz, 1H), 3.74 (d, J=31.6 Hz, 4H), 2.88-2.63 (m, 4H), 1.99 (d, J=17.8 Hz, 4H), 1.86 (d, J=13.1 Hz, 2H), 1.64 (q, J=13.9, 13.5 Hz, 2H), 1.48 (s, 9H). 13C NMR (101 MHz, CHLOROFORM-D) δ 154.79, 144.89, 141.96, 141.91, 131.69, 128.37, 126.61, 124.87, 116.84, 113.90, 106.58, 100.00, 79.73, 77.43, 77.11, 76.79, 42.31, 32.42. m/z: 399.24 [M+H].

tert-butyl 4-[3-(piperidine-1-carbonyl)pyrazolo[1,5-a]pyridin-5-yl]piperidine-1-carboxylate (5J): $^1$H NMR (500 MHz, Chloroform-d) δ 8.41 (d, J=7.5 Hz, 1H), 8.15 (s, 2H), 6.76 (dd, J=7.1, 1H), 4.30 (d, J=12.5, 2H), 3.85 (t, J=31.6 Hz, 4H), 3.18-3.02 (m, 3H), 2.01 (d J=13.0, 2H), 1.82-1.75 (m, 1H), 1.79-1.69 (m, 7H), 1.68-1.64 (m, 1H), 1.47 (s, 9H). 13C NMR (101 MHz, Chloroform-d) δ 155.63, 147.76, 142.66, 142.26, 131.37, 130.37, 125.73, 113.37, 79.77, 78.73, 77.43, 40.29, 38.32, 29.55, 26.33, 25.43, 24.26. m/z: 413.15 [M+H].

tert-butyl 4-(3-(4-methylpiperidine-1-carbonyl)pyrazolo[1,5-a]pyridin-5-yl)piperidine-1-carboxylate (5M): $^1$H NMR (400 MHz, Chloroform-d) δ 8.38 (d, J=8.6 Hz, 1H), 7.99 (s, 1H), 7.78 (s, 1H), 6.74 (d, J=7.6 Hz, 1H), 4.45 (d, J=12.9 Hz, 2H), 4.26 (s, 2H), 2.99 (d, J=13.2 Hz, 2H), 2.76 (dt, J=34.9, 12.7 Hz, 3H), 1.87 (d, J=13.1 Hz, 2H), 1.68 (dt, J=37.7, 13.0 Hz, 5H), 1.47 (s, 9H), 1.24 (p, J=13.4, 12.1 Hz, 2H), 0.99 (t, J=5.0 Hz, 3H). $^{13}$C NMR (101 MHz, CHLOROFORM-D) δ 164.46, 155.12, 144.63, 142.31, 141.64, 116.16, 113.81, 106.25, 80.07, 77.80, 77.48, 77.16, 42.64, 34.89, 32.77, 31.77, 29.02, 28.95, 28.87, 28.80, 22.25. m/z: 427.20 [M+H].

tert-butyl 4-(3-(3,5-dimethylpiperidine-1-carbonyl)pyrazolo[1,5-a]pyridin-5-yl)piperidine-1-carboxylate (5P): $^1$H NMR (400 MHz, Chloroform-d) δ 8.39 (d, J=7.1 Hz, 1H), 7.98 (s, 1H), 7.77 (s, 1H), 6.74 (d, J=7.2 Hz, 1H), 4.26 (s, 2H), 3.76 (d, J=12.2 Hz, 1H), 3.55-3.06 (m, 0H), 2.86-2.66 (m, 3H), 2.00 (s, 1H), 1.87 (d, J=12.4 Hz, 3H), 1.79-1.56 (m, 5H), 1.49 (t, 1H), 1.47 (s, 9H), 0.93 (dd, J=16.8, 6.7 Hz, 6H). $^{13}$C NMR (101 MHz, CHLOROFORM-D) δ 163.85, 154.77, 144.31, 141.98, 141.32, 128.51, 128.49, 115.77, 113.51, 105.93, 79.72, 77.44, 77.13, 76.81, 42.66, 42.28, 39.72, 32.45, 32.43, 28.55, 19.14, 18.26, 14.29. m/z: 441.20 [M+H].

tert-butyl 4-(3-(benzylcarbamoyl)pyrazolo[1,5-a]pyridin-5-yl)piperidine-1-carboxylate (5S): $^1$H NMR (400 MHz, Chloroform-d) δ 8.40-8.36 (m, 1H), 8.16 (s, 1H), 8.09 (s, 1H), 7.34 (d, J=8.9 Hz, 4H), 7.29-7.24 (m, 1H), 6.77 (d, J=8.3 Hz, 1H), 6.26 (s, 1H), 4.64 (s, 2H), 4.25 (d, J=13.1 Hz, 1H), 2.76 (dt, J=24.1, 12.3 Hz, 3H), 1.86 (d, J=13.2 Hz, 2H), 1.65 (q, J=13.3, 12.3 Hz, 3H), 1.47 (s, 9H). $^{13}$C NMR (101

MHz, CHLOROFORM-D) δ 163.40, 154.81, 145.34, 141.09, 140.69, 138.74, 128.85, 128.71, 127.69, 127.64, 116.33, 113.88, 106.05, 79.79, 77.16, 43.47, 42.41, 36.77, 32.46, 28.60, 24.90, 23.52. m/z: 457.22 [M+Na$^+$].

tert-butyl 4-(3-(azepane-1-carbonyl)pyrazolo[1,5-a]pyridin-5-yl)piperidine carboxylate (5V): $^1$H NMR (400 MHz, Chloroform-d) δ 8.39 (d, J=6.4 Hz, 1H), 8.04 (s, 1H), 7.97 (s, 1H), 6.75 (d, J=7.2 Hz, 1H), 4.26 (d, J=13.4 Hz, 2H), 3.73 (s, 4H), 2.76 (dt, J=26.0, 12.6 Hz, 3H), 1.86 (d, J=11.9 Hz, 6H), 1.65 (d, J=13.1 Hz, 6H), 1.47 (s, 9H). 13C NMR (101 MHz, CHLOROFORM-D) δ 164.99, 154.75, 144.36, 141.90, 141.54, 128.39, 116.46, 113.54, 106.28, 79.68, 77.43, 77.11, 76.80, 42.34, 32.45, 28.55. m/z: 449.25 [M+Na$^+$].

General Procedure for (6)

tert-butyl 4-[3-(diethylcarbamoyl)pyrazolo[1,5-a]pyridin-5-yl]piperidine-1-carboxylate (100 mg, 0.25 mmol) was dissolved in DCM (250 μL) and added to an argon purged round-bottom flask. TFA (2.5 mL) was added to the flask and stirred at RT for 1 hr. Reaction was diluted with DCM, and 1 M NaOH was added until aqueous solution was basic. The aqueous layer was extracted with DCM×3. The organic extracts were combined and washed with brine, followed by drying with Na$_2$SO$_4$ and then concentrated in-vacuo. Crude product was purified via flash chromatography with a 10:90 solvent mixture of MeOH:DCM.

N,N-diethyl-5-(piperidin-4-yl)pyrazolo[1,5-a]pyridine-3-carboxamide (6A): 87% yield, 66 mg, white solid. $^1$H NMR (400 MHz, Chloroform-d) δ 8.38 (d, J=7.1 Hz, 1H), 8.01 (s, 1H), 7.93 (s, 1H), 6.78 (d, J=7.5 Hz, 1H), 3.59 (d, J=7.1 Hz, 4H), 3.23 (d, J=12.2 Hz, 2H), 2.74 (q, J=15.6, 14.1 Hz, 3H), 2.48 (s, 1H), 1.89 (d, J=12.9 Hz, 2H), 1.69 (q, J=12.5, 11.0 Hz, 2H), 1.34-1.25 (m, 7H). $^{13}$C NMR (101 MHz, CHLOROFORM-D) δ 164.84, 145.37, 142.16, 141.41, 128.74, 116.64, 113.85, 106.42, 77.79, 77.48, 77.44, 77.16, 46.98, 42.80, 33.64, 30.13, 14.27. m/z: 301.05 [M+H].

The following compounds were used in step 7 without further characterization:

N,N-diethyl-2-methyl-5-(piperidin-4-yl)pyrazolo[1,5-a]pyridine-3-carboxamide (6B).
N,N-diethyl-5-(piperidin-4-yl)-2-(trifluoromethyl)pyrazolo[1,5-a]pyridine-3-carboxamide (6C).
N-methyl-5-(piperidin-4-yl)pyrazolo[1,5-a]pyridine-3-carboxamide (6D).
N,2-dimethyl-5-(piperidin-4-yl)pyrazolo[1,5-a]pyridine-3-carboxamide (6E).
N-methyl-5-(piperidin-4-yl)-2-(trifluoromethyl)pyrazolo[1,5-a]pyridine-3-carboxamide (6F).
5-(piperidin-4-yl)pyrazolo[1,5-a]pyridin-3-yl)(pyrrolidin-1-yl)methanone (6G).
2-methyl-5-(piperidin-4-yl)pyrazolo[1,5-a]pyridin-3-yl)(pyrrolidin-1-yl)methanone (6H).
5-(piperidin-4-yl)-2-(trifluoromethyl)pyrazolo[1,5-a]pyridin-3-yl)(pyrrolidin-1-yl)methanone (6I).
piperidin-1-yl(5-(piperidin-4-yl)pyrazolo[1,5-a]pyridin-3-yl)methanone (6J).
(2-methyl-5-(piperidin-4-yl)pyrazolo[1,5-a]pyridin-3-yl)(piperidin-1-yl)methanone (6K).
piperidin-1-yl(5-(piperidin-4-yl)-2-(trifluoromethyl)pyrazolo[1,5-a]pyridin-3-yl)methanone (6L).
azepan-1-yl(5-(piperidin-4-yl)pyrazolo[1,5-a]pyridin-3-yl)methanone (6M).
azepan-1-yl(2-methyl-5-(piperidin-4-yl)pyrazolo[1,5-a]pyridin-3-yl)methanone (6N).
azepan-1-yl(5-(piperidin-4-yl)-2-(trifluoromethyl)pyrazolo[1,5-a]pyridin-3-yl)methanone (6O).
N-benzyl-5-(piperidin-4-yl)pyrazolo[1,5-a]pyridine-3-carboxamide (6P).
N-benzyl-2-methyl-5-(piperidin-4-yl)pyrazolo[1,5-a]pyridine-3-carboxamide (6Q).
N-benzyl-5-(piperidin-4-yl)-2-(trifluoromethyl)pyrazolo[1,5-a]pyridine-3-carboxamide (6R).
(4-methylpiperidin-1-yl)(5-(piperidin-4-yl)pyrazolo[1,5-a]pyridin-3-yl)methanone (6S).
(2-methyl-5-(piperidin-4-yl)pyrazolo[1,5-a]pyridin-3-yl)(4-methylpiperidin-1-yl)methanone (6T)
(4-methylpiperidin-1-yl)(5-(piperidin-4-yl)-2-(trifluoromethyl)pyrazolo[1,5-a]pyridin-3-yl)methanone (6U).
(3,5-dimethylpiperidin-1-yl)(5-(piperidin-4-yl)pyrazolo[1,5-a]pyridin-3-yl)methanone (6V).
(3,5-dimethylpiperidin-1-yl)(2-methyl-5-(piperidin-4-yl)pyrazolo[1,5-a]pyridin-3-yl)methanone (6W)
(3,5-dimethylpiperidin-1-yl)(5-(piperidin-4-yl)-2-(trifluoromethyl)pyrazolo[1,5-a]pyridin-3-yl)methanone (6X).

General Procedure for (7)

N,N-diethyl-5-(piperidin-4-yl)pyrazolo[1,5-a]pyridine-3-carboxamide (82 mg, 0.27 mmol) was dissolved in DCM (900 μL, 0.3 M) and added to a flame-dried, argon purged round-bottom flask. The flask was cooled to 0° C., and TEA (90 μL) was added, followed by 4-acetamidobenzenesulfonyl chloride and stirred at RT for 1 hr. The reaction was diluted with additional DCM and washed with water twice. The aqueous extracts were combined and extracted again with ethyl acetate. Organic extracts were combined and washed with brine, followed by drying with Na$_2$SO$_4$ and then concentrated in-vacuo. Crude product was purified via flash chromatography with a 10:90 solvent mixture of MeOH:DCM.

Z231-0326: 78% yield, white solid. $^1$H NMR: (400 MHz, Chloroform-d) δ 8.40 (d, J=7.1 Hz, 1H), 8.03 (s, 1H), 7.85-7.66 (m, 6H), 6.71 (d, J=7.0 Hz, 1H), 4.13 (dd, J=7.0, 1.1 Hz, 1H), 3.98 (d, J=11.7 Hz, 2H), 3.61 (q, J=7.1 Hz, 3H), 2.55-2.39 (m, 3H), 2.24 (s, 3H), 1.88 (d, J=13.0 Hz, 2H), 1.76 (d, J=13.7 Hz, 2H), 1.32 (t, J=7.2 Hz, 5H), 1.29 (dd, J=2.4, 1.2 Hz, 1H), 1.26 (s, 6H). 13C NMR (100 MHz, Chloroform-d) δ 164.22, 143.50, 141.47, 143.11, 140.86, 132.89, 129.53, 128.33, 128.29, 127.56, 116.37, 112.69, 105.99, 46.21, 41.19, 31.56, 21.41. m/z: 497.0 [M+H].

N,N-diethyl-5-[1-(4-methylbenzenesulfonyl)piperidin-4-yl]pyrazolo[1,5-a]pyridine-3-carboxamide (7A): 63% yield across two steps, white solid. $^1$H NMR (400 MHz, Chloroform-d) δ 8.38 (dd, J=7.3, 2.2 Hz, 1H), 8.01 (dd, J=3.8, 2.0 Hz, 1H), 7.90 (d, J=2.4 Hz, 1H), 7.67 (ddd, J=8.1, 3.8, 2.0 Hz, 2H), 7.38-7.30 (m, 2H), 6.69 (ddt, J=5.7, 3.9, 2.0 Hz, 1H), 3.93 (d, 2H), 3.57 (tt, J=9.3, 5.9 Hz, 4H), 2.51 (tt, J=11.7, 3.8 Hz, 1H), 2.44 (s, 3H), 2.34 (tq, J=8.8, 2.9 Hz, 2H), 1.96-1.78 (m, 4H), 1.33-1.22 (m, 6H). $^{13}$C NMR (100 MHz, Chloroform-d) δ 164.22, 143.50, 141.47, 143.11, 140.86, 132.89, 129.53, 128.33, 128.29, 127.56, 116.37, 112.69, 105.99, 46.21, 41.19, 31.56, 21.41. m/z: 455.21 [M+H].

methyl N-[4-({4-[3-(diethylcarbamoyl)pyrazolo[1,5-a]pyridin-5-yl]piperidin yl}sulfonyl)phenyl]carbamate (7C): 44% yield across two steps, white solid. $^1$H NMR (400 MHz, Chloroform-d) δ 8.39 (d, J=7.2 Hz, 1H), 8.03 (s, 1H), 7.86 (s, 1H), 7.75 (d, J=8.2 Hz, 2H), 7.60 (d, J=8.5 Hz, 2H), 7.17 (s, 1H), 6.70 (d, J=9.1 Hz, 1H), 3.95 (d, J=11.7 Hz, 2H), 3.81 (s, 3H), 3.60 (q, J=7.1 Hz, 4H), 2.51 (t, J=12.0 Hz, 1H), 2.42 (t, J=11.3 Hz, 2H), 1.89 (d, J=13.1 Hz, 2H), 1.79 (q, J=12.1 Hz, 2H), 1.31 (t, J=7.1 Hz, 6H). $^{13}$C NMR (100 MHz, Chloroform-d) δ 164.76, 154.02, 143.83, 142.72, 142.13, 141.55, 130.98, 129.53, 128.98, 118.83, 116.92, 113.58, 106.58, 53.20, 46.89, 41.84, 32.00. m/z: 514.21 [M+H].

N-[4-({4-[3-(pyrrolidine-1-carbonyl)pyrazolo[1,5-a]pyridin-5-yl]piperidin-1-yl}sulfonyl)phenyl]acetamide (7H): 44% yield across two step, white solid. $^1$H NMR (400 MHz, Chloroform-d) δ 8.40 (dd, J=7.1, 0.9 Hz, 1H), 8.16 (s, 1H), 8.03 (s, 1H), 7.89 (s, 1H), 7.85-7.66 (m, 4H), 6.73 (dd, J=7.2, 2.1 Hz, 1H), 3.97 (d, J=12.0 Hz, 2H), 3.81-3.70 (m, 4H), 2.50 (q, J=14.0, 12.4 Hz, 3H), 2.21 (s, 3H), 2.04-1.95 (m, 4H), 1.85 (d, J=12.9 Hz, 2H), 1.79-1.66 (m, 2H). $^{13}$C NMR (101 MHz, CHLOROFORM-d) δ 164.27, 154.80, 144.39, 141.90, 141.18, 138.42, 128.51, 126.64, 124.83, 115.68, 113.49, 109.96, 105.72, 79.76, 77.43, 42.25, 32.40, 28.55, 26.33, 24.80. m/z: 496.10 [M+H].

N-[4-({4-[3-(piperidine-1-carbonyl)pyrazolo[1,5-a]pyridin-5-yl]piperidin-1-yl}sulfonyl)phenyl]acetamide (7M): 80% yield across two step, white solid. $^1$H NMR (400 MHz, Chloroform-d) δ 8.38 (dd, J=7.2, 0.9 Hz, 1H), 8.00 (s, 1H), 7.92-7.69 (m, 4H), 7.66 (s, 1H), 6.69 (dd, J=7.2, 2.0 Hz, 1H), 3.96 (d, J=11.8 Hz, 2H), 3.71 (t, J=5.4 Hz, 4H), 2.47 (ddd, J=23.6, 12.8, 9.5 Hz, 3H), 2.21 (s, 3H), 1.87 (d, J=13.1 Hz, 2H), 1.84-1.61 (m, 8H). $^{13}$C NMR (101 MHz, CHLOROFORM-D) δ 169.06, 164.21, 143.53, 142.56, 142.03, 141.12, 131.12, 128.97, 128.79, 119.74, 115.78, 113.26, 77.48, 77.16, 77.16, 76.84, 46.54, 41.39, 31.61, 26.38, 24.82, 24.74. m/z: 510.20 [M+H].

N-[4-({4-[3-(azepane-1-carbonyl)pyrazolo[1,5-a]pyridin-5-yl]piperidin-1-yl}sulfonyl)phenyl]acetamide (7R): 68% yield across two steps, white solid. $^1$H NMR (400 MHz, Chloroform-d) δ 7.93 (s, 1H), 7.83 (d, J=8.3 Hz, 1H), 7.48 (s, 1H), 7.17 (q, J=8.6 Hz, 5H), 6.15 (d, J=7.1 Hz, 1H), 3.37 (d, J=11.7 Hz, 2H), 3.17 (s, 4H), 1.96-1.80 (m, 3H), 1.60 (s, 3H), 1.30 (d, J=9.6 Hz, 6H), 1.21 (t, J=13.4 Hz, 3H), 1.08 (s, 4H). $^{13}$C NMR (101 MHz, CHLOROFORM-D) δ 168.83, 164.86, 143.32, 142.35, 141.36, 141.31, 130.69, 128.63, 128.38, 119.43, 116.05, 113.05, 105.97, 77.16, 50.66, 46.23, 41.11, 31.30, 24.39. m/z: 524.23 [M+H].

N-[4-({4-[3-(3,5-dimethylpiperidine-1-carbonyl)pyrazolo[1,5-a]pyridin yl]piperidin-1-yl}sulfonyl)phenyl]acetamide (7W): 78% yield across two steps, white solid. $^1$H NMR (400 MHz, Chloroform-d) δ 8.40 (dd, J=7.2, 1.1 Hz, 1H), 8.00 (dd, J=5.6, 1.0 Hz, 1H), 7.83-7.63 (m, 5H), 6.70 (d, J=7.3 Hz, 1H), 3.97 (d, J=12.1 Hz, 2H), 3.76 (d, J=9.4 Hz, 1H), 2.49 (dt, J=22.8, 11.7 Hz, 3H), 2.23 (s, 3H), 1.89 (d, J=11.9 Hz, 2H), 1.83-1.70 (m, 3H), 1.31-1.22 (m, 6H), 0.99-0.87 (m, 6H), 0.87-0.78 (m, 2H). $^{13}$C NMR (101 MHz, CHLOROFORM-D) δ 169.06, 164.82, 163.88, 143.53, 142.53, 142.01, 141.14, 128.93, 128.77, 119.68, 115.76, 113.26, 105.84, 77.44, 77.12, 76.81, 46.50, 42.58, 41.32, 31.57, 22.01, 24.69, 19.12, 18.25. m/z: 538.25 [M+H].

N-[4-({4-[3-(4-methylpiperidine-1-carbonyl)pyrazolo[1,5-a]pyridin-5-yl]piperidin-1-yl}sulfonyl)phenyl]acetamide (7AB): 65% yield across two steps, white solid. $^1$H NMR (400 MHz, Chloroform-d) δ 8.39 (d, J=9.3 Hz, 1H), 8.19 (s, 1H), 8.00 (s, 1H), 7.73 (s, 4H), 7.66 (s, 1H), 6.69 (d, J=7.3 Hz, 1H), 4.45 (d, J=13.1 Hz, 1H), 3.94 (d, J=11.7 Hz, 2H), 3.01 (d, J=12.9 Hz, 1H), 2.45 (dt, J=24.1, 12.0 Hz, 3H), 2.17 (s, 3H), 1.87 (d, J=13.2 Hz, 2H), 1.74 (p, J=12.0, 11.2 Hz, 6H), 1.23 (q, J=12.4, 11.2 Hz, 2H), 1.03-0.96 (m, 3H). $^{13}$C NMR (101 MHz, CHLOROFORM-D) δ 168.94, 164.13, 143.51, 142.46, 141.98, 141.14, 128.94, 128.74, 119.70, 115.79, 113.23, 105.85, 98.23, 46.49, 41.35, 34.52, 31.54, 31.38, 24.71, 21.84, 14.28. m/z: 526.21 [M+H].

N-{4-[(4-{3-[3-(hydroxymethyl)pyrrolidine-1-carbonyl]pyrazolo[1,5-a]pyridin-5-yl}piperidin-1-yl)sulfonyl]phenyl}acetamide (7AG): 40% yield across two steps, white sold. 1H NMR (400 MHz, Chloroform-d) δ 8.39 (dd, J=7.2, 2.1 Hz, 1H), 8.00 (d, J=2.2 Hz, 1H), 7.75 (td, J=8.2, 7.4, 3.2 Hz, 4H), 7.66 (s, 1H), 6.70 (dt, J=7.4, 2.2 Hz, 1H), 4.19-4.10 (m, 2H), 4.03 (s, 1H), 3.94 (d, J=11.9 Hz, 2H), 3.44 (t, J=11.3 Hz, 2H), 2.48 (dt, J=24.0, 12.1 Hz, 3H), 2.21 (dd, J=2.7, 1.6 Hz, 3H), 1.98 (d, J=12.5 Hz, 2H), 1.89 (d, J=13.1 Hz, 2H), 1.76 (q, J=12.4 Hz, 2H), 1.25 (q, J=2.7 Hz, 3H). $^{13}$C NMR (101 MHz, CHLOROFORM-D) δ 164.28, 154.77, 144.51, 141.97, 141.30, 128.58, 115.73, 113.56, 105.54, 98.05, 79.75, 77.42, 77.11, 76.79, 67.52, 42.31, 34.58, 32.44, 28.55, 14.28. m/z: 532.15 [M+H].

5-[1-(4-acetamidobenzenesulfonyl)piperidin-4-yl]-N,N-diethyl-2-methylpyrazolo[1,5-a]pyridine-3-carboxamide (7AI): 46% yield, white solid. $^1$H NMR (400 MHz, Chloroform-d) δ 8.82 (s, 1H), 8.28-8.22 (m, 1H), 7.66 (q, J=8.8 Hz, 4H), 6.54 (d, J=7.4 Hz, 1H), 3.89 (d, J=11.4 Hz, 2H), 2.43 (s, 4H), 2.34 (t, J=12.2 Hz, 3H), 2.13 (s, 3H), 1.89-1.67 (m, 8H), 1.15 (t, 7H). $^{13}$C NMR (101 MHz, Chloroform-d) δ 169.44, 166.06, 150.41, 142.78, 142.77, 139.28, 130.37, 128.82, 128.20, 119.55, 112.99, 112.05, 105.81, 50.80, 46.52, 41.14, 31.67, 24.50, 12.97. m/z: 512.23 [M+H].

5-[1-(4-acetamidobenzenesulfonyl)piperidin-4-yl]-N,N-diethyl-2-(trifluoromethyl)pyrazolo[1,5-a]pyridine-3-carboxamide (7BR): 65% yield across two steps, white solid. $^1$H NMR (400 MHz, Chloroform-d) δ 8.39 (d, J=10.8 Hz, OH), 8.10 (s, 1H), 7.68 (s, 4H), 7.20 (s, 1H), 6.78 (d, J=8.1 Hz, 1H), 3.94 (d, J=11.8 Hz, 2H), 3.28 (s, 1H), 2.49 (t, J=12.2 Hz, 1H), 2.40 (t, J=11.8 Hz, 2H), 2.18 (s, 3H), 1.88 (d, J=12.9 Hz, 2H), 1.76 (t, J=12.6 Hz, 2H), 1.33-1.20 (m, 6H). $^{13}$C NMR (100 MHz, Chloroform-d) δ 169.02, 162.77, 143.79, 142.42, 140.57, 138.79, 130.87, 128.93 (d, J=4.9 Hz), 119.60, 115.01, 113.92, 106.31, 77.32, 46.39, 41.12, 31.50, 24.68, 14.19. m/z: 566.21 [M+H].

5-[1-(benzenesulfonyl)piperidin-4-yl]-N,N-diethylpyrazolo[1,5-a]pyridine carboxamide (7DA): 57% yield across two steps, white solid. $^1$H NMR (400 MHz, Chloroform-d) δ 8.40 (dd, J=7.2, 0.9 Hz, 1H), 8.04 (s, 1H), 7.92 (dt, J=1.9, 0.9 Hz, 1H), 7.85-7.79 (m, 2H), 7.69-7.54 (m, 3H), 6.71 (dd, J=7.3, 2.0 Hz, 1H), 3.99 (dq, J=10.5, 2.7 Hz, 2H), 3.60 (q, J=7.2 Hz, 4H), 2.54 (tt, J=11.7, 4.0 Hz, 1H), 2.39 (td, J=11.9, 2.9 Hz, 2H), 2.00-1.79 (m, 4H), 1.31 (t, J=7.1 Hz, 6H). m/z: 441.19 [M+H].

N,N-diethyl-5-(1-methanesulfonylpiperidin-4-yl)pyrazolo[1,5-a]pyridine-3-carboxamide (7DE): 23% yield across two steps, white solid. 1H NMR (400 MHz, Chloroform-d) δ 8.42 (dd, J=7.2, 1.0 Hz, 1H), 8.04 (s, 1H), 7.99 (dq, J=2.0, 1.0 Hz, 1H), 6.77 (dd, J=7.2, 2.0 Hz, 1H), 3.96 (d, J=11.9 Hz, 2H), 3.60 (q, J=7.1 Hz, 4H), 2.84 (s, 3H), 2.81-2.70 (m, 3H), 2.01 (d, J=13.0 Hz, 2H), 1.94-1.82 (m, 2H), 1.31 (t, J=7.1 Hz, 6H). $^{13}$C NMR (101 MHz, Chloroform-d) δ 168.99, 142.64, 142.35, 138.37, 137.37, 126.42, 116.27, 96.58, 60.06, 41.62, 40.89, 39.76, 29.84, 22.50, 13.03. m/z: 379.17 [M+H].

N,N-diethyl-5-(1-phenylmethanesulfonylpiperidin-4-yl)pyrazolo[1,5-a]pyridine-3-carboxamide (7DJ): 23% yield across two steps. 1H NMR (400 MHz, Chloroform-d) δ 8.40 (s, 1H), 8.02 (s, 1H), 7.92 (s, 1H), 7.45-7.38 (m, 4H), 6.70 (d, J=7.0 Hz, 1H), 4.26 (s, 2H), 3.79 (d, J=12.4 Hz, 2H), 3.59 (d, J=7.2 Hz, 4H), 2.63 (dt, J=24.0, 12.0 Hz, 3H), 1.83 (d, J=13.1 Hz, 2H), 1.74-1.59 (m, 3H), 1.30 (t, 6H). $^{13}$C NMR (100 MHz, Chloroform-d) δ 164.31, 143.41, 141.77, 141.12, 130.79, 129.02, 128.94, 128.93, 128.60, 116.71, 112.97, 106.26, 57.39, 46.48, 41.77, 32.45. m/z: 455.21 [M+H].

N-benzyl-5-[1-(4-acetamidobenzenesulfonyl)piperidin-4-yl]pyrazolo[1,5-a]pyridine-3-carboxamide (7FM): 40% yield across two steps, white solid. $^1$H NMR (400 MHz, Chloroform-d) δ 8.40 (d, J=7.1 Hz, 1H), 8.10 (s, 1H), 8.04

(s, 1H), 7.94 (s, 1H), 7.75 (s, 3H), 7.37 (s, 4H), 7.26 (s, 2H), 6.74 (d, J=7.1 Hz, 1H), 6.23 (s, 1H), 4.71-4.61 (m, 2H), 3.96 (d, J=12.0 Hz, 2H), 2.58-2.40 (m, 3H), 2.19 (s, 3H), 1.87 (d, J=13.0 Hz, 2H), 1.76 (d, J=13.0 Hz, 2H). $^{13}$C NMR (101 MHz, CHLOROFORM-D) δ 168.69, 146.60, 142.34, 140.74, 129.00, 128.91, 127.89, 127.72, 119.74, 113.60, 99.66, 77.42, 77.11, 76.79, 46.46, 43.48, 41.51, 31.50, 24.86. m/z: 532.20 [M+H].

methyl N-[4-({4-[3-(methylcarbamoyl)pyrazolo[1,5-a]pyridin-5-yl]piperidin-1-yl}sulfonyl)phenyl]carbamate (7GQ): 87% yield across two steps, white solid. $^1$H NMR (400 MHz, Chloroform-d) δ 8.39 (d, J=7.1 Hz, 1H), 8.17-8.07 (m, 4H), 8.12 (d, J=9.2 Hz, 2H), 6.77 (d, J=7.2 Hz, 1H), 6.03 (s, 1H), 4.26 (d, J=13.4 Hz, 2H), 3.00 (s, 3H), 2.89-2.67 (m, 3H), 2.49 (s, 3H) 1.86 (d, J=13.1 Hz, 2H), 1.65 (q, J=13.2, 2H). $^{13}$C NMR (101 MHz, CHLOROFORM-D) δ 168.03, 164.57, 155.15, 145.44, 145.65, 144.67, 141.20, 140.98, 138.97, 137.98, 128.97, 116.53, 114.08, 106.66, 77.16, 42.69, 32.77, 28.90, 27.75, 26.56. m/z: 456.10 [M+H].

N,N-diethyl-5-[1-(4-fluorobenzenesulfonyl)piperidin-4-yl]pyrazolo[1,5-a]pyridine carboxamide (7HL): 60% yield across two steps. $^1$H NMR (400 MHz, Chloroform-d) δ 8.67 (m, 1H), 8.45 (s, 1H), 8.00 (m, 2H), 7.59 (d, J=1.5 Hz, 1H), 7.41 (m, 3H), 3.48 (q, J=6.3 Hz, 4H), 2.57 (m, 1H), 2.46 (m, 5H), 2.20 (m, 2H), 2.02 (m, 2H), 1.56 (t, J=6.3 Hz, 6H). $^{13}$C NMR (101 MHz, CHLOROFORM-D) δ 164.33, 143.04, 141.81, 141.21, 140.22, 134.83, 134.50, 128.70, 128.26, 122.01, 116.73, 112.99, 106.40, 77.48, 77.16, 76.84, 60.54, 46.55, 41.35, 31.88, 21.19, 14.33. m/z: 459.19 [M+H].

N,N-diethyl-5-{1-[4-(trifluoromethyl)benzenesulfonyl]piperidin-4-yl}pyrazolo[1,5-a]pyridine-3-carboxamide (7HM): 41% yield across two steps, white solid. $^1$H NMR (400 MHz, Chloroform-d) δ 8.40 (d, J=9.4 Hz, 1H), 8.03 (s, 1H), 7.92 (s, 3H), 7.85 (s, 1H), 7.82 (s, 1H), 6.70 (d, J=7.0 Hz, 1H), 3.99 (d, J=11.6 Hz, 2H), 3.59 (d, J=7.1 Hz, 4H), 2.55 (t, J=12.0 Hz, 1H), 2.43 (t, J=11.5 Hz, 2H), 1.97 (d, J=12.9 Hz, 2H), 1.88 (d, J=13.4 Hz, 2H), 1.32-1.26 (m, 6H). $^{13}$C NMR (101 MHz, CHLOROFORM-D) δ 164.33, 143.04, 141.81, 141.21, 140.22, 134.83, 134.50, 128.70, 128.26, 126.49 (q, J=3.8 Hz), 122.01, 116.73, 112.99, 106.40, 77.48, 77.16, 76.84, 60.54, 46.55, 41.35, 31.88, 21.19, 14.33. m/z: 509.18 [M+H].

The following compounds were synthesized in a similar manner to compounds Z231-0326 and 7A-7HM above:

benzyl N-[4-({4-[3-(diethylcarbamoyl)pyrazolo[1,5-a]pyridin-5-yl]piperidin-1-yl}sulfonyl)phenyl]carbamate (7HN). m/z: 590.35 [M+H]

4-({4-[3-(azetidine-1-carbonyl)pyrazolo[1,5-a]pyridin-5-yl]piperidin-1-yl}sulfonyl)aniline (7HO). m/z: 440.30 [M+H]

5-[1-(4-aminobenzenesulfonyl)piperidin-4-yl]-N,N-diethylpyrazolo[1,5-a]pyridine-3-carboxamide (7HP). m/z: 456.20 [M+H]

tert-butyl N-[4-({4-[3-(azetidine-1-carbonyl)pyrazolo[1,5-a]pyridin-5-yl]piperidin-1-yl}sulfonyl)phenyl]carbamate (7HQ). m/z: 540.30 [M+H]

5-{1-[4-(5-aminopentanamido)benzenesulfonyl]piperidin-4-yl}-N,N-diethylpyrazolo[1,5-a]pyridine-3-carboxamide (7HR). m/z: 555.30 [M+H]

5-{1-[4-(3-aminopropanamido)benzenesulfonyl]piperidin-4-yl}-N,N-diethylpyrazolo[1,5-a]pyridine-3-carboxamide (7HS). m/z: 525.25 [M+H]

5-{1-[4-(acetamidomethyl)benzenesulfonyl]piperidin-4-yl}-N,N-diethylpyrazolo[1,5-a]pyridine-3-carboxamide (7HT). m/z: 512.30 [M+H]

5-{1-[4-(4-aminobutanamido)benzenesulfonyl]piperidin-4-yl}-N,N-diethylpyrazolo[1,5-a]pyridine-3-carboxamide (7HU). m/z: 541.3 [M+H]

N,N-diethyl-5-{1-[4-(methylcarbamoyl)benzenesulfonyl]piperidin-4-yl}pyrazolo[1,5-a]pyridine-3-carboxamide (7HV). m/z: 498.25 [M+H]

N-[4-({4-[3-(pyrrolidine-1-carbonyl)pyrazolo[1,5-a]pyridin-5-yl]piperidin yl}sulfonyl)phenyl]cyclohexanecarboxamide (7HW). m/z: 564.75 [M+H]

N,N-diethyl-5-{1-[4-(2-oxopropyl)benzenesulfonyl]piperidin-4-yl}pyrazolo[1,5-a]pyridine carboxamide (7HX). m/z: 497.3 [M+H]

5-{1-[(1-acetyl-2,3-dihydro-1H-indol-5-yl)sulfonyl]piperidin-4-yl}-N,N-diethylpyrazolo[1,5-a]pyridine-3-carboxamide (7HY). m/z: 524.25 [M+H]

1-[6-({4-[3-(pyrrolidine-1-carbonyl)pyrazolo[1,5-a]pyridin-5-yl]piperidin-1-yl}sulfonyl)-2,3-dihydro-1H-indol-1-yl]ethan-1-one (7HZ). m/z: 522.6 [M+H]

4-({4-[3-(pyrrolidine-1-carbonyl)pyrazolo[1,5-a]pyridin-5-yl]piperidin-1-yl}sulfonyl)aniline (7IA). m/z: 454.20 [M+H]

tert-butyl N-[4-({4-[3-(pyrrolidine-1-carbonyl)pyrazolo[1,5-a]pyridin-5-yl]piperidin-1-yl}sulfonyl)phenyl]carbamate (7IB). m/z: 554.30 [M+H]

N-[4-({4-[3-(azetidine-1-carbonyl)pyrazolo[1,5-a]pyridin-5-yl]piperidin-1-yl}sulfonyl)phenyl]acetamide (7IC). m/z: 482.20 [M+H]

N-(4-{4-[3-(morpholine-4-carbonyl)pyrazolo[1,5-a]pyridin-5-yl]piperidin-1-yl}phenyl)acetamide (7ID). m/z: 512.25 [M+H]

N-[4-({4-[3-(pyrrolidine-1-carbonyl)pyrazolo[1,5-a]pyridin-5-yl]piperidin-1-yl}sulfonyl)phenyl]acetamide (7IE). m/z: 496.25 [M+H]

4-({4-[2-(diethylcarbamoyl)pyrazolo[1,5-a]pyridin-4-yl]piperidin-1-yl}sulfonyl)benzoic acid (7IF). m/z: 499.20 [M+H]

4-[1-(4-acetylbenzenesulfonyl)piperidin-4-yl]-N,N-diethylpyrazolo[1,5-a]pyridine-2-carboxamide (7IG). m/z: 483.39 [M+H]

propyl 4-({4-[2-(diethylcarbamoyl)pyrazolo[1,5-a]pyridin-4-yl]piperidin-1-yl}sulfonyl)benzoate (7IH). m/z: 527.20 [M+H]

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step not specifically disclosed.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference.

We claim:

1. An oral pharmaceutical composition comprising a therapeutically effective amount of a compound according to Formula (Ia):

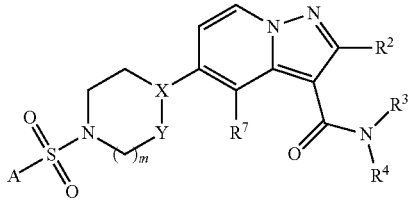
(Ia)

or pharmaceutically acceptable salt thereof, wherein:
A is $C_{1-4}$alkyl or

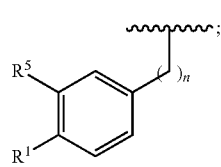
;

X is CH or N;
Y is $CH_2$ or N, and when X is N, then Y is $CH_2$;
m is 0 or 1, and when m is 1 then Y is $CH_2$;
n is 0 or 1;
R1 is H, $C_{1-6}$alkyl, $C_{0-6}$alkyleneC(=O)$R^6$, halo, cyano, aryloxy, amino, $C_{0-3}$alkylene-amido, carbamyl, S-thiocarbamyl, or ureido;
$R^2$ is H, halo, $C_{1-6}$alkyl, $C_{3-8}$cycloalkyl, or heteroaryl;
each $R^3$ and $R^4$ independently is H, $C_{1-6}$ alkyl, or $C_{1-3}$aralkyl, or $R^3$ and $R^4$ and the nitrogen to which they are attached join together to form a 3-6 membered ring optionally comprising 1 to 3 additional heteroatoms selected from N, O, and S;
$R^5$ is H, or $R^1$ and $R^5$ together with the atoms to which they are attached form a 5- or 6-membered heterocyclic ring comprising 1 to 3 ring heteroatoms selected from N, O, and S;
$R^6$ is OH, $C_{1-6}$alkyl, or $OC_{1-6}$alkyl; and
$R^7$ is H, halo or amino; and
a pharmaceutically acceptable carrier.

2. The oral pharmaceutical composition of claim 1, wherein A is methyl, ethyl, propyl, isopropyl, n-butyl, s-butyl, isobutyl, or t-butyl.

3. The oral pharmaceutical composition of claim 1, wherein A is

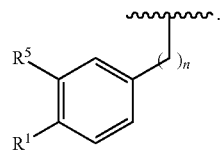
.

4. The oral pharmaceutical composition of claim 3, wherein n is 0.

5. The oral pharmaceutical composition of claim 3, where wherein $R^1$ and $R^5$ together with the atoms to which they are attached form a 5- or 6-membered heterocyclic ring comprising 1 to 3 ring heteroatoms selected from N, O, and S.

6. The oral pharmaceutical composition of claim 5, wherein A is selected from the group consisting of

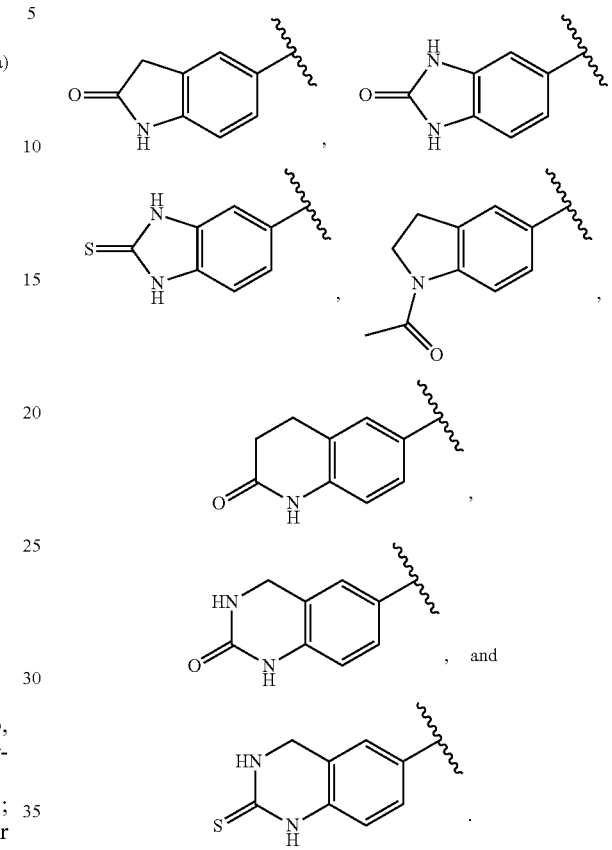

7. The oral pharmaceutical composition of claim 3, wherein $R^5$ is H.

8. The oral pharmaceutical composition of claim 7, wherein $R^1$ is:

(i) H;
(ii) methyl, ethyl, fluoromethyl, or trifluoromethyl;
(iii)

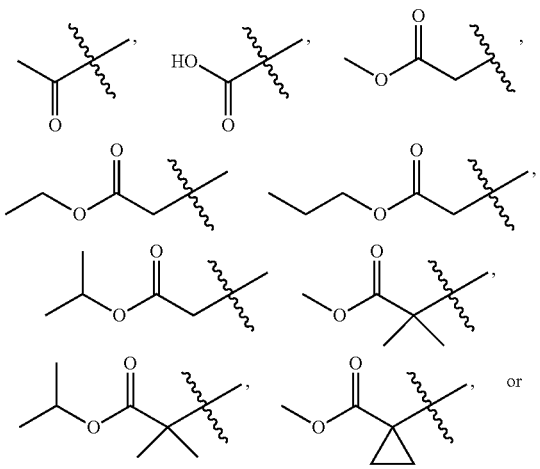

-continued
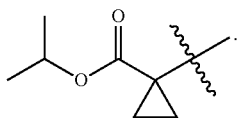
(iv) F;
(v) CN or —OPh;
(vi) —NH₂, —N(CH₃)₂ or —NH₂Ph; or
(vii)
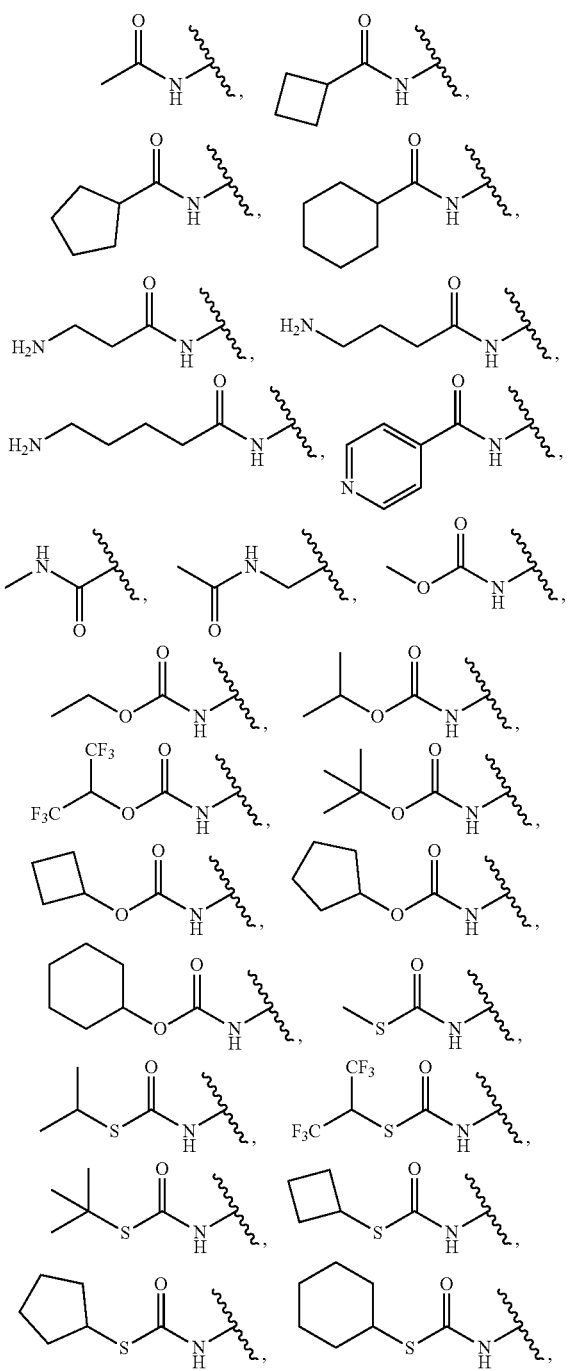
-continued
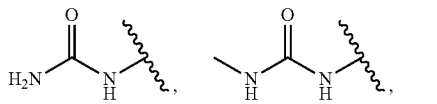
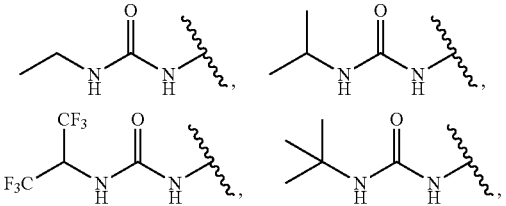
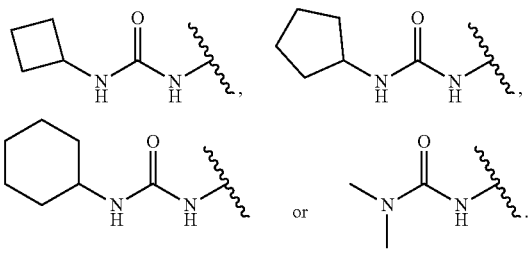
9. The oral pharmaceutical composition of claim 1, wherein A is selected from the group consisting of CH₃,
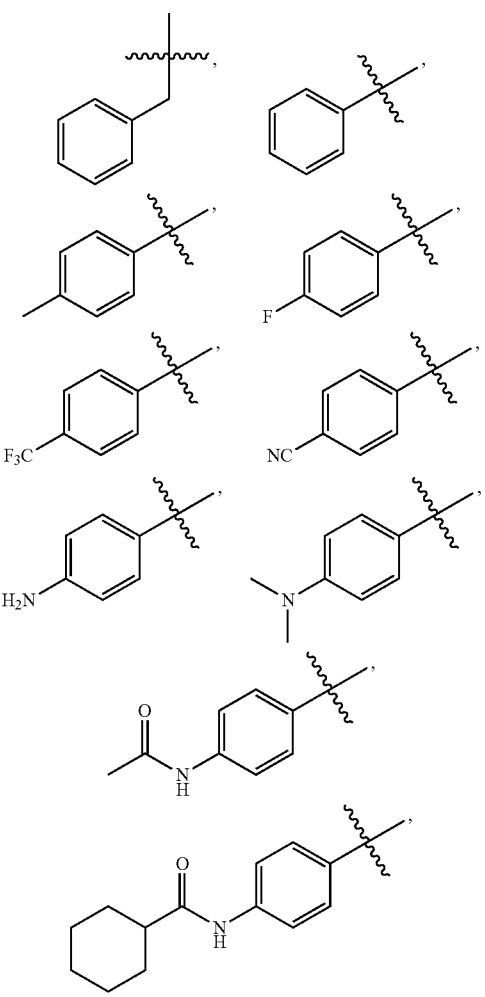

-continued

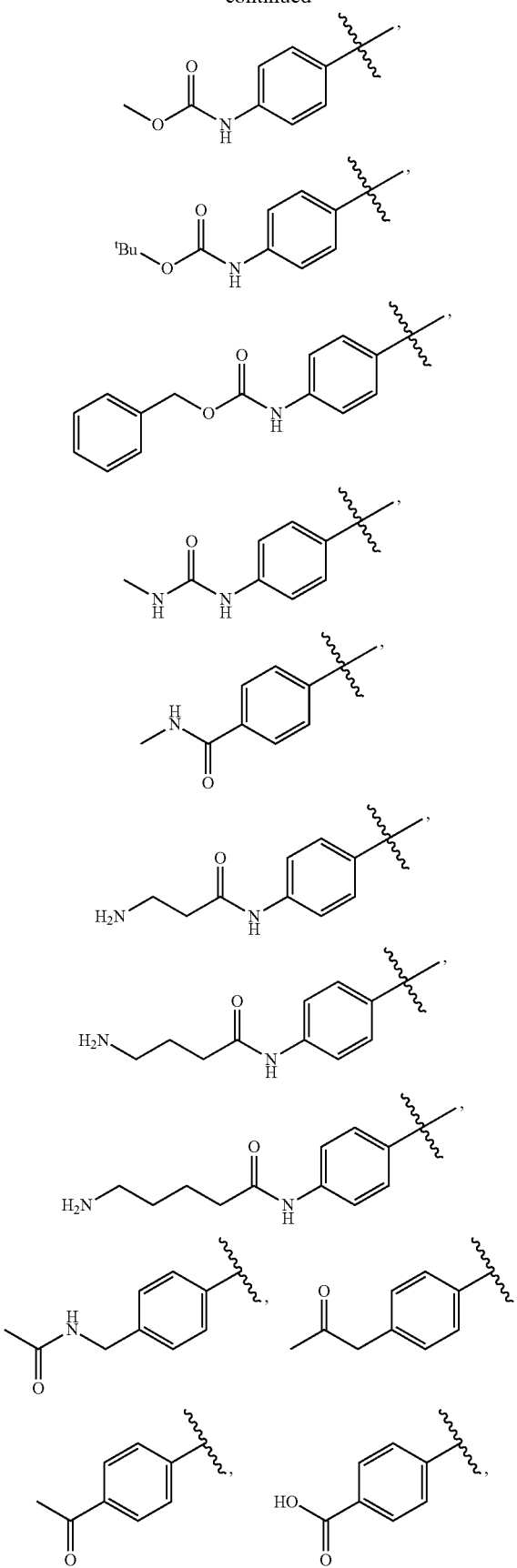

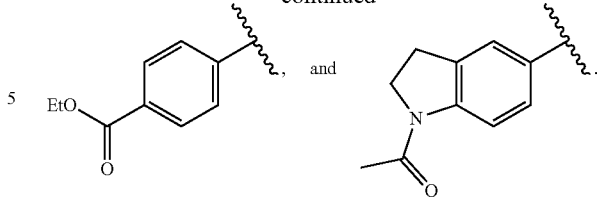

10. The oral pharmaceutical composition of claim 1, wherein $R^2$ is
   (i) H;
   (ii) Br or Cl;
   (111) $CH_3$, $CF_3$, $CH_2OH$, or $CH_2OCH_3$;
   (iv) cyclopropyl, cyclobutyl, cyclopentyl, or cyclohexyl; or
   (v) 3-furanyl.

11. The oral pharmaceutical composition of claim 1, wherein each of $R^3$ and $R^4$ independently is H, $C_{1-6}$ alkyl, or $C_{1-3}$aralkyl.

12. The oral pharmaceutical composition of claim 1, wherein

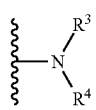

is selected from the group consisting of
   (i)

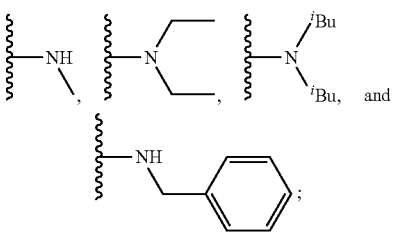

or
   (ii)

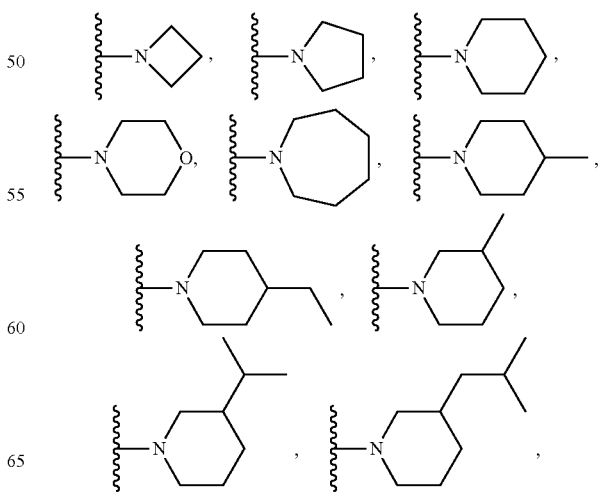

-continued

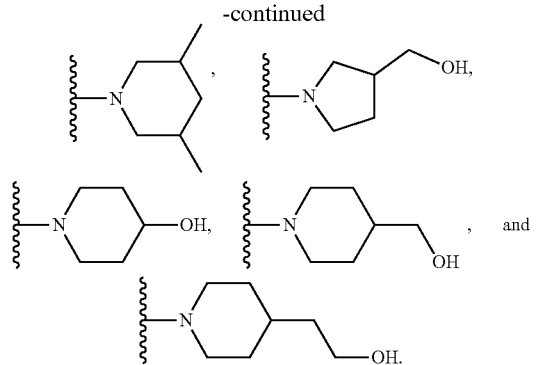

13. The oral pharmaceutical composition of claim 1, wherein R⁷ is:

(i) H; or (ii) NH₂, Br, Cl, or F.

14. The oral pharmaceutical composition of claim 1, wherein the composition is either a solid or liquid.

15. The oral pharmaceutical composition of claim 14, wherein the oral pharmaceutical composition is a solid selected from the group consisting of a capsule, tablet, powder, and granules.

16. The oral pharmaceutical composition of claim 15, further comprising an excipient, filler, binder, humectant, disintegrating agent, solution retarder, absorption accelerator, wetting agent, adsorbent, buffering agent, enteric coating, opacifying agent, sweetening, or flavoring.

17. The oral pharmaceutical composition of claim 14, wherein the oral pharmaceutical composition is a liquid selected from the group consisting of an emulsion, solution, suspension, syrup, and elixir.

18. The oral pharmaceutical composition of claim 17, further comprising a solvent, solubilizing agent, emulsifier, wetting agent, suspending agent, sweetening, or flavoring.

19. The oral pharmaceutical composition of claim 1, wherein m is 1.

* * * * *